US008236551B2

(12) United States Patent
Dhawan et al.

(10) Patent No.: US 8,236,551 B2
(45) Date of Patent: Aug. 7, 2012

(54) COMPOSITIONS AND METHODS FOR PRODUCTION OF FERMENTABLE SUGARS

(75) Inventors: Ish Kumar Dhawan, Foster City, CA (US); Dipnath Baidyaroy, Fremont, CA (US); Andrew Shaw, San Francisco, CA (US); Oleh Tanchak, Ottawa (CA); Christopher Hill, Nepean (CA); Chengsong Liu, Ottawa (CA); Amala Chokshi, Ottawa (CA); Brian R. Scott, Richmond (CA)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 13/286,972

(22) Filed: Nov. 1, 2011

(65) Prior Publication Data

US 2012/0107881 A1   May 3, 2012

Related U.S. Application Data

(60) Provisional application No. 61/409,186, filed on Nov. 2, 2010, provisional application No. 61/409,217, filed on Nov. 2, 2010, provisional application No. 61/409,472, filed on Nov. 2, 2010, provisional application No. 61/409,480, filed on Nov. 2, 2010.

(51) Int. Cl.
| C12N 1/14 | (2006.01) |
| C12N 9/04 | (2006.01) |
| C12N 15/00 | (2006.01) |
| C12N 9/02 | (2006.01) |
| C12N 9/00 | (2006.01) |
| C12Q 1/68 | (2006.01) |
| C07H 21/04 | (2006.01) |

(52) U.S. Cl. ............... 435/254.1; 435/190; 435/440; 435/6.1; 435/183; 435/189; 536/23.2

(58) Field of Classification Search ............... None
See application file for complete search history.

(56) References Cited

U.S. PATENT DOCUMENTS

| 3,953,295 A | 4/1976 | Monte et al. |
| 4,356,196 A | 10/1982 | Hultquist |
| 4,451,648 A | 5/1984 | Parsons et al. |
| 4,461,648 A | 7/1984 | Foody |
| 4,556,430 A | 12/1985 | Converse et al. |
| 4,600,590 A | 7/1986 | Dale |
| 4,683,195 A | 7/1987 | Mullis et al. |
| 4,683,202 A | 7/1987 | Mullis |
| 4,965,188 A | 10/1990 | Mullis et al. |
| 5,037,663 A | 8/1991 | Dale |
| 5,171,592 A | 12/1992 | Holtzapple et al. |
| 5,576,220 A | 11/1996 | Hudson et al. |
| 5,811,381 A | 9/1998 | Emalfarb et al. |
| 5,939,544 A | 8/1999 | Karstens et al. |
| 6,015,703 A | 1/2000 | White et al. |
| 6,015,707 A | 1/2000 | Emalfarb et al. |
| 6,090,595 A | 7/2000 | Foody et al. |
| 6,106,888 A | 8/2000 | Dale et al. |
| 6,117,679 A | 9/2000 | Stemmer |
| 6,176,176 B1 | 1/2001 | Dale et al. |
| 6,376,246 B1 | 4/2002 | Crameri et al. |
| 6,573,086 B1 | 6/2003 | Emalfrab et al. |
| 6,586,182 B1 | 7/2003 | Patten et al. |
| 6,933,133 B2 | 8/2005 | Alam et al. |
| 7,419,809 B2 | 9/2008 | Foody et al. |
| 7,465,791 B1 | 12/2008 | Hallberg et al. |
| 7,727,746 B2 | 6/2010 | Foody et al. |
| 7,754,457 B2 | 7/2010 | Foody et al. |
| 7,883,872 B2 | 2/2011 | Gusakov et al. |
| 7,910,338 B2 | 3/2011 | Hennessey et al. |
| 7,932,063 B2 | 4/2011 | Dunson et al. |
| 7,998,713 B2 | 8/2011 | Dunson et al. |
| 8,017,361 B2 | 9/2011 | Scott et al. |
| 8,017,373 B2 | 9/2011 | Hill et al. |
| 2002/0164730 A1 | 11/2002 | Perdices et al. |
| 2005/0181485 A1 | 8/2005 | Tsukamoto et al. |
| 2008/0104724 A1 | 5/2008 | Sticklen et al. |
| 2008/0194005 A1 | 8/2008 | Emalfarb et al. |
| 2008/0220990 A1 | 9/2008 | Fox |
| 2009/0099079 A1 | 4/2009 | Emalfarb et al. |
| 2009/0209009 A1 | 8/2009 | Tolan et al. |
| 2009/0312196 A1 | 12/2009 | Colbeck et al. |
| 2010/0159536 A1 | 6/2010 | Sweeney et al. |
| 2010/0304438 A1 | 12/2010 | Scott et al. |

FOREIGN PATENT DOCUMENTS

| WO | 98/15633 A1 | 4/1998 |
| WO | 2006/032282 A1 | 3/2006 |
| WO | 2006/110891 A2 | 10/2006 |
| WO | 2006/110901 A2 | 10/2006 |
| WO | 2008/073914 A2 | 6/2008 |
| WO | 2009/045651 A2 | 4/2009 |
| WO | 2010/022511 A1 | 3/2010 |
| WO | 2010/080532 A1 | 7/2010 |

OTHER PUBLICATIONS

Yoshida et al. Differential transcription of beta-glucosidase and cellobiose dehydrogenase genes in cellulose degradation by the basidiomycete *Phanerochaete chrysosporium*. FEMS Microbiol Lett. Jun. 1, 2004;235(1):177-82.*
Bhat et al. Sporotrichum thermophile Growth, Cellulose Degradation, and Cellulase Activity. Appl Environ Microbiol. Sep. 1987;53(9):2175-82.*
Stewart et al. Biotechnology and Genetic Engineering Reviews, 14:67-143, 1997.*
UniProt Database—Accession O74240—1998.*
Adachi, K., et al., "Efficient gene identification and targeted gene disruption in the wheat blotch fungus *Mycosphaerella graminicola* using TAGKO," Curr Genet., 42:123-7 [2002].
Alizadeh, H., et al., "Pretreatment of switchgrass by ammonia fiber explosion (AFEX)," Appl. Biochem. Biotechnol., 121-124:1133-1141 [2005].
Altschul, S.F., et al., "Gapped BLAST and PSI-BLAST: a new generation of protein database search programs," Nucleic Acids Res., 25(17):3389-3402 [1997].
Archibald, F., et al., "Isolation of cellobiose dehydrogenase-deficient mutant of Trametes versicolor," 7th International Conference on Biotechnology in the Pulp and Paper Industry, vol. B: B225-B228 [1998].
Awao, T., et al., "A new thermophilic species of Myceliophthora," Mycotaxon, 16(2):436-440 [1983].

(Continued)

*Primary Examiner* — Yong Pak
(74) *Attorney, Agent, or Firm* — Codexis, Inc.

(57) ABSTRACT

The present application provides genetically modified fungal organisms that produce enzyme mixtures exhibiting enhanced hydrolysis of cellulosic material to glucose, enzyme mixtures produced by the genetically modified fungal organisms, and processes for producing glucose from cellulose using such enzyme mixtures.

5 Claims, 14 Drawing Sheets

OTHER PUBLICATIONS

Bailey, M.J, et al., "Interlaboratory testing of methods for assay of xylanase activity," J. Biotechnol., 23:257-270 [1992].

Ballesteros, I., et al., "Ethanol production from steam-explosion pretreated wheat straw," Appl. Biochem. Biotechnol., 129-132: 496-508 [2006].

Bergmeyer, H. U., et al., "Enzymes as Biochemical Reagents," in Methods of Enzymatic Analysis (Bergmeyer, ed.) vol. I, 2nd Ed., pp. 457-458, Academic Press Inc., New York, NY [1974].

Biancalana, S., et al., "Fmoc chemistry compatible thio-ligation assembly of proteins," Lett. Peptide Sci., 7:291-297 [2001].

Biely, P., et al., "Recent progress in the assays of xylanolytic enzymes," J. Sci. Food Agr. 86:1636-1647 [2006].

Bjorhall, K., et al., "Comparison of different depletion strategies for improved resolution in proteomic analysis of human serum samples," Proteomics, 5:307-317 [2005].

Cannon, P.F., "Name changes in fungi of microbiological, industrial and medical importance. Part 4," Mycopathol., 111:75-83 [1990].

Cass, R., et al., "Pilot, a new peptide lead optimization technique and its application as a general library method," Proc. Thirteenth Am. Peptide Symp., Leiden, Escom, pp. 975-979 [1994].

Cavener, D.R., "GMC Oxidoreductases: A Newly Defined Family of Homologous Proteins with Diverse Catalytic Activities," J. Mol. Biol., 223:811-814 [1992].

Chandra, R.P., et al., "Substrate pretreatment: the key to effective enzymatic hydrolysis of lignocellulosics?" Adv. Biochem. Engin./Biotechnol., 108: 67-93 [2007].

Chang, X.-B., et al., "Modification of DNA ends can decrease end joining relative to homologous recombination in mammalian cells," Proc. Natl. Acad. Sci. USA, 84:4959-4963 [1987].

Chundawat, S.P.S., et al., "Effect of particle size based separation of milled corn stover on AFEX pretreatment and enzymatic digestibility," Biotechnol. Bioeng., 96(2):219-231 [2007].

Combier, J.-P., et al., "Agrobacterium tumefaciens-mediated transformation as a tool for insertional mutagenesis in the symbiotic ectomycorrhizal fungus Hebeloma cylindrosporum," FEMS Microbiol. Lett., 220:141-8 [2003].

Cook, R.M., et al, "The Preparation and Syntbctsc Application of Heterobifunctional Biocompatible Spacer Arms," Tetrahed. Lett., 35(37):6777-6780 [1994].

Davidson, R.C., et al., "A PCR-based strategy to generate integrative targeting alleles with large regions of homology," Microbiol., 148:2607-2615 [2002].

Davidson, R.C., et al., "Gene disruption by biolistic transformation in serotype D strains of *Cryptococcus neoformans*," Fung. Genet. Biol., 29:38-48 [2000].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

De Vries, R.P., et al., "aguA, the Gene Encoding an Extracellular alpha-Glucuronidase from *Aspergillus tubingensis*, is Specifically Induced on Xylose and Not on Glucuronic Acid," J. Bacteriol., 180(2):243-249 [1998].

Duff, S.J.B., et al., "Bioconversion of Forest Products Industry Waste Cellulosics to Fuel Ethanol: A Review," Biores. Technol., 55: 1-33 [1996].

Fab, S.H., et al., "Influence of Specific Signal Peptide Mutations on the Expression and Secretion of the alpha-Amylase Inhibitor Tendamistat in *Streptomyces lividans*," J. Biol. Chem., 271:15244-15252 [1996].

Fire, A., et al., "Potent and specific genetic interference by double-stranded RNA in *Caenorhabditis elegans*," Nature, 391:806-11 [1998].

Firon, A., et al., "Identification of Essential Genes in the Human Fungal Pathogen *Aspergillus fumigatus* by Transposon Mutagenesis," Eukaryot. Cell, 2:247-55 [2003].

Florea, S., et al., "Elimination of marker genes from transformed filamentous fungi by unselected transient transfection with a Cre-expressing plasmid," Fung. Genet. Biol., 46:721-730 [2009].

Foreman, P.K., et al., "Transcriptional Regulation of Biomass-degrading Enzymes in the Filamentous Fungus *Trichoderma reesei*," J. Biol. Chem., 278(34):31988-31997 [2003].

Galbe, M., et al., "A review of the production of ethanol from softwood," Appl. Microbiol. Biotechnol., 59:618-628 [2002].

Galbe, M. et al., "Pretreatment of lignocellulosic materials for efficient bioethanol production," Adv. Biochem. Engin./Biotechnol., 108: 41-65 [2007].

Garg, A.K., "An addition to the genus *Chrysosporium Corda*," Mycopathol., 30: 3-4 [1966].

Georgieva, T. I., et al., "Evaluation of continuous ethanol fermentation of dilute-acid corn stover hydrolysate using thermophilic anaerobic bacterium Thermoanaerobacter BG1L1," Appl. Microbiol, Biotech., 77: 61-68 [2007].

Ghose, T.K., "Measurement of Cellulase Activities," Pure & Appl. Chem., 59(2):257-268 [1987].

Ghosh, P., et al., "Physicochemical and Biological Treatments for Enzymatic/Microbial Conversion of Lignocellulosic Biomass," Adv. Appl. Microbiol., 39:295-333 [1993].

Glenn, J.K., et al., "Mn(II) Oxidation Is the Principal Function of the Extracellular Mn-Peroxidase from Phanerochaete chrysosporium'," Arch. Biochem. Biophys., 251(2):688-696 [1986].

Gollapalli, L.E., et al., "Predicting digestibility of ammonia fiber explosion (AFEX)-treated rice straw," Appl. Biochem. Biotechnol., 98-100:23-35 [2002].

Gong, C.S., et al., "Ethanol production from renewable resources," Adv. Biochem. Engin./Biotechnol., 65: 207-241 [1999].

Guarro, J., et al., "Myceliophthora vellerea (Chrysosporium asperatum) anamorph of Ctenomyces serratus," Mycotaxon, 23: 419-427 [1985].

Hai, P.Q., et al., "Synergistic Effects of Cellobiose Dehydrogenase, Cellulases, and Beta-Glucosidase from Irpex lacteus in the Degradation of Various Types of Cellulose,," J. Appl. Glycosci., 49:9-17 [2002].

Hallberg, B.M., et al., "Mechanism of the Reductive Half-reaction in Cellobiose Dehydrogenase", J. Biol. Chem., 278(9): 7160-7166 [2003].

Harris, P.V., et al., "Stimulation of lignocellulosic biomass hydrolysis by proteins of glycoside hydrolase family 61: structure and function of a large, enigmatic family," Biochem., 49(15):3305-16 [2010].

Harvey, P.J., et al., "Veratryl alcohol as a mediator and the role of radical cations in lignin biodegradation by *Phanerochaete chrysosporium*," FEBS Lett., 195(1,2):242-246 [1986].

Hendriks, A.T.W.M., et al., "Pretreatments to enhance the digestibility of lignocellulosic biomass," Biores. Technol., 100:10-18 [2009].

Henikoff, S., et al., "Amino acid substitution matrices from protein blocks," Proc. Natl. Acad. Sci. USA, 89:10915-10919 [1992].

Henriksson, G. et al, "Substrate specificity of cellobiose dehydrogenase from *Phanerochaete chrysosporium*," Biochim. Biophys. Acta., 1383: 48-54 [1998].

Herrmann, M.C., et al., "The beta-D-xylosidase of Trichoderma reesei is a multifunctional beta-D-xylan xylohydrolase," Biochem. J., 321:375-381 [1997].

Horton, R.M., et al., "Gene splicing by overlap extension," Meth. Enzymol., 217:270-279 [1993].

Hsu, T.-A., "Pretreatment of Biomass," in Handbook on Bioethanol: Production and Utilization (Wyman, ed.), Taylor & Francis, Washington, D.C., pp. 179-212 [1996].

Igarashi, K., et al., "Cellobiose dehydrogenase enhances Phanerochaete chrysosporium cellobiohydrolase I activity by relieving product inhibition," Eur. J. Biochem., 253: 101-106 [1998].

Kadotani, N., et al. "RNA silencing in the phytopathogenic fungus Magnaporthe oryzae," Mol. Plant Microbe Interact., 16(9):769-76 [2003].

Knutsen, J.S., et al., "Combined sedimentation and filtration process for cellulase recovery during hydrolysis of lignocellulosic biomass," Appl., Biochem. Biotech., 98-100:1161-1172 [2002].

Kotiranta, P., et al., "Adsorption and activity of *Trichoderma reesei* cellobiohydrolase I, endoglucanase II, and the corresponding core proteins on steam pretreated willow," Appl. Biochem. Biotechnol., 81: 81-90 [1999].

Kurabi, A., et al., "Enzymatic hydrolysis of steam-exploded and ethanol organosolv-pretreated Douglas-Fir by novel and commercial fungal cellulases," Appl. Biochem. Biotechnol., 121-124:219-230 [2005].

Lee et al., "Structural Characterization of Glucooligosaccharide Oxidase from Acremonium strictum," Appl. Environ. Microbiol., 71:8881-8887 [2005].

Lee, Y.Y., et al., "Dilute-Acid Hydrolysis of Lignocellulosic Biomass," Adv. Biochem. Eng. Biotechnol., 65: 93-115 [1999].

Leitner, C., et al., "Production of a Novel Pyranose 2-Oxidase by Basidiomycete Trametes multicolor," Appl Biochem Biotechnol, 70-72:237-248 [1998].

Lever, M., "A New Reaction for Calorimetric Determination of Carbohydrates," Anal. Biochem., 47:273-279 [1972].

Li, J., et al., "Crystal Structure of Cholesterol Oxidase Complexed with a Steroid Substrate: Implications for Flavin Adenine Dinucleotide Dependent Alcohol Oxidases," Biochem., 32:11507-15 [1993].

Lynd, L.R., et al., "Large-Scale Fuel Ethanol from Lignocellulose," Appl. Biochem. Biotechnol., 24/25: 695-719 [1990].

Macbeath, G., et al., "Printing Proteins as Microarrays for High-Throughput Function Determination," Science, 289:1760-1763 [2000].

Mansfield, S.D. et al., "Cellobiose Dehydrogenase, an Active Agent in Cellulose Depolymerization," Appl. Environ. Microbiol., 63(10): 3804-3809 [1997].

Martin, C., et al., "Investigation of cellulose convertibility and ethanolic fermentation of sugarcane bagasse pretreated by wet oxidation and steam explosion," J. Chem. Technol. Biotechnol., 81:1669-1677 [2006].

McMillan, J.D., "Pretreating Lignocellulosic Biomass," in Enzymatic Conversion of Biomass for Fuels Production (Himmel et al. eds.), ACS Symposium Series 566, American Chemical Society, Washington, D.C., Chapter 15 [1994].

Miyagishi, M., et al., "U6 promoter-driven siRNAs with four uridine 3' overhangs efficiently suppress targeted gene expression in mammalian cells," Nat. Biotechnol., 19:497-500 [2002].

Mores, W.D., et al., "Cellulase recovery via membrane filtration," Appl. Biochem. Biotech., 91-93:297-309 [2001].

Mosier, N., et al., "Features of promising technologies for pretreatment of lignocellulosic biomass," Biores. Technol., 96: 673-686 [2005].

Mosier, N., et al., "Reaction Kinetics, Molecular Action, and Mechanisms of Cellulolytic Proteins," Advances in Biochemical Engineering/Biotechnology, 65:23-40 [1999].

Moustafa, A.F., et al., "Thielavia aegyptiaca, a New Thermotolerant Ascomycete from Egyptian Soils," Persoonia, 14(Part2):173-175[1990].

Ngiam, C., et al., "Characterization of a Foldase, Protein Disulfide Isomerase A, in the Protein Secretory Pathway of *Aspergillus niger*," Appl Environ. Microbiol., 66(2):775-82 [2000].

Olsson, L., et al., "Fermentation of lignocellulosic hydrolysates for ethanol production," Enz. Microb. Tech., 18:312-331 [1996].

Paddison, P.J., et al., "Short hairpin RNAs (shRNAs) induce sequence-specific silencing in mammalian cells," Genes Dev. 16:948-958 [2002].

Palonen, H., et al., "Evaluation of Wet Oxidation Pretreatment for Enzymatic Hydrolysis of Softwood," Appl. Biochem. Biotechnol., 117:1-17 [2004].

Pan, X., et al., "Bioconversion of Hybrid Poplar to Ethanol and Co-Products Using an Organosolv Fractionation Process: Optimization of Process Yields," Biotechnol. Bioeng., 94(5):851-861 [2006].

Pan, X., et al., "Biorefining of Softwoods Using Ethanol Organosolv Pulping: Preliminary Evaluation of Process Streams for Manufacture of Fuel-Grade Ethanol and Co-Products," Biotechnol. Bioeng., 90(4):473-481 [2005].

Rakotomanga, S., et al., "Simultaneous determination of gluconolactone, galactonolactone and galactitol in urine by reversed-phase liquid chromatography: application to galactosemia," J. Chromatog. B., 570:277-284 [1991].

Rothstein, R.J., "One-Step Gene Disruption in Yeast," Meth. Enzymol., 101:202-211 [1983].

Rotsaert, F.A., et al., "Site-Directed Mutagenesis of the Heme Axial Ligands in the Hemoflavoenzyme Cellobiose Dehydrogenase," Arch. Biochem. Biophys., 390(2):206-14 [2001].

Rotsaert, F.A.J., et al., "Role of the flavin domain residues, His689 and Asn732, in the catalytic mechanism of cellobiose dehydrogenase from *Phanerochaete chrysosporium*," Biochem., 42:4049-4056 [2003].

Saloheimo, M., et al., "Swollenin, a *Trichoderma reesei* protein with sequence similarity to the plant expansins, exhibits disruption activity on cellulosic materials," Eur. J. Biochem., 269:4202-4211 [2002].

Sassner, P., et al., "Bioethanol production based on simultaneous saccharification and fermentation of steam-pretreated Salix at high dry-matter content," Enzyme Microb. Technol., 39:756-762 [2006].

Schell, D.J., et al., "A bioethanol process development unit: initial operating experiences and results with a corn fiber feedstock," Biores. Technol., 91:179-188 [2004].

Schell, D.J., et al., "Dilute—Sulfuric Acid Pretreatment of Corn Stover in Pilot-Scale Reactor," Appl. Biochem. Biotechnol., 105-108:69-85 [2003].

Schmidt, A.S., et al.,, "Optimization of Wet Oxidation Pretreatment of Wheat Straw," Biores. Technol., 64:139-151 [1998].

Schou, C., et al., "Characterization of a cellobiose dehydrogenase from Humicola insolens," Biochem. J., 330:565-571 [1998].

Spanikova, S., et al., "Glucuronoyl esterase—Novel carbohydrate esterase produced by Schizophyllum commune," FEBS Lett., 580:4597-4601 [2006].

Strecker, H.J., "Glucose Dehydrogenase from Liver", Meth. Enzymol., 1:335 [1955].

Taherzadeh, M.J., et al., "Pretreatment of Lignocellulosic Wastes to Improve Ethanol andBiogas Production: A Review," Int. J. Mol. Sci., 9:1621-1651 [2008].

Teeri, T.T., "Crystalline cellulose degradation: new insight into the function of cellobiohydrolases," Tr. Biotechnol., 15:160-167 [1997].

Teeri, T.T., et al., "*Trichoderma reesei* cellobiohydrolases: why so efficient on crystalline cellulose?," Biochem. Soc. Trans., 26:173-178 [1998].

Teymouri, F., et al., "Optimization of the ammonia fiber explosion (AFEX) treatment parameters for enzymatic hydrolysis of corn stover," Biores. Technol., 96:2014-2018 [2005].

Thon, M.R., et al., "Restriction Enzyme-Mediated Integration Used to Produce Pathogenicity Mutants of *Colletotrichum graminicola*," Mol. Plant Microbe Interact., 13(12):1356-65 [2000].

Trinder, P., "Determination of glucose in blood using glucose oxidase with an alternative oxygen acceptor," Ann. Clin. Biochem., 6:24-27 [1969].

Upadhyay, J.M., et al., "A new variety of thermophilic mold, *Thermoascus aurantiacus* var. levisporus," Mycopathol., 87:71-80 [1984].

Vallander, L., et al., "Production of Ethanol from Lignocellulosic Materials: State of the Art," Adv. Biochem. Eng./ Biotechnol., 42:63-95 [1990].

Van Tilbeurgh, H., et al., "Detection and differentiation of cellulase components using low molecular mass fluorogenic substrates," FEBS Lett., 187(2):283-288 [1985].

Van Tilbeurgh, H., et al., "The use of 4-methylumbelliferyl and other chromophoric glycosides in the study of cellulolytic enzymes," FEBS Lett., 149:152-156 [1982].

Varga, E., et al., "High Solid Simultaneous Saccharification and Fermentation of Wet Oxidized Corn Stover to Ethanol," Biotechnol. Bioeng., 88(5):567-574 [2004].

Varga, E., et al., "Optimization of Steam Pretreatment of Corn Stover to Enhance Enzymatic Digestibility," Appl. Biochem. Biotechnol., 113-116:509-523 [2004].

Venturi, L.L., et al., "Extracellular Beta-D-glucosidase from *Chaetomium thermophilum* var. *coprophilum*: production, purification and some biochemical properties," J. Basic Microbiol., 42: 55-66 [2002].

Viikari, L., et al., "Thermostable Enzymes in Lignocellulose Hydrolysis," Adv. Biochem. Eng. Biotechnol.,108:121-45 [2007].

Volc, J., et al., "Screening of basidiomycete fungi for the quinone-dependent sugar C-2/C-3 oxidoreductase, pyranose dehydrogenase, and properties of the enzyme from Macrolepiota rhacodes," Arch. Microbiol., 176:178-186 [2001].

Von Klopotek, A., "Revision der thermophilen Sporotrichum-Arten: *Chrysosporium thermophilum* (Apinis) comb. nov. und

*Chrysosporium fergusii* spec. nov. = status conidialis von *Corynascus thermophilus* (Fergus und Sinden).comb. nov.," Arch. Microbiol., 98:365-369 [1974].

Wang, Y., et al., "Agrobacterium-meditated gene disruption using split-marker in Grosmannia clavigera, a mountain pine beetle associated pathogen," Curr. Genet., 56:297-307 [2010].

Weil, J., et al., "Pretreatment of Yellow Poplar Sawdust by Pressure Cooking in Water," Appl. Biochem. Biotechnol., 68: 21-40 [1997].

Wiselogel, A., et al., "Biomass Feedstock Resources and Composition," in Handbook on Bioethanol, (Wyman, ed.), pp. 105-118, Taylor & Francis, Washington D.C. [1995].

Wyman, C.E., "Ethanol from Lignocellulosic Biomass: Technology, Economics, and Opportunities," Biores. Technol., 50: 3-16 [1994].

Wyman, C.E., et al., "Coordinated development of leading biomass pretreatment technologies," Biores. Technol., 96:1959-1966 [2005].

Yang, B., et al., "Pretreatment: the key to unlocking low-cost cellulosic ethanol," Biofuels Bioprod. Bioref.-Biofpr. 2: 26-40 [2008].

Zhang, Y.-H., et al., "Outlook for cellulase improvement: Screening and selection strategies," Biotechnol. Adv., 24:452-481 [2006].

Zrenner, R. et al., "Analysis of the expression of potato uridinediphosphate-glucose pyrophosphorylase and its inhibition by antisense RNA," Planta, 190:247-52 [1993].

Bentley, R., "Glucose Aerodehydrogenase (Glucose Oxidase)," Meth. Enzymol., 1:340-345 [1955].

Lin, S.-F., et al., "Purification and characterization of a novel glucooligosaccharide oxidase from Acremonium strictum T1," Biochim. Biophys. Acta., 1118:41-47 [1991].

Andric, P., et al. "Reactor design for minimizing product inhibition during enzymatic lignocellulose hydrolysis: I. Significance and mechanism of cellobiose and glucose inhibition on cellulolytic enzymes," Biotechnology Advances, 28 (3):308-324 [2010].

Kelley, R.L., et al., "Characterization of glucose oxidase-negative mutants of a lignin degrading basidiomycete Phanerochaete chrysosporium," Archives of Microbiology, 144:254-257 [1986].

Witteveen, C.F.B., et al., "Glucose oxidase overproducing and negative mutants of *Aspergillus niger*," Applied Microbiology and Biotechnology, 33:683-686 [1990].

Dumonceaux, T., et al., "Cellobiose dehydrogenase is essential for wood invasion and nonessential for kraft pulp delignification by Trametes versicolor," Enzyme and Microbial Technology, 29:478-489 [2001].

Phillips, C.M., et al., "Cellobiose dehydrogenase and a copper-dependent polysaccharide monooxygenase potentiate cellulose degradation by *Neurospora crassa*," ACS Chemical Biology, 6:1399-1406 [2011].

Roy, S.K., "Induction and Catabolite Repression of Beta-Glucosidase Synthesis in Myceliophthora thermophila D-14 (= ATCC 48104)," Applied and Environmental Microbiology, 54(8):2152-2153 [1988].

* cited by examiner

Fig. 3

(*M. thermophila* -- CDH1)

Nucleotide sequence(SEQ ID NO:5)

ATGAGGACCTCCTCTCGTTTAATCGGTGCCCTTGCGGCGGCACTCTTGCCGTCTGCCCTTGCGCAGAACAACGCGCCGGTAAC
CTTCACCGACCCGGACTCGGGCATTACCTTCAACACGTGGGGTCTCGCCGAGGATTCTCCCCAGACTAAGGGCGGTTTCACTTT
TGGTGTTGCTCTGCCCTCTGATGCCCTCACGACAGACGCCAAGGAGTTCATCGGTTACTTGAAATGCGCGAGGAACGATGAGA
GCGGTTGGTGCGGTGTCTCCCTGGGCGGCCCCATGACCAACTCGCTCCTCATCGCGGCCTGGCCCACGAGGACACCGTCTA
CACCTCTCTCCGCTTCGCCACCGGCTATGCCATGCCGGATGTCTACCAGGGGGACGCCGAGATCACCCAGGTCTCCTCCTCTG
TCAACTCGACGCACTTCAGCCTCATCTTCAGGTGCGAGAACTGCCTGCAATGGAGTCAAAGCGGCGCCACCGGCGGTGCCTCC
ACCTCGAACGGCGTGTTGGTCCTCGGCTGGGTCCAGGCATTCGCCGACCCGGCCAACCCGACCTGCCCCGACCAGATCACCC
TCGAGCAGCACGACAACGGCATGGGTATCTGGGGTGCCCAGCTCAACTCCGACGCCGCCAGCCCGTCCTACACCGAGTGGGC
CGCCCAGGCCACCAAGACCGTCACGGGTGACTGCGGCGGTCCCACCGAGACCTCTGTCGTCGGTGTCCCCGTTCCGACGGGC
GTCTCGTTCGATTACATCGTCGTGGGCGGCGGTGCCGGTGGCATCCCCGCCGCCGACAAGCTCAGCGAGGCCGGCAAGAGTG
TGCTGCTCATCGAGAAGGGCTTTGCCTCGACCGCCAACACCGGAGGCACTCTCGGCCCCGAGTGGCTCGAGGGCCACGACCT
TACCCGCTTTGACGTGCCGGGTCTGTGCAACCAGATCTGGGTTGACTCCAAGGGGATCGCTTGCGAGGATACCGACCAGATGG
CTGGCTGTGTCCTCGGCGGCGGTACCGCCGTGAATGCCGGCCTGTGGTTCAAGCCCTACTCGCTCGACTGGGACTACCTCTTC
CCTAGTGGTTGGAAGTACAAAGACGTCCAGCCGGCCATCAACCGCGCCCTCTCGCGCATCCCGGGCACCGATGCTCCCTCGAC
CGACGGCAAGCGCTACTACCAGCAGGGCTTCGACGTGCTCTCCAAGGGCCTGGCCGGCGGCGGCTGGACCTCGGTCACGGCC
AATAACGCGCCAGACAAGAAGAACCGCACCTTCTCCCATGCCCCCTTCATGTTCGCCGGCGGCGAGCGCAACGGCCCGCTGG
GCACCTACTTCCAGACCGCCAAGAAGCGCAGCAACTTCAAGCTCTGGCTCAACACGTCGGTCAAGCGCGTCATCCGCCAGGGC
GGCCACATCACCGGCGTCGAGGTCGAGCCGTTCCGCGACGGCGGTTACCAAGGCATCGTCCCCGTCACCAAGGTTACGGGCC
GCGTCATCCTCTCTGCCGGTACCTTTGGCAGTGCAAAGATCCTGCTGAGGAGCGGTATCGGTCCGAACGATCAGCTGCAGGTT
GTCGCGGCCTCGGAGAAGGATGGCCCTACCATGATCAGCAACTCGTCCTGGATCAACCTGCCTGTCGGCTACAACCTGGATGA
CCACCTGAACACCGACACTGTCATCTCCCACCCCGACGTCGTGTTCTACGACTTCTACGAGGCGTGGGACAATCCCATCCAGTC
TGACAAGGACAGCTACCTCAACTCGCGCACGGGCATCCTCGCCCAAGCCGCTCCCAACATTGGGCCTATGTTCTGGGAAGAGA
TCAAGGGTGCGGACGGCCATTGTTCGCCAGCTCCAGTGGACTGCCCGTGTCGAGGGCAGCCTGGGTGCCCCCAACGGCAAGAC
CATGACCATGTCGCAGTACCTCGGTCGTGGTGCCACCTCGCGCGGCCGATGACCATGACCCCGTCCCTGACAACTGTCGTCT
CGGACGTGCCCTACCTCAAGGACCCCAACGACAAGGAGGCCGTCATCCAGGGCATCATCAACCTGCAGAACGCCCTCAAGAAC
GTCGCCAACCTGACCTGGCTCTTCCCCAACTCGACCATCACGCCGCGCCAATACGTTGACAGCATGGTCGTCTCCCCGAGCAA
CCGGCGCTCCAACCACTGGATGGGCACCAACAAGATCGGCACCGACGACGGCCGCAAGGGCGGCTCCGCCGTCGTCGACCTC
AACACCAAGGTCTACGGCACCGACAACCTCTTCGTCATCGACGCCTCCATCTTCCCCGGCGTGCCCACCACCAACCCCACCTCG
TACATCGTGACGGCGTCGGAGCACGCCTCGGCCCGCATCCTCGCCCTGCCCGACCTCACGCCCGTCCCCAAGTACGGGCAGT
GCGGCGGCCGCGAATGGAGCGGCAGCTTCGTCTGCGCCGACGGCTCCACGTGCCAGATGCAGAACGAGTGGTACTCGCAGTG
CTTGTGA

AA sequence (SEQ ID NO:6)

MRTSSRLIGALAAALLPSALAQNNAPVTFTDPDSGITFNTWGLAEDSPQTKGGFTFGVALPSDALTTDAKEFIGYLKCARNDESGWCG
VSLGGPMTNSLLIAAWPHEDTVYTSLRFATGYAMPDVYQGDAEITQVSSSVNSTHFSLIFRCENGLQWSQSGATGGASTSNGVLVLG
WVQAFADPGNPTCPDQITLEQHDNGMGIWGAQLNSDAASPSYTEWAAQATKTVTGDCGGPTETSVVGVPVPTGVSFDYIVVGGGA
GGIPAADKLSEAGKSVLLIEKGFASTANTGGTLGPEWLEGHDLTRFDVPGLCNQIWVDSKGIACEDTDQMAGCVLGGGTAVNAGLWF
KPYSLDWDYLFPSGWKYKDVQPAINRALSRIPGTDAPSTDGKRYYQQGFDVLSKGLAGGGWTSVTANNAPDKKNRTFSHAPFMFAG
GERNGPLGTYFQTAKKRSNFKLWLNTSVKRVIRQGGHITGVEVEPFRDGGYQGIVPVTKVTGRVILSAGTFGSAKILLRSGIGPNDQL
QVVAASEKDGPTMISNSSWINLPVGYNLDDHLNTDTVISHPDVVFYDFYEAWDNPIQSDKDSYLNSRTGILAQAAPNIGPMFWEEIKG
ADGIVRQLQWTARVEGSLGAPNGKTMTMSQYLGRGATSRGRMTITPSLTTVVSDVPYLKDPNDKEAVIQGIINLQNALKNVANLTWLF
PNSTITPRQYVDSMVVSPSNRRSNHWMGTNKIGTDDGRKGGSAVVDLNTKVYGTDNLFVIDASIFPGVPTTNPTSYIVTASEHASARIL
ALPDLTPVPKYGQCGGREWSGSFVCADGSTCQMQNEWYSQCL*

Fig. 4

(*M. thermophila* -- CDH2)

Nucleotide sequence (SEQ ID NO:7)

ATGAAGCTACTCAGCCGCGTTGGGGCGACCGCCCTAGCGGCGACGTTGTCACTGCAGCAATGTGCAGCCCAGATGACCGAGG
GGACCTACACCGATGAGGCTACCGGTATCCAATTCAAGACGTGGACCGCCTCCGAGGGCGCCCCTTTCACGTTTGGCTTGACC
CTCCCCGCGGACGCGCTGGAAAAGGATGCCACCGAGTACATTGGTCTCCTGCGTTGCCAAATCACCGATCCCGCCTCGCCCAG
CTGGTGCGGTATCTCCCACGGCCAGTCCGGCCAGATGACGCAGGCGCTGCTGCTGGTCGCCTGGGCCAGCGAGGACACCGTC
TACACGTCGTTCCGCTACGCCACCGGCTACACGCTCCCCGGCCTCTACACGGGCGACGCCAAGCTGACCCAGATCTCCTCCTC
GGTCAGCGAGGACAGCTTCGAGGTGCTGTTCCGCTGCGAAAACTGCTTCTCCTGGGACCAGGATGGCACCAAGGGCAACGTCT
CGACCAGCAACGGCAACCTGGTCCTCGGCCGCGCCGCCGCGGAAAGGATGGTGTGACGGGCCCCACGTGCCCGGACACGGCCG
AGTTCGGTTTCCATGATAACGGTTTCGGACAGTGGGGTGCCGTGCTTGAGGGTGCTACTTCGGACTCGTACGAGGAGTGGGCT
AAGCTGGCCACGACCACGCCCGAGACCACCTGCGATGGCACTGGCCCCGGCGACAAGGAGTGCGTTCCGGCTCCCGAGGACA
CGTATGATTACATCGTTGTCGGTGCCGGCGCCGGTGGTATCACCGTCGCCGACAAGCTCAGCGAGGCCGGCCACAAGGTCCTT
CTCATCGAGAAGGGACCCCCTTCGACCGGCCTGTGGAACGGGACCATGAAGCCCGAGTGGCTCGAGAGCACCGACCTTACCC
GCTTCGACGTTCCCGGCCTGTGCAACCAGATCTGGGTCGACTCTGCCGGCATCGCCTGCACCGATACCGACCAGATGGCGGG
CTGCGTTCTCGGCGGTGGCACCGCTGTCAACGCTGGTTTGTGGTGGAAGCCCCACCCCGCTGACTGGGATGAGAACTTCCCCG
AAGGGTGGAAGTCGAGCGATCTCGCGGATGCGACCGAGCGTGTCTTCAAGCGCATCCCCGGCACGTCGCACCCGTCGCAGGA
CGGCAAGTTGTACCGCCAGGAGGGCTTCGAGGTCATCAGCAAGGGCCTGGCCAACGCCGGCTGGAAGGAAATCAGCGCCAAC
GAGGCGCCCAGCGAGAAGAACCACACCTATGCACACACCGAGTTCATGTTCTCGGGCGGTGAGCGTGGCGGCCCCTGGCGA
CGTACCTTGCCTCGGCTGCCGAGCGCAGCAACTTCAACCTGTGGCTCAACACTGCCGTCCGGAGGGCCGTCCGCAGCGGCAG
CAAGGTCACCGGCGTCGAGCTCGAGTGCCTCACGGACGGTGGCTTCAGCGGGACCGTCAACCTGAATGAGGGCGGTGGTGTC
ATCTTCTCGGCCGGCGCTTTCGGCTCGGCCAAGCTGCTCCTTCGCAGCGGTATCGGTCCTGAGGACCAGCTCGAGATTGTGGC
GAGCTCCAAGGACGGCGAGACCTTCACTCCCAAGGACGAGTGGATCAACCTCCCCGTCGGCCACAACCTGATCGACCATCTCA
ACACTGACCTCATTATCACGCACCCGGATGTCGTTTTCTATGACTTCTATGCGGCCTGGGACGAGCCCATCACGGAGGATAAGG
AGGCCTACCTGAACTCGCGGTCCGGCATTCTCGCCCAGGCGGCGCCCAATATCGGCCCTATGATGTGGGATCAAGTCACGCCG
TCCGACGGCATCACCCGCCAGTTCCAGTGGACATGCCGTGTTGAGGGCGACAGCTCCAAGACCAACTCGACCCACGCCATGAC
CCTCAGCCAGTACCTCGGCCGTGGCGTCGTCTCGCGCGGCCGGATGGGCATCACCTCCGGGCTGAGCACGACGGTGGCCGA
GCACCCGTACCTGCACAACAACGGCGACCTGGAGGCGGTCATCCAGGGGATCCAGAACGTGGTGGACGCGCTCAGCCAGGTG
GCCGACCTCGAGTGGGTGCTCCCGCCGCCCGACGGGACGGTGGCCGACTACGTCAACAGCCTGATCGTCTCGCCGGCCAACC
GCCGGGCCAACCACTGGATGGGCACGGCCAAGCTGGGCACCGACGACGGCCGCTCGGGCGGCACCTCGGTCGTCGACCTCG
ACACCAAGGTGTACGGCACCGACAACCTGTTCGTCGTCGACGCGTCCGTCTTCCCCGGCATGTCGACGGGCAACCCGTCGGCC
ATGATCGTCATCGTGGCCGAGCAGGCGGCGCAGCGCATCCTGGCCCTGCGGTCTTAA

AA sequence (SEQ ID NO:8)

MKLLSRVGATALAATLSLQQCAAQMTEGTYTDEATGIQFKTWTASEGAPFTFGLTLPADALEKDATEYIGLLRCQITDPASPSWCGISH
GQSGQMTQALLLVAWASEDTVYTSFRYATGYTLPGLYTGDAKLTQISSSVSEDSFEVLFRCENCFSWDQDGTKGNVSTSNGNLVLG
RAAAKDGVTGPTCPDTAEFGFHDNGFGQWGAVLEGATSDSYEEWAKLATTTPETTCDGTGPGDKECVPAPEDTYDYIVVGAGAGGI
TVADKLSEAGHKVLLIEKGPPSTGLWNGTMKPEWLESTDLTRFDVPGLCNQIWVDSAGIACTDTDQMAGCVLGGGTAVNAGLWWKP
HPADWDENFPEGWKSSDLADATERVFKRIPGTSHPSQDGKLYRQEGFEVISKGLANAGWKEISANEAPSEKNHTYAHTEFMFSGGE
RGGPLATYLASAAERSNFNLWLNTAVRRAVRSGSKVTGVELECLTDGGFSGTVNLNEGGGVIFSAGAFGSAKLLLRSGIGPEDQLEIV
ASSKDGETFTPKDEWINLPVGHNLIDHLNTDLIITHPDVVFYDFYAAWDEPITEDKEAYLNSRSGILAQAAPNIGPMMWDQVTPSDGITR
QFQWTCRVEGDSSKTNSTHAMTLSQYLGRGVVSRGRMGITSGLSTTVAEHPYLHNNGDLEAVIQGIQNVVDALSQVADLEWVLPPP
DGTVADYVNSLIVSPANRRANHWMGTAKLGTDDGRSGGTSVVDLDTKVYGTDNLFVVDASVFPGMSTGNPSAMIVIVAEQAAQRILA
LRS*

Fig.5

(*M. thermophila* -- GO1)

Nucleotide sequence (SEQ ID NO:1)

ATGGGCTTCCTCGCCGCCACTCTTGTGTCCTGTGCCGCTCTCGCGAGCGCAGCAAGCATCCCACGTCCCCATGCCAAGCGCCA
GGTCTCCCAGCTTCGCGACGATTATGACTTCGTGATCGTTGGCGGTGGAACTAGCGGCCTCACTGTAGCCGATCGGCTGACAG
AGGCCTTTCCAGCCAAGAACGTCCTTGTCATTGAGTATGGAGACGTCCACTACGCCCCGGGAACCTTCGATCCGCCGACGGAC
TGGATCACACCTCAGCCTGATGCCGCCCCTTCCTGGTCTTTCAATTCCCTCCCCAACCCAGACATGGCAAACACAACAGCGTTTG
TGCTAGCCGGCCAAGTGGTGGGTGGAAGCAGTGCCGTGAACGGCATGTTCTTTGACCGCGCATCCCGCCACGACTACGATGC
GTGGACCGCGGTCGGCGGGTCGGGGTTCGAACAGTCCAGCCACAAGTGGGACTGGGAGGGGCTGTTCCCTTTCTTCCAGAAG
AGCGTCACGTTCACGGAACCGCCGGCCGACATCGTCCAGAAGTATCACTACACCTGGGACCTGTCTGCCTACGGCAATGGCTC
AACCCCCATCTACAGCAGCTATCCGGTCTTCCAGTGGGCGGACCAGCCGTTACTTAACCAGGCATGGCAGGAGATGGGAATCA
ATCCGGTGACCGAATGCGCCGGCGGCGACAAGGAGGGTGTCTGCTGGGTTCCCGCCTCGCAGCACCCTGTCACGGCGAGGA
GGTCGCACGCCGGGCTCGGCCACTACGCCGATGTGCTCCCGCGAGCCAATTACGACCTCCTCGTTCAACACCAGGTTGTCAGG
GTAGTATTCCCCAATGGGCCGAGCCACGGACCGCCGCTTGTCGAGGCGCGGTCCCTGGCCGACAACCACCTGTTCAACGTGAC
TGTGAAGGGCGAAGTCATCATCTCGGCGGGCGCTCTGCACACCCCGACCGTCCTTCAACGGAGCGGCATCGGCCCGGCATCC
TTCTTGGACGACGCCGGGATCCCCGTGACGCTTGACCTGCCGGGCGTCGGCGCCAACCTCCAGGACCACTGCGGTCCGCCCG
TCACGTGGAACTACACCGAGCCCTACACCGGCTTCTTCCCGCTCCCCTCGGAGATGGTCAACAACGCGACCTTCAAAGCCGAA
GCCATCACCGGCTTCGACGAGGTCCCGGCCCGCGGCCCCTACACGCTCGCCGGGGGCAACAACGCCATCTTCGTATCGCTCC
CACACCTCACGGCCGACTACGGCGCCATCACCGCAAATATCCGCGCCATGGTCGCCGACGGAACCGCCGCCTCCTATCTCGCG
GCCGACGTCCGCACCATCCCGGGGATGGTGGCCGGCTACGAGGCGCCCAGCTCCTCGTGCTCGCCGACCTGCTCGACAACCCGG
AGGCGCCCAGCCTGGAGACGCCGTGGGCGACGAGCGAGGCGCCGCAGACGTCGTCGGTCCTGGCCTTCCTGCTGCACCCGC
TCAGCCGCGGCAGCGTGCGGCTCAACCTCAGCGACCCGCTCGCGCAGCCCGTGCTCGACTACCGCTCCGGGTCCAACCCGGT
CGACATCGACCTGCACCTCGCCCACGTGCGCTTCCTGCGCGGCCTGCTCGACACGCCCACCATGCAGGCCCGCGGGGCGCTC
GAGACGGCCCCCGGCTCGGCCGTGGCCGACAGCGACGAGGCGCTGGGGGAGTACGTGCGCTCGCACAGCACGCTGTCCTTC
ATGCACCCGTGCTGCACGGCCGCCATGCTGCCCGAGGACCGGGGCGGCGTCGTCGGGCCGGACCTCAAGGTGCACGGGGCC
GAGGGCCTGAGGGTCGTGGACATGAGCGTGATGCCGCTGTTGCCGGGGGCGCACCTGAGCGCCACTGCTTATGCGGTGGGG
GAGAAAGCTGCGGATATTATCATCCAGGAGTGGATGGACAAGGAGCAGTGA

AA sequence (SEQ ID NO:2)

MGFLAATLVSCAALASAASIPRPHAKRQVSQLRDDYDFVIVGGGTSGLTVADRLTEAFPAKNVLVIEYGDVHYAPGTFDPPTDWITPQ
PDAPPSWSFNSLPNPDMANTTAFVLAGQVVGGSSAVNGMFFDRASRHDYDAWTAVGGSGFEQSSHKWDWEGLFPFFQKSVTFTE
PPADIVQKYHYTWDLSAYGNGSTPIYSSYPVFQWADQPLLNQAWQEMGINPVTECAGGDKEGVCWVPASQHPVTARRSHAGLGHY
ADVLPRANYDLLVQHQVVRVVFPNGPSHGPPLVEARSLADNHLFNVTVKGEVIISAGALHTPTVLQRSGIGPASFLDDAGIPVTLDLPG
VGANLQDHCGPPVTWNYTEPYTGFFPLPSEMVNNATFKAEAITGFDEVPARGPYTLAGGNNAIFVSLPHLTADYGAITANIRAMVADG
TAASYLAADVRTIPGMVAGYEAQLLVLADLLDNPEAPSLETPWATSEAPQTSSVLAFLLHPLSRGSVRLNLSDPLAQPVLDYRSGSNP
VDIDLHLAHVRFLRGLLDTPTMQARGALETAPGSAVADSDEALGEYVRSHSTLSFMHPCCTAAMLPEDRGGVVGPDLKVHGAEGLRV
VDMSVMPLLPGAHLSATAYAVGEKAADIIIQEWMDKEQ*

Fig.6

(*M. thermophila* -- GO2)

Nucleotide sequence (SEQ ID NO:3)

ATGGAGCTGCTTCGAGTCTCCCTCGCCGCTGTTGCACTCTCCCCATTAATATTATTCGGCGTTGCAGCCGCCCACCCTACCGCC
CGATCCATTGCCCGCTCCACGATTCTTGACGGAGCCGATGGCCTTCTTCCGGAGTATGACTACATCATCGGGGGCGGCAC
GTCCGGATTGACTGTCGCCGACAGACTCACGGAGAATAGAAAGCGCAAGTTTTCCCGCTCTCCCCTCCCAACGTCACCCGCCC
GATCGTCACCGGCGTGGTGTTATTCTGTTCTTGTTTTGGAAAGAGGCATTTTCCAGAACTCTAGCTCGGTGACCACCATTTCTGG
GGGAAGCAGAGGCCTCTTCGATCCAAGTCTGACCTTCAACATCAACTCCGTTCCCCAAGCTGGCTGGACAACCGCAGCATTGC
CGTCATTGGCGGGTTGATCCTCGGCGGCAGCTCCGGCGTCAACGGGCTTCAAGTCCTCCGTGGACAAAGAGAAGACTATGACC
GCTGGGGATCGTACTTTGGGCCAAACTCTGACTGGAGTTGGAAAGGTCTCCTGCCGTATTTCAAGAAGGCATGGAATTTCCATC
CGCCCAGGCCAGAGCTGGTCAGTCAGTTCGACATCAAGTACGACCCCAGCTACTGGGGCAACACGTCTGACGTGCACGCATCT
TTCCCAACCACTTTCTGGCCGGTGCTCAAATTGGAGATGGCTGCATTTGGTGACATCCCTGGGGTCGAATATCCGCCCGACTCT
GCTTCTGGCGAGACCGGGGCGTATTGGCACCCAGCGTCCGTTGACCCAGCGACAGTCCTCGGCTCCTTCGCTCGGCCCGCGC
ATTGGGACAACATTGAGGCGGCACGTCCCAATTACCACACCCTGACCGGGCAACGCGTATTGAAGGTCGCATTTGATGGCAATC
GAGCGACCAGCGTCGTCTTCGTGCCGGCGAATGCAACGGATCACAGCACTGCCAGGTCCGTGAAGGCCAAGAAGGAGATCGT
CTTGGCCGCCGGCGGCCATTCACACGCGCCCAAATCCTACAGGCGGAGCGGAGTAGGGCCGAAGCAGGTCCTGAAGGAAGCAGGC
GTGCCGCTTGTCGTTGACGCTCCCGGTGTCGGCAGCAATTTCCAAGACCAGCCGTATGTGGTTGCTCCCACCTTCAATTTTACC
AAGTTCCCCTTCCACCCGGACTTCTACGACATGATTCTGAACCAGACTTTTATCGCCGAGGCTCAGGCCCAGTTTGAAAAGGAC
CGTACCGGACCTCACACCATCGCATCCGGCTATTGCGGCAGCTGGCTCCCCCTCCAGATCATTGCCCCAAATTCGTGGAAGGA
CATCGCTAGGCGGTACGAATCCCAAGACCCAGCCGCCTACCTCCCCGCCGGCACCGATGAGACCGTCATCGAGGGGTACAGG
GCGCAGCAGAAAGCACTAGCGAGGTCCATGAGGAGCAAGCAATCGGCAATGTATAACTTCTTCCTGAGGGGCGGCTACGAAGA
GGGTTCTGTCGTCTACTTGCACCCAACCAGCCGTGGCACCGTTCGCATCAACGGATCCGACCCCTTCTTCTCGCCGCCCGAGGT
CGACTACAGGGCACTGAGCAACCCTACCGACCTGGAGGTCCTGCTCGAATTCACTCCCTTCACCCGCAGGTACTTCTTGGAGAC
GAGGTTGAAGTCCCTCGACCCGGTCGAGCTGTCGCCCGGTGCCAACGTCACGGCGCCCGCCGACATCGAGGCCTGGCTTCGC
AGCGTCATGATCCCGTCCTCCTTCCATCCCATCGGCACGGCCGCCATGTTGCCTAGGCACCTCGGTGGTGTCGTGGACGAGAA
CCTTCTGGTGTACGGGGTCGAAGGCTTGAGTGTCGTCGACGCCAGCGTCATGCCCGACTTGCCGGGCTCATACACGCAGCAGA
CCGTGTATGCTATTGCTGAGAAGGCCGCGGATCTCATTAAGAGCAGGGCTTGA

AA sequence (SEQ ID NO:4)

MELLRVSLAAVALSPLILFGVAAAHPTARSIARSTILDGADGLLPEYDYIIGGGTSGLTVADRLTENRKRKFSRSPLPTSPARSSPAWCY
SVLVLERGIFQNSSSVTTISGGSRGLFDPSLTFNINSVPQAGLDNRSIAVIGGLILGGSSGVNGLQVLRGQREDYDRWGSYFGPNSDW
SWKGLLPYFKKAWNFHPPRPELVSQFDIKYDPSYWGNTSDVHASFPTTFWPVLKLEMAAFGDIPGVEYPPDSASGETGAYWHPASV
DPATVLRSFARPAHWDNIEAARPNYHTLTGQRVLKVAFDGNRATSVVFVPANATDHSTARSVKAKKEIVLAAGAIHTPQILQASGVGP
KQVLKEAGVPLVVDAPGVGSNFQDQPYVVAPTFNFTKFPFHPDFYDMILNQTFIAEAQAQFEKDRTGPHTIASGYCGSWLPLQIIAPNS
WKDIARRYESQDPAAYLPAGTDETVIEGYRAQQKALARSMRSKQSAMYNFFLRGGYEEGSVVYLHPTSRGTVRINRSDPFFSPPEVD
YRALSNPTDLEVLLEFTPFTRRYFLETRLKSLDPVELSPGANVTAPADIEAWLRSVMIPSSFHPIGTAAMLPRHLGGVVDENLLVYGVE
GLSVVDASVMPDLPGSYTQQTVYAIAEKAADLIKSRA*

Fig. 7

(*Aspergillus oryzae* -- Pyranose Oxidase)

Nucleotide sequence (SEQ ID NO:9)

ATGTCCATGACATCAGGACGTCAAGCGTTTACTTCCGAGTGCAGAGATTCAAATACCACAAATTCATTTTGGTTGGCTAATTCACC
GACTCTCACACTTGGCTCTACGATGCAGGTCGTGGGGTCCGGCCCCATCGGCGCCACCTATGCCAAGATTCTAGCTGACGCCG
GCAAGGATGTCCTCATGGTTGAGACTGGCACCCAGGAAAGTAAGATTGCTGGAGAGCATAAGAAGAATGCTATCAACTACCAGA
AAGATATCGATGCCTTTGTGCATGTCATTAAGGTAATCAGCTCAAGAATTAGCACCTTTGAGTGTATTTCTCTAACTTTCGATCTTC
TCCTCTTTCAGGGAAGTCTACACTACACGTCTGTACCGACCAACAAAGCCGCCGTTCCTACACTGGCTCCGATCTCCTGGAAAG
CGAACGGCCAAATTTTCAACGGACAGAATCCCCGCCAGGATCCAAACGTAAACCTGGATGCCAATGGTGTGGCACGTAATGTGG
GCGGCATGTCTACCCACTGGACTTGTGCGACTCCCCGACAGAAAGAGAAGGTTGAACGCAGCGATATATTCAGTGGTGACGAAT
GGGATAGCCTGTACAAGGAGGCAGAAAAGTTGATCGGAACCAGCAAGACTGTGCTGAATGACTCGATCCGGCAAGAATTGGTC
ATGGAGATTCTGAATGACGAGTACGGGAAGCGATCAGCCGAACCACTACCTTTGGCTGCAAAGAGGAATGGCAATACGGCCTA
CATCACTTGGTCATCCTCGTCAACTATCCTTGACGCGATGAACTGTAAGAAGAAATTTACACTATGGCCCGAGCACCACTGTGAG
AAGTTTAAAGTCGAGGAAACAGATAACGGGCCACAGGTCACCAAGGCTATAATCCGCAAACTCGCCACAGATAAACTGATTACA
GTTAAGGCGAAAGTATTTATCGCTTGCGGGGGGCCTATACTTACACCCCAGCTACTTTTCAATTCGGGCTTCGTGCCGACAAAG
CCCAACAGGGATCCCAGAACCCAAATACCATTAGAAGACGACGAGAAAGGCATCCCACCTCCACCGGATACTCTGGAGCATCTC
AAGCTTCCTGCTCTAGGACGCTATCTGACAGAGCAAAGCATGTGCTTCTGCCAAATTGTTCTGAAAAAAGAATGGATTGAGGCAG
TGGCTAATCCAAAAAAGAACCCTTATCAAAGCGATGGGGTGAAACGCAAAAAGTGGGAGAAGCTCAAGGAAGGGTGGAAGGAA
AGGGTCCAGGAACATATGAAAAGGTTTAATGACCCTATTCCCTTCCCGTTCGATGATTTGGACCCTCAGGTTACTCTACCCTTGG
ACTATCACCATCCGTGGCATACCCAAATCCATCGCGATGCCTTCTCCTATGGCGCAGCACCCCGCAGCCATTGATAAGCGGACCA
TTGTTGACCTCCGATTCTTCGGGAACGGTTGAGCCGGACTGGAAGAACTATGTGACCTTTGAAACCGACATCAGGGATGCGTACG
GCATGCCCCAGCCCACCTTCCGCTACAAGCTGAACGATGAGGATCGCAAACGGTCGCACCCAGATGATGAAAGATATGGAAGAG
GCCGCTGGTGCTCTGGGTGGCTACCTCCCAGGGTCGGAGCCTCAATTTCTAGCCCTGGCCTTGCACTGCACGTCTGTGGTAC
CACTAGAGCTCAGAAGAAGGGAGAAAGAGTGTGACCCTGATCCCAAAGAGACCTCGTGCTGCGATGAGAACTCCAAGATCTGGG
GTATCCACAACCTGTACGTGGGTGGGTTAAATGTGATCCCTGGTGCCAATGGGTCCAACCCTACCTTGACAGCAATGTGCTTCG
CCATCAAAAGCGCGAAGAGTATCCTTGAAGGGAATTCTTAG

AA sequence (SEQ ID NO:10)

MSMTSGRQAFTSECRDSNTTNSFWLANSPTLTLGSTMQVVGSGPIGATYAKILADAGKDVLMVETGTQESKIAGEHKKNAINYQKDID
AFVHVIKVISSRISTFECISLTFDLLLFQGSLHYTSVPTNKAAVPTLAPISWKANGQIFNGQNPRQDPNVNLDANGVARNVGGMSTHWT
CATPRQKEKVERSDIFSGDEWDSLYKEAEKLIGTSKTVLNDSIRQELVMEILNDEYGKRSAEPLPLAAKRNGNTAYITWSSSSTILDAM
NCKKKFTLWPEHHCEKFKVEETDNGPQVTKAIIRKLATDKLITVKAKVFIACGGPILTPQLLFNSGFVPTKPNRDPRTQIPLEDDEKGIPP
PPDTLEHLKLPALGRYLTEQSMCFCQIVLKKEWIEAVANPKKNPYQSDGVKRKKWEKLKEGWKERVQEHMKRFNDPIPFPFDDLDPQ
VTLPLDYHHPWHTQIHRDAFSYGAAPPAIDKRTIVDLRFFGTVEPDWKNYVTFETDIRDAYGMPQPTFRYKLNDEDRKRSHQMMKDM
EEAAGALGGYLPGSEPQFLAPGLALHVCGTTRAQKKEKECDPDPKETSCCDENSKIWGIHNLYVGGLNVIPGANGSNPTLTAMCFAIK
SAKSILEGNS

Fig. 8

(*Acremonium strictum* -- Glucooligosaccharide Oxidase)

Nucleotide sequence (SEQ ID NO:11)

ATGGTGCGCATCCAAGAGCTCACCGCGGCCTTGAGCCTCGCCTCAGTGGTCCAGGCTTCATGGATCCAGAAGCGCAACTCAAT
CAACGCCTGTCTCGCCGCCGCCGACGTCGAGTTCCACGAGGAAGACTCTGAAGGCTGGGACATGGACGGCACAGCCTTCAAC
CTCCGCGTCGACTACGACCCAGCTGCCATTGCCATCCCTCGCTCCACCGAGGATATCGCTGCTGCTGTCCAGTGCGGTCTTGAT
GCTGGTGTGCAGATCTCCGCCAAGGGTGGTGGTCACAGTTACGGTTCTTATGGGTTCGGTGGTGAGGATGGTCATCTTATGTTG
GAGCTGGATCGTATGTACCGTGTGTCGGTTGATGATAATAATGTGGCGACTATTCAGGGCGGTGCTCGTCTTGGATACACTGCT
CTCGAGCTTCTTGACCAGGGTAACCGTGCACTTTCTCACGGTACTTGCCCTGCCGTCGGTGTCGGCGGTCACGTCCTCGGCGG
TGGTTACGGTTTCGCAACCCACACCCACGGTCTGACCCTCGACTGGCTGATCGGCGCCACCGTCGTTCTCGCTGATGCCTCCAT
CGTGCACGTCTCCGAGACCGAGAACGCCGATCTCTTCTGGGCCCTCCGTGGCGGCGGCGGTGGTTTCGCCATCGTCTCCGAG
TTCGAGTTCAACACCTTCGAGGCCCCCGAGATCATCACCACTTACCAGGTCACCACCACCTGGAACCGGAAGCAGCACGTTGCC
GGTCTCAAGGCTCTCCAGGACTGGGCTCAGAACACCATGCCCAGGGAGCTCAGCATGCGTCTTGAGATCAACGCCAACGCTCT
CAACTGGGAGGGTAACTTCTTCGGTAACGCCAAGGACCTCAAGAAGATTCTTCAGCCTATCATGAAGAAGGCGGGTGGCAAGTC
TACCATTTCCAAGCTCGTTGAGACCGATTGGTATGGCCAGATCAACACCTACCTCTACGGTGCTGACTTGAACATCACCTACAAC
TACGACGTCCACGAGTACTTCTACGCCAACAGCTTGACGGCTCCCGTCTCTCCGACGAAGCCATCCAAGCCTTCGTCGACTAC
AAGTTCGACAACTCCTCCGTCCGCCCCGGCCGCGGCTGGTGGATTCAATGGGACTTCCACGGCGGCAAGAACTCTGCCCTGGC
CGCCGTCTCCAACGACGAAACCGCCTACGCCCACCGCGACCAGCTCTGGCTCTGGCAGTTCTACGACAGCATCTATGACTACG
AGAACAACACCTCTCCCTACCCGGAGAGCGGTTTCGAGTTCATGCAGGGCTTCGTCGCTACCATCGAGGACACTCTCCCTGAG
GACAGGAAGGGCAAGTACTTCAACTACGCCGACACCACGCTTACCAAGGAGGAGGCGCAGAAGTTGTACTGGAGGGGCAACCT
TGAGAAGTTGCAGGCTATCAAGGCCAAGTACGATCCTGAGGATGTGTTTGGTAATGTTGTCTCTGTTGAGCCCATTGCCTAG

AA sequence (SEQ ID NO:12)

MVRIQELTAALSLASVVQASWIQKRNSINACLAAADVEFHEEDSEGWDMDGTAFNLRVDYDPAAIAIPRSTEDIAAAVQCGLDAGVQIS
AKGGGHSYGSYGFGGEDGHLMLELDRMYRVSVDDNNVATIQGGARLGYTALELLDQGNRALSHGTCPAVGVGGHVLGGGYGFATH
THGLTLDWLIGATVVLADASIVHVSETENADLFWALRGGGGGFAIVSEFEFNTFEAPEIITTYQVTTTWNRKQHVAGLKALQDWAQNT
MPRELSMRLEINANALNWEGNFFGNAKDLKKILQPIMKKAGGKSTISKLVETDWYGQINTYLYGADLNITYNYDVHEYFYANSLTAPRL
SDEAIQAFVDYKFDNSSVRPGRGWWIQWDFHGGKNSALAAVSNDETAYAHRDQLWLWQFYDSIYDYENNTSPYPESGFEFMQGFV
ATIEDTLPEDRKGKYFNYADTTLTKEEAQKLYWRGNLEKLQAIKAKYDPEDVFGNVVSVEPIA

Fig. 9

(*Agaricus bisporus* -- Pyranose Dehydrogenase)

Nucleotide sequence (SEQ ID NO:13)

ATGATACCTCGAGTGGCCAAATTCAACTTTCGACTCTTGTCTCTCGCATTATTGGGGATTCAGGTTGCACGCAGTGCCATCACAT
ACCAAAACCCGACCGATTTACCTGGTGACGTTGACTATGATTTCATCGTTGCTGGCGGTGGAACTGCAGGTTTAGTTGTGGCCT
CTCGTCTCAGTGAGAATCCGGAATGGAATGTACTGGTCATCGAGGCCGGGCCTTCCAACAAGGACGTCTTCGAAACACGGGTC
CCTGGCCTTTCTTCGGAACTCCGGCCACGTTTTGATTGGAATTATACAACGATTCCTCAAGATGCTCTCGGTGGCAGGAGCCTG
AATTACTCGAGGGCGAAGCTCTTAGGCGGTTGCAGTAGCCATAATGGGATGGTTTACACACGATGTTCGAGAGACGATTGGGAC
AATTATGCCGAAATCACCGGTAATCAAGCATTTAGCTGGGACAGCATCCTACCTGTCATGAAGAGGGCTGAGAAATTCAGTAAAG
ATTCCTCTCATAAACCGGTAAAGGGCCATATTGACCCCTCCGTGCACGGTGGTGACGGAAAATTGTCCGTGGTCGCATCATACA
CCAACGCCTCTTTCAATGACTTATTACTTGAAACCGCGAAAGAATTAAGCGGTGAATTTCCGTTCAAATTGGATATGAATGACGG
GCGGCCTCTTGGATTAACTTGGACTCAGTATACGATTGATCAACGCGGGGAGCGGAGCAGCTCTGCAACAGCGTATTTAGAGG
GTACTGGAAATAACGTCCATGTCTTGGTTAACACTCTTGTTACCCGTATAGTCTCAGCAGAAAATGGGACCGACTTCGAAGCGT
CGAGTTTGCTACTGATGCCGACAGCCCAAAGATCCAATTACGAGCGAAAAAGGAAGTCATTGTATCTGGAGGAGTCATCAATTC
GCCTCAGATCCTCATGAATTCCGGCATTGGGGGCCGAGAGGTGCTTGGAGCTAATGGAATTGACACATTGGTGGATAATCCGAG
TGTCGGGAAAAATTTATCGGACCAGGCTGCAACAATTATAATGCTCGATACAACACTCCCTATTACTGATTATGATGTTGATGCAG
CGCTTATTGAATGGAAGAAGTCGCACACTGGACCTCTAGCCCAAGGAGGTCGCCTAAACCACCTTACATGGGTACGATTGCCTG
ATGACAAGCTGGATGGACTTGATCCTTCAAGTGGCGAAAATTCGCCACATATTGAGTTCCAATTCGGGCAAATTAGCCACCAGCT
CCCTCCCAGTGGTCTAACACGTTTTAGCTTCTATCGACACTGTTCTCCAATTCGCCGTTGATCAACCTCTACACTGTTTCGCGG
GGTTCTATTTCTCTCAGTAACAACGATCCGTTCTCCCACCCACTCATCGATCTCAACATGTTTGGAGAGGAAATAGATCCCGCTAT
TCTGCGTGAGGGTATTCGCAGTGCCCGAAGAATGCTTTCTTCCCAAGCATTCAAAGGCTTTGTCGGTGAAACGGTGTTTCCTCCA
AGCGACGCTACCTCTGATGAAGATTTGGATACCTTCCTCAAAACGTCAACGTTTTCTTACGTGCATGGTGTGGGAACGTTGTCTA
TGTCTCCTCAGAGTGCCTCGTGGGGTGTCGTTAACCCTGATTTCCGTGTCAAAGGAACCAGTGGCCTGCGGGTTGTCGACGCG
TCTGTGATTCCATTCGCTCCGGCGGGGCACACTCAAGAACCTGTTTATGCATTTGCTGAGCATGCAAGTGTGTTAATAGCGAAGA
GCTACAGCTAA

AA sequence (SEQ ID NO:14)

MIPRVAKFNFRLLSLALLGIQVARSAITYQNPTDLPGDVDYDFIVAGGGTAGLVVASRLSENPEWNVLVIEAGPSNKDVFETRVPGLSS
ELRPRFDWNYTTIPQDALGGRSLNYSRAKLLGGCSSHNGMVYTRCSRDDWDNYAEITGNQAFSWDSILPVMKRAEKFSKDSSHKPV
KGHIDPSVHGGDGKLSVVASYTNASFNDLLLETAKELSGEFPFKLDMNDGRPLGLTWTQYTIDQRGERSSSATAYLEGTGNNVHVLV
NTLVTRIVSAENGTDFRSVEFATDADSPKIQLRAKKEVIVSGGVINSPQILMNSGIGGREVLGANGIDTLVDNPSVGKNLSDQAATIIMLD
TTLPITDYDVDAALIEWKKSHTGPLAQGGRLNHLTWVRLPDDKLDGLDPSSGENSPHIEFQFGQISHQLPPSGLTRFSFYRHCSPIPPLI
NLYTVSRGSISLSNNDPFSHPLIDLNMFGEEIDPAILREGIRSARRMLSSQAFKGFVGETVFPPSDATSDEDLDTFLKTSTFSYVHGVGT
LSMSPQSASWGVVNPDFRVKGTSGLRVVDASVIPFAPAGHTQEPVYAFAEHASVLIAKSYS

Fig. 10

(*Talaromyces stipitatus* ATCC 10500 -- Glucose Dehydrogenase)

Nucleotide sequence (SEQ ID NO:15)

ATGCGACTTGGCTCTATCGGCGCAGGCCTCGCTCTCCTCGCTGCCCTCGCTGTCCTCGCTGCCCACGTGCACGCCTTGGCACC
GCGCACCCAGATTGCCGAGGAATACGATTTTGTCGTCGTTGGCGGCGGCCAGGCTGGTCTCGTGATCGGAGCTCGTCTGTCGG
AGATTGCAAATTATACAGTTCTCGTGCTGGAGGCAGGGACGAATGGAGACGAATTTCGAGAACGAATAGGCACGTACAACTTTT
ATACTCCCGCATATTCCTACTACGAGTCACTATGGACGACACCAATGAATTGGGCATACTATACTGTGCCTCAATCCCATGCCGA
GAATCGTCAAATTGAGTGGACCCGTGGTAAGGGGCTGGGCGGAAGTTCTGCGATCAACGGATTGTACCTGACTCGCCCCGGTA
AAGAGGAGATCAATGCATGGAAAGACCTGCTAGGAGACATGGACGGGGCGGACAATTGGTCGTGGGATTCGTTCTATGCTGCA
ATGAAGAAGAGCGAGACTTTTACTCCCCCGTCGAATGAGATTGCTACAGAAGGGAACATTACATGGGACCTTTCTACTCGTGGTA
TTCAGGGACCGATTCAGGCAACGTATCCCGGCTATACCTTCCCCCAAGTCGGCGAATGGGTCATGTCTCTGGAAGCAATGGGC
ATTGCTAGTTCTAACGATATGTACGGTGGTGAGGTGTATGGCGCCGAAGTCTCGACGTCGAGTATCAATCCCACGAACTGGACA
CGCTCGTACAGCCGGACGGGATATCTCGACCCGCTCGCAGACAACGGCAATTACGACGTTGTGGCCGATGCGTTTGTCACGCG
CATTCTCTTTGATGCTTCTTCTCCGTCGAATAATCTGACAGCAAACGGCGTGCAGTATACTCTTGACAACGGCAAGACAAACTGC
ACGGTCAAGGTCAAGAAAGAGGTGATCTTATCAGCTGGGACGGTTGGCAGTCCTGCGGTACTGCTCCACAGCGGTGTCGGTCC
GAAAGATGTTCTTTCAGATGCTGGAGTTGAGCTGGTGTCTGAACTTCCTGGTGTGGGTCACCACCTTCAGGATCATTTTAACAAC
ACCCTTTATCTCTCCTACATCGATTCAGCCATCGCCTACATCAATTCCACGCTGATGTACGGCGATAATCTGGACGCACTACAGA
AGAACATCACCACTCAAATCAACCAATTCGTGCTGAACACGACTTACGATGCTGGTGTCATTGCAGGATACAAAGCAATTGCAAA
TATGACCGCAACCACAATCCTCAGTAGTTCTATCGGGCAAATTGAGCTCTTGTTCATGAATAGTGACTTAAACGGCGATATTGGT
ATCACTGCTGCTCTTCAACATCCTTACAGCCATGGACGCATATACATCAATTCCTCGAATCCGTTGGACTATCCCGTCATTGATCC
GAATTATCTTGCTGTTTGTGCTGACTATGAAATCCTCCGCGACGGCCTCAATCTAGCCCGCCAACTCGGCAACACACAACCCCTA
AGCAGCTGTCTAATAGCCGAAACAATCCCCGGTCCCAGCGTCAAAACCGACGACGACTGGCTTGAATGGATCCGCGAAGCGAC
GGGGACAGAGTTCCACCCTTCATCGTCCTGTGCGATGCTACCCCGAGAGCAAGGCGGAGTAGTCGATGCCAACCTGCGCGTCT
ACGGTCTTGCCAATGTTCGTGTTGCGGATGCCAGCGTTGTCCCGATTTCATTGTCGACGCATCTTATGGCGTCGACGTATGGAG
TCGCAGAACAGGCTAGTAATATCATTCGTGCGCACTACACGGATAGTAGGACTACAGGCACGAGTAGTTCCGATCCTGGCTCTG
CGTCGTCACCGACAAGCAGTGCATTGGGCGCTGAAGGGACTACTGGGGCGATTAGTGCTCATACAGCGCCTTCTGGTGGTGTA
CGAAGCGTTTCTGCGGTATCCGCTTGGGTTGCTGTTGTGTTCGCTGCAGCTGTTTCCATTTTCCATTCCTTGCATTGA

AA sequence (SEQ ID NO:16)

MRLGSIGAGLALLAALAVLAAHVHALAPRTQIAEEYDFVVVGGGQAGLVIGARLSEIANYTVLVLEAGTNGDEFRERIGTYNFYTPAYS
YYESLWTTPMNWAYYTVPQSHAENRQIEWTRGKGLGGSSAINGLYLTRPGKEEINAWKDLLGDMDGADNWSWDSFYAAMKKSETF
TPPSNEIATEGNITWDLSTRGIQGPIQATYPGYTFPQVGEWVMSLEAMGIASSNDMYGGEVYGAEVSTSSINPTNWTRSYSRTGYLD
PLADNGNYDVVADAFVTRILFDASSPSNNLTANGVQYTLDNGKTNCTVKVKKEVILSAGTVGSPAVLLHSGVGPKDVLSDAGVELVSE
LPGVGHHLQDHFNNTLYLSYIDSAIAYINSTLMYGDNLDALQKNITTQINQFVLNTTYDAGVIAGYKAIANMTATTILSSSIGQIELLFMNS
DLNGDIGITAALQHPYSHGRIYINSSNPLDYPVIDPNYLAVSADYEILRDGLNLARQLGNTQPLSSCLIAETIPGPSVKTDDDWLEWIREA
TGTEFHPSSSCAMLPREQGGVVDANLRVYGLANVRVADASVVPISLSTHLMASTYGVAEQASNIIRAHYTDSRTTGTSSSDPGSASSP
TSSALGAEGTTGAISAHTAPSGGVRSVSAVSAWVAVVFAAAVSIFHSLH

Fig. 14
A
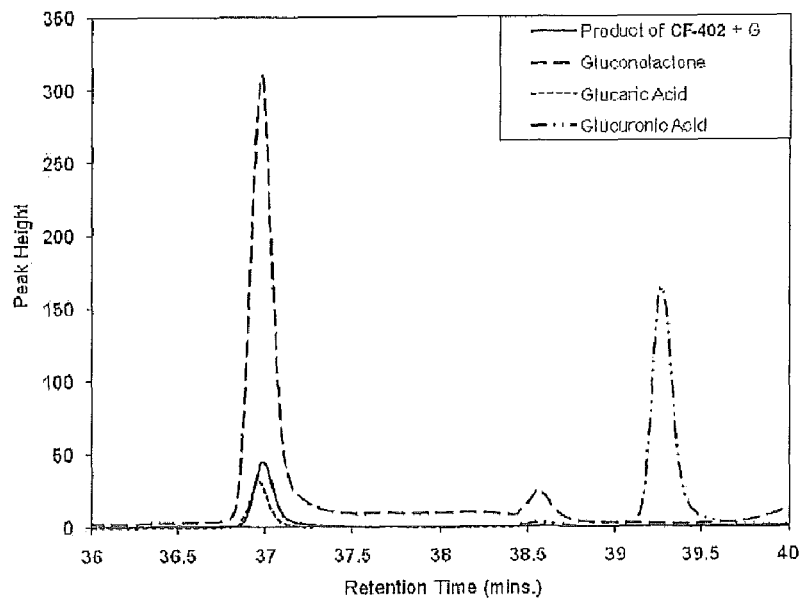
B
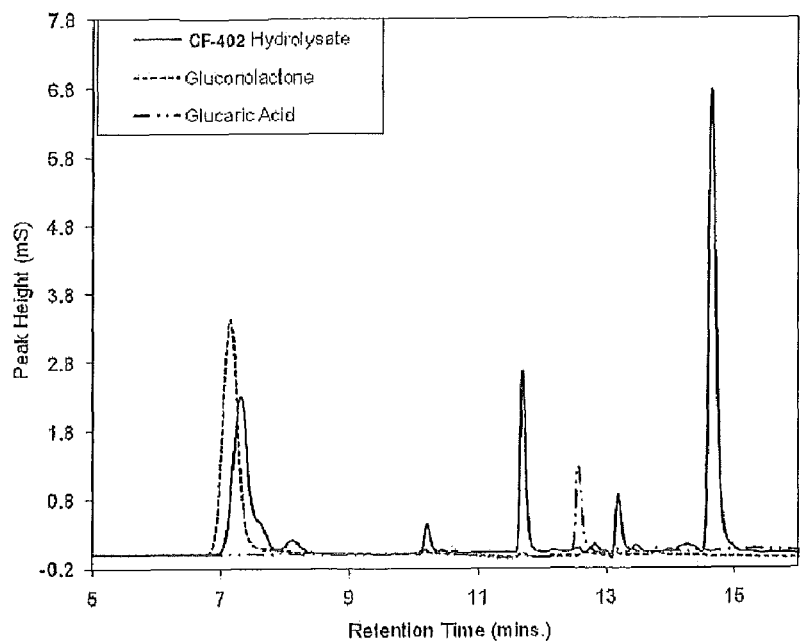

SEQUENCE LISTING

<160> NUMBER OF SEQ ID NOS: 41

<210> SEQ ID NO 1
<211> LENGTH: 1944
<212> TYPE: DNA
<213> ORGANISM: Myceliophthora thermophila

<400> SEQUENCE: 1

```
atgggcttcc tcgccgccac tcttgtgtcc tgtgccgctc tcgcgagcgc agcaagcatc    60
ccacgtcccc atgccaagcg ccaggtctcc cagcttcgcg acgattatga cttcgtgatc   120
gttggcggtg aactagcgg cctcactgta gccgatcggc tgacagaggc ctttccagcc   180
aagaacgtcc ttgtcattga gtatggagac gtccactacg ccccgggaac cttcgatccg   240
ccgacggact ggatcacacc tcagcctgat gccccccctt cctggtcttt caattccctc   300
cccaacccag acatggcaaa cacaacagcg tttgtgctag ccggccaagt ggtgggtgga   360
agcagtgccg tgaacggcat gttctttgac cgcgcatccc gccacgacta cgatgcgtgg   420
accgcggtcg gcgggtccgg gttcgaacag tccagccaca agtgggactg ggaggggctg   480
ttcccttct ccagaagag cgtcacgttc acggaaccgc cggccgacat cgtccagaag   540
tatcactaca cctgggacct gtctgcctac ggcaatggct caaccccat ctacagcagc   600
tatccggtct ccagtgggc cgaccagccg ttacttaacc aggcatgca ggagatggga   660
atcaatccgg tgaccgaatg cgccggcggc gacaaggagg gtgtctgctg ggttcccgcc   720
tcgcagcacc ctgtcacggc gaggaggtcg cacgccgggc tcggccacta cgccgatgtg   780
ctcccgcgag ccaattacga cctcctcgtt caacaccagg ttgtcagggt agtattcccc   840
aatgggccga ccacggacc gccgcttgtc gaggcgcgt ccctggccga caaccacctg   900
ttcaacgtga ctgtgaaggg cgaagtcatc atctcggcgg gcgctctgca caccccgacc   960
gtccttcaac ggagcggcat cggcccggca tccttcttgg acgacgccgg gatccccgtg  1020
acgcttgacc tgccgggcgt cggcgccaac ctccaggacc actgcggtcc gcccgtcacg  1080
tggaactaca ccgagcccta caccggcttc ttcccgctcc cctccgagat ggtcaacaac  1140
gcgaccttca agccgaagc catcaccggc ttcgacgagg tccggcccg cggcccctac  1200
acgctcgccg ggggcaacaa cgccatcttc gtatcgctcc acacctcac ggccgactac  1260
ggcgccatca ccgcaaatat ccgcgccatg gtcgccgacg gaaccgccgc ctcctatctc  1320
gcggccgacg tccgcaccat cccggggatg gtggccggct acgaggccca gctcctcgtg  1380
ctcgccgacc tgctcgacaa cccggaggcg cccagcctgg agacgccgtg ggcgacgagc  1440
gaggcgccgc agacgtcgtc ggtcctggcc ttcctgctgc acccgctcag ccgcggcagc  1500
gtgcggctca acctcagcga cccgctcgcg cagcccgtgc tcgactaccg ctccgggtcc  1560
aacccggtcg acatcgacct gcacctcgcc cacgtgcgct tcctgcgcgg cctgctcgac  1620
acgcccacca tgcaggcccg cggggcgctc gagacggccc ccggctcggc cgtggccgac  1680
agcgacgagg cgctggggga gtacgtgcgc tcgcacagca cgctgtcctt catgcacccg  1740
tgctgcacgg ccgccatgct gccgaggac cggggcggcg tcgtcgggcc ggacctcaag  1800
gtgcacgggg ccgagggcct gagggtcgtg acatgagcg tgatgccgct gttgccgggg  1860
gcgcacctga cgccactgc ttatgcggtg ggggagaag ctgcggatat tatcatccag  1920
gagtggatgg acaaggagca gtga                                          1944
```

<210> SEQ ID NO 2
<211> LENGTH: 647
<212> TYPE: PRT
<213> ORGANISM: Myceliophthora thermophila

<400> SEQUENCE: 2

```
Met Gly Phe Leu Ala Ala Thr Leu Val Ser Cys Ala Ala Leu Ala Ser
 1               5                  10                  15

Ala Ala Ser Ile Pro Arg Pro His Ala Lys Arg Gln Val Ser Gln Leu
```

```
                      20                  25                  30
Arg Asp Asp Tyr Asp Phe Val Ile Val Gly Gly Thr Ser Gly Leu
                35                  40                  45
Thr Val Ala Asp Arg Leu Thr Glu Ala Phe Pro Ala Lys Asn Val Leu
 50                  55                  60
Val Ile Glu Tyr Gly Asp Val His Tyr Ala Pro Gly Thr Phe Asp Pro
 65                  70                  75                  80
Pro Thr Asp Trp Ile Thr Pro Gln Pro Asp Ala Pro Pro Ser Trp Ser
                85                  90                  95
Phe Asn Ser Leu Pro Asn Pro Asp Met Ala Asn Thr Thr Ala Phe Val
                100                 105                 110
Leu Ala Gly Gln Val Val Gly Gly Ser Ser Ala Val Asn Gly Met Phe
                115                 120                 125
Phe Asp Arg Ala Ser Arg His Asp Tyr Asp Ala Trp Thr Ala Val Gly
                130                 135                 140
Gly Ser Gly Phe Glu Gln Ser Ser His Lys Trp Asp Trp Glu Gly Leu
145                 150                 155                 160
Phe Pro Phe Phe Gln Lys Ser Val Thr Phe Thr Glu Pro Pro Ala Asp
                165                 170                 175
Ile Val Gln Lys Tyr His Tyr Thr Trp Asp Leu Ser Ala Tyr Gly Asn
                180                 185                 190
Gly Ser Thr Pro Ile Tyr Ser Ser Tyr Pro Val Phe Gln Trp Ala Asp
                195                 200                 205
Gln Pro Leu Leu Asn Gln Ala Trp Gln Glu Met Gly Ile Asn Pro Val
                210                 215                 220
Thr Glu Cys Ala Gly Gly Asp Lys Glu Gly Val Cys Trp Val Pro Ala
225                 230                 235                 240
Ser Gln His Pro Val Thr Ala Arg Arg Ser His Ala Gly Leu Gly His
                245                 250                 255
Tyr Ala Asp Val Leu Pro Arg Ala Asn Tyr Asp Leu Leu Val Gln His
                260                 265                 270
Gln Val Val Arg Val Val Phe Pro Asn Gly Pro Ser His Gly Pro Pro
                275                 280                 285
Leu Val Glu Ala Arg Ser Leu Ala Asp Asn His Leu Phe Asn Val Thr
                290                 295                 300
Val Lys Gly Glu Val Ile Ile Ser Ala Gly Ala Leu His Thr Pro Thr
305                 310                 315                 320
Val Leu Gln Arg Ser Gly Ile Gly Pro Ala Ser Phe Leu Asp Asp Ala
                325                 330                 335
Gly Ile Pro Val Thr Leu Asp Leu Pro Gly Val Gly Ala Asn Leu Gln
                340                 345                 350
Asp His Cys Gly Pro Pro Val Thr Trp Asn Tyr Thr Glu Pro Tyr Thr
                355                 360                 365
Gly Phe Phe Pro Leu Pro Ser Glu Met Val Asn Ala Thr Phe Lys
                370                 375                 380
Ala Glu Ala Ile Thr Gly Phe Asp Glu Val Pro Ala Arg Gly Pro Tyr
385                 390                 395                 400
Thr Leu Ala Gly Gly Asn Asn Ala Ile Phe Val Ser Leu Pro His Leu
                405                 410                 415
Thr Ala Asp Tyr Gly Ala Ile Thr Ala Asn Ile Arg Ala Met Val Ala
                420                 425                 430
Asp Gly Thr Ala Ala Ser Tyr Leu Ala Ala Asp Val Arg Thr Ile Pro
                435                 440                 445
```

```
Gly Met Val Ala Gly Tyr Glu Ala Gln Leu Leu Val Leu Ala Asp Leu
            450                 455                 460

Leu Asp Asn Pro Glu Ala Pro Ser Leu Glu Thr Pro Trp Ala Thr Ser
465                 470                 475                 480

Glu Ala Pro Gln Thr Ser Ser Val Leu Ala Phe Leu Leu His Pro Leu
                    485                 490                 495

Ser Arg Gly Ser Val Arg Leu Asn Leu Ser Asp Pro Leu Ala Gln Pro
                500                 505                 510

Val Leu Asp Tyr Arg Ser Gly Ser Asn Pro Val Asp Ile Asp Leu His
            515                 520                 525

Leu Ala His Val Arg Phe Leu Arg Gly Leu Leu Asp Thr Pro Thr Met
        530                 535                 540

Gln Ala Arg Gly Ala Leu Glu Thr Ala Pro Gly Ser Ala Val Ala Asp
545                 550                 555                 560

Ser Asp Glu Ala Leu Gly Glu Tyr Val Arg Ser His Ser Thr Leu Ser
                    565                 570                 575

Phe Met His Pro Cys Cys Thr Ala Ala Met Leu Pro Glu Asp Arg Gly
                580                 585                 590

Gly Val Val Gly Pro Asp Leu Lys Val His Gly Ala Glu Gly Leu Arg
            595                 600                 605

Val Val Asp Met Ser Val Met Pro Leu Leu Pro Gly Ala His Leu Ser
        610                 615                 620

Ala Thr Ala Tyr Ala Val Gly Glu Lys Ala Ala Asp Ile Ile Ile Gln
625                 630                 635                 640

Glu Trp Met Asp Lys Glu Gln
                645

<210> SEQ ID NO 3
<211> LENGTH: 1968
<212> TYPE: DNA
<213> ORGANISM: Myceliophthora thermophila

<400> SEQUENCE: 3
atggagctgc ttcgagtctc cctcgccgct gttgcactct ccccattaat attattcggc     60
gttgcagccg cccaccctac cgcccgatcc attgcccgct ccacgattct tgacggagcc    120
gatggccttc ttccggagta tgactacatc atcatcgggg gcggcacgtc cggattgact    180
gtcgccgaca gactcacgga gaatagaaag cgcaagtttt cccgctctcc cctcccaacg    240
tcacccgccc gatcgtcacc ggcgtggtgt tattctgttc ttgttttgga aagaggcatt    300
ttccagaact ctagctcggt gaccaccatt tctgggggaa gcagaggcct cttcgatcca    360
agtctgacct tcaacatcaa ctccgttccc aagctgggc tggacaaccg cagcattgcc    420
gtcattggcg ggttgatcct cggcggcagc tccggcgtca acgggcttca agtcctccgt    480
ggacaaagag aagactatga ccgctgggga tcgtactttg gccaaactc tgactggagt    540 tggaaaggtc tcctgccgta tttcaagaag gcatggaatt ccatccgcc aggccagag    600 ctggtcagtc agttcgacat caagtacgac cccagctact ggggcaacac gtctgacgtg    660
cacgcatctt tcccaaccac tttctggccg gtgctcaaat tggagatggc tgcatttggt    720
gacatccctg gggtcgaata tccgcccgac tctgcttctg gcgagaccgg ggcgtattgg    780
cacccagcgt ccgttgaccc agcgacagtc ctccgctcct tcgctcggcc cgcgcattgg    840
gacaacattg aggcggcacg tcccaattac acaccctga ccgggcaacg cgtattgaag    900
gtcgcatttg atggcaatcg agcgaccagc gtcgtcttcg tgccggcgaa tgcaacggat    960
cacagcactg ccaggtccgt gaaggccaag aaggagatcg tcttggccgc cggcgccatt   1020
```

-continued

```
cacacgcccc aaatcctaca ggcgagcgga gtagggccga agcaggtcct gaaggaagca      1080
ggcgtgccgc ttgtcgttga cgctcccggt gtcggcagca atttccaaga ccagccgtat      1140
gtggttgctc ccaccttcaa ttttaccaag ttccccttcc acccggactt ctacgacatg      1200
attctgaacc agacttttat cgccgaggct caggcccagt ttgaaaagga ccgtaccgga      1260
cctcacacca tcgcatccgg ctattgcggc agctggctcc ccctccagat cattgcccca      1320
aattcgtgga aggacatcgc taggcggtac gaatcccaag acccagccgc ctacctcccc      1380
gccggcaccg atgagaccgt catcgagggg tacagggcgc agcagaaagc actagcgagg      1440
tccatgagga gcaagcaatc ggcaatgtat aacttcttcc tgaggggcgg ctacgaagag      1500
ggttctgtcg tctacttgca cccaaccagc cgtggcaccg ttcgcatcaa ccgatccgac      1560
cccttcttct cgccgcccga ggtcgactac agggcactga gcaaccctac cgacctggag      1620
gtcctgctcg aattcactcc cttcacccgc aggtacttct ggagacgag gttgaagtcc       1680 ctcgacccgg tcgagctgtc gcccggtgcc aacgtcacgg cgcccgccga catcgaggcc      1740
tggcttcgca gcgtcatgat cccgtcctcc ttccatccca tcggcacggc cgccatgttg      1800
cctaggcacc tcggtggtgt cgtggacgag aaccttctgg tgtacggggt cgaaggcttg      1860
agtgtcgtcg acgccagcgt catgcccgac ttgccgggct catacacgca gcagaccgtg      1920
tatgctattg ctgagaaggc cgcggatctc attaagagca gggcttga                  1968
```

<210> SEQ ID NO 4
<211> LENGTH: 655
<212> TYPE: PRT
<213> ORGANISM: Myceliophthora thermophila

<400> SEQUENCE: 4

```
Met Glu Leu Leu Arg Val Ser Leu Ala Ala Val Ala Leu Ser Pro Leu
1               5                   10                  15

Ile Leu Phe Gly Val Ala Ala His Pro Thr Ala Arg Ser Ile Ala
                20                  25                  30

Arg Ser Thr Ile Leu Asp Gly Ala Asp Gly Leu Leu Pro Glu Tyr Asp
        35                  40                  45

Tyr Ile Ile Ile Gly Gly Gly Thr Ser Gly Leu Thr Val Ala Asp Arg
    50                  55                  60

Leu Thr Glu Asn Arg Lys Arg Lys Phe Ser Arg Ser Pro Leu Pro Thr
65                  70                  75                  80

Ser Pro Ala Arg Ser Ser Pro Ala Trp Cys Tyr Ser Val Leu Val Leu
                85                  90                  95

Glu Arg Gly Ile Phe Gln Asn Ser Ser Ser Val Thr Thr Ile Ser Gly
            100                 105                 110

Gly Ser Arg Gly Leu Phe Asp Pro Ser Leu Thr Phe Asn Ile Asn Ser
        115                 120                 125

Val Pro Gln Ala Gly Leu Asp Asn Arg Ser Ile Ala Val Ile Gly Gly
    130                 135                 140

Leu Ile Leu Gly Gly Ser Ser Gly Val Asn Gly Leu Gln Val Leu Arg
145                 150                 155                 160

Gly Gln Arg Glu Asp Tyr Asp Arg Trp Gly Ser Tyr Phe Gly Pro Asn
                165                 170                 175

Ser Asp Trp Ser Trp Lys Gly Leu Leu Pro Tyr Phe Lys Lys Ala Trp
            180                 185                 190

Asn Phe His Pro Pro Arg Pro Glu Leu Val Ser Gln Phe Asp Ile Lys
        195                 200                 205
```

-continued

| | | | | | | | | | | | | | |
|---|---|---|---|---|---|---|---|---|---|---|---|---|---|
|Tyr|Asp|Pro|Ser|Tyr|Trp|Gly|Asn|Thr|Ser|Asp|Val|His|Ala|Ser|Phe
| |210| | | |215| | | |220| | | | | |

Tyr Asp Pro Ser Tyr Trp Gly Asn Thr Ser Asp Val His Ala Ser Phe
    210             215             220

Pro Thr Thr Phe Trp Pro Val Leu Lys Leu Glu Met Ala Ala Phe Gly
225             230             235             240

Asp Ile Pro Gly Val Glu Tyr Pro Pro Asp Ser Ala Ser Gly Glu Thr
            245             250             255

Gly Ala Tyr Trp His Pro Ala Ser Val Asp Pro Ala Thr Val Leu Arg
            260             265             270

Ser Phe Ala Arg Pro Ala His Trp Asp Asn Ile Glu Ala Ala Arg Pro
        275             280             285

Asn Tyr His Thr Leu Thr Gly Gln Arg Val Leu Lys Val Ala Phe Asp
    290             295             300

Gly Asn Arg Ala Thr Ser Val Val Phe Val Pro Ala Asn Ala Thr Asp
305             310             315             320

His Ser Thr Ala Arg Ser Val Lys Ala Lys Glu Ile Val Leu Ala
            325             330             335

Ala Gly Ala Ile His Thr Pro Gln Ile Leu Gln Ala Ser Gly Val Gly
            340             345             350

Pro Lys Gln Val Leu Lys Glu Ala Gly Val Pro Leu Val Val Asp Ala
        355             360             365

Pro Gly Val Gly Ser Asn Phe Gln Asp Gln Pro Tyr Val Val Ala Pro
    370             375             380

Thr Phe Asn Phe Thr Lys Phe Pro Phe His Pro Asp Phe Tyr Asp Met
385             390             395             400

Ile Leu Asn Gln Thr Phe Ile Ala Glu Ala Gln Ala Gln Phe Glu Lys
            405             410             415

Asp Arg Thr Gly Pro His Thr Ile Ala Ser Gly Tyr Cys Gly Ser Trp
            420             425             430

Leu Pro Leu Gln Ile Ile Ala Pro Asn Ser Trp Lys Asp Ile Ala Arg
        435             440             445

Arg Tyr Glu Ser Gln Asp Pro Ala Ala Tyr Leu Pro Ala Gly Thr Asp
    450             455             460

Glu Thr Val Ile Glu Gly Tyr Arg Ala Gln Gln Lys Ala Leu Ala Arg
465             470             475             480

Ser Met Arg Ser Lys Gln Ser Ala Met Tyr Asn Phe Phe Leu Arg Gly
            485             490             495

Gly Tyr Glu Glu Gly Ser Val Val Tyr Leu His Pro Thr Ser Arg Gly
            500             505             510

Thr Val Arg Ile Asn Arg Ser Asp Pro Phe Phe Ser Pro Pro Glu Val
        515             520             525

Asp Tyr Arg Ala Leu Ser Asn Pro Thr Asp Leu Glu Val Leu Leu Glu
    530             535             540

Phe Thr Pro Phe Thr Arg Arg Tyr Phe Leu Glu Thr Arg Leu Lys Ser
545             550             555             560

Leu Asp Pro Val Glu Leu Ser Pro Gly Ala Asn Val Thr Ala Pro Ala
            565             570             575

Asp Ile Glu Ala Trp Leu Arg Ser Val Met Ile Pro Ser Ser Phe His
            580             585             590

Pro Ile Gly Thr Ala Ala Met Leu Pro Arg His Leu Gly Gly Val Val
        595             600             605

Asp Glu Asn Leu Leu Val Tyr Gly Val Glu Gly Leu Ser Val Val Asp
    610             615             620

Ala Ser Val Met Pro Asp Leu Pro Gly Ser Tyr Thr Gln Gln Thr Val
625             630             635             640

Tyr Ala Ile Ala Glu Lys Ala Ala Asp Leu Ile Lys Ser Arg Ala
            645                 650                 655

<210> SEQ ID NO 5
<211> LENGTH: 2487
<212> TYPE: DNA
<213> ORGANISM: Myceliophthora thermophila

<400> SEQUENCE: 5

| | | | | | |
|---|---|---|---|---|---|
| atgaggacct | cctctcgttt | aatcggtgcc | cttgcggcgg | cactcttgcc | gtctgccctt | 60 |
| gcgcagaaca | acgcgccggt | aaccttcacc | gacccggact | cgggcattac | cttcaacacg | 120 |
| tggggtctcg | ccgaggattc | tccccagact | aagggcggtt | tcacttttgg | tgttgctctg | 180 |
| ccctctgatg | ccctcacgac | agacgccaag | gagttcatcg | gttacttgaa | atgcgcgagg | 240 |
| aacgatgaga | gcggttggtg | cggtgtctcc | ctgggcggcc | ccatgaccaa | ctcgctcctc | 300 |
| atcgcggcct | ggccccacga | ggacaccgtc | tacacctctc | tccgcttcgc | caccggctat | 360 |
| gccatgccgg | atgtctacca | gggggacgcc | gagatcaccc | aggtctcctc | ctctgtcaac | 420 |
| tcgacgcact | tcagcctcat | cttcaggtgc | gagaactgcc | tgcaatggag | tcaaagcggc | 480 |
| gccaccggcg | gtgcctccac | ctcgaacggc | gtgttggtcc | tcggctgggt | ccaggcattc | 540 |
| gccgaccccg | gcaacccgac | ctgccccgac | cagatcaccc | tcgagcagca | cgacaacggc | 600 |
| atgggtatct | ggggtgccca | gctcaactcc | gacgccgcca | gcccgtccta | caccgagtgg | 660 |
| gccgcccagg | ccaccaagac | cgtcacgggt | gactgcggcg | gtcccaccga | gacctctgtc | 720 |
| gtcggtgtcc | ccgttccgac | gggcgtctcg | ttcgattaca | tcgtcgtggg | cggcggtgcc | 780 |
| ggtggcatcc | ccgccgccga | caagctcagc | gaggccggca | agagtgtgct | gctcatcgag | 840 |
| aagggctttg | cctcgaccgc | caacaccgga | ggcactctcg | gccccgagtg | gctcgagggc | 900 |
| cacgacctta | cccgctttga | cgtgccgggt | ctgtgcaacc | agatctgggt | tgactccaag | 960 |
| gggatcgctt | gcgaggatac | cgaccagatg | gctggctgtg | tcctcggcgg | cggtaccgcc | 1020 |
| gtgaatgccg | gctgtggtt | caagccctac | tcgctcgact | gggactacct | cttccctagt | 1080 |
| ggttggaagt | acaaagacgt | ccagccggcc | atcaaccgcg | ccctctcgcg | catcccgggc | 1140 |
| accgatgctc | cctcgaccga | cggcaagcgc | tactaccaac | agggcttcga | cgtcctctcc | 1200 |
| aagggcctgg | ccggcggcgg | ctggaccctcg | gtcacggcca | taacgcgcc | agacaagaag | 1260 |
| aaccgcacct | tctcccatgc | ccccttcatg | ttcgccggcg | gcgagcgcaa | cggcccgctg | 1320 |
| ggcacctact | tccagaccgc | caagaagcgc | agcaacttca | agctctggct | caacacgtcg | 1380 |
| gtcaagcgcg | tcatccgcca | gggcggccac | atcaccggcg | tcgaggtcga | gccgttccgc | 1440 |
| gacgcggtt | accaaggcat | cgtccccgtc | accaaggtta | cgggccgcgt | catcctctct | 1500 |
| gccggtacct | ttggcagtgc | aaagatcctg | ctgaggagcg | gtatcggtcc | gaacgatcag | 1560 |
| ctgcaggttg | tcgcggcctc | ggagaaggat | ggccctacca | tgatcagcaa | ctcgtcctgg | 1620 |
| atcaacctgc | ctgtcggcta | caacctggat | gaccacctca | acaccgacac | tgtcatctcc | 1680 |
| caccccgacg | tcgtgttcta | cgacttctac | gaggcgtggg | acaatcccat | ccagtctgac | 1740 |
| aaggacagct | acctcaactc | gcgcacgggc | atcctcgccc | aagccgctcc | caacattggg | 1800 |
| cctatgttct | gggaagagat | caagggtgcg | gacggcattg | ttcgccagct | ccagtggact | 1860 |
| gcccgtgtcg | agggcagcct | gggtgccccc | aacggcaaga | ccatgaccat | gtcgcagtac | 1920 |
| ctcggtcgtg | gtgccacctc | gcgcggccgc | atgaccatca | cccgtccct | gacaactgtc | 1980 |
| gtctcggacg | tgccctacct | caaggacccc | aacgacaagg | aggccgtcat | ccagggcatc | 2040 |

```
atcaacctgc agaacgccct caagaacgtc gccaacctga cctggctctt ccccaactcg    2100
accatcacgc cgcgccaata cgttgacagc atggtcgtct ccccgagcaa ccggcgctcc    2160
aaccactgga tgggcaccaa caagatcggc accgacgacg ggcgcaaggg cggctccgcc    2220
gtcgtcgacc tcaacaccaa ggtctacggc accgacaacc tcttcgtcat cgacgcctcc    2280
atcttccccg gcgtgcccac caccaacccc acctcgtaca tcgtgacggc gtcggagcac    2340
gcctcggccc gcatcctcgc cctgcccgac ctcacgcccg tccccaagta cgggcagtgc    2400
ggcggccgcg aatggagcgg cagcttcgtc tgcgccgacg gctccacgtg ccagatgcag    2460
aacgagtggt actcgcagtg cttgtga                                        2487
```

<210> SEQ ID NO 6
<211> LENGTH: 828
<212> TYPE: PRT
<213> ORGANISM: Myceliophthora thermophila

<400> SEQUENCE: 6

```
Met Arg Thr Ser Ser Arg Leu Ile Gly Ala Leu Ala Ala Ala Leu Leu
1               5                   10                  15

Pro Ser Ala Leu Ala Gln Asn Asn Ala Pro Val Thr Phe Thr Asp Pro
            20                  25                  30

Asp Ser Gly Ile Thr Phe Asn Thr Trp Gly Leu Ala Glu Asp Ser Pro
        35                  40                  45

Gln Thr Lys Gly Gly Phe Thr Phe Gly Val Ala Leu Pro Ser Asp Ala
    50                  55                  60

Leu Thr Thr Asp Ala Lys Glu Phe Ile Gly Tyr Leu Lys Cys Ala Arg
65                  70                  75                  80

Asn Asp Glu Ser Gly Trp Cys Gly Val Ser Leu Gly Gly Pro Met Thr
                85                  90                  95

Asn Ser Leu Leu Ile Ala Ala Trp Pro His Glu Asp Thr Val Tyr Thr
            100                 105                 110

Ser Leu Arg Phe Ala Thr Gly Tyr Ala Met Pro Asp Val Tyr Gln Gly
        115                 120                 125

Asp Ala Glu Ile Thr Gln Val Ser Ser Ser Val Asn Ser Thr His Phe
    130                 135                 140

Ser Leu Ile Phe Arg Cys Glu Asn Cys Leu Gln Trp Ser Gln Ser Gly
145                 150                 155                 160

Ala Thr Gly Gly Ala Ser Thr Ser Asn Gly Val Leu Val Leu Gly Trp
                165                 170                 175

Val Gln Ala Phe Ala Asp Pro Gly Asn Pro Thr Cys Pro Asp Gln Ile
            180                 185                 190

Thr Leu Glu Gln His Asp Asn Gly Met Gly Ile Trp Gly Ala Gln Leu
        195                 200                 205

Asn Ser Asp Ala Ala Ser Pro Ser Tyr Thr Glu Trp Ala Ala Gln Ala
    210                 215                 220

Thr Lys Thr Val Thr Gly Asp Cys Gly Gly Pro Thr Glu Thr Ser Val
225                 230                 235                 240

Val Gly Val Pro Val Pro Thr Gly Val Ser Phe Asp Tyr Ile Val Val
                245                 250                 255

Gly Gly Gly Ala Gly Gly Ile Pro Ala Ala Asp Lys Leu Ser Glu Ala
            260                 265                 270

Gly Lys Ser Val Leu Leu Ile Glu Lys Gly Phe Ala Ser Thr Ala Asn
        275                 280                 285

Thr Gly Gly Thr Leu Gly Pro Glu Trp Leu Glu Gly His Asp Leu Thr
    290                 295                 300
```

-continued

```
Arg Phe Asp Val Pro Gly Leu Cys Asn Gln Ile Trp Val Asp Ser Lys
305                 310                 315                 320
Gly Ile Ala Cys Glu Asp Thr Asp Gln Met Ala Gly Cys Val Leu Gly
                325                 330                 335
Gly Gly Thr Ala Val Asn Ala Gly Leu Trp Phe Lys Pro Tyr Ser Leu
            340                 345                 350
Asp Trp Asp Tyr Leu Phe Pro Ser Gly Trp Lys Tyr Lys Asp Val Gln
        355                 360                 365
Pro Ala Ile Asn Arg Ala Leu Ser Arg Ile Pro Gly Thr Asp Ala Pro
    370                 375                 380
Ser Thr Asp Gly Lys Arg Tyr Tyr Gln Gln Gly Phe Asp Val Leu Ser
385                 390                 395                 400
Lys Gly Leu Ala Gly Gly Trp Thr Ser Val Thr Ala Asn Asn Ala
                405                 410                 415
Pro Asp Lys Lys Asn Arg Thr Phe Ser His Ala Pro Phe Met Phe Ala
            420                 425                 430
Gly Gly Glu Arg Asn Gly Pro Leu Gly Thr Tyr Phe Gln Thr Ala Lys
        435                 440                 445
Lys Arg Ser Asn Phe Lys Leu Trp Leu Asn Thr Ser Val Lys Arg Val
    450                 455                 460
Ile Arg Gln Gly Gly His Ile Thr Gly Val Glu Val Glu Pro Phe Arg
465                 470                 475                 480
Asp Gly Gly Tyr Gln Gly Ile Val Pro Val Thr Lys Val Thr Gly Arg
                485                 490                 495
Val Ile Leu Ser Ala Gly Thr Phe Gly Ser Ala Lys Ile Leu Leu Arg
            500                 505                 510
Ser Gly Ile Gly Pro Asn Asp Gln Leu Gln Val Val Ala Ala Ser Glu
        515                 520                 525
Lys Asp Gly Pro Thr Met Ile Ser Asn Ser Ser Trp Ile Asn Leu Pro
    530                 535                 540
Val Gly Tyr Asn Leu Asp Asp His Leu Asn Thr Asp Thr Val Ile Ser
545                 550                 555                 560
His Pro Asp Val Val Phe Tyr Asp Phe Tyr Glu Ala Trp Asp Asn Pro
                565                 570                 575
Ile Gln Ser Asp Lys Asp Ser Tyr Leu Asn Ser Arg Thr Gly Ile Leu
            580                 585                 590
Ala Gln Ala Ala Pro Asn Ile Gly Pro Met Phe Trp Glu Glu Ile Lys
        595                 600                 605
Gly Ala Asp Gly Ile Val Arg Gln Leu Gln Trp Thr Ala Arg Val Glu
    610                 615                 620
Gly Ser Leu Gly Ala Pro Asn Gly Lys Thr Met Thr Met Ser Gln Tyr
625                 630                 635                 640
Leu Gly Arg Gly Ala Thr Ser Arg Gly Arg Met Thr Ile Thr Pro Ser
                645                 650                 655
Leu Thr Thr Val Val Ser Asp Val Pro Tyr Leu Lys Asp Pro Asn Asp
            660                 665                 670
Lys Glu Ala Val Ile Gln Gly Ile Ile Asn Leu Gln Asn Ala Leu Lys
        675                 680                 685
Asn Val Ala Asn Leu Thr Trp Leu Phe Pro Asn Ser Thr Ile Thr Pro
    690                 695                 700
Arg Gln Tyr Val Asp Ser Met Val Val Ser Pro Ser Asn Arg Arg Ser
705                 710                 715                 720
Asn His Trp Met Gly Thr Asn Lys Ile Gly Thr Asp Asp Gly Arg Lys
```

```
                725                 730                 735
Gly Gly Ser Ala Val Val Asp Leu Asn Thr Lys Val Tyr Gly Thr Asp
                    740                 745                 750

Asn Leu Phe Val Ile Asp Ala Ser Ile Phe Pro Gly Val Pro Thr Thr
                755                 760                 765

Asn Pro Thr Ser Tyr Ile Val Thr Ala Ser Glu His Ala Ser Ala Arg
            770                 775                 780

Ile Leu Ala Leu Pro Asp Leu Thr Pro Val Pro Lys Tyr Gly Gln Cys
785                 790                 795                 800

Gly Gly Arg Glu Trp Ser Gly Ser Phe Val Cys Ala Asp Gly Ser Thr
                805                 810                 815

Cys Gln Met Gln Asn Glu Trp Tyr Ser Gln Cys Leu
            820                 825
```

<210> SEQ ID NO 7
<211> LENGTH: 2364
<212> TYPE: DNA
<213> ORGANISM: Myceliophthora thermophila

<400> SEQUENCE: 7

```
atgaagctac tcagccgcgt tgggcgacc gccctagcgg cgacgttgtc actgcagcaa      60
tgtgcagccc agatgaccga ggggacctac accgatgagg ctaccggtat ccaattcaag    120
acgtggaccg cctccgaggg cgcccctttc acgtttggct tgaccctccc cgcggacgcg    180
ctggaaaagg atgccaccga gtacattggt ctcctgcgtt gccaaatcac cgatcccgcc    240
tcgcccagct ggtgcggtat ctcccacggc cagtccggcc agatgacgca ggcgctgctg    300
ctggtcgcct gggccagcga ggacaccgtc tacacgtcgt tccgctacgc caccggctac    360
acgctccccg gcctctacac gggcgacgcc aagctgaccc agatctcctc ctcggtcagc    420
gaggacagct cgaggtgct gttccgctgc gaaaactgct tctcctggga ccaggatggc    480
accaagggca acgtctcgac cagcaacggc aacctggtcc tcggccgcgc cgccgcgaag    540
gatggtgtga cgggccccac gtgcccggac acggccgagt tcggtttcca tgataacggt    600
ttcggacagt ggggtgccgt gcttgagggt gctacttcgg actcgtacga ggagtgggct    660
aagctggcca cgaccacgcc cgagaccacc tgcgatggca ctggccccgg cgacaaggag    720
tgcgttccgg ctcccgagga cacgtatgat tacatcgttg tcggtgccgg cgccggtggt    780
atcaccgtcg ccgacaagct cagcgaggcc ggccacaagg tccttctcat cgagaaggga    840
ccccttcga ccgcctgtg aacgggacc atgaagcccg agtggctcga gagcaccgac    900
cttaccgct cgacgttcc cggcctgtgc aaccagatct gggtcgactc tgccggcatc    960
gcctgcaccg ataccgacca gatggcgggc tgcgttctcg gcggtggcac cgctgtcaac   1020
gctggtttgt ggtggaagcc ccaccccgct gactgggatg agaacttccc cgaagggtgg   1080
aagtcgagcg atctcgcgga tgcgaccgag cgtgtcttca gcgcatccc cggcacgtcg   1140
cacccgtcgc aggacggcaa gttgtaccgc caggagggct cgaggtcat cagcaagggc   1200
ctggccaacg ccggctggaa ggaaatcagc gccaacgagg cgcccagcga aagaaccac   1260
acctatgcac acaccgagtt catgttctcg ggcggtgagc gtggcggccc cctggcgacg   1320
taccttgcct cggctgccga gcgcagcaac ttcaacctgt ggctcaacac tgccgtccgg   1380
agggccgtcc gcagcggcag caaggtcacc ggcgtcgagc tcgagtgcct cacggacggt   1440
ggcttcagcg gaccgtcaa cctgaatgag ggcggtggtg tcatcttctc ggccggcgct   1500
ttcggctcgg ccaagctgct ccttcgcagc ggtatcggtc ctgaggacca gctcgagatt   1560
```

-continued

```
gtggcgagct ccaaggacgg cgagaccttc actcccaagg acgagtggat caacctcccc    1620
gtcggccaca acctgatcga ccatctcaac actgacctca ttatcacgca cccggatgtc    1680
gttttctatg acttctatgc ggcctgggac gagcccatca cggaggataa ggaggcctac    1740
ctgaactcgc ggtccggcat tctcgcccag gcggcgccca atatcggccc tatgatgtgg    1800
gatcaagtca cgccgtccga cggcatcacc cgccagttcc agtggacatg ccgtgttgag    1860
ggcgacagct ccaagaccaa ctcgacccac gccatgaccc tcagccagta cctcggccgt    1920
ggcgtcgtct cgcgcggccg gatgggcatc acctccgggc tgagcacgac ggtggccgag    1980
cacccgtacc tgcacaacaa cggcgacctg gaggcggtca tccagggat ccagaacgtg     2040 gtggacgcgc tcagccaggt ggccgacctc gagtgggtgc tcccgccgcc cgacgggacg    2100
gtggccgact acgtcaacag cctgatcgtc tcgccggcca accgccgggc caaccactgg    2160
atgggcacgg ccaagctggg caccgacgac ggccgctcgg cggcacctc ggtcgtcgac      2220 ctcgacacca aggtgtacgg caccgacaac ctgttcgtcg tcgacgcgtc cgtcttcccc    2280
ggcatgtcga cgggcaaccc gtcggccatg atcgtcatcg tggccgagca ggcggcgcag    2340
cgcatcctgg ccctgcggtc ttaa                                           2364
```

<210> SEQ ID NO 8
<211> LENGTH: 787
<212> TYPE: PRT
<213> ORGANISM: Myceliophthora thermophila

<400> SEQUENCE: 8

```
Met Lys Leu Leu Ser Arg Val Gly Ala Thr Ala Leu Ala Ala Thr Leu
1               5                   10                  15

Ser Leu Gln Gln Cys Ala Ala Gln Met Thr Glu Gly Thr Tyr Thr Asp
            20                  25                  30

Glu Ala Thr Gly Ile Gln Phe Lys Thr Trp Thr Ala Ser Glu Gly Ala
        35                  40                  45

Pro Phe Thr Phe Gly Leu Thr Leu Pro Ala Asp Ala Leu Glu Lys Asp
    50                  55                  60

Ala Thr Glu Tyr Ile Gly Leu Leu Arg Cys Gln Ile Thr Asp Pro Ala
65                  70                  75                  80

Ser Pro Ser Trp Cys Gly Ile Ser His Gly Gln Ser Gly Gln Met Thr
                85                  90                  95

Gln Ala Leu Leu Leu Val Ala Trp Ala Ser Glu Asp Thr Val Tyr Thr
            100                 105                 110

Ser Phe Arg Tyr Ala Thr Gly Tyr Thr Leu Pro Gly Leu Tyr Thr Gly
        115                 120                 125

Asp Ala Lys Leu Thr Gln Ile Ser Ser Ser Val Ser Glu Asp Ser Phe
    130                 135                 140

Glu Val Leu Phe Arg Cys Glu Asn Cys Phe Ser Trp Asp Gln Asp Gly
145                 150                 155                 160

Thr Lys Gly Asn Val Ser Thr Ser Asn Gly Asn Leu Val Leu Gly Arg
                165                 170                 175

Ala Ala Ala Lys Asp Gly Val Thr Gly Pro Thr Cys Pro Asp Thr Ala
            180                 185                 190

Glu Phe Gly Phe His Asp Asn Gly Phe Gly Gln Trp Gly Ala Val Leu
        195                 200                 205

Glu Gly Ala Thr Ser Asp Ser Tyr Glu Glu Trp Ala Lys Leu Ala Thr
    210                 215                 220

Thr Thr Pro Glu Thr Thr Cys Asp Gly Thr Gly Pro Gly Asp Lys Glu
225                 230                 235                 240
```

```
Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285

Gly Thr Met Lys Pro Glu Trp Leu Glu Ser Thr Asp Leu Thr Arg Phe
    290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
            340                 345                 350

Asp Glu Asn Phe Pro Glu Gly Trp Lys Ser Ser Asp Leu Ala Asp Ala
        355                 360                 365

Thr Glu Arg Val Phe Lys Arg Ile Pro Gly Thr Ser His Pro Ser Gln
    370                 375                 380

Asp Gly Lys Leu Tyr Arg Gln Glu Gly Phe Glu Val Ile Ser Lys Gly
385                 390                 395                 400

Leu Ala Asn Ala Gly Trp Lys Glu Ile Ser Ala Asn Glu Ala Pro Ser
                405                 410                 415

Glu Lys Asn His Thr Tyr Ala His Thr Glu Phe Met Phe Ser Gly Gly
            420                 425                 430

Glu Arg Gly Gly Pro Leu Ala Thr Tyr Leu Ala Ser Ala Ala Glu Arg
        435                 440                 445

Ser Asn Phe Asn Leu Trp Leu Asn Thr Ala Val Arg Arg Ala Val Arg
    450                 455                 460

Ser Gly Ser Lys Val Thr Gly Val Glu Leu Glu Cys Leu Thr Asp Gly
465                 470                 475                 480

Gly Phe Ser Gly Thr Val Asn Leu Asn Glu Gly Gly Val Ile Phe
                485                 490                 495

Ser Ala Gly Ala Phe Gly Ser Ala Lys Leu Leu Leu Arg Ser Gly Ile
            500                 505                 510

Gly Pro Glu Asp Gln Leu Glu Ile Val Ala Ser Ser Lys Asp Gly Glu
        515                 520                 525

Thr Phe Thr Pro Lys Asp Glu Trp Ile Asn Leu Pro Val Gly His Asn
    530                 535                 540

Leu Ile Asp His Leu Asn Thr Asp Leu Ile Ile Thr His Pro Asp Val
545                 550                 555                 560

Val Phe Tyr Asp Phe Tyr Ala Ala Trp Asp Pro Ile Thr Glu Asp
                565                 570                 575

Lys Glu Ala Tyr Leu Asn Ser Arg Ser Gly Ile Leu Ala Gln Ala Ala
            580                 585                 590

Pro Asn Ile Gly Pro Met Met Trp Asp Gln Val Thr Pro Ser Asp Gly
        595                 600                 605

Ile Thr Arg Gln Phe Gln Trp Thr Cys Arg Val Glu Gly Asp Ser Ser
    610                 615                 620

Lys Thr Asn Ser Thr His Ala Met Thr Leu Ser Gln Tyr Leu Gly Arg
625                 630                 635                 640

Gly Val Val Ser Arg Gly Arg Met Gly Ile Thr Ser Gly Leu Ser Thr
                645                 650                 655

Thr Val Ala Glu His Pro Tyr Leu His Asn Asn Gly Asp Leu Glu Ala
```

```
                660               665                670
Val Ile Gln Gly Ile Gln Asn Val Val Asp Ala Leu Ser Gln Val Ala
            675                 680                 685
Asp Leu Glu Trp Val Leu Pro Pro Pro Asp Gly Thr Val Ala Asp Tyr
    690                 695                 700
Val Asn Ser Leu Ile Val Ser Pro Ala Asn Arg Arg Ala Asn His Trp
705                 710                 715                 720
Met Gly Thr Ala Lys Leu Gly Thr Asp Asp Gly Arg Ser Gly Gly Thr
                725                 730                 735
Ser Val Val Asp Leu Asp Thr Lys Val Tyr Gly Thr Asp Asn Leu Phe
            740                 745                 750
Val Val Asp Ala Ser Val Phe Pro Gly Met Ser Thr Gly Asn Pro Ser
        755                 760                 765
Ala Met Ile Val Ile Val Ala Glu Gln Ala Ala Gln Arg Ile Leu Ala
        770                 775                 780
Leu Arg Ser
785

<210> SEQ ID NO 9
<211> LENGTH: 1890
<212> TYPE: DNA
<213> ORGANISM: Aspergillus oryzae

<400> SEQUENCE: 9
atgtccatga catcaggacg tcaagcgttt acttccgagt gcagagattc aaataccaca      60
aattcatttt ggttggctaa ttcaccgact ctcacacttg gctctacgat gcaggtcgtg     120
gggtccggcc ccatcggcgc cacctatgcc aagattctag ctgacgccgg caaggatgtc     180
ctcatggttg agactggcac ccaggaaagt aagattgctg agagcataa  gaagaatgct     240
atcaactacc agaaagatat cgatgccttt gtgcatgtca ttaaggtaat cagctcaaga     300
attagcacct ttgagtgtat ttctctaact ttcgatcttc cctctttca gggaagtcta     360
cactacacgt ctgtaccgac caacaaagcc gccgttccta cactggctcc gatctcctgg     420
aaagcgaacg gccaaatttt caacggacag aatccccgcc aggatccaaa cgtaaacctg     480
gatgccaatg gtgtggcacg taatgtgggc ggcatgtcta cccactggac ttgtgcgact     540
ccccgacaga aagagaaggt tgaacgcagc gatatattca gtggtgacga atgggatagc     600
ctgtacaagg aggcagaaaa gttgatcgga accagcaaga ctgtgctgaa tgactcgatc     660
cggcaagaat tggtcatgga gattctgaat gacgagtacg ggaagcgatc agccgaacca     720
ctaccttggg ctgcaaagag gaatggcaat acggcctaca tcacttggtc atcctcgtca     780
actatccttg acgcgatgaa ctgtaagaag aaatttacac tatggcccga gcaccactgt     840
gagaagttta agtcgaggaa acagataaac gggccacagg tcaccaaggc tataatccgc     900
aaactcgcca cagataaact gattacagtt aaggcgaaag tatttatcgc ttgcgggggg     960
cctatactta caccccagct acttttcaat tcgggcttcg tgccgacaaa gcccaacagg    1020
gatcccagaa cccaaatacc attagaagac gacgagaaag gcatcccacc tccaccggat    1080
actctggagc atctcaagct tcctgctcta ggacgctatc tgacagagca aagcatgtgc    1140
ttctgccaaa tgttctgaa  aaagaatgg  attgaggcag tggctaatcc aaaaaagaac    1200
ccttatcaaa gcgatggggt gaaacgcaaa agtgggaga  agctcaagga agggtggaag    1260
gaaagggtcc aggaacatat gaaaaggttt aatgaccctt tcccttccc  gttcgatgat    1320
ttggacccct caggttactc taccccttgg acatcaccat cgtggcatac ccaaatccat    1380
```

-continued

```
cgcgatgcct tctcctatgg cgcagcaccc ccagccattg ataagcggac cattgttgac    1440
ctccgattct tcggaacggt tgagccggac tggaagaact atgtgacctt tgaaaccgac    1500
atcagggatg cgtacggcat gccccagccc accttccgct acaagctgaa cgatgaggat    1560
cgcaaacggt cgcaccagat gatgaaagat atggaagagg ccgctggtgc tctgggtggc    1620
tacctcccag ggtcggagcc tcaatttcta gctcctggcc ttgcactgca cgtctgtggt    1680
accactagag ctcagaagaa ggagaaagag tgtgaccctg atcccaaaga gacctcgtgc    1740
tgcgatgaga actccaagat ctggggtatc cacaacctgt acgtgggtgg gttaaatgtg    1800
atccctggtg ccaatgggtc caaccctacc ttgacagcaa tgtgcttcgc catcaaaagc    1860
gcgaagagta tccttgaagg gaattcttag                                    1890
```

<210> SEQ ID NO 10
<211> LENGTH: 629
<212> TYPE: PRT
<213> ORGANISM: Aspergillus oryzae

<400> SEQUENCE: 10

```
Met Ser Met Thr Ser Gly Arg Gln Ala Phe Thr Ser Glu Cys Arg Asp
1               5                   10                  15

Ser Asn Thr Thr Asn Ser Phe Trp Leu Ala Asn Ser Pro Thr Leu Thr
            20                  25                  30

Leu Gly Ser Thr Met Gln Val Val Gly Ser Gly Pro Ile Gly Ala Thr
        35                  40                  45

Tyr Ala Lys Ile Leu Ala Asp Ala Gly Lys Asp Val Leu Met Val Glu
    50                  55                  60

Thr Gly Thr Gln Glu Ser Lys Ile Ala Gly Glu His Lys Lys Asn Ala
65                  70                  75                  80

Ile Asn Tyr Gln Lys Asp Ile Asp Ala Phe Val His Val Ile Lys Val
                85                  90                  95

Ile Ser Ser Arg Ile Ser Thr Phe Glu Cys Ile Ser Leu Thr Phe Asp
            100                 105                 110

Leu Leu Leu Phe Gln Gly Ser Leu His Tyr Thr Ser Val Pro Thr Asn
        115                 120                 125

Lys Ala Ala Val Pro Thr Leu Ala Pro Ile Ser Trp Lys Ala Asn Gly
    130                 135                 140

Gln Ile Phe Asn Gly Gln Asn Pro Arg Gln Asp Pro Asn Val Asn Leu
145                 150                 155                 160

Asp Ala Asn Gly Val Ala Arg Asn Val Gly Gly Met Ser Thr His Trp
                165                 170                 175

Thr Cys Ala Thr Pro Arg Gln Lys Glu Lys Val Glu Arg Ser Asp Ile
            180                 185                 190

Phe Ser Gly Asp Glu Trp Asp Ser Leu Tyr Lys Glu Ala Glu Lys Leu
        195                 200                 205

Ile Gly Thr Ser Lys Thr Val Leu Asn Asp Ser Ile Arg Gln Glu Leu
    210                 215                 220

Val Met Glu Ile Leu Asn Asp Glu Tyr Gly Lys Arg Ser Ala Glu Pro
225                 230                 235                 240

Leu Pro Leu Ala Ala Lys Arg Asn Gly Asn Thr Ala Tyr Ile Thr Trp
                245                 250                 255

Ser Ser Ser Ser Thr Ile Leu Asp Ala Met Asn Cys Lys Lys Lys Phe
            260                 265                 270

Thr Leu Trp Pro Glu His His Cys Glu Lys Phe Lys Val Glu Glu Thr
        275                 280                 285
```

```
Asp Asn Gly Pro Gln Val Thr Lys Ala Ile Ile Arg Lys Leu Ala Thr
            290                 295                 300

Asp Lys Leu Ile Thr Val Lys Ala Lys Val Phe Ile Ala Cys Gly Gly
305                 310                 315                 320

Pro Ile Leu Thr Pro Gln Leu Leu Phe Asn Ser Gly Phe Val Pro Thr
                325                 330                 335

Lys Pro Asn Arg Asp Pro Arg Thr Gln Ile Pro Leu Glu Asp Asp Glu
            340                 345                 350

Lys Gly Ile Pro Pro Pro Asp Thr Leu Glu His Leu Lys Leu Pro
            355                 360                 365

Ala Leu Gly Arg Tyr Leu Thr Glu Gln Ser Met Cys Phe Cys Gln Ile
    370                 375                 380

Val Leu Lys Lys Glu Trp Ile Glu Ala Val Ala Asn Pro Lys Lys Asn
385                 390                 395                 400

Pro Tyr Gln Ser Asp Gly Val Lys Arg Lys Trp Glu Lys Leu Lys
            405                 410                 415

Glu Gly Trp Lys Glu Arg Val Gln Glu His Met Lys Arg Phe Asn Asp
                420                 425                 430

Pro Ile Pro Phe Pro Phe Asp Asp Leu Asp Pro Gln Val Thr Leu Pro
            435                 440                 445

Leu Asp Tyr His His Pro Trp His Thr Gln Ile His Arg Asp Ala Phe
    450                 455                 460

Ser Tyr Gly Ala Ala Pro Pro Ala Ile Asp Lys Arg Thr Ile Val Asp
465                 470                 475                 480

Leu Arg Phe Phe Gly Thr Val Glu Pro Asp Trp Lys Asn Tyr Val Thr
                485                 490                 495

Phe Glu Thr Asp Ile Arg Asp Ala Tyr Gly Met Pro Gln Pro Thr Phe
            500                 505                 510

Arg Tyr Lys Leu Asn Asp Glu Asp Arg Lys Arg Ser His Gln Met Met
    515                 520                 525

Lys Asp Met Glu Glu Ala Ala Gly Ala Leu Gly Gly Tyr Leu Pro Gly
530                 535                 540

Ser Glu Pro Gln Phe Leu Ala Pro Gly Leu Ala Leu His Val Cys Gly
545                 550                 555                 560

Thr Thr Arg Ala Gln Lys Lys Glu Lys Glu Cys Asp Pro Asp Pro Lys
                565                 570                 575

Glu Thr Ser Cys Cys Asp Glu Asn Ser Lys Ile Trp Gly Ile His Asn
            580                 585                 590

Leu Tyr Val Gly Gly Leu Asn Val Ile Pro Gly Ala Asn Gly Ser Asn
    595                 600                 605

Pro Thr Leu Thr Ala Met Cys Phe Ala Ile Lys Ser Ala Lys Ser Ile
    610                 615                 620

Leu Glu Gly Asn Ser
625

<210> SEQ ID NO 11
<211> LENGTH: 1500
<212> TYPE: DNA
<213> ORGANISM: Acremonium strictum

<400> SEQUENCE: 11
atggtgcgca tccaagagct caccgcggcc ttgagcctcg cctcagtggt ccaggcttca     60
tggatccaga agcgcaactc aatcaacgcc tgtctcgccg ccgccgacgt cgagttccac    120
gaggaagact ctgaaggctg ggacatggac ggcacagcct tcaacctccg cgtcgactac    180
```

```
gacccagctg ccattgccat ccctcgctcc accgaggata tcgctgctgc tgtccagtgc    240
ggtcttgatg ctggtgtgca gatctccgcc aagggtggtg gtcacagtta cggttcttat    300
gggttcggtg gtgaggatgg tcatcttatg ttggagctgg atcgtatgta ccgtgtgtcg    360
gttgatgata taatgtggc gactattcag ggcggtgctc gtcttggata cactgctctc    420
gagcttcttg accagggtaa ccgtgcactt tctcacggta cttgccctgc cgtcggtgtc    480
ggcggtcacg tcctcggcgg tggttacggt ttcgcaaccc acacccacgg tctgaccctc    540
gactggctga tcggcgccac cgtcgttctc gctgatgcct ccatcgtgca cgtctccgag    600
accgagaacg ccgatctctt ctgggcccct cgtggcggcg cggtggtttt cgccatcgtc    660
tccgagttcg agttcaacac cttcgaggcc cccgagatca tcaccactta ccaggtcacc    720
accacctgga accggaagca gcacgttgcc ggtctcaagg ctctccagga ctgggctcag    780
aacaccatgc ccagggagct cagcatgcgt cttgagatca cgccaacgc tctcaactgg    840
gagggtaact tcttcggtaa cgccaaggac ctcaagaaga ttcttcagcc tatcatgaag    900
aaggcgggtg gcaagtctac catttccaag ctcgttgaga ccgattggta tggccagatc    960
aacacctacc tctacggtgc tgacttgaac atcacctaca actacgacgt ccacgagtac   1020
ttctacgcca acagcttgac cgctccccgt ctctccgacg aagccatcca agccttcgtc   1080
gactacaagt tcgacaactc ctccgtccgc cccggccgcg gctggtggat tcaatgggac   1140
ttccacggcg gcaagaactc tgccctggcc gccgtctcca cgacgaaac cgcctacgcc   1200
caccgcgacc agctctggct ctggcagttc tacgacagca tctatgacta cgagaacaac   1260
acctctcccct acccggagag cggtttcgag ttcatgcagg gcttcgtcgc taccatcgag   1320
gacactctcc ctgaggacag gaagggcaag tacttcaact acgccgacac cacgcttacc   1380
aaggaggagg cgcagaagtt gtactggagg ggcaaccttg agaagttgca ggctatcaag   1440
gccaagtacg atcctgagga tgtgtttggt aatgttgtct ctgttgagcc cattgcctag   1500
```

<210> SEQ ID NO 12
<211> LENGTH: 499
<212> TYPE: PRT
<213> ORGANISM: Acremonium strictum

<400> SEQUENCE: 12

```
Met Val Arg Ile Gln Glu Leu Thr Ala Ala Leu Ser Leu Ala Ser Val
1               5                   10                  15

Val Gln Ala Ser Trp Ile Gln Lys Arg Asn Ser Ile Asn Ala Cys Leu
            20                  25                  30

Ala Ala Ala Asp Val Glu Phe His Glu Glu Asp Ser Glu Gly Trp Asp
        35                  40                  45

Met Asp Gly Thr Ala Phe Asn Leu Arg Val Asp Tyr Asp Pro Ala Ala
    50                  55                  60

Ile Ala Ile Pro Arg Ser Thr Glu Asp Ile Ala Ala Val Gln Cys
65                  70                  75                  80

Gly Leu Asp Ala Gly Val Gln Ile Ser Ala Lys Gly Gly His Ser
            85                  90                  95

Tyr Gly Ser Tyr Gly Phe Gly Gly Glu Asp Gly His Leu Met Leu Glu
            100                 105                 110

Leu Asp Arg Met Tyr Arg Val Ser Val Asp Asp Asn Val Ala Thr
        115                 120                 125

Ile Gln Gly Gly Ala Arg Leu Gly Tyr Thr Ala Leu Glu Leu Leu Asp
    130                 135                 140

Gln Gly Asn Arg Ala Leu Ser His Gly Thr Cys Pro Ala Val Gly Val
```

```
                145                 150                 155                 160
Gly Gly His Val Leu Gly Gly Gly Tyr Gly Phe Ala Thr His Thr His
                    165                 170                 175
Gly Leu Thr Leu Asp Trp Leu Ile Gly Ala Thr Val Val Leu Ala Asp
                180                 185                 190
Ala Ser Ile Val His Val Ser Glu Thr Glu Asn Ala Asp Leu Phe Trp
                195                 200                 205
Ala Leu Arg Gly Gly Gly Gly Phe Ala Ile Val Ser Glu Phe Glu
            210                 215                 220
Phe Asn Thr Phe Glu Ala Pro Glu Ile Ile Thr Thr Tyr Gln Val Thr
225                 230                 235                 240
Thr Thr Trp Asn Arg Lys Gln His Val Ala Gly Leu Lys Ala Leu Gln
                245                 250                 255
Asp Trp Ala Gln Asn Thr Met Pro Arg Glu Leu Ser Met Arg Leu Glu
                260                 265                 270
Ile Asn Ala Asn Ala Leu Asn Trp Glu Gly Asn Phe Phe Gly Asn Ala
                275                 280                 285
Lys Asp Leu Lys Lys Ile Leu Gln Pro Ile Met Lys Lys Ala Gly Gly
    290                 295                 300
Lys Ser Thr Ile Ser Lys Leu Val Glu Thr Asp Trp Tyr Gly Gln Ile
305                 310                 315                 320
Asn Thr Tyr Leu Tyr Gly Ala Asp Leu Asn Ile Thr Tyr Asn Tyr Asp
                    325                 330                 335
Val His Glu Tyr Phe Tyr Ala Asn Ser Leu Thr Ala Pro Arg Leu Ser
                340                 345                 350
Asp Glu Ala Ile Gln Ala Phe Val Asp Tyr Lys Phe Asp Asn Ser Ser
                355                 360                 365
Val Arg Pro Gly Arg Gly Trp Trp Ile Gln Trp Asp Phe His Gly Gly
            370                 375                 380
Lys Asn Ser Ala Leu Ala Ala Val Ser Asn Asp Glu Thr Ala Tyr Ala
385                 390                 395                 400
His Arg Asp Gln Leu Trp Leu Trp Gln Phe Tyr Asp Ser Ile Tyr Asp
                    405                 410                 415
Tyr Glu Asn Asn Thr Ser Pro Tyr Pro Glu Ser Gly Phe Glu Phe Met
                420                 425                 430
Gln Gly Phe Val Ala Thr Ile Glu Asp Thr Leu Pro Glu Asp Arg Lys
            435                 440                 445
Gly Lys Tyr Phe Asn Tyr Ala Asp Thr Thr Leu Thr Lys Glu Glu Ala
450                 455                 460
Gln Lys Leu Tyr Trp Arg Gly Asn Leu Glu Lys Leu Gln Ala Ile Lys
465                 470                 475                 480
Ala Lys Tyr Asp Pro Glu Asp Val Phe Gly Asn Val Val Ser Val Glu
                    485                 490                 495
Pro Ile Ala

<210> SEQ ID NO 13
<211> LENGTH: 1785
<212> TYPE: DNA
<213> ORGANISM: Agaricus bisporus

<400> SEQUENCE: 13
atgatacctc gagtggccaa attcaacttt cgactcttgt ctctcgcatt attggggatt      60
caggttgcac gcagtgccat cacataccaa aacccgaccg atttacctgg tgacgttgac     120
tatgatttca tcgttgctgg cggtggaact gcaggtttag ttgtggcctc tcgtctcagt     180
```

```
gagaatccgg aatggaatgt actggtcatc gaggccgggc cttccaacaa ggacgtcttc    240
gaaacacggg tccctggcct ttcttcggaa ctccggccac gttttgattg aattataca    300 acgattcctc aagatgctct cggtggcagg agcctgaatt actcgagggc gaagctctta    360
ggcggttgca gtagccataa tgggatggtt tacacacgat gttcgagaga cgattgggac    420
aattatgccg aaatcaccgg taatcaagca tttagctggg acagcatcct acctgtcatg    480
aagagggctg agaaattcag taaagattcc tctcataaac cggtaaaggg ccatattgac    540
ccctccgtgc acggtggtga cggaaaattg tccgtggtcg catcatacac caacgcctct    600
ttcaatgact tattacttga aaccgcgaaa gaattaagcg gtgaatttcc gttcaaattg    660
gatatgaatg acgggcggcc tcttggatta acttggactc agtatacgat tgatcaacgc    720
ggggagcgga gcagctctgc aacagcgtat ttagagggta ctggaaataa cgtccatgtc    780
ttggttaaca ctcttgttac ccgtatagtc tcagcagaaa atgggaccga cttccgaagc    840
gtcgagtttg ctactgatgc cgacagccca aagatccaat tacgagcgaa aaaggaagtc    900
attgtatctg gaggagtcat caattcgcct cagatcctca tgaattccgg cattgggggc    960
cgagaggtgc ttggagctaa tggaattgac acattggtgg ataatccgag tgtcgggaaa   1020
aatttatcgg accaggctgc aacaattata atgctcgata caacactccc tattactgat   1080
tatgatgttg atgcagcgct tattgaatgg aagaagtcgc acactggacc tctagcccaa   1140
ggaggtcgcc taaccaccct tacatgggta cgattgcctg atgacaagct ggatggactt   1200
gatccttcaa gtggcgaaaa ttcgccacat attgagttcc aattcgggca aattagccac   1260
cagctccctc ccagtggtct aacacgtttt agcttctatc gacactgttc tccaattccg   1320
ccgttgatca acctctacac tgtttcgcgg ggttctattt ctctcagtaa caacgatccg   1380
ttctcccacc cactcatcga tctcaacatg tttggagagg aaatagatcc cgctattctg   1440
cgtgagggta ttcgcagtgc ccgaagaatg ctttcttccc aagcattcaa aggctttgtc   1500
ggtgaaacgg tgtttcctcc aagcgacgct acctctgatg aagatttgga taccttcctc   1560
aaaacgtcaa cgtttctta cgtgcatggt gtgggaacgt tgtctatgtc tcctcagagt   1620
gcctcgtggg gtgtcgttaa ccctgatttc cgtgtcaaag gaaccagtgg cctgcgggtt   1680
gtcgacgcgt ctgtgattcc attcgctccg gcggggcaca ctcaagaacc tgtttatgca   1740
tttgctgagc atgcaagtgt gttaatagcg aagagctaca gctaa                  1785
```

<210> SEQ ID NO 14
<211> LENGTH: 594
<212> TYPE: PRT
<213> ORGANISM: Agaricus bisporus

<400> SEQUENCE: 14

Met Ile Pro Arg Val Ala Lys Phe Asn Phe Arg Leu Leu Ser Leu Ala
1               5                   10                  15

Leu Leu Gly Ile Gln Val Ala Arg Ser Ala Ile Thr Tyr Gln Asn Pro
            20                  25                  30

Thr Asp Leu Pro Gly Asp Val Asp Tyr Asp Phe Ile Val Ala Gly Gly
        35                  40                  45

Gly Thr Ala Gly Leu Val Val Ala Ser Arg Leu Ser Glu Asn Pro Glu
    50                  55                  60

Trp Asn Val Leu Val Ile Glu Ala Gly Pro Ser Asn Lys Asp Val Phe
65                  70                  75                  80

Glu Thr Arg Val Pro Gly Leu Ser Ser Glu Leu Arg Pro Arg Phe Asp
                85                  90                  95

```
Trp Asn Tyr Thr Thr Ile Pro Gln Asp Ala Leu Gly Gly Arg Ser Leu
            100                 105                 110

Asn Tyr Ser Arg Ala Lys Leu Leu Gly Gly Cys Ser Ser His Asn Gly
            115                 120                 125

Met Val Tyr Thr Arg Cys Ser Arg Asp Asp Trp Asp Asn Tyr Ala Glu
            130                 135                 140

Ile Thr Gly Asn Gln Ala Phe Ser Trp Asp Ser Ile Leu Pro Val Met
145                 150                 155                 160

Lys Arg Ala Glu Lys Phe Ser Lys Asp Ser His Lys Pro Val Lys
                165                 170                 175

Gly His Ile Asp Pro Ser Val His Gly Asp Gly Lys Leu Ser Val
                180                 185                 190

Val Ala Ser Tyr Thr Asn Ala Ser Phe Asn Asp Leu Leu Glu Thr
                195                 200                 205

Ala Lys Glu Leu Ser Gly Glu Phe Pro Phe Lys Leu Asp Met Asn Asp
            210                 215                 220

Gly Arg Pro Leu Gly Leu Thr Trp Thr Gln Tyr Thr Ile Asp Gln Arg
225                 230                 235                 240

Gly Glu Arg Ser Ser Ala Thr Ala Tyr Leu Glu Gly Thr Gly Asn
                245                 250                 255

Asn Val His Val Leu Val Asn Thr Leu Val Thr Arg Ile Val Ser Ala
            260                 265                 270

Glu Asn Gly Thr Asp Phe Arg Ser Val Glu Phe Ala Thr Asp Ala Asp
            275                 280                 285

Ser Pro Lys Ile Gln Leu Arg Ala Lys Lys Glu Val Ile Val Ser Gly
            290                 295                 300

Gly Val Ile Asn Ser Pro Gln Ile Leu Met Asn Ser Gly Ile Gly Gly
305                 310                 315                 320

Arg Glu Val Leu Gly Ala Asn Gly Ile Asp Thr Leu Val Asp Asn Pro
                325                 330                 335

Ser Val Gly Lys Asn Leu Ser Asp Gln Ala Ala Thr Ile Ile Met Leu
            340                 345                 350

Asp Thr Thr Leu Pro Ile Thr Asp Tyr Asp Val Asp Ala Ala Leu Ile
            355                 360                 365

Glu Trp Lys Lys Ser His Thr Gly Pro Leu Ala Gln Gly Gly Arg Leu
            370                 375                 380

Asn His Leu Thr Trp Val Arg Leu Pro Asp Asp Lys Leu Asp Gly Leu
385                 390                 395                 400

Asp Pro Ser Ser Gly Glu Asn Ser Pro His Ile Glu Phe Gln Phe Gly
                405                 410                 415

Gln Ile Ser His Gln Leu Pro Pro Ser Gly Leu Thr Arg Phe Ser Phe
            420                 425                 430

Tyr Arg His Cys Ser Pro Ile Pro Pro Leu Ile Asn Leu Tyr Thr Val
            435                 440                 445

Ser Arg Gly Ser Ile Ser Leu Ser Asn Asn Asp Pro Phe Ser His Pro
            450                 455                 460

Leu Ile Asp Leu Asn Met Phe Gly Glu Glu Ile Asp Pro Ala Ile Leu
465                 470                 475                 480

Arg Glu Gly Ile Arg Ser Ala Arg Met Leu Ser Ser Gln Ala Phe
                485                 490                 495

Lys Gly Phe Val Gly Glu Thr Val Phe Pro Pro Ser Asp Ala Thr Ser
            500                 505                 510

Asp Glu Asp Leu Asp Thr Phe Leu Lys Thr Ser Thr Phe Ser Tyr Val
```

```
                515                 520                 525
His Gly Val Gly Thr Leu Ser Met Ser Pro Gln Ser Ala Ser Trp Gly
        530                 535                 540

Val Val Asn Pro Asp Phe Arg Val Lys Gly Thr Ser Gly Leu Arg Val
545                 550                 555                 560

Val Asp Ala Ser Val Ile Pro Phe Ala Pro Ala Gly His Thr Gln Glu
                565                 570                 575

Pro Val Tyr Ala Phe Ala Glu His Ala Ser Val Leu Ile Ala Lys Ser
            580                 585                 590

Tyr Ser

<210> SEQ ID NO 15
<211> LENGTH: 2010
<212> TYPE: DNA
<213> ORGANISM: Talaromyces stipitatus

<400> SEQUENCE: 15
```

| | | | | | |
|---|---|---|---|---|---|
| atgcgacttg | gctctatcgg | cgcaggcctc | gctctcctcg | ctgccctcgc | tgtcctcgct | 60 |
| gcccacgtgc | acgccttggc | accgcgcacc | cagattgccg | aggaatacga | ttttgtcgtc | 120 |
| gttggcggcg | gccaggctgg | tctcgtgatc | ggagctcgtc | tgtcggagat | tgcaaattat | 180 |
| acagttctcg | tgctggaggc | agggacgaat | ggagacgaat | tcgagaacg | aataggcacg | 240 |
| tacaactttt | atactcccgc | atattcctac | tacgagtcac | tatggacgac | accaatgaat | 300 |
| tgggcatact | atactgtgcc | tcaatcccat | gccgagaatc | gtcaaattga | gtggacccgt | 360 |
| ggtaagggc | tgggcggaag | ttctgcgatc | aacggattgt | acctgactcg | ccccggtaaa | 420 |
| gaggagatca | atgcatggaa | agacctgcta | ggagacatgg | acggggcgga | caattggtcg | 480 |
| tgggattcgt | tctatgctgc | aatgaagaag | agcgagactt | ttactccccc | gtcgaatgag | 540 |
| attgctacag | aagggaacat | tacatggac | ctttctactc | gtggtattca | gggaccgatt | 600 |
| caggcaacgt | atcccggcta | taccttcccc | caagtcggcg | aatgggtcat | gtctctggaa | 660 |
| gcaatgggca | ttgctagttc | taacgatatg | tacggtggtg | aggtgtatgg | cgccgaagtc | 720 |
| tcgacgtcga | gtatcaatcc | cacgaactgg | acacgctcgt | acagccggac | gggatatctc | 780 |
| gacccgctcg | cagacaacgg | caattacgac | gttgtggccg | atgcgtttgt | cacgcgcatt | 840 |
| ctctttgatg | cttcttctcc | gtcgaataat | ctgacagcaa | acggcgtgca | gtatactctt | 900 |
| gacaacggca | agacaaactg | cacggtcaag | gtcaagaaag | aggtgatctt | atcagctggg | 960 |
| acggttggca | gtcctgcggt | actgctccac | agcggtgtcg | gtccgaaaga | tgttctttca | 1020 |
| gatgctggag | ttgagctggt | gtctgaactt | cctggtgtgg | gtcaccacct | tcaggatcat | 1080 |
| tttaacaaca | ccctttatct | ctcctacatc | gattcagcca | tcgcctacat | caattccacg | 1140 |
| ctgatgtacg | gcgataatct | ggacgcacta | cagaagaaca | tcaccactca | aatcaaccaa | 1200 |
| ttcgtgctga | acacgactta | cgatgctggt | gtcattgcag | atacaaagc | aattgcaaat | 1260 |
| atgaccgcaa | ccacaatcct | cagtagttct | atcgggcaaa | ttgagctctt | gttcatgaat | 1320 |
| agtgacttaa | acggcgatat | tggtatcact | gctgctcttc | aacatcctta | cagccatgga | 1380 |
| cgcatataca | tcaattcctc | gaatccgttg | gactatcccg | tcattgatcc | gaattatctt | 1440 |
| gctgtttctg | ctgactatga | aatcctccgc | gacggcctca | atctagcccg | ccaactcggc | 1500 |
| aacacacaac | ccctaagcag | ctgtctaata | gccgaaacaa | tccccggtcc | cagcgtcaaa | 1560 |
| accgacgacg | actggcttga | atggatccgc | gaagcgacgg | ggacagagtt | ccacccttca | 1620 |
| tcgtcctgtg | cgatgctacc | ccgagagcaa | ggcggagtag | tcgatgccaa | cctgcgcgtc | 1680 |

-continued

```
tacggtcttg ccaatgttcg tgttgcggat gccagcgttg tcccgatttc attgtcgacg    1740
catcttatgg cgtcgacgta tggagtcgca gaacaggcta gtaatatcat tcgtgcgcac    1800
tacacggata gtaggactac aggcacgagt agttccgatc ctggctctgc gtcgtcaccg    1860
acaagcagtg cattgggcgc tgaagggact actggggcga ttagtgctca tacagcgcct    1920
tctggtggtg tacgaagcgt tctgcggta tccgcttggg ttgctgttgt gttcgctgca    1980
gctgtttcca ttttccattc cttgcattga                                    2010
```

<210> SEQ ID NO 16
<211> LENGTH: 669
<212> TYPE: PRT
<213> ORGANISM: Talaromyces stipitatus

<400> SEQUENCE: 16

```
Met Arg Leu Gly Ser Ile Gly Ala Gly Leu Ala Leu Leu Ala Ala Leu
1               5                   10                  15

Ala Val Leu Ala Ala His Val His Ala Leu Ala Pro Arg Thr Gln Ile
            20                  25                  30

Ala Glu Glu Tyr Asp Phe Val Val Gly Gly Gln Ala Gly Leu
        35                  40                  45

Val Ile Gly Ala Arg Leu Ser Glu Ile Ala Asn Tyr Thr Val Leu Val
    50                  55                  60

Leu Glu Ala Gly Thr Asn Gly Asp Glu Phe Arg Glu Arg Ile Gly Thr
65                  70                  75                  80

Tyr Asn Phe Tyr Thr Pro Ala Tyr Ser Tyr Tyr Glu Ser Leu Trp Thr
                85                  90                  95

Thr Pro Met Asn Trp Ala Tyr Tyr Thr Val Pro Gln Ser His Ala Glu
            100                 105                 110

Asn Arg Gln Ile Glu Trp Thr Arg Gly Lys Gly Leu Gly Gly Ser Ser
        115                 120                 125

Ala Ile Asn Gly Leu Tyr Leu Thr Arg Pro Gly Lys Glu Glu Ile Asn
    130                 135                 140

Ala Trp Lys Asp Leu Leu Gly Asp Met Asp Gly Ala Asp Asn Trp Ser
145                 150                 155                 160

Trp Asp Ser Phe Tyr Ala Ala Met Lys Lys Ser Glu Thr Phe Thr Pro
                165                 170                 175

Pro Ser Asn Glu Ile Ala Thr Glu Gly Asn Ile Thr Trp Asp Leu Ser
            180                 185                 190

Thr Arg Gly Ile Gln Gly Pro Ile Gln Ala Thr Tyr Pro Gly Tyr Thr
        195                 200                 205

Phe Pro Gln Val Gly Glu Trp Val Met Ser Leu Glu Ala Met Gly Ile
    210                 215                 220

Ala Ser Ser Asn Asp Met Tyr Gly Gly Glu Val Tyr Gly Ala Glu Val
225                 230                 235                 240

Ser Thr Ser Ser Ile Asn Pro Thr Asn Trp Thr Arg Ser Tyr Ser Arg
                245                 250                 255

Thr Gly Tyr Leu Asp Pro Leu Ala Asp Asn Gly Asn Tyr Asp Val Val
            260                 265                 270

Ala Asp Ala Phe Val Thr Arg Ile Leu Phe Asp Ala Ser Ser Pro Ser
        275                 280                 285

Asn Asn Leu Thr Ala Asn Gly Val Gln Tyr Thr Leu Asp Asn Gly Lys
    290                 295                 300

Thr Asn Cys Thr Val Lys Val Lys Lys Glu Val Ile Leu Ser Ala Gly
305                 310                 315                 320
```

-continued

Thr Val Gly Ser Pro Ala Val Leu Leu His Ser Gly Val Gly Pro Lys
            325                 330                 335

Asp Val Leu Ser Asp Ala Gly Val Glu Leu Val Ser Glu Leu Pro Gly
        340                 345                 350

Val Gly His His Leu Gln Asp His Phe Asn Asn Thr Leu Tyr Leu Ser
            355                 360                 365

Tyr Ile Asp Ser Ala Ile Ala Tyr Ile Asn Ser Thr Leu Met Tyr Gly
        370                 375                 380

Asp Asn Leu Asp Ala Leu Gln Lys Asn Ile Thr Thr Gln Ile Asn Gln
385                 390                 395                 400

Phe Val Leu Asn Thr Thr Tyr Asp Ala Gly Val Ile Ala Gly Tyr Lys
                405                 410                 415

Ala Ile Ala Asn Met Thr Ala Thr Thr Ile Leu Ser Ser Ile Gly
            420                 425                 430

Gln Ile Glu Leu Leu Phe Met Asn Ser Asp Leu Asn Gly Asp Ile Gly
            435                 440                 445

Ile Thr Ala Ala Leu Gln His Pro Tyr Ser His Gly Arg Ile Tyr Ile
        450                 455                 460

Asn Ser Ser Asn Pro Leu Asp Tyr Pro Val Ile Asp Pro Asn Tyr Leu
465                 470                 475                 480

Ala Val Ser Ala Asp Tyr Glu Ile Leu Arg Asp Gly Leu Asn Leu Ala
                485                 490                 495

Arg Gln Leu Gly Asn Thr Gln Pro Leu Ser Ser Cys Leu Ile Ala Glu
            500                 505                 510

Thr Ile Pro Gly Pro Ser Val Lys Thr Asp Asp Trp Leu Glu Trp
        515                 520                 525

Ile Arg Glu Ala Thr Gly Thr Glu Phe His Pro Ser Ser Ser Cys Ala
        530                 535                 540

Met Leu Pro Arg Glu Gln Gly Gly Val Val Asp Ala Asn Leu Arg Val
545                 550                 555                 560

Tyr Gly Leu Ala Asn Val Arg Val Ala Asp Ala Ser Val Val Pro Ile
                565                 570                 575

Ser Leu Ser Thr His Leu Met Ala Ser Thr Tyr Gly Val Ala Glu Gln
            580                 585                 590

Ala Ser Asn Ile Ile Arg Ala His Tyr Thr Asp Ser Arg Thr Thr Gly
            595                 600                 605

Thr Ser Ser Ser Asp Pro Gly Ser Ala Ser Pro Thr Ser Ser Ala
        610                 615                 620

Leu Gly Ala Glu Gly Thr Gly Ala Ile Ser Ala His Thr Ala Pro
625                 630                 635                 640

Ser Gly Gly Val Arg Ser Val Ser Ala Val Ser Ala Trp Val Ala Val
                645                 650                 655

Val Phe Ala Ala Ala Val Ser Ile Phe His Ser Leu His
            660                 665

<210> SEQ ID NO 17
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 17
cacgcggggt ctttctcca tctc                                        24

<210> SEQ ID NO 18

```
<211> LENGTH: 47
<212> TYPE: DNA
<213> ORGANISM: Artificial sequence
<220> FEATURE:
<223> OTHER INFORMATION: Synthetic DNA primer

<400> SEQUENCE: 18
tgaggaaaac gccgagactg agctcgactc tgccggccta cctacga           47

<210> SEQ ID NO 19
<211> LENGTH: 48
<212> TYPE: DNA
<213> ORGANISM: Artificial sequence
<220> FEATURE:
<223> OTHER INFORMATION: Synthetic DNA primer

<400> SEQUENCE: 19
atcagttggg tgcacgagtg ggttttgatg gggagttgag tttgtgaa          48

<210> SEQ ID NO 20
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 20
ggatggatga ggttgttttt gagc                                    24

<210> SEQ ID NO 21
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 21
aacccactcg tgcacccaac tgat                                    24

<210> SEQ ID NO 22
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 22
gaccacgatg ccggctacga tacc                                    24

<210> SEQ ID NO 23
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 23
acatggcccc actcgcttct taca                                    24

<210> SEQ ID NO 24
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 24
```

```
aagcgtgccg attttcctga tttc                                      24
```

<210> SEQ ID NO 25
<211> LENGTH: 21
<212> TYPE: DNA
<213> ORGANISM: Artificial sequence
<220> FEATURE:
<223> OTHER INFORMATION: Synthetic DNA primer

<400> SEQUENCE: 25

```
gcatttctgg ggcggttagc a                                         21
```

<210> SEQ ID NO 26
<211> LENGTH: 21
<212> TYPE: DNA
<213> ORGANISM: Artificial sequence
<220> FEATURE:
<223> OTHER INFORMATION: Synthetic DNA primer

<400> SEQUENCE: 26

```
tcatcgacgc ctccatcttc c                                         21
```

<210> SEQ ID NO 27
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 27

```
tttcggttgt cgtgtttcca ttat                                      24
```

<210> SEQ ID NO 28
<211> LENGTH: 20
<212> TYPE: DNA
<213> ORGANISM: Artificial sequence
<220> FEATURE:
<223> OTHER INFORMATION: Synthetic DNA primer

<400> SEQUENCE: 28

```
ggagatcctg gaggatttcc                                           20
```

<210> SEQ ID NO 29
<211> LENGTH: 22
<212> TYPE: DNA
<213> ORGANISM: Artificial sequence
<220> FEATURE:
<223> OTHER INFORMATION: Synthetic DNA primer

<400> SEQUENCE: 29

```
caggcggtgt gcgttatcaa aa                                        22
```

<210> SEQ ID NO 30
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 30

```
ttcagcacgg ccggggattt tatcca                                    26
```

<210> SEQ ID NO 31
<211> LENGTH: 48
<212> TYPE: DNA
<213> ORGANISM: Artificial sequence
<220> FEATURE:

<223> OTHER INFORMATION: Synthetic DNA primer

<400> SEQUENCE: 31
gtaacaccca atacgccggc cgaacataag agcggaggtc aggaataa          48

<210> SEQ ID NO 32
<211> LENGTH: 48
<212> TYPE: DNA
<213> ORGANISM: Artificial sequence
<220> FEATURE:
<223> OTHER INFORMATION: Synthetic DNA primer

<400> SEQUENCE: 32
ccgtctctcc gcatgccaga aagagctgtc aacgctggtt tgtggtgg          48

<210> SEQ ID NO 33
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 33
aatgccggac cgcgagttca ggta                                    24

<210> SEQ ID NO 34
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 34
tctttctggc atgcggagag acgg                                    24

<210> SEQ ID NO 35
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 35
tgttggcgac ctcgtattgg gaat                                    24

<210> SEQ ID NO 36
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 36
tctcggaggg cgaagaatct cgtg                                    24

<210> SEQ ID NO 37
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 37
ttcggccggc gtattgggtg ttac                                    24

<210> SEQ ID NO 38

```
<211> LENGTH: 25
<212> TYPE: DNA
<213> ORGANISM: Artificial sequence
<220> FEATURE:
<223> OTHER INFORMATION: Synthetic DNA primer

<400> SEQUENCE: 38
gcgctggaaa aggatgccac cgagt                                        25

<210> SEQ ID NO 39
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 39
gcaccccact gtccgaaacc gtta                                         24

<210> SEQ ID NO 40
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 40
agcgcgtctg ctgctccata caag                                         24

<210> SEQ ID NO 41
<211> LENGTH: 24
<212> TYPE: DNA
<213> ORGANISM: Artificial sequence
<220> FEATURE:
<223> OTHER INFORMATION: Synthetic DNA primer

<400> SEQUENCE: 41
caaagccacg tccaggttga taga                                         24
```

COMPOSITIONS AND METHODS FOR PRODUCTION OF FERMENTABLE SUGARS

The present application claims priority to U.S. Prov. Patent Appln. Ser. Nos. 61/409,186, 61/409,217, 61/409,472, and 61/409,480, all of which were filed on Nov. 2, 2010, and are hereby incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX35-069US2_ST25.TXT, created on Jan. 5, 2012, 72,869 bytes, machine format IBM-PC, MS-Windows operating system, is hereby incorporated by reference.

FIELD OF THE INVENTION

The present invention provides compositions and methods for the production of fermentable sugars. In some embodiments, the present invention provides genetically modified fungal organisms. In some additional embodiments, the present invention provides enzymes that find use in enhancing hydrolysis of cellulosic material to fermentable sugars (e.g., glucose), and methods for using the enzymes. In some further embodiments, the present invention provides enzyme mixtures useful for the hydrolysis of cellulosic materials.

BACKGROUND

Cellulose is a polymer of the simple sugar glucose linked by beta-1,4 glycosidic bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and lower overall greenhouse gas production. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Although progress has been made in increasing the efficiency of enzymatic degradation of lignocellulosic feedstocks, there remains a great need to improve yield of fermentable sugars using enzymatic processes.

SUMMARY OF THE INVENTION

The present invention provides genetically modified fungal organisms, as well as enzymes that enhance hydrolysis of cellulosic material to glucose, and methods for using the enzymes.

The present invention provides fungal cells that have been genetically modified to reduce the amount of endogenous glucose and/or cellobiose oxidizing enzyme activity that is produced by the fungal cells. In some embodiments, the fungal cell is an Ascomycete belonging to the subdivision Pezizomycotina, and/or wherein the fungal cell is from the family Chaetomiaceae. In some embodiments, the fungal cell is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium, Corynascus, Acremonium, Ctenomyces, Chrysosporium, Scytalidium, Talaromyces, Thermoascus,* or *Aspergillus.* In some additional embodiments, the fungal cell is a species of *Myceliophthora, Thielavia, Sporotrichum, Chrysosporium, Corynascus, Acremonium, Chaetomium, Ctenomyces, Scytalidium, Talaromyces,* or *Thermoascus,* while in some other embodiments, the fungal cell is *Sporotrichum thermophile Sporotrichum cellulophilum, Thielavia heterothallica, Thielavia terrestris, Corynascus heterothallicus,* or *Myceliophthora thermophila.* In some embodiments, the fungal cell has been genetically modified to reduce the amount of endogenous glucose oxidase and/or cellobiose dehydrogenase that is produced by the fungal cell. In some additional embodiments, the fungal cell has been genetically modified to reduce the amount of endogenous glucose oxidase and/or cellobiose dehydrogenase that is produced by the fungal cell and to increase the production of at least one saccharide hydrolyzing enzyme. In some further embodiments, the fungal cell has been genetically modified to reduce the amount of endogenous glucose oxidase and/or cellobiose dehydrogenase that is produced by the fungal cell and to increase the production of at least one saccharide hydrolyzing enzyme, and wherein the fungal cell is a Basidiomycete belonging to the class Agaricomycetes. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex.* In some embodiments, the fungal cell has been genetically modified to reduce the amount of the endogenous glucose oxidase and/or cellobiose dehydrogenase that is secreted by the fungal cell. In some additional embodiments, the fungal cell has been genetically modified to disrupt the secretion signal peptide of the glucose and/or cellobiose oxidizing enzyme. In some further embodiments, the fungal cell has been genetically modified to reduce the amount of the endogenous glucose and/or cellobiose oxidizing enzyme that is expressed by the fungal cell. In still some additional embodiments, the fungal cell has been genetically modified to disrupt a translation initiation sequence in the transcript encoding the endogenous glucose and/or cellobiose oxidizing enzyme. In some additional embodiments, the fungal cell has been genetically modified to introduce a frameshift mutation in the transcript encoding the endogenous glucose and/or cellobiose oxidizing enzyme. In some further embodiments, the fungal cell has been genetically modified to reduce the transcription level of a gene encoding the endogenous glucose and/or cellobiose oxidizing enzyme. In some embodiments, the fungal cell has been genetically modified to disrupt the promoter of a gene encoding the endogenous glucose and/or cellobiose oxidizing enzyme. In still some additional embodiments, the fungal cell has been genetically modified to at least partially delete at least one gene encoding the endogenous glucose and/or cellobiose oxidizing enzyme. In some further embodiments, the fungal cell has been genetically modified to reduce the catalytic efficiency of the endogenous glucose and/or cellobiose oxidizing enzyme. In some additional embodiments, the fungal cell has been genetically modified to mutate one or more residues in an active site of the glucose and/or cellobiose oxidizing enzyme. In some further embodiments, the fungal cell has been genetically modified to mutate one or more residues in a heme binding domain of the glucose and/or cellobiose oxidizing enzyme. In some embodiments of the fungal cells provided herein, the glucose and/or cellobiose oxidizing enzyme is selected from cellobiose dehydrogenase (EC 1.1.99.18), glucose oxidase (EC 1.1.3.4), pyranose oxidase (EC1.1.3.10), glucooligosaccharide oxidase (EC 1.1.99.B3), pyranose dehydrogenase (EC 1.1.99.29), and glucose dehydrogenase (EC 1.1.99.10). In some additional embodiments, the glucose and/or cellobiose oxidizing enzyme comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NOS:2, 4, 6, 8, 10, 12, 14, and/or 16. In some further embodiments, the glucose and/or cellobiose oxidizing enzyme is cellobiose dehydrogenase (EC 1.1.99.18). In some embodiments, the fungal cell has been genetically modified to reduce the amount of glucose and/or cellobiose oxidizing enzyme activity of two or more endogenous glucose and/or cellobiose oxidizing enzymes that are produced by the fungal cell prior to genetic modification. In some further embodiments, the first of the two or more the glucose and/or cellobiose oxidizing enzymes comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NOS: 2, 4, 6, 8, 10, 12, 14, and/or 16, and a second of the two or more the glucose and/or cellobiose oxidizing enzymes comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NOS: 2, 4, 6, 8, 10, 12, 14, and/or 16.

The present invention also provides enzyme mixtures comprising two or more cellulose hydrolyzing enzymes, wherein at least one of the two or more cellulose hydrolyzing enzymes is expressed by at least one of the fungal cells provided herein.

The present invention also provides enzyme mixtures comprising two or more cellulose hydrolyzing enzymes, wherein at least one of the two or more cellulose hydrolyzing enzymes is produced by a fungal cell that has been genetically modified to reduce the amount of endogenous glucose and/or cellobiose oxidizing enzyme activity that is secreted by the fungal cell, and wherein the fungal cell is an Ascomycete belonging to the subdivision Pezizomycotina. In some embodiments, the fungal cell is a species of *Myceliophthora, Thielavia, Sporotrichum, Corynascus, Acremonium, Chaetomium, Ctenomyces, Scytalidium, Talaromyces*, or *Thermoascus*.

The present invention also provides enzyme mixtures comprising two or more cellulose hydrolyzing enzymes, wherein at least one of the two or more cellulose hydrolyzing enzymes is produced by a fungal cell that has been genetically modified to reduce the amount of endogenous glucose and/or cellobiose oxidizing enzyme activity that is secreted by the fungal cell and to increase the production of at least one saccharide hydrolyzing enzyme, wherein the fungal cell is a Basidiomycete belonging to the class Agaricomycetes.

In some embodiments, the enzyme mixtures are cell-free mixtures. In some additional embodiments, a substrate of the enzyme mixture comprises pretreated lignocellulose. In some further embodiments, the pretreated lignocellulose comprises lignocellulose treated by a treatment method selected from acid pretreatment, ammonium pretreatment, steam explosion and/or organic solvent extraction.

The present invention also provides enzyme mixtures comprising two or more cellulose hydrolyzing enzymes, wherein the fungal cellulase enzyme mixture is modified relative to a parental (or reference) enzyme mixture to be at least partially deficient in glucose and/or cellobiose oxidizing enzyme activity.

The present invention further provides enzyme mixtures comprising two or more cellulose hydrolyzing enzymes, at least one of the cellulose hydrolyzing enzymes being endogenous to a fungal cell, wherein the fungal cell is a Basidiomycete belonging to the class Agaricomycetes or an Ascomycete belonging to the subdivision Pezizomycotina and wherein the enzyme mixture is characterized in that, when the enzyme mixture is contacted with cellobiose and/or glucose, no more than about 10%, about 15% or about 20%, of the cellobiose and/or glucose is oxidized after 10 hours.

In some embodiments of the enzyme mixtures, the fungal cell has been genetically modified to reduce the amount of glucose and/or cellobiose oxidase enzyme activity that is secreted by the fungal cell. In some further embodiments, the enzyme mixture is a cell-free mixture. In some additional embodiments, the enzyme mixture comprises at least one beta-glucosidase. In some further embodiments, the enzyme mixture comprises at least one cellulase enzyme selected from endoglucanases (EGs), beta-glucosidases (BGLs), Type 1 cellobiohydrolases (CBH1s), Type 2 cellobiohydrolases (CBH2s), and/or glycoside hydrolase 61s (GH61s), and/or variants of the cellulase enzyme. In some embodiments, the enzyme mixture further comprises at least one cellobiose dehydrogenase. In some embodiments, the cellobiose dehydrogenase is CDH1 and/or CDH2. In some additional embodiments, the enzyme mixture further comprises at least one cellulase enzyme and/or at least one additional enzyme. In some further embodiments, the enzyme mixture has been subjected to a purification process to selectively remove one or more glucose and/or cellobiose oxidizing enzymes from the enzyme mixture. In some embodiments, the purification process comprises selective precipitation to separate the glucose and/or cellobiose oxidizing enzymes from other enzymes present in the enzyme mixture. In some additional embodiments, the enzyme mixtures comprise at least one inhibitor of one or more glucose and/or cellobiose oxidizing enzymes.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungal cell that is an Ascomycete belonging to the subdivision Pezizomycotina, and wherein the enzyme mixture is characterized in that, when the enzyme mixture is contacted with cellobiose and/or glucose, no more than about 10%, about 15%, or about 20% of the cellobiose and/or glucose is oxidized after 10 hours. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium*, or *Aspergillus*.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungal cell that is a Basidiomycete belonging to the class Agaricomycetes, and wherein the enzyme mixture is characterized in that, when the enzyme mixture is contacted with cellobiose and/or glucose, no more than about 10%, about 15% or about 20% of the cellobiose and/or glucose is oxidized after 10 hours. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota*, or *Irpex*.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungal cell that is an Ascomycete belonging to the subdivision Pezizomycotina, and wherein, of the cellulose hydrolyzed by the enzyme mixture, at least about 80%, about 85%, or about 90% is present in the form of cellobiose and/or glucose. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium*, or *Aspergillus*. In some embodiments, the Ascomycete is *Myceliophthora thermophila, Thielavia heterothallica* or *Sporotrichum thermophile*. In some embodiments, the fungal cell is *Myceliophthora thermophila*.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungal cell that is a Basidiomycete belonging to the class Agaricomycetes, and wherein, of the cellulose hydrolyzed by the enzyme mixture, at least about 80%, about 85%, or about 90% is present in the form of cellobiose and/or glucose. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota*, or *Irpex*.

The present invention also provides methods for producing cellobiose and/or glucose from cellulose comprising treating a cellulose substrate with an enzyme mixture to generate glucose, wherein the enzyme mixture is modified relative to a secreted enzyme mixture from a reference (or parental) fungal cell to be at least partially deficient in glucose and/or cellobiose oxidizing enzyme activity. In some embodiments of the methods, the enzyme mixture is a cell-free mixture. In some additional embodiments, the cellulose substrate comprises pretreated lignocellulose. In some further embodiments, the pretreated lignocellulose comprises lignocellulose treated by a treatment method selected from acid pretreatment, ammonium pretreatment, steam explosion and/or organic solvent extraction. In some further embodiments, the methods further comprise fermentation of the cellobiose and/or glucose to at least one end product. In some embodiments, the end product is at least one fuel alcohol and/or at least one precursor industrial chemical. In some additional embodiments, the fuel alcohol is ethanol or butanol. In some embodiments, the process for producing cellobiose and/or glucose from cellulose and said fermentation are conducted in a simultaneous saccharification and fermentation (SSF) process. In some further additional embodiments, the enzyme mixture is produced by a fungal cell has that been genetically modified to reduce the amount of one or more endogenous glucose and/or cellobiose oxidizing enzymes that is secreted by the fungal cell. In some embodiments, the enzyme mixture has been subjected to a purification process to selectively remove at least one glucose and/or cellobiose oxidizing enzyme from the enzyme mixture. In some further embodiments, the purification process comprises selective precipitation to separate the glucose and/or cellobiose oxidizing enzyme from other enzymes present in the enzyme mixture. In still some additional embodiments, the enzyme mixture comprises at least one inhibitor of the glucose and/or cellobiose oxidizing enzyme. In some embodiments, the inhibitor comprises a broad-spectrum oxidase inhibitor selected from sodium azide, potassium cyanide, a metal anion, and a combination thereof. In some embodiments, the inhibitor comprises a specific inhibitor of cellobiose dehydrogenase (EC 1.1.99.18) selected from cellobioimidazole, gentiobiose, lactobiono-1,5-lactone, celliobono-1,5-lactone, tri-N-acetylchitortriose, methyl-beta-D cellobiosidase, 2,2-bipyridine, cytochrome C, and a combination thereof. In some embodiments, the method is a batch process, while in some other embodiments it is a continuous process, and in some further embodiments it is a fed-batch process and in still further embodiments, it is a combination of batch, continuous and/or fed-batch processes conducted in any order. In some embodiments, the method is conducted in a reaction volume of at least 10,000 liters, while in some other embodiments, the method is conducted in a reaction volume of at least 100,000 liters. In some embodiments, the enzyme mixture comprises at least one beta-glucosidase, while in some other embodiments, the enzyme mixture does not comprise a beta-glucosidase. In some embodiments, the enzyme mixture comprises at least one endoglucanase, while in some other embodiments, the enzyme mixture does not comprise an endoglucanase. In some embodiments, the enzyme mixture comprises at least one cellulase enzyme selected from endoglucanases (EGs), beta-glucosidases (BGLs), Type 1 cellobiohydrolases (CBH1s), Type 2 cellobiohydrolases (CBH2s), and/or glycoside hydrolase 61s (GH61s), and/or variants of said cellulase enzyme.

The present invention also provides methods for generating glucose comprising contacting cellulose with an enzyme mixture comprising two or more cellulose hydrolyzing enzymes, wherein at least one of the two or more cellulose hydrolyzing enzymes is produced by the fungal cells provided herein.

The present invention also provides methods for generating glucose comprising contacting cellulose with an enzyme mixture comprising two or more cellulose hydrolyzing enzymes, wherein at least one of the two or more cellulose hydrolyzing enzymes is produced by a fungal cell that has been genetically modified to reduce the amount of endogenous glucose and/or cellobiose oxidizing enzyme activity that is secreted by the fungal cell, wherein the fungal cell is an Ascomycete belonging to the subdivision Pezizomycotina. In some embodiments, the fungal cell is a species of *Myceliophthora, Thielavia, Sporotrichum, Corynascus, Acremonium, Chaetomium, Ctenomyces, Scytalidium, Talaromyces*, or *Thermoascus*.

The present invention also provides methods for generating glucose comprising contacting cellulose with an enzyme mixture comprising two or more cellulose hydrolyzing enzymes, wherein at least one of the two or more cellulose hydrolyzing enzymes is produced by a fungal cell that has been genetically modified to reduce the amount of endogenous glucose and/or cellobiose oxidizing enzyme activity that is secreted by the fungal cell and to increase the production of at least one saccharide hydrolyzing enzyme, wherein the fungal cell is a Basidiomycete belonging to the class Agaricomycetes.

The present invention further provides methods for generating glucose comprising contacting cellulose with at least one enzyme mixture as provided herein. In some embodiments, the cellulose comprises pretreated lignocellulose. In some additional embodiments, the pretreated lignocellulose comprises lignocellulose treated by a treatment method selected from acid pretreatment, ammonium pretreatment, steam explosion and/or organic solvent extraction. In some additional embodiments, the enzyme mixture is a cell-free mixture. In some further embodiments, the methods further comprise fermentation of the glucose to an end product. In some embodiments, the end product is a fuel alcohol or a precursor industrial chemical. In some embodiments, the fuel alcohol is ethanol or butanol.

The present invention further provides the fungal cells provided herein, as well as the enzyme mixtures provided herein, and the methods provided herein, further comprising a cellulose degrading enzyme that is heterologous to the fungal cell.

The present invention also provides fermentation media comprising at least one fungal cell provided herein.

The present invention also provides fermentation media comprising at least one enzyme mixture provided herein.

The present invention further provides fermentation media comprising at least one fungal cell and/or at least one enzyme mixture, as provided herein.

The present invention also provides methods of producing at least one cellulase, comprising at least one fungal cell provided herein, under conditions such that said at least one cellulase is produced. In some embodiments, the fungal cell is recombinant.

The present invention also provides compositions comprising at least one cellulase as provided herein.

DESCRIPTION OF THE DRAWINGS

FIGS. 3 and 4 provide the nucleotide and amino acid sequences of *M. thermophila* CDH1 and CDH2 (SEQ ID NOS:5-8).

FIGS. 5 and 6 provide the nucleotide and amino acid sequences of *M. thermophila* GO1 and GO2 (SEQ ID NOS:1-4).

FIG. 7 provides the nucleotide and amino acid sequences of *A. oryzae* pyranose oxidase (SEQ ID NOS:9-10).

FIG. 8 provides the nucleotide and amino acid sequences of *A. strictum* glucooligosaccharide oxidase (SEQ ID NOS:11-12).

FIG. 9 provides the nucleotide and amino acid sequences of *A. bisporus* pyranose dehydrogenase (SEQ ID NOS:13-14).

FIG. 10 provides the nucleotide and amino acid sequences of *T. stipitatus* ATCC10500 glucose dehydrogenase (SEQ ID NOS:15-16).

FIGS. 14A and 14B are HPLC chromatograms that identify an oxidized glucose product produced from glucose (FIG. 5A) or from cellulose hydrolysate using cellulase enzymes secreted by strain CF-402, as described in Example 13.

DESCRIPTION OF THE INVENTION

Figure 1:
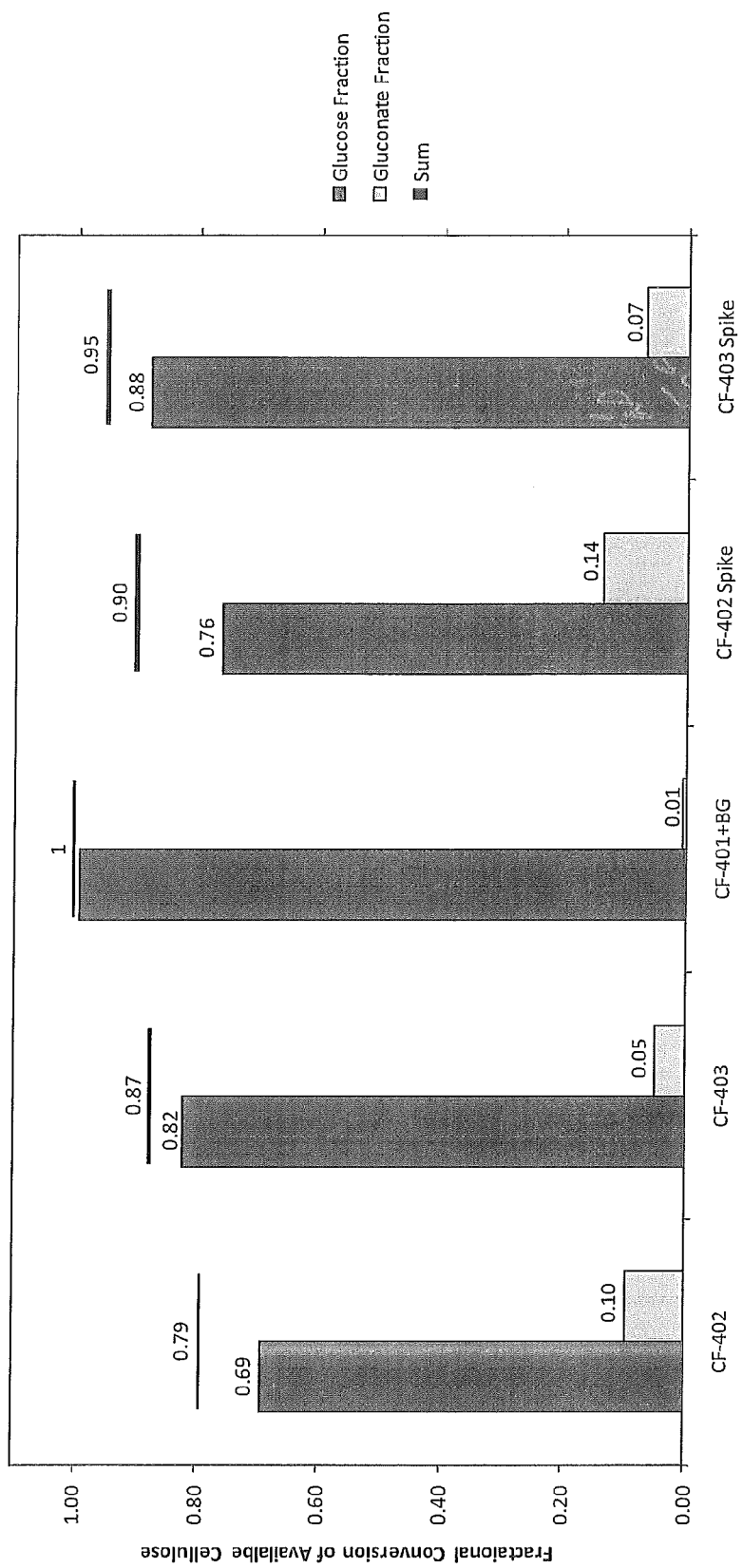
FIG. 1 is a chart that shows the products of cellulose hydrolysis using enzyme mixtures obtained from strains CF-402, CF-403, and CF-401 as further described in Example 1 and Example 7. Dark bars represent measured glucose production. Light bars represent measured gluconate production. Numbers above horizontal bars indicate the sum of glucose and gluconate fractions.

The present invention provides genetically modified fungal organisms, as well as enzymes that enhance hydrolysis of cellulosic material to glucose, and methods for using the enzymes.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, some suitable methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, "substrate" refers to a substance or compound that is converted or meant to be converted into another compound by the action of an enzyme. The term includes not only a single compound but also combinations of compounds, such as solutions, mixtures and other materials which contain at least one substrate.

As used herein, "conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a cellobiose dehydrogenase ("CDH" or "cdh") polypeptide can be expressed as "percent conversion" of the substrate to the product.

As used herein, "secreted activity" refers to enzymatic activity of glucose and/or cellobiose oxidizing enzymes produced by a fungal cell that is present in an extracellular environment. An extracellular environment can be, for example, an extracellular milieu such as a culture medium. The secreted activity is influenced by the total amount of glucose and/or cellobiose oxidizing enzyme secreted, and also is influenced by the catalytic efficiency of the secreted glucose and/or cellobiose oxidizing enzyme.

As used herein, a "reduction in catalytic efficiency" refers to a reduction in the activity of the glucose and/or cellobiose oxidizing enzyme, relative to unmodified glucose and/or cellobiose oxidizing enzyme, as measured using standard techniques, as provided herein or otherwise known in the art.

As used herein, the term "enzyme mixture" refers to a combination of at least two enzymes. In some embodiments, at least two enzymes are present in a composition. In some additional embodiments, the enzyme mixtures are present within a cell (e.g., a fungal cell). In some embodiments, each or some of the enzymes present in an enzyme mixture are produced by different fungal cells and/or different fungal cultures. In some further embodiments, all of the enzymes present in an enzyme mixture are produced by the same cell. In some embodiments, the enzyme mixtures comprise cellulase enzymes, while in some additional embodiments, the enzyme mixtures comprise enzymes other than cellulases. In some embodiments, the enzyme mixtures comprise at least one cellulase and at least one enzyme other than a cellulase. In some embodiments, the enzyme mixtures comprise enzymes including, but not limited to endoxylanases (EC 3.2.1.8), beta-xylosidases (EC 3.2.1.37), alpha-L-arabinofuranosidases (EC 3.2.1.55), alpha-glucuronidases (EC 3.2.1.139), acetylxylanesterases (EC 3.1.1.72), feruloyl esterases (EC 3.1.1.73), coumaroyl esterases (EC 3.1.1.73), alpha-galactosidases (EC 3.2.1.22), beta-galactosidases (EC 3.2.1.23), beta-mannanases (EC 3.2.1.78), beta-mannosidases (EC 3.2.1.25), endo-polygalacturonases (EC 3.2.1.15), pectin methyl esterases (EC 3.1.1.11), endo-galactanases (EC 3.2.1.89), pectin acetyl esterases (EC 3.1.1.6), endo-pectin lyases (EC 4.2.2.10), pectate lyases (EC 4.2.2.2), alpha rhamnosidases (EC 3.2.1.40), exo-galacturonases (EC 3.2.1.82), exo-galacturonases (EC 3.2.1.67), exopolygalacturonate lyases (EC 4.2.2.9), rhamnogalacturonan endolyases EC (4.2.2.B3), rhamnogalacturonan acetylesterases (EC 3.2.1.B11), rhamnogalacturonan galacturonohydrolases (EC 3.2.1.B11), endo-arabinanases (EC 3.2.1.99), laccases (EC 1.10.3.2), manganese-dependent peroxidases (EC 1.10.3.2), amylases (EC 3.2.1.1), glucoamylases (EC 3.2.1.3), lipases, lignin peroxidases (EC 1.11.1.14), and/or proteases.

In some additional embodiments, the present invention further provides enzyme mixtures comprising at least one expansin and/or expansin-like protein, such as a swollenin (See e.g., Salheimo et al., Eur. J. Biochem., 269:4202-4211 [2002]) and/or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein and/or swollenin-like protein comprises one or both of such domains and/or disrupts the structure of cell walls (e.g., disrupting cellulose structure), optionally without producing detectable amounts of reducing sugars. In some additional embodiments, the enzyme mixtures comprise at least one polypeptide product of a cellulose integrating protein, scaffoldin and/or a scaffoldin-like protein (e.g., CipA or CipC from *Clostridium thermocellum* or *Clostridium cellulolyticum* respectively). In some additional embodiments, the enzyme mixtures comprise at least one cellulose induced protein and/or modulating protein (e.g., as encoded by cip1 or cip2 gene and/or similar genes from *Trichoderma reesei*; See e.g., Foreman et al., J. Biol. Chem., 278:31988-31997 [2003]). In some additional embodiments, the enzyme mixtures comprise at least one member of each of the classes of the polypeptides described above, several members of one polypeptide class, or any combination of these polypeptide classes to provide enzyme mixtures suitable for various uses.

Any combination of at least one two, three, four, five, or more than five enzymes and/or polypeptides find use in various enzyme mixtures provided herein. Indeed, it is not intended that the enzyme mixtures of the present invention be limited to any particular enzymes, polypeptides, nor combinations, as any suitable enzyme mixture finds use in the present invention.

As used herein, the term "saccharide" refers to any carbohydrate comprising monosaccharides (e.g., glucose, ribose, fructose, galactose, etc.), disaccharides (e.g., sucrose, lactose, maltose, cellobiose, trehalose, melibiose, etc.), oligosaccharides (e.g., raffinose, stachyose, amylose, etc.), and polysaccharides (e.g., starch, glycogen, cellulose, chitin, xylan, arabinoxylan, mannan, fucoidan, galactomannan, callose, laminarin, chrysolaminarin, amylopectin, dextran, dextrins, maltodextrins, inulin, oligofructose, polydextrose, etc.). The term encompasses simple carbohydrates, as well as complex carbohydrates. Indeed, it is not intended that the present invention be limited to any particular saccharide, as various saccharides and forms of saccharides find use in the present invention.

As used herein, the term "saccharide hydrolyzing enzyme" refers to any enzyme that hydrolyzes at least one saccharide.

As used herein, the terms "glucose oxidizing enzyme" and "cellobiose oxidizing enzyme" refer to enzymes that oxidize glucose and/or cellobiose. For example, glucose and/or cellobiose oxidizing enzymes include glucose oxidase (EC 1.1.3.4), cellobiose dehydrogenase (EC 1.1.99.18), pyranose oxidase (EC 1.1.3.10), glucooligosaccharide oxidase (EC 1.1.99.B3), pyranose dehydrogenase (EC 1.1.99.29), and glucose dehydrogenase (EC 1.1.99.10).

As used herein, the terms "glucose oxidase" and "GO" refer to an enzyme that is an oxido-reductase that catalyses the oxidation of β-D-glucose into D-glucono-1,5-lactone, which is a cyclic ester existing at a pH-dependent equilibrium in aqueous solution with gluconic acid or gluconate. Exemplary glucose oxidases fall into the enzyme classification (EC 1.1.3.4). In order to work as a catalyst, glucose oxidases typically utilize a co-substrate oxidant, such as flavin adenine dinucleotide (FAD). The enzyme is highly specific for β-D-glucose. However, glucose oxidase also can demonstrate some lesser oxidase activity for substrates 2-deoxy-D-glucose, D-mannose and D-galactose (See e.g., Bentley, Meth. Enzymol., 9:86 [1996]).

As used herein, the terms "cellobiose dehydrogenase" and "CDH" refer to a cellobiose:acceptor 1-oxidoreductase that catalyzes the conversion of cellobiose in the presence of an acceptor to cellobiono-1,5-lactone and a reduced acceptor. Examples of cellobiose dehydrogenases fall into the enzyme classification (E.C. 1.1.99.18). Typically 2,6-Dichloroindophenol can act as acceptor, as can iron, especially Fe(SCN)$_3$, molecular oxygen, ubiquinone, or cytochrome C, and other polyphenolics, such as lignin. Substrates of the enzyme include cellobiose, cello-oligosaccharides, lactose, and D-glucosyl-1,4-β-D-mannose, glucose, maltose, mannobiose, thiocellobiose, galactosyl-mannose, xylobiose, xylose. Electron donors include beta-1-4 dihexoses with glucose or mannose at the reducing end, though alpha-1-4 hexosides, hexoses, pentoses, and beta-1-4 pentomers can act as substrates for at least some of these enzymes (See e.g., Henriksson et al, Biochim. Biophys. Acta—Prot. Struct. Mol. Enzymol., 1383: 48-54 [1998]; and Schou et al., Biochem. J., 330: 565-571 [1998]).

As used herein, the terms "oxidation", "oxidize(d)" and the like as used herein refer to the enzymatic formation of one or more glucose or cellobiose oxidation products including, but not limited to, cellobionolactone, cellobionic acid, gluconolactone, gluconate and/or gluconic acid. When used in reference to a percentage of oxidized cellobiose and/or glucose, those percentages reflect a weight percent (w/w) relative to the initial amount of substrate. For example, when the enzyme mixture is contacted with cellobiose and/or glucose, the percentage of oxidized cellobiose and/or glucose reflects a weight percent (w/w) relative to the initial amount of cellobiose and/or glucose present in solution. Where the enzyme mixture is contacted with a cellulose substrate, the percentage of oxidized cellobiose and/or glucose reflects a weight percent (w/w) based on the maximum amount (wt %) of glucose that could be produced from the total hydrolyzed cellulose (i.e., Gmax).

As used herein, the terms "cellobiose dehydrogenase" and "CDH" refer to a cellobiose:acceptor 1-oxidoreductase that catalyzes the conversion of cellobiose in the presence of an acceptor to cellobiono-1,5-lactone and a reduced acceptor. Examples of cellobiose dehydrogenases are included in the enzyme classification (E.C. 1.1.99.18). In some embodiments, the cellobiose dehydrogenase of interest in the present invention is CDH1, which is encoded by the cdh1 gene. In some embodiments, the cellobiose dehydrogenase of interest in the present invention is CDH2, which is encoded by the cdh2 gene. In some embodiments, both CDH1 and CDH2 are of interest.

As used herein, the terms "pyranose oxidase" and "PO" refer to an enzyme that catalyzes the conversion of D-glucose and $O_2$ to 2-dehydro-D-glucose and $H_2O_2$. Examples of pyranose oxidases fall into the enzyme classification (E.C. 1.1.3.10). The systematic name of this enzyme class is pyranose:oxygen 2-oxidoreductase. Other names in common use include glucose 2-oxidase, and pyranose-2-oxidase. Substrates of the enzyme include D-glucose, D-xylose, L-arabinose, L-sorbose, D-glucono-1,5-lactone, cellobiose and gentiobiose.

As used herein, the terms "glucooligosaccharide oxidase" and "GOOX" refer to an enzyme that catalyzes the oxidation of oligosaccharides with glucose on the reducing end and each sugar residue joined by an alpha- or beta-1,4 glucosidic bond. Examples of glucooligosaccharide oxidase fall into the enzyme classification (E.C. 1.1.99.B3). The systematic name of this enzyme class is carbohydrate:acceptor oxidoreductase. Substrates of the enzyme include maltose, lactose, cellobiose and maltose derivatives up to seven residues.

As used herein, the terms "pyranose dehydrogenase" and "PDH" refer to an enzyme that catalyzes the reaction of pyranose and an acceptor to yield 2-dehydropyranose (or 3-dehydropyranose or 2,3-didehydropyranose) and a reduced acceptor. PDH also catalyzes the reaction of a pyranoside and an acceptor to yield a 3-dehydropyranoside (or 3,4-didehydropyranoside) and a reduced acceptor. Examples of pyranose dehydrogenases fall into the enzyme classification (E.C. 1.1.99.29). The systematic name of this enzyme class is pyranose:acceptor oxidoreductase. Other names in common use include pyranose 2,3-dehydrogenase. PDH utilizes FAD as a cofactor. A number of aldoses and ketoses in pyranose form, as well as glycosides, gluco-oligosaccharides, sucrose and lactose can act as a donor. 1,4-Benzoquinone or ferricenium ion (ferrocene oxidized by removal of one electron) can serve as acceptor. Unlike EC 1.1.3.10 (pyranose oxidase), pyranose dehydrogenase does not interact with $O_2$ and exhibits extremely broad substrate tolerance with variable regioselectivity (C-3, C-2 or C-3+C-2 or C-3+C-4) for (di)oxidation of different sugars. D-Glucose is exclusively or preferentially oxidized at C-3 (depending on the enzyme source), but can also be oxidized at C-2+C-3. Pyranose dehydrogenase also acts on 1->4-alpha- and 1->4-beta-gluco-oligosaccharides, non-reducing gluco-oligosaccharides and L-arabinose, which are not substrates of EC 1.1.3.10. Sugars are oxidized by pyranose dehydrogenase in their pyranose but not in their furanose form.

As used herein, the terms "glucose dehydrogenase" and "GDH" refer to an enzyme that catalyzes the reaction of D-glucose and an acceptor to yield D-glucono-1,5-lactone and a reduced acceptor. Examples of glucose dehydrogenase fall into the enzyme classification (E.C. 1.1.99.10). The systematic name of this enzyme class is D-glucose:acceptor 1-oxidoreductase. GDH utilizes FAD as a cofactor.

As used herein, the term "cellulase" refers to any enzyme that is capable of degrading cellulose. Thus, the term encompasses enzymes capable of hydrolyzing cellulose (β-1,4-glucan or β-D-glucosidic linkages) to shorter cellulose chains, oligosaccharides, cellobiose and/or glucose. "Cellulases" are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," "BG," or "BGL"). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. Beta-glucosidases split the cellobiose into glucose monomers.

Cellulases often comprise a mixture of different types of cellulolytic enzymes (endoglucanases and cellobiohydrolases) that act synergistically to break down the cellulose to soluble di- or oligosaccharides such as cellobiose, which are then further hydrolyzed to glucose by beta-glucosidase. Cellulase enzymes are produced by a wide variety of microorganisms. Cellulases (and hemicellulases) from filamentous fungi and some bacteria are widely exploited for many industrial applications that involve processing of natural fibers to sugars.

As used herein, a "cellulase-producing fungal cell" is a fungal cell that produces at least one cellulase enzyme (i.e., "cellulose hydrolyzing enzyme"). In some embodiments, the cellulase-producing fungal cells provided herein express and secrete a mixture of cellulose hydrolyzing enzymes. As used herein, the terms "cellulose hydrolyzing enzyme," "cellulolytic enzyme," and like terms refer to an enzyme that acts in the process of breaking down cellulose to soluble di- or oligosaccharides such as cellobiose, which are then further hydrolyzed to glucose by beta-glucosidase. A mixture of cellulose hydrolyzing enzymes is also referred to herein as "cellulases," a "cellulase-containing mixture," and/or a "cellulase mixture."

As used herein, the terms "endoglucanase" and "EG" refer to a category of cellulases (EC 3.2.1.4) that catalyze the hydrolysis of internal β-1,4 glucosidic bonds of cellulose. The term "endoglucanase" is further defined herein as an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1,3 glucans such as cereal beta-D-glucans or xyloglucans, and other plant material containing cellulosic components. Endoglucanase activity can be determined based on a reduction in substrate viscosity or increase in reducing ends determined by a reducing sugar assay (See e.g., Zhang et al., Biotechnol. Adv., 24:452-481 [2006]). For purposes of the present invention, endoglucanase activity is determined using carboxymethyl cellulose (CMC) hydrolysis (See e.g., Ghose, Pur. Appl. Chem., 59:257-268 [1987]).

As used herein, "EG1" refers to a carbohydrate active enzyme expressed from a nucleic acid sequence coding for a glycohydrolase (GH) Family 7 catalytic domain classified under EC 3.2.1.4 or any protein, polypeptide or catalytically active fragment thereof. In some embodiments, the EG1 is functionally linked to a carbohydrate binding module (CBM), such as a Family 1 cellulose binding domain.

As used herein, the term "EG2" refers to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, the EG2 is functionally linked to a carbohydrate binding module (CBM), such as a Family 1 cellulose binding domain.

As used herein, the term "EG3" refers to a carbohydrate active enzyme expressed from a nucleic acid sequence coding for a glycohydrolase (GH) Family 12 catalytic domain classified under EC 3.2.1.4 or any protein, polypeptide or catalytically active fragment thereof. In some embodiments, the EG3 is functionally linked to a carbohydrate binding module (CBM), such as a Family 1 cellulose binding domain.

As used herein, the term "EG4" refers to a carbohydrate active enzyme expressed from a nucleic acid sequence coding for a glycohydrolase (GH) Family 61 catalytic domain classified under EC 3.2.1.4 or any protein, polypeptide or fragment thereof. In some embodiments, the EG4 is functionally linked to a carbohydrate binding module (CBM), such as a Family 1 cellulose binding domain.

As used herein, the term "EG5" refers to a carbohydrate active enzyme expressed from a nucleic acid sequence coding for a glycohydrolase (GH) Family 45 catalytic domain classified under EC 3.2.1.4 or any protein, polypeptide or fragment thereof. In some embodiments, the EG5 is functionally linked to a carbohydrate binding module (CBM), such as a Family 1 cellulose binding domain.

As used herein, the term "EG6" refers to a carbohydrate active enzyme expressed from a nucleic acid sequence coding for a glycohydrolase (GH) Family 6 catalytic domain classified under EC 3.2.1.4 or any protein, polypeptide or fragment thereof. In some embodiments, the EG6 is functionally linked to a carbohydrate binding module (CBM), such as a Family 1 cellulose binding domain.

As used herein, the terms "cellobiohydrolase" and "CBH" refer to a category of cellulases (EC 3.2.1.91) that hydrolyze glycosidic bonds in cellulose. The term "cellobiohydrolase" is further defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (See e.g., Teeri, Tr. Biotechnol., 15:160-167 [1997]; and Teeri et al., Biochem. Soc. Trans., 26:173-178 [1998]). In some embodiments, cellobiohydrolase activity is determined using a fluorescent disaccharide derivative 4-methylumbelliferyl-.beta.-D-lactoside (See e.g., van Tilbeurgh et al., FEBS Lett., 149:152-156 [1982]; and van Tilbeurgh and Claeyssens, FEBS Lett., 187:283-288 [1985]).

As used herein, the terms "CBH1" and "type 1 cellobiohydrolase" refer to a carbohydrate active enzyme expressed from a nucleic acid sequence coding for a glycohydrolase (GH) Family 7 catalytic domain classified under EC 3.2.1.91 or any protein, polypeptide or catalytically active fragment thereof. In some embodiments, the CBH1 is functionally linked to a carbohydrate binding module (CBM), such as a Family 1 cellulose binding domain.

As used herein, the terms "CBH2" and "type 2 cellobiohydrolase" refer to a carbohydrate active enzyme expressed from a nucleic sequence coding for a glycohydrolase (GH) Family 6 catalytic domain classified under EC 3.2.1.91 or any protein, polypeptide or catalytically active fragment thereof. Type 2 cellobiohydrolases are also commonly referred to as "the Cel6 family." In some embodiments, the CBH2 is functionally linked to a carbohydrate binding module (CBM), such as a Family 1 cellulose binding domain.

As used herein, the terms "beta-glucosidase," "cellobiase," and "BGL" refers to a category of cellulases (EC 3.2.1.21) that catalyze the hydrolysis of cellobiose to glucose. The term "beta-glucosidase" is further defined herein as a beta-D-glucoside glucohydrolase (E.C. 3.2.1.21), which catalyzes the hydrolysis of terminal non-reducing beta-D-glucose residues with the release of beta-D-glucose. Beta-glucosidase activity can be determined using any suitable method (See e.g., J. Basic Microbiol., 42: 55-66 [2002]). One unit of beta-glucosidase activity is defined as 1.0 pmole of p-nitrophenol produced per minute at 40° C., pH 5 from 1 mM p-nitrophenyl-beta-D-glucopyranoside as substrate in 100 mM sodium citrate containing 0.01% TWEEN® 20.

As used herein, the term "glycoside hydrolase 61" and "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, beta-xylosidases, alpha-L-arabinofuranosidases, alpha-D-glucuronidases, feruloyl esterases, coumaroyl esterases, alpha-galactosidases, beta-galactosidases, beta-mannanases, and beta-mannosidases.

As used herein, the terms "xylan degrading activity" and "xylanolytic activity" are defined herein as a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases) (See e.g., Biely and Puchard, J. Sci. Food Agr. 86:1636-1647 [2006]; Spanikova and Biely, FEBS Lett., 580: 4597-4601 [2006]; and Herrmann et al., Biochem. J., 321: 375-381 [1997]).

Total xylan degrading activity can be measured by determining the reducing sugars formed from various types of xylan, including oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan (See e.g., Bailey et al., J. Biotechnol., 23:257-270 [1992]). In some embodiments, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 mL reactions, 5 mg/mL substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay (See e.g., Lever, Anal. Biochem., 47:273-279 [1972]).

As used herein the term "xylanase activity" refers to a 1,4-beta-D-xylan-xylohydrolase activity (E.C. 3.2.1.8) that catalyzes the endo-hydrolysis of 1,4-beta-D-xylosidic linkages in xylans. In some embodiments, xylanase activity is determined using birchwood xylan as substrate. One unit of xylanase activity is defined as 1.0 μmole of reducing sugar (measured in glucose equivalents; See e.g., Lever, Anal. Biochem., 47:273-279 [1972]) produced per minute during the initial period of hydrolysis at 50° C., pH 5 from 2 g of birchwood xylan per liter as substrate in 50 mM sodium acetate containing 0.01% TWEEN® 20.

As used herein, the term "beta-xylosidase activity" refers to a beta-D-xyloside xylohydrolase (E.C. 3.2.1.37) that catalyzes the exo-hydrolysis of short beta (1→4)-xylooligosaccharides, to remove successive D-xylose residues from the non-reducing termini. In some embodiments of the present invention, one unit of beta-xylosidase activity is defined as 1.0 μmole of p-nitrophenol produced per minute at 40° C., pH 5 from 1 mM p-nitrophenyl-beta-D-xyloside as substrate in 100 mM sodium citrate containing 0.01% TWEEN® 20.

As used herein, the term "acetylxylan esterase activity" refers to a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. In some embodiments of the present invention, acetylxylan esterase activity is determined using 0.5 mM p-nitrophenylacetate as substrate in 50 mM sodium acetate pH 5.0 containing 0.01% TWEEN® 20. One unit of acetylxylan esterase activity is defined as the amount of enzyme capable of releasing 1 pmole of p-nitrophenolate anion per minute at pH 5, 25° C.

As used herein, the term "feruloyl esterase activity" refers to a 4-hydroxy-3-methoxycinnamoyl-sugar hydrolase activity (EC 3.1.1.73) that catalyzes the hydrolysis of the 4-hydroxy-3-methoxycinnamoyl(feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. In some embodiments of the present invention, feruloyl esterase activity is determined using 0.5 mM p-nitrophenylferulate as substrate in 50 mM sodium acetate pH 5.0. One unit of feruloyl esterase activity equals the amount of enzyme capable of releasing 1 μmole of p-nitrophenolate anion per minute at pH 5, 25° C.

As used herein, the term "alpha-glucuronidase activity" refers to an alpha-D-glucosiduronate glucuronohydrolase activity (EC 3.2.1.139) that catalyzes the hydrolysis of an alpha-D-glucuronoside to D-glucuronate and an alcohol. One unit of alpha-glucuronidase activity equals the amount of enzyme capable of releasing 1 pmole of glucuronic or 4-O-methylglucuronic acid per minute at pH 5, 40° C. (See e.g., de Vries, J. Bacteriol., 180:243-249 [1998]).

As used herein the term "alpha-L-arabinofuranosidase activity" refers to an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per mL of 100 mM sodium acetate pH 5 in a total volume of 200 μL for 30 minutes at 40° C. followed by arabinose analysis by AMINEX®. HPX-87H column chromatography (Bio-Rad Laboratories, Inc., Hercules, Calif., USA).

Enzymatic lignin depolymerization can be accomplished by lignin peroxidases, manganese peroxidases, laccases and cellobiose dehydrogenases (CDH), often working in synergy. These extracellular enzymes, essential for lignin degradation, are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC). Although the details of the reaction scheme of lignin biodegradation are not fully understood to date, without being bound by theory, it is suggested that these enzymes employ free radicals for depolymerization reactions.

As used herein, the term "laccase" refers to the copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

As used herein, the term "Mn-dependent peroxidase" refers to peroxidases that require Mn. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al. Arch. Biochem. Biophys., 251:688-696 [1986]). Subsequently, phenolic substrates are oxidized by the $Mn^{3+}$ generated.

As used herein, the term "lignin peroxidase" refers to an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalysed oxidation of lignin in vivo (See e.g., Harvey et al., FEBS Lett. 195:242-246 [1986]).

As used herein, the term "glucoamylase" (EC 3.2.1.3) refers to enzymes that catalyze the release of D-glucose from non-reducing ends of oligo- and poly-saccharide molecules. Glucoamylase is also generally considered a type of amylase known as amylo-gludosidase.

As used herein, the term "amylase" (EC 3.2.1.1) refers to starch cleaving enzymes that degrade starch and related compounds by hydrolyzing the alpha-1,4 and/or alpha-1,6 glucosidic linkages in an endo- or an exo-acting fashion. Amylases include alpha-amylases (EC 3.2.1.1); beta-amylases (3.2.1.2), amylo-amylases (EC 3.2.1.3), alpha-glucosidases (EC 3.2.1.20), pullulanases (EC 3.2.1.41), and isoamylases (EC 3.2.1.68). In some embodiments, the amylase is an alpha-amylase.

As used herein, the term "pectinase" refers to enzymes that catalyze the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

As used herein, the term "endo-polygalacturonase" (EC 3.2.1.15) refers to enzymes that catalyze the random hydrolysis of 1,4-alpha-D-galactosiduronic linkages in pectate and other galacturonans. This enzyme may also be referred to as "polygalacturonase pectin depolymerase," "pectinase," "endopolygalacturonase," "pectolase," "pectin hydrolase," "pectin polygalacturonase," "poly-alpha-1,4-galacturonide glycanohydrolase," "endogalacturonase," "endo-D-galacturonase," or "poly(1,4-alpha-D-galacturonide) glycanohydrolase."

As used herein, the term "pectin methyl esterase" (EC 3.1.1.11) refers to enzymes that catalyze the reaction: pectin+n $H_2O$=n methanol+pectate. The enzyme may also been known as "pectin esterase," "pectin demethoxylase," "pectin methoxylase," "pectin methylesterase," "pectase," "pectinoesterase," or "pectin pectylhydrolase."

As used herein, the term "endo-galactanase" (EC 3.2.1.89) refers to enzymes that catalyze the endohydrolysis of 1,4-beta-D-galactosidic linkages in arabinogalactans. The enzyme may also be known as "arabinogalactan endo-1,4-beta-galactosidase," "endo-1,4-beta-galactanase," galactanase," "arabinogalactanase," or "arabinogalactan 4-β-D-galactanohydrolase."

As used herein, the term "pectin acetyl esterase" refers to enzymes that catalyze the deacetylation of the acetyl groups at the hydroxyl groups of GaIUA residues of pectin.

As used herein, the term "one endo-pectin lyase" (EC 4.2.2.10) refers to enzymes that catalyze the eliminative cleavage of (1→4)-alpha-D-galacturonan methyl ester to give oligosaccharides with 4-deoxy-6-O-methyl-alpha-D-galact-4-enuronosyl groups at their non-reducing ends. The enzyme may also be known as "pectin lyase," "pectin transeliminase," "endo-pectin lyase," "polymethylgalacturonic transeliminase," "pectin methyltranseliminase," "pectolyase," "PL," "PNL," "PMGL," or "(1→4)-6-O-methyl-α-D-galacturonan lyase."

As used herein, the term "pectate lyase" (EC 4.2.2.2) refers to enzymes that catalyze the eliminative cleavage of (1→4)-alpha-D-galacturonan to give oligosaccharides with 4-deoxy-alpha-D-galact-4-enuronosyl groups at their non-reducing ends. The enzyme may also be known as "polygalacturonic transeliminase," "pectic acid transeliminase," "polygalacturonate lyase," "endopectin methyltranseliminase," "pectate transeliminase," "endogalacturonate transeliminase," "pectic acid lyase," "pectic lyase," "alpha-1,4-endopolygalacturonic acid lyase," "PGA lyase," "PPase-N," "endo-alpha-1,4-polygalacturonic acid lyase," "polygalacturonic acid lyase," "pectin trans-eliminase," "polygalacturonic acid trans-eliminase," or "(1→4)-alpha-D-galacturonan lyase."

As used herein, the term "alpha-rhamnosidase" (EC 3.2.1.40) refers to enzymes that catalyze the hydrolysis of terminal non-reducing alpha-L-rhamnose residues in alpha-L-rhamnosides or alternatively in rhamnogalacturonan. This enzyme may also be known as "alpha-L-rhamnosidase T," "alpha-L-rhamnosidase N," or "alpha-L-rhamnoside rhamnohydrolase."

As used herein, the term "exo-galacturonase" (EC 3.2.1.82) refers to enzymes that hydrolyze pectic acid from the non-reducing end, releasing digalacturonate. The enzyme may also be known as "exo-poly-alpha-galacturonosidase," "exopolygalacturonosidase," or "exopolygalacturanosidase."

As used herein, the term "exo-galacturan 1,4-alpha galacturonidase" (EC 3.2.1.67) refers to enzymes that catalyze reactions of the following types: (1,4-alpha-D-galacturonide) n+H2O=(1,4-alpha-D-galacturonide)n-i+D-galacturonate. The enzyme may also be known as "poly[1->4) alpha-D-galacturonide]galacturonohydrolase," "exopolygalacturonase," "poly(galacturonate) hydrolase," "exo-D-galacturonase," "exo-D-galacturonanase," "exopoly-D-galacturonase," or "poly(1,4-alpha-D-galacturonide) galacturonohydrolase."

As used herein, the term "exopolygalacturonate lyase" (EC 4.2.2.9) refers to enzymes that catalyze eliminative cleavage of 4-(4-deoxy-α-D-galact-4-enuronosyl)-D-galacturonate from the reducing end of pectate (i.e. de-esterified pectin). This enzyme may be known as "pectate disaccharide-lyase," "pectate exo-lyase," "exopectic acid transeliminase," "exopectate lyase," "exopolygalacturonic acid-trans-eliminase," "PATE," "exo-PATE," "exo-PGL," or "(1→4)-alpha-D-galacturonan reducing-end-disaccharide-lyase."

As used herein, the term "rhamnogalacturonanase" refers to enzymes that hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, the term "rhamnogalacturonan lyase" refers to enzymes that cleave alpha-L-Rhap-(1→4)-alpha-D-GalpA linkages in an endo-fashion in rhamnogalacturonan by beta-elimination.

As used herein, the term "rhamnogalacturonan acetyl esterase" refers to enzymes that catalyze the deacetylation of the backbone of alternating rhamnose and galacturonic acid residues in rhamnogalacturonan.

As used herein, the term "rhamnogalacturonan galacturonohydrolase" refers to enzymes that hydrolyze galacturonic acid from the non-reducing end of strictly alternating rhamnogalacturonan structures in an exo-fashion. This enzyme may also be known as "xylogalacturonan hydrolase."

As used herein, the term "endo-arabinanase" (EC 3.2.1.99) refers to enzymes that catalyze endohydrolysis of 1,5-alpha-arabinofuranosidic linkages in 1,5-arabinans. The enzyme may also be known as "endo-arabinase," "arabinan endo-1, 5-α-L-arabinosidase," "endo-1,5-alpha-L-arabinanase," "endo-alpha-1,5-arabanase," "endo-arabanase," or "1,5-alpha-L-arabinan 1,5-alpha-L-arabinanohydrolase."

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include but are not limited to, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

As used herein, the terms "isolated" and "purified" are used to refer to a molecule (e.g., an isolated nucleic acid, polypeptide [including, but not limited to enzymes], etc.) or other component that is removed from at least one other component with which it is naturally associated. It is intended that the term encompass any suitable method for removing at least one component with which the molecule is naturally associated. In some embodiments, the terms also encompass cells that are separated from other cells and/or media components. It is intended that any suitable separation method finds use in the present invention.

As used herein, the term "purification process" used in reference to an enzyme mixture encompasses any process that physically removes an undesired component of the enzyme mixture. Thus, in some embodiments, purification processes provided herein include purification methodologies that physically remove one or more glucose and/or cellobiose oxidizing enzymes from the enzyme mixture or vice versa. It is contemplated that any suitable purification process known in the art will find use in the present invention. Indeed, it is not intended that the present invention be limited to any particular purification process.

As used herein, the term "cell-free enzyme mixture" comprises enzymes that have been separated from any cells, including the cells that secreted the enzymes. Cell-free enzyme mixtures can be prepared by any of a variety of methodologies that are known in the art, such as filtration or centrifugation methodologies. In some embodiments, the enzyme mixture can be, for example, partially cell-free, substantially cell-free, or entirely cell-free.

As used herein, "polynucleotide" refers to a polymer of deoxyribonucleotides or ribonucleotides in either single- or double-stranded form, and complements thereof.

The terms "protein" and "polypeptide" are used interchangeably herein to refer to a polymer of amino acid residues.

In addition, the terms "amino acid" "polypeptide," and "peptide" encompass naturally-occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine). As used herein, the term "amino acid analogs" refers to compounds that have the same basic chemical structure as a naturally occurring amino acid (i.e., an α-carbon that is bound to a hydrogen, a carboxyl group, an amino group, and an R group, including but not limited to homoserine, norleucine, methionine sulfoxide, and methionine methyl sulfonium). In some embodiments, these analogs have modified R groups (e.g., norleucine) and/or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a test sequence has a deletion relative to an aligned reference sequence, there will be no amino acid in the variant that corresponds to a position in the reference sequence at the site of deletion. Where there is an insertion in an aligned test sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "reference enzyme" refers to an enzyme to which another enzyme of the present invention (e.g., a "test" enzyme) is compared in order to determine the presence of an improved property in the other enzyme being evaluated. In some embodiments, a reference enzyme is a wild-type enzyme. In some embodiments, the reference enzyme is an enzyme to which a test enzyme of the present invention is compared in order to determine the presence of an improved property in the test enzyme being evaluated, including but not limited to improved thermoactivity, improved thermostability, and/or improved stability. In some embodiments, a reference enzyme is a wild-type enzyme.

As used herein, the term "biologically active fragment," refers to a polypeptide that has an amino-terminal and/or carboxy-terminal deletion(s) and/or internal deletion(s), but where the remaining amino acid sequence is identical to the corresponding positions in the sequence to which it is being compared and that retains substantially all of the activity of the full-length polypeptide.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. A nucleic acid construct, nucleic acid (e.g., a polynucleotide), polypeptide, or host cell is referred to herein as "recombinant" when it is non-naturally occurring, artificial or engineered. "Recombination," "recombining" and generating a "recombined" nucleic acid generally encompass the assembly of at least two nucleic acid fragments.

The present invention also provides a recombinant nucleic acid construct comprising at least one CDH polynucleotide sequence that hybridizes under stringent hybridization conditions to the complement of a polynucleotide which encodes a polypeptide having the amino acid sequence of SEQ ID NOS:6 and/or 8.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

Moderately stringent conditions encompass those known in the art and described in various standard texts and include the use of washing solution and hybridization conditions (e.g., temperature, ionic strength and % SDS). An example of moderately stringent conditions involves overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used in some embodiments herein, stringent conditions or high stringency conditions utilize: (1) low ionic strength and high temperature for washing, for example 0.015 M sodium chloride/0.0015 M sodium citrate/0.1% sodium dodecyl sulfate at 50° C.; (2) during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "similarity" refers to an identical or conservative amino acid substitution thereof as defined below. Accordingly, a change to an identical or conservative substitution for the purposes of similarity is viewed as not comprising a change. A deletion of an amino acid or a non-conservative amino acid substitution is viewed herein as comprising a change. Calculation of percent similarity is performed in the same manner as performed for percent identity. A conservative amino acid substitution can be a substitution such as the conservative substitutions shown in Table A. The substitutions shown are based on amino acid physical-chemical properties, and as such, are independent of organism. In some embodiments, the conservative amino acid substitution is a substitution listed under the heading of exemplary substitutions.

TABLE A

| | Substitutions | |
| --- | --- | --- |
| Original Residue | Conservative Substitutions | Exemplary Substitutions |
| Ala (A) | val; leu; ile | Val |
| Arg (R) | lys; gln; asn | Lys |
| Asn (N) | gln; his; lys; arg | Gln |
| Asp (D) | Glu | Glu |
| Cys (C) | Ser | Ser |
| Gln (Q) | Asn | Asn |
| Glu (E) | Asp | Asp |
| Gly (G) | pro; ala | Ala |
| His (H) | asn; gln; lys; arg | Arg |
| Ile (I) | leu; val; met; ala; phe | Leu |
| Leu (L) | ile; val; met; ala; phe | Ile |
| Lys (K) | arg; gln; asn | Arg |
| Met (M) | leu; phe; ile | Leu |
| Phe (F) | leu; val; ile; ala; tyr | Leu |
| Pro (P) | Ala | Ala |
| Ser (S) | Thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala | Leu |

As used herein, "identity" and "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

In some embodiments, the terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/more accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure,"* Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising a CDH polynucleotide sequence that hybridizes under stringent hybridization conditions to the complement of a polynucleotide which encodes a polypeptide having the amino acid sequence of SEQ ID NO:6 and/or 8. Two nucleic acid or polypeptide sequences that have 100% sequence identity are said to be "identical." A nucleic acid or polypeptide sequence is said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters.

As used herein, a "secretion signal peptide" can be a propeptide, a prepeptide or both. For example, the term "propeptide" refers to a protein precursor that is cleaved to yield a "mature protein." The signal peptide is cleaved from the pre-protein by a signal peptidase prior to secretion to result in the "mature" or "secreted" protein. The terms "prepeptide" ad "pre-protein" refer to a polypeptide synthesized with an N-terminal signal peptide that targets it for secretion. Accordingly, a "pre-pro-peptide" is a polypeptide that contains a signal peptide that targets the polypeptide for secretion and which is cleaved off to yield a mature polypeptide. Signal peptides are found at the N-terminus of the protein and are typically composed of between 6 to 136 basic and hydrophobic amino acids.

As used herein, "transcription" and like terms refer to the conversion of the information encoded in a gene to an RNA transcript. Accordingly, a reduction of the transcription level of a glucose and/or cellobiose oxidizing enzyme is a reduction in the amount of RNA transcript of an RNA coding for a glucose and/or cellobiose oxidizing enzyme.

As used herein, a "vector" is a polynucleotide construct for introducing a polynucleotide sequence into a cell. In some embodiments, the vector comprises a suitable control sequence operably linked to and capable of effecting the expression of the polypeptide encoded in the polynucleotide sequence in a suitable host. An "expression vector" has a promoter sequence operably linked to the polynucleotide sequence (e.g., transgene) to drive expression in a host cell, and in some embodiments a transcription terminator sequence. In some embodiments, the vectors are deletion vectors. In some embodiments, vectors comprise polynucleotide sequences that produce small interfering RNA or antisense RNA transcripts that interfere with the translation of a target polynucleotide sequence.

As used herein, a "deletion vector" comprises polynucleotide sequences homologous to a polynucleotide sequences 5' and 3' to a target sequence to be deleted from a host genome so as to direct recombination and replacement of the target sequence with a polynucleotide between the 5' and 3' targeting sequences.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell. In general the term, "expression" refers to conversion of the information encoded in a gene to the protein encoded by that gene. Thus, a "reduction of the amount of an expressed glucose and/or cellobiose oxidizing enzyme" is a reduction in the amount of the glucose and/or cellobiose oxidizing enzyme that is eventually translated by the cell.

As used herein, the term "overexpress" is intended to encompass increasing the expression of a protein to a level greater than the cell normally produces. It is intended that the term encompass overexpression of endogenous, as well as heterologous proteins. In some embodiments, overexpression includes an elevated transcription rate and/or level of the gene compared to the endogenous transcription rate and/or level for that gene. For example, in some embodiments, a heterologous gene is introduced into a fungal cell to express a gene encoding a heterologous enzyme such as a beta-glucosidase from another organism. In some other embodiments, a heterologous gene is introduced into a fungal cell to overexpress a gene encoding a homologous enzyme such as a beta-glucosidase.

In some embodiments, the heterologous gene is a gene that has been modified to overexpress the gene product. In some embodiments, "overexpression" refers to any state in which a gene is caused to be expressed at an elevated rate or level as compared to the endogenous expression rate or level for that gene. In some embodiments, overexpression includes elevated translation rate and/or level of the gene compared to the endogenous translation rate and/or level for that gene. As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, a "polynucleotide sequence that has been adapted for expression" is a polynucleotide sequence that has been inserted into an expression vector or otherwise modified to contain regulatory elements necessary for expression of the polynucleotide in the host cell, positioned in such a manner as to permit expression of the polynucleotide in the host cell. Such regulatory elements required for expression include promoter sequences, transcription initiation sequences and, optionally, enhancer sequences. For example, in some embodiments, a polynucleotide sequence is inserted into a plasmid vector adapted for expression in the fungal host cell.

As used herein, the term "operably linked" refers to a configuration in which a control sequence is appropriately placed at a position relative to the coding sequence of the DNA sequence such that the control sequence influences the expression of a polypeptide.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, a "heterologous enzyme" refers to an enzyme that is encoded by a "heterologous gene." However, it is also contemplated that a heterologous gene encodes an endogenous or homologous enzyme, as explained below. In general, the term "heterologous gene" refers to a gene that occurs in a form not found in a parental strain of the host fungal cell (including but not limited to wild-type). Thus, in some embodiments, a heterologous gene is a gene that is derived from a species that is different from the species of the fungal cell expressing the gene and recognized anamorphs, teleomorphs or taxonomic equivalents of the fungal cell expressing the gene. In some embodiments, a heterologous gene is a modified version of a gene that is endogenous to the host fungal cell, which endogenous gene has been subjected to manipulation and then introduced or transformed into the host cell. For example, in some embodiments, a heterologous gene has an endogenous coding sequence, but has modifications to the promoter sequence. Similarly, in some embodiments, a heterologous gene encodes the same amino acid sequence as an endogenous gene, but has modifications to the codon usage or to noncoding regions such as introns, or a combination thereof. For example, in some embodiments, a heterologous gene comprises modifications to the coding sequence to encode a non-wild type polypeptide. In some other embodiments, a heterologous gene has the same promoter sequence, 5' and 3' untranslated regions and coding regions as a parental strain, but be located in another region of the same chromosome, or on an entirely different chromosome as compared to a parental strain of the host cell.

As used herein, an "endogenous" or "homologous" gene refers to a gene that is found in a parental strain of the host fungal cell (including, but not limited to wild-type).

As used herein, the term "introduced" used in the context of inserting a nucleic acid sequence into a cell, means transformation, transduction, conjugation, transfection, and/or any other suitable method(s) known in the art for inserting nucleic acid sequences into host cells. Any suitable means for the introduction of nucleic acid into host cells find use in the present invention.

As used herein, the terms "transformed" and "transformation" used in reference to a cell refer to a cell that has a non-native nucleic acid sequence integrated into its genome or has an episomal plasmid that is maintained through multiple generations.

As used herein, the terms "host cell" and "host strain" refer to suitable hosts for expression vectors comprising polynucleotide sequences (e.g., DNA) as provided herein. In some embodiments, the host cells are prokaryotic or eukaryotic cells that have been transformed or transfected with vectors constructed using recombinant techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of enzyme within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

As used herein, "gene deletion" and "deletion mutation" refer to a mutation in which part of a gene is missing. Thus, a deletion is a loss or replacement of genetic material resulting in a complete or partial disruption of the sequence of the DNA making up the gene. Any number of nucleotides can be deleted, from a single base to an entire piece of a chromosome. In some embodiments, complete or near-complete deletion of the gene sequence is contemplated. However, a deletion mutation need not completely remove the entire gene sequence for the glucose and/or cellobiose oxidizing enzyme in order to reduce the endogenous glucose and/or cellobiose oxidizing enzyme activity secreted by the fungal cell. For example, a partial deletion that removes one or more nucleotides encoding an amino acid in a glucose and/or cellobiose oxidizing enzyme active site, encoding a secretion signal, or encoding another portion of the glucose and/or cellobiose oxidizing enzyme that plays a role in endogenous glucose and/or cellobiose oxidizing enzyme activity being secreted by the fungal cell.

As used herein, a "conditional mutation" is a mutation that has wild-type phenotype under certain environmental conditions and a mutant phenotype under certain other conditions.

As used herein, the terms "amplification" and "gene amplification" refer to a method by which specific DNA sequences are disproportionately replicated such that the amplified gene becomes present in a higher copy number than was initially present in the genome. In some embodiments, selection of cells by growth in the presence of a drug (e.g., an inhibitor of an inhabitable enzyme) results in the amplification of either the endogenous gene encoding the gene product required for growth in the presence of the drug or by amplification of exogenous (i.e., input) sequences encoding this gene product, or both. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, that is capable of acting as a synthesis initiation point when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. As known in the art, the exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This method for amplifying the target sequence is well known in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In some embodiments of the invention, restriction sites are engineered into the selective marker and into 5' and 3' ends of the DNA construct.

As used herein, "homologous recombination" means the exchange of DNA fragments between two DNA molecules or paired chromosomes at the site of identical or nearly identical nucleotide sequences. In some embodiments, chromosomal integration is homologous recombination.

As used herein, the term "C1" refers to *Myceliophthora thermophilia*, including the fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO 2008073914 and WO 2010107303, each of which is incorporated herein by reference.

As used herein, a "genetically modified" and/or "genetically engineered cell" (e.g., a "genetically engineered fungal cell" and/or a "genetically modified fungal cell") is a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA; another example of a genetic modification as a result of genetic engineering techniques includes introduction of a stable heterologous nucleic acid into the cell. For example, as provided herein, a genetically modified fungal cell as provided herein is a fungal cell that whose genetic material has been altered in such a way as to either reduce the amount of secreted glucose and/or cellobiose oxidizing enzyme activity, or to reduce the ability of the secreted enzyme to oxidize cellobiose or glucose.

As used herein, the term "culturing" refers to growing a population of microbial cells under suitable conditions in a liquid or solid medium. It is contemplated that the culturing be carried out in any suitable format, equipment (e.g., shake flasks, fermentation tanks, bioreactors, etc.). It is also intended that the culturing be conducted using any suitable process methods, including but not limited to batch, fed-batch, and/or continuous culturing. Indeed, it is contemplated that any combination of suitable methods will find use.

In a "batch process," all the necessary materials, with the exception of oxygen for aerobic processes, are placed in a reactor at the start of the operation and the fermentation is allowed to proceed until completion, at which point the product is harvested. In some embodiments, batch processes for producing the fungal cells, enzymes, and/or enzyme mixtures of the present invention are carried out in a shake-flask or a bioreactor.

In a "fed-batch process," the culture is fed continuously or sequentially with one or more media components without the removal of the culture fluid.

In a "continuous process," fresh medium is supplied and culture fluid is removed continuously at volumetrically equal rates to maintain the culture at a steady growth rate. In reference to continuous processes, "steady state" refers to a state in which the concentration of reactants does not vary appreciably, and "quasi-steady state" refers to a state in which, subsequent to the initiation of the reaction, the concentration of reactants fluctuates within a range consistent with normal operation of the continuous hydrolysis process.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein the term "soluble sugars" refers to water-soluble pentose and hexose monomers and oligomers of up to about six monomer units. It is intended that the term encompass any water soluble mono- and/or oligosaccharides.

As used herein, the term "fermentation" is used broadly to refer to the process of obtaining energy from the oxidation of organic compounds (e.g., carbohydrates). Indeed, "fermentation" broadly refers to the chemical conversion of a sugar source to an end product through the use of a fermenting organism. In some embodiments, the term encompasses cultivation of a microorganism or a culture of microorganisms that use sugars, such as fermentable sugars, as an energy source to obtain a desired product.

As used herein, the term "fermenting organism" refers to any organism, including prokaryotic, as well as eukaryotic organisms (e.g., bacterial organisms, as well as fungal organisms such as yeast and filamentous fungi), suitable for producing a desired end product. Especially suitable fermenting organisms are able to ferment (i.e., convert) sugars, including but not limited to glucose, fructose, maltose, xylose, mannose and/or arabinose, directly or indirectly into at least one desired end product. In some embodiments, yeast that find use in the present invention include, but are not limited to strains of the genus *Saccharomyces* (e.g., strains of *Saccharomyces cerevisiae* and *Saccharomyces uvarum*), strains of the genus *Pichia* (e.g., *Pichia stipitis* such as *Pichia stipitis* CBS 5773 and *Pichia pastoris*), and strains of the genus *Candida* (e.g., *Candida utilis, Candida arabinofermentans, Candida diddensii, Candida sonorensis, Candida shehatae, Candida tropicalis,* and *Candida boidinii*). Other fermenting organisms include, but are not limited to strains of *Zymomonas, Hansenula* (e.g., *Hansenula polymorphs* and *Hansenula anomala*), *Kluyveromyces* (e.g., *Kluyveromyces fragilis*), and *Schizosaccharomyces* (e.g., *Schizosaccharomyces pombe*).

As used herein, the term "slurry" refers to an aqueous solution in which are dispersed one or more solid components, such as a cellulosic substrate. Thus, the term "slurry" refers to a suspension of solids in a liquid. In some embodiments, the cellulosic substrate is slurried in a liquid at a concentration that is thick, but can still be pumped. For example, in some embodiments, the liquid is water, a recycled process stream, and/or a treated effluent. However, it is not intended that the present invention be limited to any particular liquid and/or solid.

As used herein, "cellulose" refers to a polymer of the simple sugar glucose linked by beta-1,4 glycosidic bonds.

As used herein, "cellobiose" refers to a water-soluble beta-1,4-linked dimer of glucose.

The terms "biomass," and "biomass substrate," encompass any suitable materials for use in saccharification reactions. The terms encompass, but are not limited to, materials that comprise cellulose (i.e., "cellulosic biomass," "cellulosic feedstock," and "cellulosic substrate"), as well as lignocellulosic biomass. Indeed, the term "biomass" encompasses any living or dead biological material that contains a polysaccharide substrate, including but not limited to cellulose, starch, other forms of long-chain carbohydrate polymers, and mixtures of such sources. In some embodiments, it is assembled entirely or primarily from glucose or xylose, and in some embodiments, optionally also contains various other pentose and/or hexose monomers. Biomass can be derived from plants, animals, or microorganisms, and includes, but is not limited to agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass also comprises transgenic plants that express ligninase and/or cellulase enzymes (See e.g., US 2008/0104724 A1).

As used herein, "lignocellulose" refers to a matrix of cellulose, hemicellulose and lignin. Economic production of biofuels from lignocellulosic biomass typically involves conversion of the cellulose and hemicellulose components to fermentable sugars, typically monosaccharides such as glucose (from the cellulose) and xylose and arabinose (from the hemicelluloses). Nearly complete conversion can be achieved by a chemical pretreatment of the lignocellulose followed by enzymatic hydrolysis with cellulase enzymes. The chemical pretreatment step renders the cellulose more susceptible to enzymatic hydrolysis and, in some cases, also hydrolyzes the hemicellulose component. Numerous chemical pretreatment processes are known in the art, and include, but are not limited to, mild acid pretreatment at high temperatures and dilute acid, ammonium pretreatment or organic solvent extraction.

Lignin is a more complex and heterogeneous biopolymer than either cellulose or hemicellulose and comprises a variety of phenolic subunits. Enzymatic lignin depolymerization can be accomplished by lignin peroxidases, manganese peroxidases, laccases and cellobiose dehydrogenases (CDH), often working in synergy. However, as the name suggests, CDH enzymes also oxidize cellobiose to cellobionolactone. Several reports indicate that the oxidation of cellobiose by CDH enhances the rate of cellulose hydrolysis by cellulases by virtue of reducing the concentrations of cellobiose, which is a potent inhibitor of some cellulase components (Mansfield et al., Appl. Environ. Microbiol., 63: 3804-3809 [1997]; and Igarishi et al., Eur. J. Biochem., 253: 101-106 [1998]). Recently, it has been reported that CDHs can enhance the activity of cellulolytic enhancing proteins from Glycosyl Hydrolase family 61 (See e.g., WO2010/080532A1).

As used herein, the term "lignocellulosic biomass" refers to any plant biomass comprising cellulose and hemicellulose, bound to lignin In some embodiments, the biomass is optionally pretreated to increase the susceptibility of cellulose to hydrolysis by chemical, physical and biological pretreatments (such as steam explosion, pulping, grinding, acid hydrolysis, solvent exposure, and the like, as well as combinations thereof). Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "lignocellulosic feedstock" refers to any type of lignocellulosic biomass that is suitable for use as feedstock in saccharification reactions.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

As used herein, the terms "lignocellulose-competent," "lignocellulose-utilizing" and like terms refer to an organism that secretes enzymes that participate in lignin breakdown and hydrolysis. For example, in some embodiments, lignocellulose-competent fungal cells secrete one or more lignin peroxidases, manganese peroxidases, laccases and/or cellobiose dehydrogenases (CDH). These extracellular enzymes, essential for lignin degradation, are often referred to as "lignin-modifying enzymes" or "LMEs."

A biomass substrate is said to be "pretreated" when it has been processed by some physical and/or chemical means to facilitate saccharification. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis.

In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in lignocellulose to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663; and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO 2009/045651 and US 2007/0031953). This pretreatment process may or may not produce any monosaccharides.

An additional pretreatment process for use in the present invention includes chemical treatment of the cellulosic substrate with organic solvents, in methods such as those utilizing organic liquids in pretreatment systems (See e.g., U.S. Pat. No. 4,556,430). These methods have the advantage that the low boiling point liquids easily can be recovered and reused. Other pretreatments, such as the Organosolv™ process, also use organic liquids (See e.g., U.S. Pat. No. 7,465,791). Subjecting the substrate to pressurized water may also be a suitable pretreatment method (See e.g., Weil et al., Appl. Biochem. Biotechnol., 68: 21-40 [1997]). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

As used herein, the term "chemical treatment" refers to any chemical pretreatment that promotes the separation and/or release of cellulose, hemicellulose, and/or lignin.

As used herein, the term "physical pretreatment" refers to any pretreatment that promotes the separation and/or release of cellulose, hemicellulose, and/or lignin from cellulosic material.

As used herein, the term "mechanical pretreatment" refers to any mechanical means for treating biomass, including but not limited to various types of grinding or milling (e.g., dry milling, wet milling, or vibratory ball milling).

As used herein, the term "biological pretreatment" refers to any biological pretreatment that promotes the separation and/or release of cellulose, hemicellulose, and/or lignin from cellulosic material.

As used herein, the term "recovered" refers to the harvesting, isolating, collecting, or recovering of protein from a cell and/or culture medium. In the context of saccharification, it is used in reference to the harvesting of fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharification) if the process includes separating the product from other components of a reaction mixture subsequent to at least some of the product being generated in the reaction.

As used herein, "increasing" the yield of a product (such as a fermentable sugar) from a reaction occurs when a particular component of interest is present during the reaction (e.g., enzyme) causes more product to be produced, compared with a reaction conducted under the same conditions with the same substrate and other substituents, but in the absence of the component of interest (e.g., without enzyme).

As used herein, a reaction is said to be "substantially free" of a particular enzyme if the amount of that enzyme compared with other enzymes that participate in catalyzing the reaction is less than about 2%, about 1%, or about 0.1% (wt/wt).

As used herein, "fractionating" a liquid (e.g., a culture broth) means applying a separation process (e.g., salt precipitation, column chromatography, size exclusion, and filtration) or a combination of such processes to provide a solution in which a desired protein (e.g., a cellulase enzyme, and/or a combination thereof) comprises a greater percentage of total protein in the solution than in the initial liquid product.

As used herein, the term "enzymatic hydrolysis," refers to the hydrolysis of a substrate by an enzyme. In some embodiments, the hydrolysis comprises methods in which at least one enzyme is contacted with at least one substrate to produce an end product. In some embodiments, the enzymatic hydrolysis methods comprise at least one cellulase and at least one glycosidase enzyme and/or a mixture glycosidases that act on polysaccharides, (e.g., cellulose), to convert all or a portion thereof to fermentable sugars. "Hydrolyzing" and/or "hydrolysis" of cellulose or other polysaccharide occurs when at least some of the glycosidic bonds between two monosaccharides present in the substrate are hydrolyzed, thereby detaching from each other the two monomers that were previously bonded.

It is intended that the enzymatic hydrolysis be carried out with any suitable type of enzyme(s) capable of hydrolyzing at least one substrate to at least one end-product. In some embodiments, the substrate is cellulose, while in some other embodiments, it is lignocelluloses, and in still further embodiments, it is another composition (e.g., starch). In some embodiments, the end-product comprises at least one fermentable sugar. It is further intended that the enzymatic hydrolysis encompass processes carried out with any suitable type of cellulase enzymes capable of hydrolyzing the cellulose to glucose, regardless of their source. It is intended that any suitable source of enzyme will find use in the present invention, including but not limited to enzymes obtained from fungi, such as *Trichoderma* spp., *Aspergillus* spp., *Hypocrea* spp., *Humicola* spp., *Neurospora* spp., *Orpinomyces* spp., *Gibberella* spp., *Emericella* spp., *Chaetomium* spp., *Chrysosporium* spp., *Fusarium* spp., *Penicillium* spp., *Magnaporthe* spp., *Phanerochaete* spp., *Trametes* spp., *Lentinula edodes*, *Gleophyllum trabeiu*, *Ophiostoma piliferum*, *Corpinus cinereus*, *Geomyces pannorum*, *Cryptococcus laurentii*, *Aureobasidium pullulans*, *Amorphotheca resinae*, *Leucosporidium scotti*, *Cunninghamella elegans*, *Thermomyces lanuginosus*, *Myceliopthora thermophila*, and *Sporotrichum thermophile*, as well as those obtained from bacteria of the genera *Bacillus*, *Thermomyces*, *Clostridium*, *Streptomyces* and *Thermobifida*.

In some embodiments, the enzymatic hydrolysis is carried out at a pH and temperature that is at or near the optimum for the cellulase enzymes being used. For example, in some embodiments, the enzymatic hydrolysis is carried out at about 30° C. to about 75° C., or any suitable temperature therebetween, for example a temperature of about 30° C., about 35° C., about 40° C., about 45° C., about 50° C., about 55° C., about 60° C., about 65° C., about 70° C., about 75° C., or any temperature therebetween, and a pH of about 3.5 to about 7.5, or any pH therebetween (e.g., about 3.5, about 4.0, about 4.5, about 5.0, about 5.5, about 6.0, about 6.5, about 7.0, about 7.5, or any suitable pH therebetween). In some embodiments, the initial concentration of cellulose, prior to the start of enzymatic hydrolysis, is preferably about 0.1% (w/w) to about 20% (w/w), or any suitable amount therebetween (e.g., about 0.1%, about 0.5%, about 1%, about 2%, about 4%, about 6%, about 8%, about 10%, about 12%, about 14%, about 15%, about 18%, about 20%, or any suitable amount therebetween). In some embodiments, the combined dosage of all cellulase enzymes is about 0.001 to about 100 mg protein per gram cellulose, or any suitable amount therebetween (e.g., about 0.001, about 0.01, about 0.1, about 1, about 5, about 10, about 15, about 20, about 25, about 30, about 40, about 50, about 60, about 70, about 80, about 90, about 100 mg protein per gram cellulose or any amount therebetween). The enzymatic hydrolysis is carried out for any suitable time period. In some embodiments, the enzymatic hydrolysis is carried out for a time period of about 0.5 hours to about 200 hours, or any time therebetween (e.g., about 2 hours to about 100 hours, or any suitable time therebetween). For example, in some embodiments, it is carried out for about 0.5, about 1, about 2, about 5, about 7, about 10, about 12, about 14, about 15, about 20, about 25, about 30, about 35, about 40, about 45, about 50, about 55, about 60, about 65, about 70, about 75, about 80, about 85, about 90, about 95, about 100, about 120, about 140, about 160, about 180, about 200, or any suitable time therebetween.

In some embodiments, the enzymatic hydrolysis is batch hydrolysis, continuous hydrolysis, and/or a combination thereof. In some embodiments, the hydrolysis is agitated, unmixed, or a combination thereof. The enzymatic hydrolysis is typically carried out in a hydrolysis reactor. The cellulase enzyme composition is added to the pretreated lignocellulosic substrate prior to, during, or after the addition of the substrate to the hydrolysis reactor. Indeed it is not intended that reaction conditions be limited to those provided herein, as modifications are well-within the knowledge of those skilled in the art. In some embodiments, following cellulose hydrolysis, any insoluble solids present in the resulting lignocellulosic hydrolysate, including but not limited to lignin, are removed using conventional solid-liquid separation techniques prior to any further processing. In some embodiments, these solids are burned to provide energy for the entire process.

As used herein, the "total available cellulose" is the amount (wt %) of cellulose that is accessible to enzymatic hydrolysis. Total available cellulose is typically equal to, or very close to being equal to, the amount of initial cellulose present in a hydrolysis reaction.

As used herein, the "residual cellulose" is the portion (wt %) of the total available cellulose in the hydrolysis mixture that remains unhydrolyzed. Residual cellulose can be measured using any suitable method known in the art. For example, it can be directly measured using IR spectroscopy, or it can be measured by determining the amount of glucose generated by concentrated acid hydrolysis of the residual solids.

As used herein, the "total hydrolyzed cellulose" is the portion of the total available cellulose that is hydrolyzed in the hydrolysis mixture. For example, the total hydrolyzed cellulose can be calculated as the difference between the "total available cellulose" and the "residual cellulose."

As used herein, the "theoretical maximum glucose yield" is the maximum amount (wt %) of glucose that could be produced under given conditions from the total available cellulose.

As used herein, "Gmax" refers to the maximum amount (wt %) of glucose that could be produced from the total hydrolyzed cellulose. Gmax can be calculated, for example, by directly measuring the amount of residual cellulose remaining at the end of a reaction under a given reaction conditions, subtracting the amount of residual cellulose from the total available cellulose to determine the total hydrolyzed cellulose, and then calculating the amount of glucose that could be produced from the total hydrolyzed cellulose.

It will be appreciated by those skilled in the art that when calculating theoretical values such as Gmax and theoretical maximum glucose yield, the mass of two hydrogen atoms and one oxygen atom that are added to the glucose molecule in the course of the hydrolysis reaction are taken into account. For example, when a polymer of "n" glucose units is hydrolyzed, (n-1) units of water are added to the glucose molecules formed in the hydrolysis, so the weight of the glucose produced is about 10% greater than the weight of cellulose consumed in the hydrolysis (e.g., hydrolysis of 1 g cellulose would produce about 1.1 g glucose).

Thus, as an example, where 5 g of total available cellulose is present at the beginning of a hydrolysis reaction, and 2 g of residual cellulose remains after the reaction, the total hydrolyzed cellulose is 3 g cellulose. A theoretical maximum glucose yield of 100% (w/w) under the reaction conditions is about 5.5 g of glucose. Gmax is calculated based on the 3 g of cellulose that was released or converted in the reaction by hydrolysis. Thus, in this example, a Gmax of 100% (w/w) is about 3.3 g of glucose. Cellulose levels, either the total available amount present in the substrate or the amount of unhydrolyzed or residual cellulose, can be quantified by any of a variety of methods known in the art, such as by IR spectroscopy or by measuring the amount of glucose generated by concentrated acid hydrolysis of the cellulose (See e.g., U.S. Pat. Nos. 6,090,595 and 7,419,809).

As used herein, the term "undissolved solids" refers to solid material which is suspended, but not dissolved, in a liquid. As is well known in the art, the concentration of suspended or undissolved solids can be determined by any suitable method (e.g., by filtering a sample of the slurry using glass microfiber filter paper, washing the filter cake with water, and drying the cake overnight at about 105° C.).

As used herein, the terms "unhydrolyzed solids," "unconverted solids," and the like refer to cellulose that is not digested by the cellulase enzyme(s), as well as non-cellulosic, or other, materials that are inert to the cellulase enzyme(s), present in the feedstock.

As used herein, the term "by-product" refers to an organic molecule that is an undesired product of a particular process (e.g., saccharification).

In some embodiments, the present invention provides fungal organisms and methods for the conversion of cellulose to glucose. In some embodiments, the conversion is improved by genetically modifying a fungus to reduce the amount of endogenous glucose and/or cellobiose oxidizing enzyme activity that is secreted by the cell. Prior to this invention, it was generally believed that cellobiose dehydrogenase enhances the rate of cellulose hydrolysis by reducing the concentration of cellobiose, which is a potent inhibitor of some cellulase components (See e.g., Mansfield et al., Appl. Environ. Microbiol., 63: 3804-3809 [1997]; Igarishi et al., Eur. J. Biochem., 253: 101-106 [1998]). Further, cellobiose dehydrogenase has been reported as playing a critical role contributing to synergistic enhancement in degradation of cellulose by preventing product inhibition of hydrolysis (See e.g., Hai et al., J. Appl. Glycosci., 49:9-17 [2002]). As a result, genetic modification of *Trametes versicolor* (See, Archibald, 7$^{th}$ International Conference on Biotechnology in the Pulp and Paper Industry, Vol. B: B225-B228 [1998]) and *Coriolus hirsutus* (See, U.S. Pat. Appln. Publn. No. 2005/0181485) has been carried out in order to produce cellulase systems with reduced cellolytic activities for pulp and paper applications. It was also generally believed that cellobiose dehydrogenase was useful in delignifying lignocellulose, and thereby enhance cellulose degradation. Recently, it has been reported that cellobiose dehydrogenases can enhance the activity of cellulolytic enhancing proteins from Glycosyl Hydrolase Family 61 (See e.g., WO 2010/080532A1).

Contrary to general understanding in the art, the present invention provides fungal cells with genetic modification (such as deletion) of glucose and/or cellobiose oxidizing enzyme-encoding genes in cellulase-producing fungal cells that results in an improvement in the yield of fermentable sugars from enzyme mixtures secreted by the genetically modified cells. Thus, reduction of glucose and/or cellobiose oxidizing enzyme activity secreted by a cellulase-producing organism results in a mixture of cellulase enzymes that can improve yield of fermentable sugars during enzymatic hydrolysis of cellulose-containing substrates.

The present invention provides a fungal cell that has been genetically modified to reduce the amount of endogenous glucose and/or cellobiose oxidizing enzyme activity that is secreted by the cell, wherein the fungal cell is an Ascomycete belonging to the subdivision Pezizomycotina, and where the fungal cell is capable of secreting a cellulase-containing enzyme mixture. Also provided herein is a fungal cell that has been genetically modified to reduce the amount of endogenous glucose and/or cellobiose oxidizing enzyme activity that is secreted by the cell and to increase the expression of at least one saccharide hydrolyzing enzyme, wherein the fungal cell is a Basidiomycete belonging to the class Agaricomycetes, and where the fungal cell is capable of secreting a cellulase-containing enzyme mixture. Also provided herein is a fungal cell that has been genetically modified to reduce the amount of endogenous glucose and/or cellobiose oxidizing enzyme activity that is secreted by the cell, wherein the fungal cell is a Basidiomycete, and where the fungal cell is the fungal cell is capable of secreting a cellulase-containing enzyme mixture. In some embodiments, the endogenous glucose and/or cellobiose oxidizing enzyme is a cellobiose dehydrogenase, while in some alternative embodiments, the endogenous glucose and/or cellobiose oxidizing enzyme is an enzyme other than cellobiose dehydrogenase.

In some embodiments, the fungal cell is capable of secreting an enzyme mixture comprising at least two or more cellulase enzymes. In some embodiments, the Basidiomycete is a species of *Pleurotus, Peniophora, Trametes, Athelia, Sclerotium, Termitomyces, Flammulina, Chrysosporium, Coniphora, Ganoderma, Pycnoporus, Ceriporiopsis, Phanerochaete, Gloeophyllum, Hericium, Heterobasidion, Gelatoporia, Lepiota,* or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium,* or *Aspergillus*.

The present invention also provides a fungal cell that has been genetically modified to reduce the amount of endogenous glucose and/or cellobiose oxidizing enzyme activity that is secreted by the cell, wherein the fungal cell is a Basidiomycete species *Pleurotus, Peniophora, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex*.

In some embodiments, the fungal cell has been genetically modified to reduce the amount of endogenous cellobiose dehydrogenase activity that is secreted by the cell. In some embodiments, the fungal cell has been genetically modified to reduce the amount of endogenous glucose oxidase activity that is secreted by the cell. In some embodiments, the fungal cell has been genetically modified to reduce the amount of endogenous pyranose oxidase activity that is secreted by the cell. In some embodiments, the fungal cell has been genetically modified to reduce the amount of endogenous glucooligosaccharide oxidase activity that is secreted by the cell. In some embodiments, the fungal cell has been genetically modified to reduce the amount of endogenous pyranose dehydrogenase activity that is secreted by the cell. In some embodiments, the fungal cell has been genetically modified to reduce the amount of endogenous glucose dehydrogenase activity that is secreted by the cell.

In some embodiments, the fungal cell is a species of *Myceliophthora, Thielavia, Chrysosporium, Sporotrichum, Corynascus, Acremonium, Chaetomium, Ctenomyces, Scytalidium, Talaromyces,* or *Thermoascus*. In some embodiments the fungal cell is a species of *Myceliophthora, Thielavia, Sporotrichum, Corynascus, Acremonium, Chaetomium,* or *Talaromyces*. In some embodiments, the fungal cell is *Sporotrichum thermophile, Sporotrichum cellulophilum, Thielavia terrestris, Corynascus heterothallicus, Thielavia heterothallica, Chaetomium globosum, Talaromyces stipitatus,* or *Myceliophthora thermophila*. In some embodiments, the fungal cell is an isolated fungal cell.

In some embodiments, the fungal cell has been genetically modified to reduce the amount of the endogenous glucose and/or cellobiose oxidizing enzyme that is secreted by the cell. Thus, in some embodiments, the fungal cell has been genetically modified to disrupt the secretion signal peptide of the glucose and/or cellobiose oxidizing enzyme. In some embodiments, the fungal cell has been genetically modified to reduce the amount of the endogenous glucose and/or cellobiose oxidizing enzyme that is expressed by the cell. For example, the fungal cell can be genetically modified to disrupt a translation initiation sequence or to introduce a frameshift mutation in the transcript encoding the endogenous glucose and/or cellobiose oxidizing enzyme. In some other embodiments, the fungal cell has been genetically modified to reduce the transcription level of a gene encoding the endogenous glucose and/or cellobiose oxidizing enzyme. For example, the fungal cell can be genetically modified to disrupt the promoter of a gene encoding the endogenous glucose and/or cellobiose oxidizing enzyme. In some embodiments, the fungal cell has been genetically modified to at least partially delete a gene encoding the endogenous glucose and/or cellobiose oxidizing enzyme. In some other embodiments, the fungal cell has been genetically modified to reduce the catalytic efficiency of the endogenous glucose and/or cellobiose oxidizing enzyme. In some embodiments, the fungal cell has been genetically modified to mutate one or more residues in an active site of the glucose and/or cellobiose oxidizing enzyme. In some embodiments, the fungal cell has been genetically modified to mutate one or more residues in a heme binding domain of the glucose and/or cellobiose oxidizing enzyme.

In some embodiments, the glucose and/or cellobiose oxidizing enzyme is glucose oxidase (EC 1.1.3.4). In some other embodiments, the glucose and/or cellobiose oxidizing enzyme is cellobiose dehydrogenase (EC 1.1.99.18). In some other embodiments, the glucose and/or cellobiose oxidizing enzyme is pyranose oxidase (EC1.1.3.10). In some other embodiments, the glucose and/or cellobiose oxidizing enzyme is glucooligosaccharide oxidase (EC 1.1.99.B3). In some additional embodiments, the glucose and/or cellobiose oxidizing enzyme is pyranose dehydrogenase (EC 1.1.99.29). In some further embodiments, the glucose and/or cellobiose oxidizing enzyme is glucose dehydrogenase (EC 1.1.99.10).

In some embodiments, the glucose and/or cellobiose oxidizing enzyme comprises an amino acid sequence that is at least about 85%, about 86%, about 87%, about 88%, about 89%, about 90%, about 91%, about 92%, about 93%, about 94%, about 95%, about 96%, about 97%, about 98%, or at least about 99% identical to SEQ ID NOS:2, 4, 6, 8, 10, 12, 14, and/or 16.

In some embodiments, the cell has been genetically modified to reduce the amount of glucose and/or cellobiose oxidizing enzyme activity of two or more endogenous glucose and/or cellobiose oxidizing enzymes that are secreted by the cell. In certain such embodiments, a first of the two or more the glucose and/or cellobiose oxidizing enzymes comprises an amino acid sequence that is at least about 85%, about 86%, about 87%, about 88%, about 89%, about 90%, about 91%, about 92%, about 93%, about 94%, about 95%, about 96%, about 97%, about 98%, or at least about 99% identical to SEQ ID NO:2, 4, 6, 8, 10, 12, 14, and/or 16, and a second of the two or more the glucose and/or cellobiose oxidizing enzymes comprises an amino acid sequence that is at least about 85%, about 86%, about 87%, about 88%, about 89%, about 90%, about 91%, about 92%, about 93%, about 94%, about 95%, about 96%, about 97%, about 98%, or at least about 99% identical to SEQ ID NOS:2, 4, 6, 8, 10, 12, 14, and/or 16.

In some embodiments, the fungal cell further comprises at least one gene encoding at least one cellulose degrading enzyme that is heterologous to the fungal cell. For example, the fungal cell can overexpress a homologous or heterologous gene encoding a cellulose degrading enzyme such as beta-glucosidase. In some embodiments, the fungal cell overexpresses beta-glucosidase and has been genetically modified to reduce the amount of endogenous glucose and/or cellobiose oxidizing enzyme activity that is secreted by the cell.

The present invention also provides enzyme mixtures comprising two or more cellulose hydrolyzing enzymes, wherein at least one of the two or more cellulose hydrolyzing enzymes is expressed by a fungal cell as described herein. For example, in some embodiments, the fungal cell is a cell that has been genetically modified to reduce the amount of endogenous glucose and/or cellobiose oxidizing enzyme activity that is secreted by the cell, wherein the fungal cell is an Ascomycete belonging to the subdivision Pezizomycotina. In some other embodiments, the fungal cell has been genetically modified to reduce the activity of an endogenous glucose and/or cellobiose oxidizing enzyme that is secreted by the cell and to increase the expression of at least one saccharide hydrolyzing enzyme, wherein the fungal cell is a Basidiomycete belonging to the class Agaricomycetes. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium,* or *Aspergillus*. In some embodiments, the fungal cell can be a species of *Myceliophthora, Thielavia, Sporotrichum, Corynascus, Acremonium, Chaetomium, Ctenomyces, Scytalidium, Talaromyces,* or *Thermoascus*. In some embodiments the fungal cell is a species of *Myceliophthora, Thielavia, Sporotrichum, Corynascus, Acremonium,* or *Chaetomium*. In some embodiments, the fungal cell is *Sporotrichum cellulophilum, Thielavia terrestris, Corynascus heterothallicus, Thielavia heterothallica,* or *Myceliophthora thermophila*.

In some embodiments, the fungal cell is a species of *Myceliophthora, Thielavia, Sporotrichum, Chrysoporium, Corynascus, Acremonium, Chaetomium, Ctenomyces, Scytalidium, Talaromyces,* or *Thermoascus*. In some embodiments the fungal cell is a species of *Myceliophthora, Chrysosporium, Thielavia, Sporotrichum, Corynascus, Acremonium,* or *Chaetomium*. In some embodiments, the fungal cell is *Sporotrichum cellulophilum, Thielavia terrestris, Corynascus heterothallicus, Thielavia heterothallica, Chaetomium globosum, Talaromyces stipitatus,* or *Myceliophthora thermophila*. In some embodiments, the fungal cell is an isolated fungal cell.

In some additional embodiments, the enzyme mixture is a cell-free mixture. In some embodiments, a substrate of the enzyme mixture comprises pretreated lignocellulose. In some additional embodiments, the pretreated lignocellulose comprises lignocellulose treated by a treatment method selected from acid pretreatment, ammonia pretreatment, steam explosion, organic solvent extraction, and/or any other suitable pretreatment method(s). In some embodiments, the enzyme mixture further comprises a cellulose degrading enzyme that is heterologous to the fungal cell. In some embodiments, at least one of the two or more cellulose hydrolyzing enzymes is expressed by an isolated fungal cell.

The present invention also provides methods for generating cellobiose and/or glucose comprising contacting a cellulosic substrate with the enzyme mixture described herein. For example, in some embodiments, the methods comprise contacting cellulose with an enzyme mixture comprising two or more cellulose hydrolyzing enzymes, wherein at least one of the two or more cellulose hydrolyzing enzymes is expressed by a fungal cell as described herein. In some embodiments, the methods comprise contacting cellulose with an enzyme mixture comprising two or more cellulose hydrolyzing enzymes, wherein at least one of the two or more cellulose hydrolyzing enzymes is expressed by a cell that has been genetically modified to reduce the amount of endogenous glucose and/or cellobiose oxidizing enzyme activity that is secreted by the cell, wherein the fungal cell is a an Ascomycete belonging to the subdivision Pezizomycotina.

In some other embodiments, the fungal cell has been genetically modified to reduce the activity of an endogenous glucose and/or cellobiose oxidizing enzyme that is secreted by the cell and to increase the expression of at least one saccharide hydrolyzing enzyme, wherein the fungal cell is a Basidiomycete belonging to the class Agaricomycetes. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium,* or *Aspergillus*. In some embodiments, the fungal cell is a species of *Myceliophthora, Thielavia, Sporotrichum, Corynascus, Acremonium, Chaetomium, Ctenomyces, Scytalidium, Talaromyces,* or *Thermoascus*. In some embodiments the fungal cell is a species of *Myceliophthora, Thielavia, Sporotrichum, Corynascus, Acremonium,* or *Chaetomium*. In some embodiments, the fungal cell is *Sporotrichum cellulophilum, Thielavia terrestris, Corynascus heterothallicus, Thielavia heterothallica,* or *Myceliophthora thermophila*.

In some embodiments, the fungal cell is a species of *Myceliophthora, Thielavia, Sporotrichum, Corynascus, Acremonium, Chaetomium, Ctenomyces, Scytalidium, Talaromyces,* or *Thermoascus*. In some embodiments the fungal cell is a species of *Myceliophthora, Thielavia, Sporotrichum, Corynascus, Acremonium,* or *Chaetomium*. In some embodiments, the fungal cell is *Sporotrichum cellulophilum, Thielavia terrestris, Corynascus heterothallicus, Thielavia heterothallica, Chaetomium globosum, Talaromyces stipitatus,* or *Myceliophthora thermophila*. In some embodiments, the fungal cell is an isolated fungal cell.

The present invention provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus that is an Ascomycete belonging to the subdivision Pezizomycotina, and wherein the enzyme mixture is characterized in that, when the enzyme mixture is contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus that is a Basidiomycete belonging to the class Agaricomycetes, and wherein the enzyme mixture is characterized in that, when the enzyme mixture is contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

The present invention further provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus of a species of *Myceliophthora, Thielavia, Sporotrichum, Corynascus, Acremonium, Chaetomium* or *Ctenomyces, Scytalidium* or *Thermoascus*, and wherein the enzyme mixture is characterized in that, when the enzyme mixture is contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

In some embodiments of the methods provided herein, when the enzyme mixture is contacted with a cellulose substrate, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or 20% (wt %) of the cellobiose and/or glucose resulting from the hydrolysis of the cellulose substrate is oxidized. For example, when the enzyme mixture is contacted with a cellulose substrate, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20% (wt %) of the cellobiose and/or glucose resulting from the hydrolysis of the cellulose substrate is oxidized to form cellobionolactone, cellobionic acid, gluconolactone, gluconate or gluconic acid after a period of time during which hydrolysis occurs. For example, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of cellobiose and/or glucose is oxidized after about 1, about 5, about 10, about 20, about 30, about 40, about 50 or about 60 minutes, or after about 1.5, about 2, about 3, about 4, about 5, about 6, about 7, about 8, about 9, about 10, about 12, about 14, about 16, about 18, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 395, about 300 hours, or longer.

The present invention provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus that is an Ascomycete belonging to the subdivision Pezizomycotina, and wherein, of the cellulose hydrolyzed by the enzyme mixture, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 98%, about 99% or 100% (wt %) is present in the form of cellobiose and/or glucose.

The present invention also provides methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus that is a Basidiomycete belonging to the class Agaricomycetes, and wherein, of the cellulose hydrolyzed by the enzyme mixture, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 98%, about 99%, or about 100% (wt %) is present in the form of cellobiose and/or glucose.

In some embodiments, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellulose hydrolyzed by the enzyme mixture is present in the form of gluconolactone or gluconic acid. In some embodiments, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellulose hydrolyzed by the enzyme mixture is present in the form of gluconolactone, gluconic acid, cellobionolactone or cellobionic acid.

Further provided herein are methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus of a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex,* and wherein, of the cellulose hydrolyzed by the enzyme mixture, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 98%, about 99%, or about 100% (wt %) is present in the form of cellobiose and/or glucose.

Further provided herein are methods for generating cellobiose and/or glucose comprising contacting a cellulose substrate with an enzyme mixture comprising two or more cellulose hydrolyzing enzymes to generate glucose and/or cellobiose, wherein at least one of the cellulose hydrolyzing enzymes is endogenous to a fungus of a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium,* or *Aspergillus,* and wherein, of the cellulose hydrolyzed by the enzyme mixture, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 98%, about 99%, or about 100% (wt %) is present in the form of cellobiose and/or glucose.

In some embodiments, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellulose hydrolyzed by the enzyme mixture is present in the form of gluconolactone or gluconic acid. In some embodiments, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellulose hydrolyzed by the enzyme mixture is present in the form of gluconolactone, gluconic acid, cellobionolactone or cellobionic acid.

In some embodiments, the methods result in an increased yield of glucose and/or cellobiose from the hydrolyzed cellulose and a decreased oxidation of the glucose and/or cellobiose to oxidized sugar products, such as gluconolactone, gluconate, gluconic acid, cellobionolactone, and/or cellobionic acid from the hydrolyzed cellulose. In some embodiments, the methods result in an increased yield of glucose and/or cellobiose from the hydrolyzed cellulose and a decreased oxidation of the glucose and/or cellobiose to oxidized sugar products, such as gluconolactone, gluconate, gluconic acid, cellobionolactone, and/or cellobionic acid from the hydrolyzed cellulose, relative to an enzyme mixture with an unmodified amount of glucose and/or cellobiose oxidizing enzyme activity, or relative to a parental enzyme mixture.

In some embodiments, the present invention provides methods for producing cellobiose and/or glucose from cellulose comprising treating a cellulose substrate with an enzyme mixture to generate glucose and/or cellobiose, wherein the enzyme mixture is modified relative to a secreted enzyme mixture from a wild type or reference (e.g., parental) fungal cell to be at least partially deficient in glucose and/or cellobiose oxidizing enzyme activity.

In some aspects of the above embodiments, the enzyme mixture is a cell-free mixture. In some other aspects, the cellulose substrate comprises pretreated lignocellulose. In some embodiments, the pretreated lignocellulose comprises lignocellulose treated by a treatment method selected from acid pretreatment, ammonia pretreatment, steam explosion, and organic solvent extraction.

In some aspects of the above embodiments, the methods further comprise fermentation of the glucose to an end product such as a fuel alcohol or a precursor industrial chemical. In some aspects, the fuel alcohol is ethanol or butanol. Accordingly, in some embodiments, increased glucose yield can result in lower fuel production costs. In some aspects, the methods comprise contacting cellulose with an enzyme mixture that further comprises a cellulose degrading enzyme that is heterologous to the fungal cell.

In some embodiments, the enzyme mixture is produced by a fungal cell has that been genetically modified to reduce the amount of one or more endogenous glucose and/or cellobiose oxidizing enzymes that is secreted by the cell.

In some embodiments, the enzyme mixture is subjected to a purification process to selectively remove one or more glucose and/or cellobiose oxidizing enzymes from the enzyme mixture. In some such aspects, the purification process comprises selective precipitation to separate the glucose and/or cellobiose oxidizing enzymes from other enzymes present in the enzyme mixture.

In some embodiments, the enzyme mixture comprises an inhibitor of one or more glucose and/or cellobiose oxidizing enzymes. In some embodiments, the inhibitor includes a broad-spectrum oxidase inhibitor selected from sodium azide, potassium cyanide and a number of metal anions such as $Ag^+$, $Hg^{2+}$, $Zn^{2+}$. In some additional embodiments, the inhibitor includes a specific inhibitor of cellobiose dehydrogenase (EC 1.1.99.18) such as gentiobiose, lactobiono-1,5-lactone, celliobono-1,5-lactone, tri-N-acetylchitortriose, methyl-beta-D-cellobioside, 2,2-bipyridine and cytochrome C.

In some embodiments, the enzyme mixture comprises at least one beta-glucosidase. In some additional embodiments, the enzyme mixture comprises at least one cellulase enzyme selected from endoglucanases (EGs), β-glucosidases (BGLs), Type 1 cellobiohydrolases (CBH1s), Type 2 cellobiohydrolases (CBH2s), and/or glycoside hydrolase 61s (GH61s), and/or variants of said cellulase enzyme.

The present invention also provides enzyme mixtures comprising two or more cellulose hydrolyzing enzymes, at least one of the cellulose hydrolyzing enzymes being endogenous to a fungal cell, wherein the fungal cell is an Ascomycete belonging to the subdivision Pezizomycotina and wherein the enzyme mixtures are characterized in that, when the enzyme mixtures are contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours. In some aspects of the above embodiments, the fungal cell is a species of *Myceliophthora*, *Thielavia*, *Sporotrichum*, *Corynascus*, *Acremonium*, *Chaetomium*, *Ctenomyces*, *Scytalidium*, *Talaromyces* or *Thermoascus*.

The present invention also provides enzyme mixtures comprising two or more cellulose hydrolyzing enzymes, at least one of the cellulose hydrolyzing enzymes being endogenous to a fungal cell, wherein the fungal cell is a Basidiomycete belonging to the class Agaricomycetes and wherein the enzyme mixtures are characterized in that, when the enzyme mixtures are contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

The present invention further provides enzyme mixtures comprising two or more cellulose hydrolyzing enzymes, at least one of the cellulose hydrolyzing enzymes being endogenous to a fungal cell, wherein the fungal cell is *Pleurotus*, *Peniophora*, *Trametes*, *Athelia*, *Sclerotium*, *Termitomyces*, *Flammulina*, *Coniphora*, *Ganoderma*, *Pycnoporus*, *Ceriporiopsis*, *Phanerochaete*, *Gloeophyllum*, *Hericium*, *Heterobasidion*, *Gelatoporia*, *Lepiota*, or *Irpex*, and wherein the enzyme mixtures are characterized in that, when the enzyme mixtures are contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

The present invention also provides enzyme mixtures comprising two or more cellulose hydrolyzing enzymes, at least one of the cellulose hydrolyzing enzymes being endogenous to a fungal cell, wherein the fungal cell is *Myceliophthora*, *Thielavia*, *Sporotrichum*, *Neurospora*, *Sordaria*, *Podospora*, *Magnaporthe*, *Fusarium*, *Gibberella*, *Botryotinia*, *Humicola*, *Neosartorya*, *Pyrenophora*, *Phaeosphaeria*, *Sclerotinia*, *Chaetomium*, *Nectria*, *Verticillium*, or *Aspergillus*, and wherein the enzyme mixtures are characterized in that, when the enzyme mixtures are contacted with cellobiose and/or glucose, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized after 10 hours.

In some aspects of the above embodiments, the fungal cell has been genetically modified to reduce the amount of one or more endogenous glucose and/or cellobiose oxidizing enzymes that is secreted by the cell. In some embodiments, the enzyme mixtures are cell-free mixtures. In some embodiments, the enzyme mixtures contain a beta-glucosidase. In some additional embodiments, the enzyme mixtures comprise at least one cellulase enzyme selected from endoglucanases (EGs), β-glucosidases (BGLs), Type 1 cellobiohydrolases (CBH1s), Type 2 cellobiohydrolases (CBH2s), and/or glycoside hydrolase 61s (GH61s), and/or variants of said cellulase enzyme.

In some embodiments, the enzyme mixtures are subjected to a purification process to selectively remove one or more glucose and/or cellobiose oxidizing enzymes from the enzyme mixture. In some embodiments, the purification process comprises selective precipitation to separate the glucose and/or cellobiose oxidizing enzymes from other enzymes present in the enzyme mixture. In some embodiments, the enzyme mixtures comprise at least one inhibitor of one or more glucose and/or cellobiose oxidizing enzymes.

The present invention also provides compositions comprising the fungal cell of any of the above embodiments, and/or comprising the enzyme mixture derived from the fungal cell of any of the above embodiments.

In some embodiments, the present invention provides methods for the production of fungal cells. In some further embodiments, the present invention provides methods for the production of at least one enzyme from fungal cells. In some embodiments, these methods comprise fermentation methods, including but not limited to, batch process, continuous process, fed-batch and/or a combination of methods. In some embodiments, the methods are conducted in a reaction volume of at least about 0.01 mL, about 0.1 mL, about 1 mL, about 10 mL, about 100 mL, about 1000 mL, or at least about 10 L, about 50 L, about 100 L, about 200 L, about 300 L, about 400 L, about 500 L, about 600 L, about 700 L, about 800 L, about 900 L, about 1000 L, about 10,000 L, about 50,000 L, about 100,000 L, about 250,000 L, about 500,000 L, or greater than about 1,000,000 L.

DETAILED DESCRIPTION OF THE INVENTION

The present invention provides genetically modified cellulase-producing fungal cells that have reduced secreted activity of an endogenous glucose and/or cellobiose oxidizing enzyme, and which are therefore able to secrete enzyme mixtures that improve the yield of fermentable sugars from cellulose. Previous reports have indicated that the oxidation of cellobiose by cellobiose dehydrogenase enhances the rate of cellulose hydrolysis by cellulases. In contrast to the traditional thinking in the art, the present invention provides fungal cells with genomic deletion(s) or other genetic modification(s) to reduce glucose and/or cellobiose oxidizing enzyme activity that results in improved yield of fermentable sugars from cellulose. Advantageously, the genetically modified cellulase-producing fungal cells provided herein secrete enzyme mixtures that result in vastly improved yields of fermentable sugars such as glucose from cellulose.

Among the cellulase-producing filamentous fungi, there are those that also produce a variety of enzymes involved in lignin degradation. For example, organisms of such genera as *Myceliophthora*, *Chrysosporium*, *Sporotrichum*, *Thielavia*, *Phanerochaete* and *Trametes* produce and secrete a mixture of cellulases, hemicellulases and lignin degrading enzymes. These types of organisms are commonly called "white rot fungi" by virtue of their ability to digest lignin and to distinguish them from the "brown rot" fungi (such as *Trichoderma*) which typically cannot digest lignin. The genera *Myceliophthora*, *Chrysosporium*, *Sporotrichum*, and *Thielavia* are closely related and in some cases different genus/species identifiers have been used interchangeably for strains of the same species (e.g., *M. thermophila* and *S. thermophile*). Continuing developments in the methods to establish the taxonomy of filamentous fungi has led to reclassification of some strains from one genus to another or has identified an "anamorph-teleomorph" relationship between strains of two genera (e.g., *M. thermophila* and *T. heterothallica*).

The present invention provides cells, enzyme mixtures and methods in which the activity of glucose and/or cellobiose oxidizing enzyme(s) is reduced so as to improve the yield of fermentable sugars from an enzymatic cellulose hydrolysis process. In view of this, as described herein, the present invention provides for removal or inactivation of glucose and/or cellobiose oxidizing enzyme from a mixture of cellulase enzymes to improve the yield of fermentable sugars from cellulose or biomass.

Genetically Modified Fungal Cells

The genetically modified fungal cells provided herein permit a reduction in the amount of endogenous glucose and/or cellobiose oxidizing enzyme activity that is secreted by the cell.

In some embodiments of the genetically modified fungal cells provided herein, glucose and/or cellobiose oxidizing enzyme activity that is secreted by the cell is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the level of glucose and/or cellobiose oxidizing enzyme activity secreted by the unmodified parental fungal cell grown or cultured under essentially the same culture conditions.

In some embodiments, the genetic modification results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total glucose and/or cellobiose oxidizing enzyme activity secreted by the fungal cell.

It will be readily appreciated that any genetic modification known in the art can be employed to reduce the secreted activity of the endogenous glucose and/or cellobiose oxidizing enzyme. For example, as described below, modifications contemplated herein include modifications that reduce the amount of glucose and/or cellobiose oxidizing enzyme secreted by the cell. Further contemplated are modifications that reduce the amount of glucose and/or cellobiose oxidizing enzyme that is expressed by the cell. Additional embodiments include modifications that reduce the transcription level of glucose and/or cellobiose oxidizing enzyme. Still further embodiments include the complete or partial deletion of a gene encoding glucose and/or cellobiose oxidizing enzyme. Other embodiments include modifications that reduce the catalytic efficiency of glucose and/or cellobiose oxidizing enzyme.

Secreted Enzyme(s). Accordingly, in some embodiments, the fungal cell has been genetically modified to reduce the amount of the endogenous glucose and/or cellobiose oxidizing enzyme that is secreted by the cell. The glucose and/or cellobiose oxidizing enzyme that is secreted by a cell is a glucose and/or cellobiose oxidizing enzyme produced by the cell in a manner such that the glucose and/or cellobiose oxidizing enzyme is exported across a cell membrane and then subsequently released into the extracellular milieu, such as into culture media. Thus, a reduction in the amount of secreted glucose and/or cellobiose oxidizing enzyme can be a complete or partial reduction of the glucose and/or cellobiose oxidizing enzyme secreted to the extracellular milieu. Reduction in the amount of secreted glucose and/or cellobiose oxidizing enzyme can be accomplished by reducing the amount of glucose and/or cellobiose oxidizing enzyme produced by the cell and/or by reducing the ability of the cell to secrete the glucose and/or cellobiose oxidizing enzyme that is produced by the cell. Methods for reducing the ability of the cell to secrete a polypeptide can be performed according to any of a variety of methods known in the art (See e.g., Fass and Engels, J. Biol. Chem., 271, 15244-15252 [1996]). For example, the gene encoding a secreted polypeptide can be modified to delete or inactivate a secretion signal peptide. Thus, in some embodiments, the fungal cell has been genetically modified to disrupt the N-terminal secretion signal peptide of the glucose and/or cellobiose oxidizing enzyme. The amount of glucose and/or cellobiose oxidizing enzyme that is secreted by the cell can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the secretion of glucose and/or cellobiose oxidizing enzyme in an unmodified organism grown or cultured under essentially the same culture conditions.

Furthermore, the total amount of glucose and/or cellobiose oxidizing enzyme activity can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more, relative to the total amount of glucose and/or cellobiose oxidizing enzyme secreted in an unmodified organism grown or cultured under essentially the same culture conditions.

Decreased secretion of a glucose and/or cellobiose oxidizing enzyme can be determined by any of a variety of methods known in the art for detection of protein or enzyme levels. For example, the levels of glucose and/or cellobiose oxidizing enzyme in the supernatant of a fungal culture can be detected using Western blotting techniques or other protein detection techniques that use an antibody specific to the glucose and/or cellobiose oxidizing enzyme. Similarly, secreted glucose and/or cellobiose oxidizing enzyme activity in the supernatant of a fungal culture can be measured using assays for glucose and/or cellobiose oxidizing enzyme activity as described in greater detail herein.

Expression Level. In some embodiments, the fungal cell has been genetically modified to reduce the amount of the endogenous glucose and/or cellobiose oxidizing enzyme that is expressed by the cell. In some embodiments, the reduction in the expression is accomplished by reducing the amount of mRNA that is transcribed from a gene encoding the glucose and/or cellobiose oxidizing enzyme. In some other embodiments, the reduction in the expression is accomplished by reducing the amount of protein that is translated from a mRNA encoding the glucose and/or cellobiose oxidizing enzyme.

The amount of glucose and/or cellobiose oxidizing enzyme that is expressed by the cell can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the expression of glucose and/or cellobiose oxidizing enzyme in an unmodified fungal cell. In some embodiments, the reduction in the expression is accomplished by reducing the amount of mRNA that is transcribed from a gene encoding cellobiose dehydrogenase or glucose oxidase in an unmodified organism grown or cultured under essentially the same culture conditions.

Furthermore, in some embodiments a reduction in the expression level of a glucose and/or cellobiose oxidizing enzyme will result in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total expression level of glucose and/or cellobiose oxidizing enzyme activity by the fungal cell relative to an unmodified fungal cell grown or cultured under essentially the same culture conditions.

Decreased expression of a glucose and/or cellobiose oxidizing enzyme can be determined by any of a variety of methods known in the art for detection of protein or enzyme levels. For example, the levels of glucose and/or cellobiose oxidizing enzyme in the supernatant of a fungal culture can be detected using Western blotting techniques or other protein detection techniques that use an antibody specific to the glucose and/or cellobiose oxidizing enzyme.

Methods for reducing expression of a polypeptide are well known and can be performed using any of a variety of methods known in the art. For example, the gene encoding a secreted polypeptide can be modified to disrupt a translation initiation sequence such as a Shine-Delgarno sequence or a Kozak consensus sequence. Furthermore, the gene encoding a secreted polypeptide can be modified to introduce a frameshift mutation in the transcript encoding the endogenous glucose and/or cellobiose oxidizing enzyme. It will also be recognized that usage of uncommon codons can result in reduced expression of a polypeptide. It will be appreciated that in some embodiments, the gene encoding the glucose and/or cellobiose oxidizing enzyme can have a nonsense mutation that results in the translation of a truncated protein.

Other methods of reducing the amount of expressed polypeptide include post-transcriptional RNA silencing methodologies such as antisense RNA and RNA interference. Antisense techniques are well-established, and include using a nucleotide sequence complementary to the nucleic acid sequence of the gene. More specifically, in some embodiments, expression of the gene by a fungal cell is reduced or eliminated by introducing a nucleotide sequence complementary to the nucleic acid sequence, which is transcribed in the cell and is capable of hybridizing to the mRNA produced in the cell. Under conditions allowing the complementary antisense nucleotide sequence to hybridize to the mRNA, the amount of protein translated is thus reduced or eliminated (See e.g., Ngiam et al., Appl Environ. Microbiol., 66:775-82 [2000]; and Zrenner et al., Planta 190:247-52 [1993]).

In some further embodiments, modification, downregulation and/or inactivation of the gene is achieved via any suitable RNA interference (RNAi) technique (See e.g., Kadotani et al. Mol. Plant Microbe Interact., 16:769-76 [2003]). RNA interference methodologies include double stranded RNA (dsRNA), short hairpin RNAs (shRNAs) and small interfering RNAs (siRNAs). Potent silencing using dsRNA may be obtained (See e.g., Fire et al., Nature 391:806-11 [1998]). Silencing using shRNAs is also well-established (See e.g., Paddison et al., Genes Dev. 16:948-958 [2002]). Silencing using siRNA techniques are also known (See e.g., Miyagishi et al., Nat. Biotechnol., 20:497-500 [2002].

Transcription Level. In some embodiments, the fungal cell has been genetically modified to reduce the transcription level of a gene encoding the endogenous glucose and/or cellobiose oxidizing enzyme. The transcription level can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the transcription level of a glucose and/or cellobiose oxidizing enzyme in an unmodified organism grown or cultured under essentially the same culture conditions.

Furthermore, a reduction in the transcription level of a glucose and/or cellobiose oxidizing enzyme will result in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total glucose and/or cellobiose oxidizing enzyme activity secreted by the fungal cell relative to an unmodified organism grown or cultured under essentially the same culture conditions.

Decreased transcription can be determined by any of a variety of methods known in the art for detection of transcription levels. For example, the levels of transcription of a particular mRNA in a fungal cell can be detected using quantitative RT-PCR techniques or other RNA detection techniques that specifically detect a particular mRNA.

Methods for reducing transcription level of a gene can be performed according to any method known in the art, and include partial or complete deletion of the gene, and disruption or replacement of the promoter of the gene such that transcription of the gene is greatly reduced or even inhibited. For example, the promoter of the gene can be replaced with a weak promoter (See e.g., U.S. Pat. No. 6,933,133). Thus, where the weak promoter is operably linked with the coding sequence of an endogenous polypeptide, transcription of that gene will be greatly reduced or even inhibited.

Gene Deletion. In some embodiments, the fungal cell has been genetically modified to at least partially delete a gene encoding the endogenous glucose and/or cellobiose oxidizing enzyme. In some embodiments, this deletion reduces or eliminates the total amount of endogenous glucose and/or cellobiose oxidizing enzyme activity secreted by the fungal cell.

A deletion in a gene encoding a glucose and/or cellobiose oxidizing enzyme in accordance with the embodiments provided herein can be a deletion of one or more nucleotides in the gene encoding the glucose and/or cellobiose oxidizing enzyme, and is often a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% of the gene encoding the glucose and/or cellobiose oxidizing enzyme, where the amount of glucose and/or cellobiose oxidizing enzyme activity secreted by the cell is reduced.

Thus, for example, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the activity of the endogenous glucose and/or cellobiose oxidizing enzyme secreted by the fungal cell, relative to the activity of the glucose and/or cellobiose oxidizing enzyme secreted by an unmodified organism grown or cultured under essentially the same culture conditions.

Furthermore, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total glucose and/or cellobiose oxidizing enzyme activity secreted by the fungal cell relative to an unmodified fungal cell grown or cultured under essentially the same culture conditions.

Deletion of a glucose and/or cellobiose oxidizing enzyme gene can be detected and confirmed by any of a variety of methods known in the art for detection of gene deletions. For example, as exemplified in the Example section below, gene deletion can be confirmed using PCR amplification of the modified genomic region. It will be appreciated that additional techniques for confirming deletion can be used and are well known, including Southern blot techniques, DNA sequencing of the modified genomic region, and screening for positive or negative markers incorporated during recombination events.

Methods for complete and/or partial deletion of a gene are well-known and the genetically modified fungal cell described herein can be generated using any of a variety of deletion methods known in the art that permits a reduction in the amount of endogenous glucose and/or cellobiose oxidizing enzyme activity that is secreted by the cell. Such methods may advantageously include standard gene disruption using homologous flanking markers (See e.g., Rothstein, Meth. Enzymol., 101:202-211 [1983]). Another technique for gene deletion includes PCR-based methods for standard deletion (See e.g., Davidson et al., Microbiol., 148:2607-2615 [2002], which describes a PCR-based strategy to generate integrative targeting alleles with large regions of homology).

Further gene deletion techniques include "positive-negative" cassettes; cre/lox based deletion, biolistic transformation to increase homologous recombination, and *agrobacterium*-mediated gene disruption. The "positive-negative" method employs cassettes which consist of one marker gene for positive screening and another marker gene for negative screening (See e.g., Chang et al., Proc. Natl. Acad. Sci. USA 84:4959-4963 [1987]). Cre/lox based methodologies employ elimination of marker genes using expression of Cre recombinase (See e.g., Florea et al., Fung. Genet. Biol., 46:721-730 [2009]).

Methods to introduce DNA or RNA into fungal cells are known to those of skill in the art and include PEG-mediated transformation of protoplasts, electroporation, biolistic transformation, and *Agrobacterium*-mediated transformation. Biolistic transformation employs a unique process in which DNA or RNA is introduced into cells on micron-sized particles, thus increasing delivery of a deletion construct to the fungal cell (See e.g., Davidson et al., Fung. Genet. Biol., 29:38-48 [2000]. Similarly, *Agrobacterium*-mediated transformation in conjunction with linear or split-marker deletion cassettes can facilitate delivery of deletion constructs to the target cell (See e.g., Wang et al., Curr. Genet., 56:297-307 [2010]).

Additional methods for complete or partial gene deletion include, but are not limited to, disruption of the gene. Such gene disruption techniques are known to those of skill in the art, and include the use of, for example, insertional mutagenesis, the use of transposons and marked integration. However, it will be appreciated that any technique that provides for disruption of the coding sequence or any other functional aspect of a gene can be utilized to generate the genetically modified fungal cells provided herein. Methods of insertional mutagenesis can be performed according to any such method known in the art (See e.g., Combier et al., FEMS Microbiol. Lett., 220:141-8 [2003]). For example, *Agrobacterium*-mediated insertional mutagenesis can be used to insert a sequence that disrupts the function of the encoded gene, such as disruption of the coding sequence or any other functional aspect of the gene.

Transposon mutagenesis methodologies are another manner for disruption of a gene. Transposon mutagenesis is well known in the art, and can be performed using in vivo techniques (See e.g., Firon et al., Eukaryot. Cell 2:247-55 [2003]); or by the use of in vitro techniques (See e.g., Adachi et al., Curr Genet., 42:123-7 [2002]). The content of each of these references is incorporated by reference in its entirety. Thus, targeted gene disruption using transposon mutagenesis can be used to insert a sequence that disrupts the function of the encoded gene, such as disruption of the coding sequence or any other functional aspect of the gene.

Restriction enzyme-mediated integration (REMI) is another methodology for gene disruption, and is well known in the art (See e.g., Thon et al., Mol. Plant. Microbe Interact., 13:1356-65 [2000], which is incorporated by reference herein in its entirety). REMI generates insertions into genomic restriction sites in an apparently random manner, some of which cause mutations. Thus, insertional mutants that demonstrate a disruption in the gene encoding the endogenous glucose and/or cellobiose oxidizing enzyme can be selected and utilized as provided herein.

Catalytic Disruption. In some other embodiments, the fungal cell is genetically modified to reduce the catalytic efficiency of the endogenous glucose and/or cellobiose oxidizing enzyme. In some embodiments, a genetic modification that reduces catalytic efficiency can result in, for example, a translated protein product that has a reduction in enzymatic activity.

In some embodiments, a reduction in catalytic efficiency is a reduction of glucose and/or cellobiose oxidizing enzyme activity of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to unmodified glucose and/or cellobiose oxidizing enzyme, as measured using standard techniques.

In some further embodiments, the genetic modification results in a reduction of glucose and/or cellobiose oxidizing enzyme activity of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total glucose and/or cellobiose oxidizing enzyme activity secreted by the fungal cell.

Methods for reducing catalytic efficiency of dehydrogenases and oxidases are well known, and as such, any of a variety of suitable methods known in the art for reducing catalytic efficiency can be utilized in the genetic modification of the fungal cells provided herein. Thus, for example, the fungal cell can be genetically modified to inactivate one or more residues in an active site of the glucose and/or cellobiose oxidizing enzyme (See e.g., Frederik et al., Biochem., 42:4049-4056 [2003]). For example, one or more residues can be modified to decrease substrate binding, and/or one or more residues can be modified to decrease the catalytic activity of the glucose and/or cellobiose oxidizing enzyme. Accordingly, one or more residues in the electron acceptor (e.g., flavin) binding domain, saccharide binding domain or other substrate binding domain of glucose and/or cellobiose oxidizing enzyme can be performed to reduce or inactivate the catalytic efficiency of the glucose and/or cellobiose oxidizing enzyme. Similarly, it will be apparent that mutation of residues outside an active site can result in allosteric change in the shape or activity of the glucose and/or cellobiose oxidizing enzyme.

In some additional embodiments, other domains are targeted for a mutation which results in reducing catalytic efficiency of the endogenous glucose and/or cellobiose oxidizing enzyme. For example, in some embodiments, a mutation to one or more residues in a heme binding domain of a glucose and/or cellobiose oxidizing enzyme can result in reduced catalytic efficiency (See e.g., Rotsaert et al., Arch. Biochem. Biophys., 390:206-14 [2001]).

Similarly, in some embodiments, the genetic modification is a conditional mutation to a glucose and/or cellobiose oxidizing enzyme. In some embodiments, the glucose and/or cellobiose oxidizing enzyme has a temperature sensitive mutation that renders the protein non-functional (i.e., inactive or less active) at (e.g. warm temperatures, such as 37-42° C.), and functional (i.e., active) at colder temperatures.

Fungal Cells

In some embodiments, the present invention provides a fungal cell that is a Basidiomycete belonging to the class Agaricomycetes or an Ascomycete belonging to the subdivision Pezizomycotina that has been genetically modified to reduce the amount of endogenous glucose and/or cellobiose oxidizing enzyme activity that is secreted by the cell, where the fungal cell is capable of secreting a cellulase-containing enzyme mixture. In some embodiments, the genetically modified fungal cell provided herein is a Basidiomycete belonging to the class Agaricomycetes or an Ascomycete belonging to the subdivision Pezizomycotina. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota*, or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium*, or *Aspergillus*.

The classification of a given fungal cell as belonging to the Basidiomycete class Agaricomycetes or to the Ascomycetes subdivision Pezizomycotina is done as is recognized in the art, as exemplified in the NCBI taxonomy database.

In some embodiments, the fungal cell is a Chaetomiaceae family member. The Chaetomiaceae are a family of fungi in the Ascomycota, class Sordariomycetes. The family Chaetomiaceae includes the genera *Achaetomium, Aporothielavia, Chaetomidium, Chaetomium, Corylomyces, Corynascus, Farrowia, Thielavia, Zopfiella*, and *Myceliophthora*.

In some embodiments, the genetically modified fungal cell is an anamorph or teleomorph of a Basidiomycete belonging to the class Agaricomycetes or an Ascomycete belonging to the subdivision Pezizomycotina. In some embodiments, the genetically modified fungal cell is an anamorph or teleomorph of a Chaetomiaceae family member selected from the genera *Myceliophthora, Thielavia, Corynascus, Chaetomium*. As such, the genetically modified fungal cell can also be selected from the genera *Sporotrichum, Chrysosporium, Paecilomyces, Talaromyces* or *Acremonium*. It is also contemplated that the genetically modified fungal cell be selected from the genera *Ctenomyces, Thermoascus*, and *Scytalidium*, including anamorphs and teleomorphs of fungal cells from those genera.

In some further embodiments, the genetically modified fungal cell is a thermophilic member of the genera *Acremonium, Arthroderma, Corynascus, Thielavia, Myceliophthora, Thermoascus, Chromocleista, Byssochlamys, Sporotrichum, Chaetomium, Chrysosporium, Scytalidium, Ctenomyces, Paecilomyces*, and *Talaromyces*. By "thermophilic fungus" is meant any fungus which exhibits optimum growth at a temperature of at least about 37° C., and generally below about 80° C., such as for example between about 37-80° C., also between about 37-75° C., also between about 40-65° C., and also between about 40-60° C. In some embodiments, the optimum growth is exhibited at a temperature of at least 40°-60° C.

In some embodiments, the genetically modified fungal cell is selected from the strains of *Sporotrichum cellulophilum, Thielavia heterothallica, Corynascus heterothallicus, Thielavia terrestris*, and *Myceliophthora thermophila*, including anamorphs and teleomorphs thereof. It will be understood that for the aforementioned species, the genetically modified fungal cell presented herein encompasses both the perfect and imperfect states, and other taxonomic equivalents (e.g., anamorphs), regardless of the species name by which they are known. For example, the following species are anamorphs or teleomorphs and may therefore be considered as synonymous: *Myceliophthora thermophila, Sporotrichum thermophile, Sporotrichum thermophilum, Sporotrichum cellulophilum, Chrysosporium thermophile, Corynascus heterothallicus*, and *Thielavia* heterothallica. Additionally, the following species may be considered synonymous with each other: *Thielavia terrestris, Allscheria terrestris*, and *Acremonium alabamense*. Further examples of taxonomic equivalents are known in the art (See e.g., Cannon, Mycopathol., 111:75-83 [1990]; Moustafa et al., Persoonia 14:173-175 [1990]; Stalpers, Stud. Mycol., 24, [1984]; Upadhyay et al., Mycopathol., 87:71-80 [1984]; Guarro et al., Mycotaxon 23: 419-427 [1985]; Awao et al., Mycotaxon 16:436-440 [1983]; von Klopotek, Arch. Microbiol., 98:365-369 [1974]; and Long et al., *ATCC Names of Industrial Fungi*, ATCC, Rockville Md. [1994]). Those skilled in the art will readily recognize the identity of appropriate equivalents. Accordingly, it will be understood that, unless otherwise stated, the use of a particular species designation in the present disclosure also refers to species that are related by anamorphic or teleomorphic relationship.

In some embodiments, the genetically modified fungal cell is a cellulase-producing fungal cell that is a Basidiomycete belonging to the class Agaricomycetes or an Ascomycete belonging to the subdivision Pezizomycotina. For example, in some embodiments, the genetically modified fungal cell is a Basidiomycete belonging to the class Agaricomycetes or an Ascomycete belonging to the subdivision Pezizomycotina that secretes two or more cellulose hydrolyzing enzymes, such as, for example, endoglucanase, cellobiohydrolase, or beta-glucosidase, It will be appreciated that cellulase can include hemicellulose-hydrolyzing enzymes such as endoxylanase, beta-xylosidase, arabinofuranosidase, alpha-glucuronidase, acetylxylan esterase, feruloyl esterase, and alpha-glucuronyl esterase. It will also be appreciated that a cellulase-producing fungal cell can produce two or more of these enzymes, in any combination.

Additionally, in some embodiments, the genetically modified fungal cell is derived from a lignocellulose-competent parental fungal cell The present invention also provides a fungal culture in a vessel comprising a genetically modified fungal cell as described hereinabove. In some embodiments, the vessel comprises a liquid medium, such as fermentation medium. For example, the vessel can be a flask, bioprocess reactor, and the like. In some embodiments, the vessel comprises a solid growth medium. For example, the solid medium can be an agar medium such as potato dextrose agar, carboxymethylcellulose, cornmeal agar, and the like. In some embodiments, the fungal cell described herein is an isolated fungal cell.

Sugar Oxidizing Enzymes

The present invention provides fungal cells that have been genetically modified to reduce the amount of endogenous glucose and/or cellobiose oxidizing enzyme secreted by the fungal cell. Examples of some suitable glucose and/or cellobiose oxidizing enzymes that find use in the present invention are described in greater detail below.

Glucose Oxidase. As indicated herein, in some embodiments, glucose oxidase and fungal cells producing reduced levels of glucose oxidase activity find use in the present invention. Glucose oxidase is known to function via a so-called ping-pong mechanism of enzymatic catalysis, which involves successive binding on two different sites. One site is a saccharide binding domain that is capable of binding β-D-glucose. The other site is a relatively non-selective co-substrate site for binding an oxidant such as FAD.

One of skill in the art will appreciate that glucose oxidase enzyme activity typically employs the presence of oxygen or an equivalent redox acceptor (e.g., lignin, molecular oxygen, cytochrome c, redox dyes, benzoquinones and $Fe^{2+}$ complexes). Glucose oxidase (GO) activity can be measured using any of a variety of methods known in the art. For example, GO activity assays can be performed using any suitable method known in the art (See e.g., Bergmeyer et al., in *Methods of Enzymatic Analysis* (Bergmeyer, ed.) Volume 1, $2^{nd}$ Ed., pp. 457-458, Academic Press Inc., New York, N.Y. [1974]; and U.S. Pat. No. 3,953,295). For example, GO activity is determined by an increase in absorbance at 460 nm resulting from the oxidation of o-dianisidine through a peroxidase coupled system.

In some embodiments, the present invention provides fungal cells that have been genetically modified to reduce the secreted activity of a glucose oxidase and have reduced secreted activity of an endogenous glucose oxidase. Accordingly, one or more glucose oxidase enzymes from each of the fungal species described herein can be targeted for genetic modification.

In some embodiments, the glucose oxidase is from a fungal species from the division Basidiomycete and belonging to the class Agaricomycetes; or from the division Ascomycete and belonging to the subdivision Pezizomycotina. Some examples of glucose oxidase enzymes identified from division Basidiomycete belonging to the class Agaricomycetes; and division Ascomycete belonging to the subdivision Pezizomycotina are set forth in the Table B, below.

In some embodiments, the glucose oxidase is from a fungal species selected from *Chaetomium globosum, Thielavia heterothallica, Thielavia terrestris, Talaromyces stipitatus* and *Myceliophthora thermophila*. Some glucose oxidase enzymes identified from these and other species are set forth in Table B, below. The proteins listed in Table B are examples of glucose oxidase that are known in the art, or identified herein as being a glucose oxidase.

TABLE B

Glucose Oxidase Sequences

| Accession Number | Organism | GMC oxred N Domain | GMC oxred C Domain |
|---|---|---|---|
| chr1-56652m21GM (SEQ ID NO.: 2) | *Myceliophthora thermophila* | 36-356 | 495-634 |
| XP_001227361.1 | *Chaetomium globosum* CBS 148.51 | 36-355 | 465-604 |
| JGIThite5217 | *Thielavia terrestris* | 36-355 | 466-605 |
| |XP_001223540.1 | *Chaetomium globosum* CBS 148.51 | 185-380 | 514-655 |
| XP_001910674.1 | *Podospora anserina* S mat+ | 39-373 | 506-644 |
| XP_001220376.1 | *Chaetomium globosum* CBS 148.51 | 38-342 | 481-620 |
| XP_001226009.1 | *Chaetomium globosum* CBS 148.51 | 214-289 | 323-464 |
| CBI59558.1 | *Sordaria macrospora* | 43-373 | 480-619 |
| XP_383916.1 | *Gibberella zeae* PH-1 | 35-345 | 466-603 |
| CBI59559.1 | *Sordaria macrospora* | 43-356 | 440-579 |
| JGIThite6377 | *Thielavia terrestris* | 40-363 | 490-630 |
| XP_001549389.1 | *Botryotinia fuckeliana* B05.10 | 39-347 | 438-578 |
| XP_001903685.1 | *Podospora anserina* S mat+ | 36-337 | 465-606 |
| XP_002792207.1 | *Paracoccidioides brasiliensis* Pb01 | 68-290 | 414-556 |
| XP_003001656.1 | *Verticillium albo-atrum* VaMs.102 | 46-359 | 488-627 |
| XP_361250.1 | *Magnaporthe oryzae* 70-15 | 113-324 | 450-594 |
| JGIThite5048 | *Thielavia terrestris* | 45-354 | 480-619 |
| XP_001226113.1 | *Chaetomium globosum* CBS 148.51 | 44-353 | 480-619 |
| XP_001906345.1 | *Podospora anserina* S mat+ | 39-352 | 480-620 |
| chr4-293m24GM (SEQ ID NO.: 4) | *Myceliophthora thermophila* | 81-380 | 508-647 |
| CAJ85791.1 | *Fusarium oxysporum* f. sp. *Lycopersici* | 34-344 | 465-602 |
| XP_661610.1 | *Aspergillus nidulans* FGSC A4 | 35-346 | 467-604 |
| XP_003041895.1 | *Nectria haematococca* mpVI 77-13-4 | 35-346 | 467-604 |
| XP_001912227.1 | *Podospora anserina* S mat+ | 27-333 | 443-584 |
| XP_681267.1 | *Aspergillus nidulans* FGSC A4 | 38-343 | 471-609 |
| XP_001227424.1 | *Chaetomium globosum* CBS 148.51 | 42-374 | 500-640 |
| CBI58590.1 | *Sordaria macrospora* | 46-351 | 477-588 |
| EEH49925.1 | *Paracoccidioides brasiliensis* Pb18 | 176-397 | NA |
| XP_001223186.1 | *Chaetomium globosum* CBS 148.51 | 37-292 | 424-599 |
| XP_001791201.1 | *Phaeosphaeria nodorum* SN15 | 60-223 | 349-480 |
| XP_001905375.1 | *Podospora anserina* S mat+ | 49-370 | 495-633 |
| XP_001592050.1 | *Sclerotinia sclerotiorum* 1980 | 227-296 | 314-446 |
| XP_003002940.1 | *Verticillium albo-atrum* VaMs.102 | 43-355 | 462-600 |
| XP_366260.2 | *Magnaporthe oryzae* 70-15 | 42-351 | 491-631 |
| XP_003048882.1 | *Nectria haematococca* mpVI 77-13-4 | 121-295 | 394-530 |
| XP_001796868.1 | *Phaeosphaeria nodorum* SN15 | 38-350 | 475-615 |
| XP_001805358.1 | *Phaeosphaeria nodorum* SN15 | 20-328 | 454-593 |
| XP_001931252.1 | *Pyrenophora tritici-repentis* Pt-1C-BFP | 23-318 | 508-595 |
| XP_001218113.1 | *Aspergillus terreus* NIH2624 | 43-354 | 475-612 |
| XP_001224467.1 | *Chaetomium globosum* CBS 148.51 | 218-318 | 446-552 |
| XP_003049247.1 | *Nectria haematococca* mpVI 77-13-4 | 25-323 | 451-589 |
| XP_001906627.1 | *Podospora anserina* S mat+ | 37-349 | 473-618 |
| XP_001804484.1 | *Phaeosphaeria nodorum* SN15 | 29-319 | 449-586 |
| JGIThite9772 | *Thielavia terrestris* | 33-357 | 460-599 |
| EEH08138.1 | *Ajellomyces capsulatus* G186AR | 181-256 | 366-509 |
| XP_002565293.1 | *Penicillium chrysogenum* Wisconsin 54-1255 | 34-355 | 458-595 |
| CBI52485.1 | *Sordaria macrospora* | 28-338 | NA |
| XP_001273036.1 | *Aspergillus clavatus* NRRL 1 | 14-322 | 421-560 |
| AAF31169.1|AF143814_1 | *Pleurotus pulmonarius* | 30-342 | 446-585 |
| EER39780.1 | *Ajellomyces capsulatus* H143 | 228-301 | 411-554 |
| XP_001558188.1 | *Botryotinia fuckeliana* B05.10 | 37-358 | 482-619 |
| XP_001904543.1 | *Podospora anserina* S mat+ | 27-344 | 453-596 |
| XP_001544530.1 | *Ajellomyces capsulatus* NAm1 | 228-301 | 411-554 |
| JGIThite8281 | *Thielavia terrestris* | 5-301 | 456-624 |
| XP_383802.1 | *Gibberella zeae* PH-1 | 24-324 | 452-589 |
| XP_001833868.1 | *Coprinopsis cinerea* okayama7#130 | 35-341 | 430-568 |
| XP_001836103.1 | *Coprinopsis cinerea* okayama7#130 | 39-366 | 462-535 |
| XP_001597615.1 | *Sclerotinia sclerotiorum* 1980 | 134-290 | 295-422 |
| ADD14021.1 | *Pleurotus eryngii* | 30-342 | 446-585 |
| EEH50230.1 | *Paracoccidioides brasiliensis* Pb18 | 131-252 | 366-484 |
| JGIThite6435 | *Thielavia terrestris* | 100-404 | 509-658 |
| XP_362999.2 | *Magnaporthe oryzae* 70-15 | 31-327 | 431-575 |
| XP_761104.1 | *Ustilago maydis* 521 | 54-372 | 485-603 |
| XP_002482522.1 | *Talaromyces stipitatus* ATCC 10500 | 36-362 | 456-593 |
| XP_001879270.1 | *Laccaria bicolor* S238N-H82 | 35-345 | 451-581 |
| XP_001584680.1 | *Sclerotinia sclerotiorum* 1980 | 24-335 | 440-581 |
| XP_001798598.1 | *Phaeosphaeria nodorum* SN15 | 35-337 | 440-584 |
| XP_661816.1 | *Aspergillus nidulans* FGSC A4 | 33-350 | 461-599 |
| XP_001883085.1 | *Laccaria bicolor* S238N-H82 | 34-348 | 450-594 |
| XP_001556658.1 | *Botryotinia fuckeliana* B05.10 | 39-364 | 464-603 |
| XP_001833865.1 | *Coprinopsis cinerea* okayama7#130 | 34-345 | 432-570 |

TABLE B-continued

Glucose Oxidase Sequences

| Accession Number | Organism | GMC oxred N Domain | GMC oxred C Domain |
|---|---|---|---|
| XP_002390024.1 | Moniliophthora perniciosa FA553 | 36-298 | 411-536 |
| XP_001801353.1 | Phaeosphaeria nodorum SN15 | 22-332 | 436-579 |
| XP_001817515.1 | Aspergillus oryzae RIB40 | 28-335 | 436-577 |
| XP_568317.1 | Cryptococcus neoformans var. neoformans JEC21 | 55-373 | 507-643 |
| XP_001273087.1 | Aspergillus clavatus NRRL 1 | 51-369 | 481-620 |
| XP_002372599.1 | Aspergillus flavus NRRL3357 | 28-340 | 441-582 |
| XP_001806098.1 | Phaeosphaeria nodorum SN15 | 62-382 | 494-634 |
| XP_001835456.1 | Coprinopsis cinerea okayama7#130 | 34-345 | 433-569 |
| XP_001586361.1 | Sclerotinia sclerotiorum 1980 | 32-346 | 446-586 |
| XP_001884302.1 | Laccaria bicolor S238N-H82 | 36-348 | 452-589 |
| XP_001821530.1 | Aspergillus oryzae RIB40 | 75-394 | 496-635 |
| XP_760191.1 | Ustilago maydis 521 | 59-366 | 497-628 |
| XP_002375018.1 | Aspergillus flavus NRRL3357 | 53-358 | 466-631 |
| XP_391162.1 | Gibberella zeae PH-1 | 21-316 | 442-579 |
| XP_759762.1 | Ustilago maydis 521 | 84-408 | 530-667 |
| CBI51995.1 | Sordaria macrospora | 30-326 | 469-610 |
| XP_002376612.1 | Aspergillus flavus NRRL3357 | 22-321 | 457-599 |
| XP_660833.1 | Aspergillus nidulans FGSC A4 | 41-358 | 466-603 |
| EDP53840.1 | Aspergillus fumigatus A1163 | 36-347 | 448-589 |
| XP_001911514.1 | Podospora anserina S mat+ | 77-396 | 498-637 |
| XP_002471526.1 | Postia placenta Mad-698-R | 86-400 | 517-660 |
| XP_367669.2 | Magnaporthe oryzae 70-15 | 21-323 | 427-568 |
| XP_001389920.1 | Aspergillus niger | 5-289 | 391-528 |
| XP_001732158.1 | Malassezia globosa CBS 7966 | 52-370 | 481-618 |
| XP_001826806.1 | Aspergillus oryzae RIB40 | 27-338 | 439-580 |
| XP_001216916.1 | Aspergillus terreus NIH2624 | 26-338 | 439-580 |
| XP_003000545.1 | Verticillium albo-atrum VaMs.102 | 21-339 | 440-581 |
| XP_391184.1 | Gibberella zeae PH-1 | 264-389 | 491-631 |
| XP_002148263.1 | Penicillium marneffei ATCC 18224 | 30-351 | 469-606 |
| XP_749312.1 | Aspergillus fumigatus Af293 | 36-347 | 448-589 |
| JGIThite9811 | Thielavia terrestris | 22-337 | 440-579 |
| XP_001907031.1 | Podospora anserina S mat+ | 29-322 | 451-590 |
| XP_001550244.1 | Botryotinia fuckeliana B05.10 | 24-336 | 451-484 |
| XP_002479433.1 | Talaromyces stipitatus ATCC 10500 | 42-367 | 467-606 |
| XP_001390806.1 | Aspergillus niger | 38-356 | 466-605 |
| XP_681081.1 | Aspergillus nidulans FGSC A4 | 143-367 | 469-608 |
| XP_001882478.1 | Laccaria bicolor S238N-H82 | 33-345 | 451-588 |
| XP_664049.1 | Aspergillus nidulans FGSC A4 | 36-353 | 464-603 |
| XP_002373928.1 | Aspergillus flavus NRRL3357 | 41-353 | 465-604 |
| XP_001592756.1 | Sclerotinia sclerotiorum 1980 | 42-358 | 469-539 |
| YP_914851.1 | Paracoccus denitrificans PD1222 | 13-304 | 394-530 |
| XP_002622246.1 | Ajellomyces dermatitidis SLH14081 | 39-349 | 459-602 |
| XP_002565328.1 | Penicillium chrysogenum Wisconsin 54-1255 | 34-338 | 450-589 |
| XP_001215452.1 | Aspergillus terreus NIH2624 | 46-350 | 454-589 |
| XP_001820476.1 | Aspergillus oryzae RIB40 | 41-343 | 455-594 |
| XP_001732090.1 | Malassezia globosa CBS 7966 | 55-373 | 484-621 |
| XP_002388554.1 | Moniliophthora perniciosa FA553 | 46-367 | 487-624 |
| XP_001265740.1 | Neosartorya fischeri NRRL 181 | 34-345 | 446-587 |
| XP_381957.1 | Gibberella zeae PH-1 | 53-320 | 432-553 |
| XP_001587168.1 | Sclerotinia sclerotiorum 1980 | 33-351 | 464-603 |
| XP_660308.1 | Aspergillus nidulans FGSC A4 | 27-334 | 437-568 |
| YP_001923964.1 | Methylobacterium populi BJ001 | 67-360 | 428-563 |
| XP_001559357.1 | Botryotinia fuckeliana B05.10 | 50-370 | 482-621 |
| XP_002389049.1 | Moniliophthora perniciosa FA553 | 33-345 | NA |
| XP_001394544.1 | Aspergillus niger | 27-338 | 439-580 |
| XP_760250.1 | Ustilago maydis 521 | 38-293 | 419-556 |
| XP_359722.1 | Magnaporthe oryzae 70-15 | 39-365 | 476-616 |
| XP_001800211.1 | Phaeosphaeria nodorum SN15 | 122-375 | 485-623 |
| XP_002481914.1 | Talaromyces stipitatus ATCC 10500 | 5-303 | 416-553 |
| XP_001398576.1 | Aspergillus niger | 40-353 | 465-604 |
| XP_003040786.1 | Nectria haematococca mpVI 77-13-4 | 61-379 | 493-631 |
| XP_001904483.1 | Podospora anserina S mat+ | 120-397 | 510-649 |
| XP_759393.1 | Ustilago maydis 521 | 40-366 | 478-618 |
| XP_002388140.1 | Moniliophthora perniciosa FA553 | 25-346 | NA |
| XP_002373140.1 | Aspergillus flavus NRRL3357 | 43-357 | 469-603 |
| XP_002143250.1 | Penicillium marneffei ATCC 18224 | 37-355 | 466-605 |
| XP_001729093.1 | Malassezia globosa CBS 7966 | 35-351 | 454-604 |
| XP_001793977.1 | Phaeosphaeria nodorum SN15 | 25-345 | 451-587 |
| XP_002476910.1 | Postia placenta Mad-698-R | 5-307 | 431-563 |
| XP_001559633.1 | Botryotinia fuckeliana B05.10 | 33-352 | 465-604 |
| XP_001732157.1 | Malassezia globosa CBS 7966 | 49-368 | 480-617 |
| XP_002149622.1 | Penicillium marneffei ATCC 18224 | 43-324 | 400-532 |

TABLE B-continued

Glucose Oxidase Sequences

| Accession Number | Organism | GMC oxred N Domain | GMC oxred C Domain |
|---|---|---|---|
| XP_001910399.1 | Podospora anserina S mat+ | 51-369 | 480-620 |
| XP_391404.1 | Gibberella zeae PH-1 | 64-382 | 496-634 |
| XP_002794971.1 | Paracoccidioides brasiliensis Pb01 | 5-300 | 414-551 |
| XP_001270826.1 | Aspergillus clavatus NRRL 1 | 48-372 | 484-623 |
| XP_001548196.1 | Botryotinia fuckeliana B05.10 | 41-349 | 477-617 |
| XP_001215424.1 | Aspergillus terreus NIH2624 | 41-351 | 450-591 |
| XP_758019.1 | Ustilago maydis 521 | 36-343 | 457-608 |
| BAI66412.1 | Fusarium oxysporum | 66-382 | 496-634 |
| EDP52931.1 | Aspergillus fumigatus A1163 | 46-370 | 482-621 |
| XP_002387978.1 | Moniliophthora perniciosa FA553 | 224-327 | NA |
| XP_001216137.1 | Aspergillus terreus NIH2624 | 27-340 | 441-525 |
| XP_002375706.1 | Aspergillus flavus NRRL3357 | 51-359 | 471-608 |
| XP_001598641.1 | Sclerotinia sclerotiorum 1980 | 50-370 | 482-621 |
| gi|71002308|ref|XP_755835.1 | Aspergillus fumigatus Af293 | 38-354 | 466-602 |
| gi|119481873|ref|XP_001260965.1 | Neosartorya fischeri NRRL 181 | 38-354 | 466-605 |
| XP_001817967.1 | Aspergillus oryzae RIB40 | 43-357 | 469-608 |
| XP_001275639.1 | Aspergillus clavatus NRRL 1 | 39-356 | 468-607 |
| XP_002148584.1 | Penicillium marneffei ATCC 18224 | 54-377 | 490-629 |
| XP_002485672.1 | Talaromyces stipitatus ATCC 10500 | 54-377 | 476-605 |
| EDP55006.1 | Aspergillus fumigatus A1163 | 38-354 | 466-602 |
| XP_754807.1 | Aspergillus fumigatus Af293 | 46-370 | 482-621 |
| CBF78527.1 | Aspergillus nidulans FGSC A4 | 21-324 | 436-575 |
| XP_002556907.1 | Penicillium chrysogenum Wisconsin 54-1255 | 28-339 | NA |
| XP_002567445.1 | Penicillium chrysogenum Wisconsin 54-1255 | 53-377 | 485-622 |
| XP_001396848.1 | Aspergillus niger | 60-366 | 454-593 |
| XP_001397016.1 | Aspergillus niger | 51-381 | 502-641 |
| XP_001023507.1 | Tetrahymena thermophila | 8-309 | 403-539 |
| XP_001263633.1 | Neosartorya fischeri NRRL 181 | 46-370 | 482-621 |
| XP_001400283.1 | Aspergillus niger | 49-372 | 477-616 |
| XP_001261659.1 | Neosartorya fischeri NRRL 181 | 44-369 | 477-612 |
| XP_001797048.1 | Phaeosphaeria nodorum SN15 | 39-366 | 458-598 |
| XP_001211074.1 | Aspergillus terreus NIH2624 | 44-320 | 430-565 |
| XP_001398522.1 | Aspergillus niger | 50-373 | 475-614 |

*Accession numbers for Thielavia terrestris refer to the U.S. Department of Energy (DOE) Joint Genome Institute (JGI) genome sequence Some amino acid sequences encoding glucose oxidase are provided herein. For example, the nucleotide sequence encoding Myceliophthora thermophila GO1 is set forth herein as SEQ ID NO:1, and the encoded amino acid sequence of Myceliophthora thermophila GO1 is set forth as SEQ ID NO:2. Furthermore, the nucleotide sequence encoding Myceliophthora thermophila GO2 is set forth herein as SEQ ID NO:3, and the encoded amino acid sequence of Myceliophthora thermophila GO2 is set forth as SEQ ID NO:4.

In some embodiments, the glucose oxidase is glucose oxidase (EC 1.1.3.4). In some embodiments, the glucose oxidase is a glucose oxidase with the amino acid sequence of Myceliophthora thermophila GO1 as set forth in SEQ ID NO:2. In some embodiments, the glucose oxidase is a glucose oxidase with the amino acid sequence of Myceliophthora thermophila GO2 as set forth in SEQ ID NO:4. In other embodiments, the glucose oxidase comprises an amino acid sequence provided in the GenBank entry of any one of the accession numbers set forth in Table B. In some embodiments, the glucose oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NOS:1 and/or 3. In some embodiments, the glucose oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NOS:2 and/or 4, or an amino acid sequence provided in the GenBank entry of any one of the accession numbers set forth in Table B. In some embodiments, the glucose oxidase is encoded by a nucleic acid sequence that can selectively hybridize to SEQ ID NOS:1 and/or 3 under moderately stringent or stringent conditions, as described below. In some embodiments, the glucose oxidase is encoded by a nucleic acid sequence that can selectively hybridize under moderately stringent or stringent conditions to a nucleic acid sequence that encodes SEQ ID NOS:2 and/or 4, or an amino acid sequence provided in the GenBank entry of any one of the accession numbers set forth in Table B.

In some embodiments, the glucose oxidase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NOS:2 and/or 4, or an amino acid sequence provided in the GenBank entry of any one of the accession numbers set forth in Table B.

Cellobiose Dehydrogenase. In some embodiments, the CDH contains both the conserved glucose-methanol-choline (GMC) oxido-reductase N and the GMC oxido-reductase C domains. In some other embodiments, a CDH contains the GMC oxido-reductase N domain alone. The GMC oxidoreductases are FAD flavoproteins oxidoreductases (See e.g., Cavener, J. Mol. Biol., 223:811-814 [1992]; and Vrielink and Blow, Biochem., 32:11507-15 [1993]). The GMC oxidoreductases include a variety of proteins; choline dehydrogenase (CHD), methanol oxidase (MOX) and cellobiose dehydrogenase (CDH) which share a number of regions of sequence similarities. One of these regions, located in the N-terminal section, corresponds to the FAD ADP-binding domain, as further defined by the Pfam database under the entry GMC_oxred_N (PF00732). Similarly, the C-terminal conserved domain (GMC oxido-reductase C domain) is defined as set forth in the Pfam database under the entry GMC_oxred_C (PF05199).

Cellobiose dehydrogenases can be categorized into two families, where a first family contains a catalytic portion and a second family contains a catalytic portion and a cellulose binding motif (CBM). The three-dimensional structure of an example cellobiose dehydrogenase features two globular domains, each containing one of two cofactors: a heme or a flavin. The active site lies at a cleft between the two domains. Oxidation of cellobiose typically occurs via 2-electron transfer from cellobiose to the flavin, generating cellobiono-1,5-lactone and reduced flavin. Active FAD is regenerated by electron transfer to the heme group, leaving a reduced heme. The native state heme is regenerated by reaction with the oxidizing substrate at the second active site.

The acceptor is preferentially iron ferricyanide, cytochrome C, or an oxidized phenolic compound such as dichloroindophenol (DCIP), an acceptor commonly used for colorimetric assays. Metal ions and $O_2$ are also acceptors, but for most cellobiose dehydrogenases the reaction rate of cellobiose oxidase for these acceptors is several orders of magnitude lower than that observed for iron or organic oxidants. Following cellobionolactone release, the product may undergo spontaneous ring-opening to generate cellobionic acid (Hallberg et al., 2003, J. Biol. Chem. 278: 7160-7166).

Those of skill in the art will appreciate that cellobiose dehydrogenase enzyme activity typically employs the presence of oxygen or an equivalent redox acceptor (e.g., lignin, molecular oxygen, cytochrome c, redox dyes, benzoquinones and $Fe^{2+}$ complexes).

Cellobiose dehydrogenase activity can be measured using any of a variety of methods known in the art. For example, CDH activity assays can be performed using any suitable method known in the art (See e.g., Schou et al., Biochem J., 220:565-71 [1998]). For example, DCPIP (2,6-dichlorophenolindophenol) reduction by CDH activity in the presence of cellobiose can be monitored by absorbance at 530 nm.

In some embodiments, the fungal cells provided herein that have been genetically modified to reduce the secreted activity of a cellobiose dehydrogenase have reduced secreted activity of an endogenous cellobiose dehydrogenase. Accordingly, one or more cellobiose dehydrogenase enzymes from each of the fungal species described herein can be targeted for genetic modification.

In some embodiments, the cellobiose dehydrogenase is from a fungal species in the division Basidiomycete and belonging to the class Agaricomycetes; or in the division Ascomycete and belonging to the subdivision Pezizomycotina. Some examples of cellobiose dehydrogenase enzymes identified from division Basidiomycete belonging to the class Agaricomycetes; and division Ascomycete belonging to the subdivision Pezizomycotina are set forth in Table C, below.

In some embodiments, the cellobiose dehydrogenase is from a fungal species selected from *Thielavia heterothallica, Thielavia terrestris, Chaetomium globosum* and *Myceliophthora thermophila*. Some cellobiose dehydrogenase enzymes identified from these and other species are set forth in the table below. The proteins listed in Table C are examples of cellobiose dehydrogenase that are known in the art, or identified herein as being a cellobiose dehydrogenase.

TABLE C

| Cellobiose Dehydrogenase Sequences | | | |
|---|---|---|---|
| Accession Number | Organism | GMC oxred N Domain | GMC oxred C Domain |
| AC26221 (SEQ ID NO.: 6) | *Myceliophthora thermophila* | 251-554 | 645-781 |
| AAC26221 | *Myceliophthora thermophila* | 251-554 | 645-781 |
| ABS45566 | *Myriococcum thermophilum* | 251-554 | 645-781 |
| ABS45567 | *Myriococcum thermophilum* | 251-554 | 645-781 |
| CHGT_03380 | *Chaetomium globosum* | 226-529 | 620-757 |
| XP_001229896.1 | *Chaetomium globosum* CBS 148.51 | 226-529 | 620-757 |
| JGIThite5441 | *Thielavia terrestris* | 253-555 | 647-783 |
| CAP68427 | *Podospora anserina* | 247-550 | 643-779 |
| CBI53519.1 | *Sordaria macrospora* | 252-554 | 645-782 |
| XP_956591.1 | *Neurospora crassa* OR74A | 253-555 | 646-782 |
| XP_360402.2 | *Magnaporthe oryzae* 70-15 | 264-566 | 657-794 |
| EDP55266 | *Aspergillus fumigatus* A1163 | 265-568 | 661-796 |
| BAE61169 | *Aspergillus oryzae* | 254-556 | 647-782 |
| CBI59551.1 | *Sordaria macrospora* | 167-295 | 382-518 |
| EAW14611 | *Aspergillus clavatus* NRRL 1 | 254-556 | 647-783 |
| XP_001209295.1 | *Aspergillus terreus* NIH2624 | 253-474 | 586-720 |
| JGIThite4524 | *Thielavia terrestris* | 36-337 | NA |

TABLE C-continued

Cellobiose Dehydrogenase Sequences

| Accession Number | Organism | GMC oxred N Domain | GMC oxred C Domain |
|---|---|---|---|
| CHGT_08276 | *Chaetomium globosum* | 36-338 | NA |
| XP_001225932.1 | *Chaetomium globosum* CBS 148.51 | 36-338 | NA |
| JGIThite6738 | *Thielavia terrestris* | 249-550 | 642-779 |
| CAP61651 | *Podospora anserina* | 254-555 | 647-783 |
| AAF69005 | *Humicola insolens* | 247-548 | 640-776 |
| XP_389261.1 | *Gibberella zeae* PH-1 | 213-516 | 607-743 |
| XP_958234.1 | *Neurospora crassa* OR74A | 274-576 | 668-804 |
| CDH2 derived from a C1 strain (SEQ ID NO.: 8) | *Myceliophthora thermophila* | 249-550 | NA |
| CBI54739.1 | *Sordaria macrospora* | 272-574 | 666-802 |
| XP_001800470.1 | *Phaeosphaeria nodorum* SN15 | 36-343 | 366-502 |
| XP_001939778.1 | *Pyrenophora tritici-repentis* Pt-1C-BFP | 247-550 | 640-776 |
| CHGT_08622 | *Chaetomium globosum* | 249-521 | 549-667 |
| XP_001226549.1 | *Chaetomium globosum* CBS 148.51 | 249-521 | 549-667 |
| XP_001801490.1 | *Phaeosphaeria nodorum* SN15 | 245-543 | 633-769 |
| XP_001553707.1 | *Botryotinia fuckeliana* B05.10 | 265-570 | 656-796 |
| XP_002999803.1 | *Verticillium albo-atrum* VaMs.102 | 393-534 | 590-681 |
| XP_001591237.1 | *Sclerotinia sclerotiorum* 1980 | 265-570 | 655-796 |
| XP_001273175.1 | *Aspergillus clavatus* NRRL 1 | 244-543 | 627-752 |
| XP_749254.1 | *Aspergillus fumigatus* Af293 | 247-546 | 637-755 |
| ACF60617 | *Ceriporiopsis subvermispora* | 236-519 | 634-763 |
| BAC20641 | *Grifola frondosa* | 230-509 | 628-757 |
| AAC50004 | *Trametes versicolor* | 230-512 | 628-757 |
| BAD32781 | *Coniophora puteana* | 236-519 | 634-763 |
| XP_367658.1 | *Magnaporthe oryzae* 70-15 | 39-334 | 426-551 |
| BAD36748 | *Irpex lacteus* | 239-516 | 637-766 |
| AAB61455 | *Phanerochaete chrysosporium* | 235-517 | 633-762 |
| CAA61359 | *Phanerochaete chrysosporium* | 234-516 | 632-761 |
| AAO32063 | *Trametes versicolor* | 230-512 | 628-757 |
| AAO64483 | *Athelia rolfsii* | 233-520 | 631-760 |
| XP_001265679.1 | *Neosartorya fischeri* NRRL 181 | 247-546 | 639-755 |
| AAC32197 | *Pycnoporus cinnabarinus* | 231-517 | 628-758 |
| XP_383093.1 | *Gibberella zeae* PH-1 | 27-325 | 408-528 |
| 2118247A | *Phanerochaete chrysosporium* | 234-515 | 631-759 |
| XP_001937164.1 | *Pyrenophora tritici-repentis* Pt-1C-BFP | 245-542 | 625-754 |
| XP_001400060.1 | *Aspergillus niger* | 33-329 | 415-542 |
| CAP85828 | *Penicillium chrysogenum* Wisconsin 54-1255 | 30-327 | 393-537 |
| XP_001803287.1 | *Phaeosphaeria nodorum* SN15 | 243-516 | NA |
| XP_003006847.1 | *Verticillium albo-atrum* VaMs.102 | 27-317 | 411-529 |
| XP_001402432.1 | *Aspergillus niger* CBS 513.88 | 245-495 | 598-726 |
| XP_003042062.1 | *Nectria haematococca* mpVI 77-13-4 | 241-540 | 597-754 |
| XP_001210806.1 | *Aspergillus terreus* NIH2624 | 32-329 | 413-541 |
| XP_386159.1 | *Gibberella zeae* PH-1 | 25-323 | 406-530 |
| BAE63115 | *Aspergillus oryzae* | 24-317 | 401-527 |
| XP_001559563.1 | *Botryotinia fuckeliana* B05.10 | 232-534 | 620-746 |
| XP_003003908.1 | *Verticillium albo-atrum* VaMs.102 | 232-507 | NA |
| XP_003042935.1 | *Nectria haematococca* mpVI 77-13-4 | 233-531 | 614-739 |
| XP_383918.1 | *Gibberella zeae* PH-1 | 234-533 | 615-740 |
| XP_001793048.1 | *Phaeosphaeria nodorum* SN15 | 28-314 | 408-542 |
| BAE79276 | *Fusarium oxysporum* f. sp. *Lycopersici* | 27-325 | 408-532 |
| XP_364344.1 | *Magnaporthe oryzae* 70-15 | 49-321 | 426-560 |
| XP_001547235.1 | *Botryotinia fuckeliana* B05.10 | 30-313 | 422-548 |
| XP_001593342.1 | *Sclerotinia sclerotiorum* 1980 | 232-536 | 622-748 |
| XP_385048.1 | *Gibberella zeae* PH-1 | 239-538 | 595-752 |
| XP_362950.1 | *Magnaporthe oryzae* 70-15 | 30-327 | 415-537 |
| XP_003052041.1 | *Nectria haematococca* mpVI 77-13-4 | 32-332 | 415-539 |
| XP_001940494.1 | *Pyrenophora tritici-repentis* Pt-1C-BFP | 90-271 | 363-479 |

*Accession numbers for *Thielavia terrestris* refer to the U.S. Department of Energy (DOE) Joint Genome Institute (JGI) genome sequence Some amino acid sequences encoding cellobiose dehydrogenase are provided herein. For example, the nucleotide sequence encoding *Myceliophthora thermophila* CDH1 is set forth herein as SEQ ID NO:5, and the encoded amino acid sequence of *Myceliophthora thermophila* CDH1 is set forth as SEQ ID NO:6. Furthermore, the nucleotide sequence encoding *Myceliophthora thermophila* CDH2 is set forth herein as SEQ ID NO:7, and the encoded amino acid sequence of *Myceliophthora thermophila* CDH2 is set forth as SEQ ID NO:8.

In some embodiments, the cellobiose dehydrogenase is cellobiose dehydrogenase (EC 1.1.99.18). In some embodiments, the cellobiose dehydrogenase is a cellobiose dehydrogenase with the amino acid sequence of *Myceliophthora thermophila* CDH1 as set forth in SEQ ID NO:6. In some embodiments, the cellobiose dehydrogenase is a cellobiose dehydrogenase with the amino acid sequence of *Myceliophthora thermophila* CDH2 as set forth in SEQ ID NO:8. In other embodiments, the cellobiose dehydrogenase comprises an amino acid sequence provided in the GenBank entry of any one of the accession numbers set forth in Table C. In some embodiments, the cellobiose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NOS:5 and/or 7. In some embodiments, the cellobiose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NOS:6 and/or 8, or an amino acid sequence provided in the GenBank entry of any one of the accession numbers set forth in Table D. In some embodiments, the cellobiose dehydrogenase is encoded by a nucleic acid sequence that can selectively hybridize to SEQ ID NOS:5 and/or 7 under moderately stringent or stringent conditions, as described hereinabove. In some embodiments, the cellobiose dehydrogenase is encoded by a nucleic acid sequence that can selectively hybridize under moderately stringent or stringent conditions to a nucleic acid sequence that encodes SEQ ID NOS:6 and/or 8, or an amino acid sequence provided in the GenBank entry of any one of the accession numbers set forth in Table C.

In some embodiments, the cellobiose dehydrogenase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NOS:6 and/or 8, or an amino acid sequence provided in the GenBank entry of any one of the accession numbers set forth in Table C. Similarity as used herein is described in greater detail hereinabove.

Cellobiose dehydrogenase sequences can be identified by any of a variety of methods known in the art. For example, a sequence alignment can be conducted against a database, for example against the NCBI database, and sequences with the lowest HMM E-value can be selected.

Pyranose Oxidase. As indicated herein, pyranose oxidases and fungal cells that have been modified to have reduced pyranose oxidase activity find use in the present invention. Pyranose oxidase activity can be measured using any of a variety of methods known in the art. For example, PO activity assays can be performed as described by Leitner et al., Appl Biochem Biotechnol 1998, 70-72:237-248), which is incorporated by reference in its entirety. For example, 2'-azinobis (3-ethylbenzthiazolinesulfonic acid) (ABTS) reduction by PO activity can be monitored by absorbance at 530 nm. In some additional embodiments, PO activity is determined by an increase in absorbance at 420 nm resulting from the oxidation of 2,2'-azinobis(3-ethylbenzthiazolinesulfonic acid) (ABTS) through a peroxidase coupled system.

In some embodiments, the fungal cells provided herein that have been genetically modified to reduce the secreted activity of a pyranose oxidase have reduced secreted activity of an endogenous pyranose oxidase. Accordingly, one or more pyranose oxidase enzymes from each of the fungal species described herein can be targeted for genetic modification.

In some embodiments, the pyranose oxidase is from a fungal species in the division Basidiomycete and belonging to the class Agaricomycetes; or in the division Ascomycete and belonging to the subdivision Pezizomycotina. Some examples of pyranose oxidase enzymes identified from division Basidiomycete belonging to the class Agaricomycetes; and division Ascomycete belonging to the subdivision Pezizomycotina are set forth in Table D, below.

In some embodiments, the pyranose oxidase is from a fungal species selected from *Peniophora gigantean, Phanerochaete chrysosporium, Trametes ochracea, Trametes pubescens, Emericella nidulans, Aspergillus oryzae, Gloeophyllum trabeum, Tricholoma matsutake, Trametes hirsute, Gloeophyllum trabeum, Phanerochaete chrysosporium, Peniophora sp., Trametes versicolor, Lyophyllum shimeji, Trametes pubescens, Phlebiopsis gigantea, Aspergillus parasiticus, Auricularia polytricha, Coriolus hirsutus, Coriolus versicolor, Gloeophyllum sepiarum, Iridophycus faccidum, Irpex lactus, Oudemansiella mucida, Phanerochaete gigantea, Pleurotus ostreatus, Polyporus obtusus, Saxidomus giganteus, Todus multicolor, Trametes cinnabarinus* and *Trametes* multicolor. Some pyranose oxidase enzymes identified from these species are set forth in Table D, below. The proteins listed in the table below are examples of pyranose oxidase that are known in the art, or identified herein as being a pyranose oxidase.

TABLE D

Pyranose Oxidase Sequences

| Database | Accession Number | Organism | Reference |
|---|---|---|---|
| Swiss Prot | Q6UG02 | Peniophora gigantea | |
| Swiss Prot | Q6QWR1 | Phanerochaete chrysosporium | |
| Swiss Prot | Q7ZA32 | Trametes ochracea | |
| Swiss Prot | Q5G234 | Trametes pubescens | |
| GenPept | Q5B2E9 | Emericella nidulans | |
| GenPept | BAE56707.1 (SEQ ID NO: 10) | Aspergillus oryzae | |
| GenPept | ACJ54278.1 | Gloeophyllum trabeum | |
| GenPept | BAC24805.1 | Tricholoma matsutake | |
| GenPept | P59097 | Trametes hirsuta | |
| GenPept | ACM47528.1 | Gloeophyllum trabeum | |
| GenPept | AAS93628.1 | Phanerochaete chrysosporium | |
| GenPept | AAO13382.1 | Peniophora sp. | |
| GenPept | BAA11119.1 | Trametes versicolor | |
| GenPept | BAD1079.1 | Lyophyllum shimeji | |
| GenPept | AAW57304.1 | Trametes pubescens | |
| GenPept | AAQ72486.1 | Phlebiopsis gigantea | |
| | | Aspergillus parasiticus | GiffhornAppl. Microbiol. Biotechnol., 54: 727-740 (2000) |
| | | Auricularia polytricha | Izumi et al., Agric. Biol. Chem., 54: 799-801 (1990) |
| | | Coriolus hirsutus | Machida et al., Agric. Biol. Chem.. 48: 2463-2470 (1984) |
| | | Coriolus versicolor | Taguchi et al., J. Appl. Biochem., 7: 289-295 (1985) |
| | | Gloeophyllum sepiarum | Izumi et al., Agric. Biol. Chem., 54: 799-801 (1990) |
| | | Iridophycus faccidum | Giffhorn, Appl. Microbiol. Biotechnol., 54: 727-740 (2000) |
| | | Irpex lactus | Izumi et al., Agric. Biol. Chem., 54: 799-801 (1990) |
| | | Oudemansiella mucida | Giffhorn, Appl. Microbiol. Biotechnol., 54: 727-740 (2000) |
| | | Phanerochaete gigantean | Giffhorn, Appl. Microbiol. Biotechnol., 54: 727-740 (2000) |
| | | Pleurotus ostreatus | Giffhorn, Appl. Microbiol. Biotechnol., 54: 727-740 (2000) |
| | | Polyporus obtusus | Janssen et al., Methods Enzymol., 41B: 170-173) 1975_ |
| | | Saxidomus giganteus | Giffhorn, Appl. Microbiol. Biotechnol., 54: 727-740 (2000) |
| | | Todus multicolor | Giffhorn, Appl. Microbiol. Biotechnol., 54: 727-740 (2000) |
| | | Trametes cinnabarinus | Izumi et al., Biol. Chem., 54: 799-801 (1990) |
| | | Trametes multicolor | Tasca et al., Electroanal., 19: 294-302 (2007) |

Some amino acid sequences encoding pyranose oxidase are provided herein. For example, the nucleotide sequence encoding *Aspergillus oryzae* PO1 is set forth herein as SEQ ID NO:9, and the encoded amino acid sequence of *Aspergillus oryzae* PO1 is set forth as SEQ ID NO:10.

In some embodiments, the pyranose oxidase is pyranose oxidase (E.C. 1.1.3.10). In some embodiments, the pyranose oxidase is a pyranose oxidase with the amino acid sequence of *Aspergillus oryzae* PO1 as set forth in SEQ ID NO: 10. In other embodiments, the pyranose oxidase comprises an amino acid sequence provided in the literature reference and/or GenBank entry of any one of the accession numbers set forth in Table D. In some embodiments, the pyranose oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:9. In some embodiments, the pyranose oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NO:10, or an amino acid sequence provided in the literature reference and/or GenBank entry of any one of the accession numbers set forth in Table D. In some embodiments, the pyranose oxidase is encoded by a nucleic acid sequence that can selectively hybridize to SEQ ID NO:9 under moderately stringent or stringent conditions, as described hereinabove. In some embodiments, the pyranose oxidase is encoded by a nucleic acid sequence that can selectively hybridize under moderately stringent or stringent conditions to a nucleic acid sequence that encodes SEQ ID NO:10, or an amino acid sequence provided in the literature reference and/or GenBank entry of any one of the accession numbers set forth in Table D.

In some embodiments, the pyranose oxidase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NO:10, or an amino acid sequence provided in the literature reference and/or GenBank entry of any one of the accession numbers set forth in Table D. Similarity as used herein is described in greater detail hereinabove.

Pyranose oxidase sequences can be identified by any of a variety of methods known in the art. For example, a sequence alignment can be conducted against a database, for example against the NCBI database, and sequences with the lowest HMM E-value can be selected.

Glucooligosaccharide Oxidase. As indicated herein, glucooligosaccharide oxidases and fungal cells modified to have reduced GOOX activity find use in the present invention. Glucooligosaccharide oxidase activity can be measured using any of a variety of methods known in the art. For example, GOOX activity assays can be performed as described by Lin et al., (Biochim. Biophys. Acta. 1991, 11:417-427), or Lee et al. (Appl. Environ. Microbiol. 2005, 71:8881-8887) each of which is incorporated by reference in its entirety. For example, activity can be measured by determining $H_2O_2$ production by coupling to a peroxidase enzyme assay.

In some embodiments, the fungal cells provided herein that have been genetically modified to reduce the secreted activity of at least one glucooligosaccharide oxidase have reduced secreted activity of an endogenous glucooligosaccharide oxidase. Accordingly, one or more glucooligosaccharide oxidase enzymes from each of the fungal species described herein can be targeted for genetic modification.

In some embodiments, the glucooligosaccharide oxidase is from a fungal species in the division Basidiomycete and belonging to the class Agaricomycetes; or in the division Ascomycete and belonging to the subdivision Pezizomycotina. Some examples of glucooligosaccharide oxidase identified from division Basidiomycete belonging to the class Agaricomycetes; and division Ascomycete belonging to the subdivision Pezizomycotina are set forth in the table below.

In some embodiments, the glucooligosaccharide oxidase is from a fungal species selected from *Acremonium strictum* and *Paraconiothyrium* sp. Some glucooligosaccharide oxidase enzymes identified from these species are set forth in Table E, below. The proteins listed in the table below are examples of glucooligosaccharide oxidase that are known in the art, or identified herein as being a glucooligosaccharide oxidase.

TABLE E

Glucooligosaccharide Oxidase Sequences

| Database | Accession Number | Organism | Reference |
|---|---|---|---|
| TrEMBL UniProt | Q6PW77 (SEQ ID NO: 12) | *Acremonium strictum* | |
| | | *Paraconiothyrium* sp. | Kiryu et al., 2008, Biosci. Biotechnol. Biochem., 72: 833-841 (2008) |

Some amino acid sequences encoding glucooligosaccharide oxidase are provided herein. For example, the nucleotide sequence encoding *Acremonium strictum* GOOX1 is set forth herein as SEQ ID NO:11, and the encoded amino acid sequence of *Acremonium strictum* GOOX1 is set forth as SEQ ID NO:12.

In some embodiments, the glucooligosaccharide oxidase is glucooligosaccharide oxidase (E.C. 1.1.99.B3). In some embodiments, the glucooligosaccharide oxidase is a glucooligosaccharide oxidase with the amino acid sequence of *Acremonium strictum* GOOX1 as set forth in SEQ ID NO:12. In other embodiments, the glucooligosaccharide oxidase comprises an amino acid sequence provided in the literature reference and/or GenBank entry of any one of the accession numbers set forth in Table E. In some embodiments, the glucooligosaccharide oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:11. In some embodiments, the glucooligosaccharide oxidase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NO:12, or an amino acid sequence provided in the literature reference and/or the GenBank entry of any one of the accession numbers set forth in Table E. In some embodiments, the glucooligosaccharide oxidase is encoded by a nucleic acid sequence that can selectively hybridize to SEQ ID NO:11 under moderately stringent or stringent conditions, as described hereinabove. In some embodiments, the glucooligosaccharide oxidase is encoded by a nucleic acid sequence that can selectively hybridize under moderately stringent or stringent conditions to a nucleic acid sequence that encodes SEQ ID NO:12, or an amino acid sequence provided in the literature reference and/or GenBank entry of any one of the accession numbers set forth in Table E.

In some embodiments, the glucooligosaccharide oxidase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NO:12, or an amino acid sequence provided in the literature reference and/or the GenBank entry of any one of the accession numbers set forth in Table E. Similarity as used herein is described in greater detail hereinabove.

Glucooligosaccharide oxidase sequences can be identified by any of a variety of methods known in the art. For example, a sequence alignment can be conducted against a database, for example against the NCBI database, and sequences with the lowest HMM E-value can be selected.

Pyranose Dehydrogenase. In some embodiments, pyranose dehydrogenases and fungal cells that have reduced pyranose dehydrogenase activity find use in the present invention. Pyranose dehydrogenases activity can be measured using any of a variety of methods known in the art. For example, PDH activity assays can be performed using any suitable method (See e.g., Volc et al., Arch. Microbiol., 176:178-186 [2001]).

In some embodiments, the fungal cells that have been genetically modified to reduce the secreted activity of a pyranose dehydrogenase have reduced secreted activity of an endogenous pyranose dehydrogenase. Accordingly, one or more pyranose dehydrogenase enzymes from each of the fungal species described herein can be targeted for genetic modification.

In some embodiments, the pyranose dehydrogenase is from a fungal species in the division Basidiomycete and belonging to the class Agaricomycetes; or in the division Ascomycete and belonging to the subdivision Pezizomycotina. Some examples of pyranose dehydrogenase identified from division Basidiomycete belonging to the class Agaricomycetes; and division Ascomycete belonging to the subdivision Pezizomycotina are set forth in the table below.

In some embodiments, the pyranose dehydrogenase is from a fungal species selected from *Agaricus bisporus*, *Agaricus meleagris*, *Agaricus xanthoderma*, *Macroleplota rhacodes* and *Leucoagaricus meleagris*. Some pyranose dehydrogenase enzymes identified from these species are set forth in Table F, below. The proteins listed in the table below are examples of pyranose dehydrogenase that are known in the art, or identified herein as being a pyranose dehydrogenase.

TABLE F

Pyranose Dehydrogenase Sequences

| Database | Accession Number | Organism | Reference |
|---|---|---|---|
| TrEMBL UniProt | Q3L1D1 (SEQ ID NO: 14) | *Agaricus bisporus* | |
| TrEMBL UniProt | Q3L245 | *Agaricus meleagris* | |
| TrEMBL UniProt | Q0R4L2 | *Agaricus meleagris* | |
| TrEMBL UniProt | Q3L243 | *Agaricus meleagris* | |

TABLE F-continued

Pyranose Dehydrogenase Sequences

| Database | Accession Number | Organism | Reference |
|---|---|---|---|
| TrEMBL UniProt | Q3L1D2 | *Agaricus xanthoderma Macroleplota rhacodes* | Volc et al., Arch. Microbiol., 176: 178-186 (2001) |
| GenBank | AAW82996.1 | *Leucoagaricus meleagris* | |
| GenBank | AAW82998.1 | *Leucoagaricus meleagris* | |
| GenBank | AAZ94874.1 | *Leucoagaricus meleagris* | |

Some amino acid sequences encoding pyranose dehydrogenase are provided herein. For example, the nucleotide sequence encoding *Agaricus bisporus* PDH1 is set forth herein as SEQ ID NO:13, and the encoded amino acid sequence of *Agaricus bisporus* PDH1 is set forth as SEQ ID NO:14.

In some embodiments, the pyranose dehydrogenase is pyranose dehydrogenase (E.C. 1.1.99.29). In some embodiments, the pyranose dehydrogenase is a pyranose dehydrogenase with the amino acid sequence of *Agaricus bisporus* PDH1 as set forth in SEQ ID NO:14. In some other embodiments, the pyranose dehydrogenase comprises an amino acid sequence provided in the literature reference and/or GenBank entry of any one of the accession numbers set forth in Table F. In some embodiments, the pyranose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:13. In some embodiments, the pyranose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NO:14, or an amino acid sequence provided in the literature reference and/or GenBank entry of any one of the accession numbers set forth in Table F. In some embodiments, the pyranose dehydrogenase is encoded by a nucleic acid sequence that can selectively hybridize to SEQ ID NO:13 under moderately stringent or stringent conditions, as described hereinabove. In some embodiments, the pyranose dehydrogenase is encoded by a nucleic acid sequence that can selectively hybridize under moderately stringent or stringent conditions to a nucleic acid sequence that encodes SEQ ID NO:14, or an amino acid sequence provided in the literature reference and/or GenBank entry of any one of the accession numbers set forth in Table F.

In some embodiments, the pyranose dehydrogenase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NO:14, or an amino acid sequence provided in the literature reference and/or the GenBank entry of any one of the accession numbers set forth in Table F. Similarity as used herein is described in greater detail hereinabove.

Pyranose dehydrogenase sequences can be identified by any of a variety of methods known in the art. For example, a sequence alignment can be conducted against a database, for example against the NCBI database, and sequences with the lowest HMM E-value can be selected.

Glucose Dehydrogenase. As indicated herein, glucose dehydrogenases and fungal cells that have been modified to have reduced glucose dehydrogenase activity find use in the present invention. Glucose dehydrogenase activity can be measured using any of a variety of methods known in the art (See e.g., Strecker, Meth. Enzymol., 1:335 [1955]). In some embodiments, GDH activity is determined by an increase in absorbance at 340 nm resulting from the generation of NADH from NAD when beta-D-glucose is provided as a substrate and NAD as an acceptor.

In some embodiments, the fungal cells provided herein that have been genetically modified to reduce the secreted activity of a glucose dehydrogenase have reduced secreted activity of an endogenous glucose dehydrogenase. Accordingly, one or more glucose dehydrogenase enzymes from each of the fungal species described herein can be targeted for genetic modification.

In some embodiments, the glucose dehydrogenase is from a fungal species in the division Basidiomycete and belonging to the class Agaricomycetes; or in the division Ascomycete and belonging to the subdivision Pezizomycotina. Some examples of glucose dehydrogenase identified from division Basidiomycete belonging to the class Agaricomycetes; and division Ascomycete belonging to the subdivision Pezizomycotina are set forth in the table below.

In some embodiments, the glucose dehydrogenase is from a fungal species selected from *Aspergillus niger, Aspergillus oryzae, Aspergillus terreus* and *Talaromyces stipatus*. Some glucose dehydrogenase enzymes identified from these species are set forth in Table G, below. The proteins listed in the table below are examples of glucose dehydrogenase that are known in the art, or identified herein as being a glucose dehydrogenase.

TABLE G

Glucose Dehydrogenase Sequences

| Database | Accession Number | Organism | Reference |
|---|---|---|---|
| | | *Aspergillus niger* | Muller, Zentralbl. Bacteriol. Parasienkd. Infectionskr Hyg., 132(a): 14-24 (1977) |
| | | *Aspergillus oryzae* | Bak, Biochim. Biophys. Acta 139: 277-293 (1967) |

TABLE G-continued

Glucose Dehydrogenase Sequences

| Database | Accession Number | Organism | Reference |
|---|---|---|---|
| | | *Aspergillus terreus* | Tsujimura et al., (2006) Biosci. Biotechnol. Biochem., 70: 654-659 (2006) |
| GenBank | XP_002482522.1 (SEQ ID NO: 16) | *Talaromyces stipitatus* ATCC 10500 | |
| GenBank | XP_002479433.1 | *Talaromyces stipitatus* ATCC 10500 | |
| GenBank | XP_002481914.1 | *Talaromyces stipitatus* ATCC 10500 | |

Some amino acid sequences encoding glucose dehydrogenase are provided herein. For example, the nucleotide sequence encoding *Myceliophthora thermophila* GDH1 is set forth herein as SEQ ID NO:15, and the encoded amino acid sequence of *Myceliophthora thermophila* GDH1 is set forth as SEQ ID NO:16.

In some embodiments, the glucose dehydrogenase is glucose dehydrogenase (E.C. 1.1.99.10). In some embodiments, the glucose dehydrogenase is a glucose dehydrogenase with the amino acid sequence of *Myceliophthora thermophila* GDH1 as set forth in SEQ ID NO:16. In some other embodiments, the glucose dehydrogenase comprises an amino acid sequence provided in the literature reference and/or GenBank entry of any one of the accession numbers set forth in Table G. In some embodiments, the glucose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:15. In some embodiments, the glucose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NO:16, or an amino acid sequence provided in the literature reference and/or GenBank entry of any one of the accession numbers set forth in Table G. In some embodiments, the glucose dehydrogenase is encoded by a nucleic acid sequence that can selectively hybridize to SEQ ID NO:15 under moderately stringent or stringent conditions, as described hereinabove. In some embodiments, the glucose dehydrogenase is encoded by a nucleic acid sequence that can selectively hybridize under moderately stringent or stringent conditions to a nucleic acid sequence that encodes SEQ ID NO:16, or an amino acid sequence provided in the literature reference and/ or GenBank entry of any one of the accession numbers set forth in Table G.

In some embodiments, the glucose dehydrogenase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NO:16, or an amino acid sequence provided in the literature reference or the GenBank entry of any one of the accession numbers set forth in Table G. Similarity as used herein is described in greater detail hereinabove.

Glucose dehydrogenase sequences can be identified by any of a variety of methods known in the art. For example, a sequence alignment can be conducted against a database, for example against the NCBI database, and sequences with the lowest HMM E-value selected, as desired.

In some embodiments, the cell has been genetically modified to reduce the amount of glucose and/or cellobiose oxidizing enzyme activity from two or more endogenous glucose and/or cellobiose oxidizing enzymes that are secreted by the cell. In certain such embodiments, a first of the two or more the glucose and/or cellobiose oxidizing enzymes comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to any one of SEQ ID NOS:2, 4, 6, 8, 10, 12, 14 and/or 16 and a second of the two or more the glucose and/or cellobiose oxidizing enzymes comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to any one of SEQ ID NOS: 2, 4, 6, 8, 10, 12, 14 and/or 16.

Enzyme Mixtures

Also provided herein are enzyme mixtures that comprise at least one or more cellulose hydrolyzing enzymes expressed by a fungal cell that has been genetically modified to reduce the amount of endogenous glucose and/or cellobiose oxidizing enzyme activity that is secreted by the cell, as described hereinabove.

In some embodiments the enzyme mixture is in a vessel comprising a genetically modified fungal cell as described hereinabove. In some embodiments, the vessel comprises a liquid medium. For example, the vessel can be a flask, bioprocess reactor, and the like. In some embodiments, the enzyme mixture is in a liquid volume. For example, the liquid volume can be greater than about 0.01 mL, 0.1 mL, 1 mL, 10 mL, 100 mL, 1000 mL, or greater than about 10 L, 50 L, 100 L, 200 L, 300 L, 400 L, 500 L, 600 L, 700 L, 800 L, 900 L, 1000 L, 10,000 L, 50,000 L, 100,000 L, 250,000 L, and 500,000 L or greater than about 1,000,000 L.

In some embodiments, the fungal cell is a lignocellulose-utilizing cell that is a Basidiomycete belonging to the class Agaricomycetes or an Ascomycete belonging to the subdivision Pezizomycotina, and where the fungal cell is capable of secreting a cellulase-containing enzyme mixture. In some embodiments, the fungal cell is capable of secreting an enzyme mixture comprising two or more cellulase enzymes. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota*, or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium*, or *Aspergillus*.

In some embodiments, the fungal cell is a lignocellulose-utilizing cell from the family Chaetomiaceae. In some embodiments, the genetically modified fungal cell provided herein is a Chaetomiaceae family member selected from the genera *Myceliophthora, Thielavia, Corynascus*, or *Chaetomium*. The genetically modified fungal cell can also be an anamorph or teleomorph of a Chaetomiaceae family member selected from the genera *Myceliophthora, Thielavia, Corynascus*, or *Chaetomium*. As such, the genetically modified fungal cell can also be selected from the genera *Sporotrichum, Acremonium* or *Talaromyces*. It is also contemplated that the genetically modified fungal cell be selected from the genera *Ctenomyces, Thermoascus*, and *Scytalidium*, including anamorphs and teleomorphs of fungal cells from those genera. In some embodiments, the fungal cell is a species selected from *Sporotrichum cellulophilum, Thielavia heterothallica, Corynascus heterothallicus, Thielavia terrestris, Chaetomium globosum, Talaromyces stipitatus* and *Myceliophthora thermophila*, including anamorphs and teleomorphs thereof.

In some embodiments, the present invention provides enzyme mixtures that are cell-free. In some embodiments, two or more cellulases and any additional enzymes and/or other components present in the cellulase enzyme mixtures are produced by a single type of genetically modified fungal cells, while in some embodiments the cellulases and/or other enzymes and/or other components are produced by different microbes. In some embodiments, the fermentations comprise single genetically modified cells and/or different microorganisms in combination, while in some other embodiments, the cells are grown in separate fermentations. Similarly, in some embodiments, the two or more cellulases and/or any additional enzymes and/or other components present in the cellulase enzyme mixture are expressed individually or in sub-groups from different strains of different organisms and the enzymes combined in vitro to produce the cellulase enzyme mixture. In some embodiments, cellulases and/or any additional enzymes and/or other components in the enzyme mixture are expressed individually or in sub-groups from different strains of a single organism, and the enzymes combined to make the cellulase enzyme mixture. In some embodiments, all of the enzymes and/or other components are expressed from a single host organism, such the genetically modified fungal cell as describe herein above.

In some embodiments, the enzyme mixtures comprise at least one or more cellulose hydrolyzing enzymes expressed by a fungal cell that has been genetically modified to reduce the amount of endogenous glucose and/or cellobiose oxidizing enzyme activity that is secreted by the cell, as described hereinabove.

In some embodiments, the fungal cell is a lignocellulose-utilizing cell that is a Basidiomycete belonging to the class Agaricomycetes or an Ascomycete belonging to the subdivision Pezizomycotina, and where the fungal cell is capable of secreting a cellulase-containing enzyme mixture. In some embodiments, the fungal cell is capable of secreting an enzyme mixture comprising two or more cellulase enzymes. In some embodiments, the Basidiomycete is a species of *Pleurotus, Peniophora, Trametes, Athelia, Sclerotium, Termitomyces, Flammulina, Coniphora, Ganoderma, Pycnoporus, Ceriporiopsis, Phanerochaete, Gloeophyllum, Hericium, Heterobasidion, Gelatoporia, Lepiota,* or *Irpex*. In some embodiments, the Ascomycete is a species of *Myceliophthora, Thielavia, Sporotrichum, Neurospora, Sordaria, Podospora, Magnaporthe, Fusarium, Gibberella, Botryotinia, Humicola, Neosartorya, Pyrenophora, Phaeosphaeria, Sclerotinia, Chaetomium, Nectria, Verticillium,* or *Aspergillus*.

In some embodiments, the fungal cell is a lignocellulose-utilizing cell from the family Chaetomiaceae. In some embodiments, the genetically modified fungal cell provided herein is a Chaetomiaceae family member selected from the genera *Myceliophthora, Thielavia, Corynascus,* and *Chaetomium*. The genetically modified fungal cell can also be an anamorph or teleomorph of a Chaetomiaceae family member selected from the genera *Myceliophthora, Thielavia, Corynascus,* and *Chaetomium*. As such, the genetically modified fungal cell can also be selected from the genera *Sporotrichum* or *Acremonium*. It is also contemplated that the genetically modified fungal cell can also be selected from the genera *Ctenomyces, Scytalidium* and *Thermoascus*, including anamorphs and teleomorphs of fungal cells from those genera. Typically, the fungal cell is a species selected from *Sporotrichum cellulophilum, Thielavia heterothallica, Corynascus heterothallicus, Thielavia terrestris, Chaetomium globosum, Talaromyces stipitatus,* and *Myceliophthora thermophila*, including anamorphs and teleomorphs thereof.

Some cellulase mixtures for efficient enzymatic hydrolysis of cellulose that are known (See e.g., Viikari et al., Adv. Biochem. Eng. Biotechnol., 108:121-45 [2007]; and US Pat. Appln. Publn. Nos. US 2009/0061484, US 2008/0057541, and US 2009/0209009) find use as components of some enzyme mixtures provided herein. In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, are combined with cellulosic feedstock or a product of cellulose hydrolysis. In some embodiments, the enzyme mixture comprises commercially available purified cellulases. Commercial cellulases are known and available to the art. In some embodiments, the enzyme mixtures do not comprise an endoglucanase.

In some embodiments, the enzyme mixture comprises at least 5%, at least 10%, at last 15%, at least 20%, at least 25%, at least 30%, at least 35%, at least 40%, at least 45%, or at least 50% GH61. In some embodiments, the enzyme mixture further comprises a cellobiohydrolase 1a (e.g., CBH1a) and GH61, wherein the enzymes together comprise at least 25%, at least 30%, at least 35%, at least 40%, at least 45%, at least 50%, at least 55%, at least 60%, at least 65%, at least 70%, at least 75%, or at least 80% of the enzyme mixture. In some embodiments, the enzyme mixture further comprises a β-glucosidase (Bgl), GH61, and CBH, wherein the three enzymes together comprise at least 30%, at least 35%, at least 40%, at least 45%, at least 50%, at least 55%, at least 60%, at least 65%, at least 70%, at least 75%, at least 80%, or at least 85% of the enzyme mixture. In some embodiments, the enzyme mixture further comprises an endoglucanase (EG), GH61, CBH2b, CBH1a, Bgl, wherein the five enzymes together comprise at least 35%, at least 40%, at least 45%, at least 50%, at least 55%, at least 60%, at least 65%, at least 70%, at least 75%, at least 80%, at least 85%, or at least 90% of the enzyme mixture. In some embodiments, the enzyme mixture comprises GH61, CBH2b, CBH1, Bgl, and at least one EG, in any suitable proportion for the desired reaction.

In some embodiments, the enzyme mixture composition comprises isolated cellulases in the following proportions by weight (wherein the total weight of the cellulases is 100%), about 20%-10% of Bgl, about 30%-25% of CBH1a, about 10%-30% of GH61, about 20%-10% of EG, and about 20%-25% of CBH2b. In some embodiments, the enzyme mixture composition comprises isolated cellulases in the following proportions by weight: about 20%-10% of GH61, about 25%-15% of Bgl, about 20%-30% of CBH1a, about 10%-15% of EG, and about 25%-30% of CBH2b. In some embodiments, the enzyme mixture composition comprises isolated cellulases in the following proportions by weight: about 30%-20% of GH61, about 15%-10% of Bgl, about 25%-10% of CBH1a, about 25%-10% of CBH2b, about 15%-10% of EG. In some embodiments, the enzyme mixture composition comprises isolated cellulases in the following proportions by weight: about 40-30% of GH61, about 15%-10% of Bgl, about 20%-10% of CBH1a, about 20%-10% of CBH2b, and about 15%-10% of EG. In some embodiments, the enzyme mixture composition comprises isolated cellulases in the following proportions by weight: about 50%-40% of GH61, about 15%-10% of Bgl, about 20%-10% of CBH1a, about 15%-10% of CBH2b, and about 10%-5% of EG. In some embodiments, the enzyme mixture composition comprises isolated cellulases in the following proportions by weight: about 10%-15% of GH61, about 20%-25% of Bgl, about 30%-20% of CBH1a, about 15%-5% of EG, and about 25%-35% of CBH2b. In some embodiments, the enzyme mixture composition comprises isolated cellulases in the following proportions by weight: about 15%-5% of GH61, about 15%-10% of Bgl, about 45%-30% of CBH1a, about 25%-5% of EG, and about 40%-10% of CBH2b. In some embodiments, the enzyme mixture composition comprises isolated cellulases in the following proportions by weight: about 10% of GH61, about 15% of Bgl, about 40% of CBH1a, about 25% of EG, and about 10% of CBH2b.

In some embodiments, the enzyme component comprises more than one CBH1a, CBH2b, EG, Bgl, and/or GH61 enzyme (e.g., 2, 3, 4, or more different variants), in any suitable combination. In some embodiments, an enzyme mixture composition of the invention further comprises at least one additional protein and/or enzyme. In some embodiments, enzyme mixture compositions of the present invention further comprise at least one additional enzyme other than the GH61, Bgl, CBH1a, GH61, and/or CBH2b. In some embodiments, the enzyme mixture compositions of the invention further comprise at least one additional cellulase, other than the GH61, Bgl, CBH1a, GH61, and/or CBH2b variant recited herein. In some embodiments, the GH61 polypeptide of the invention is also present in mixtures with non-cellulase enzymes that degrade cellulose, hemicellulose, pectin, and/or lignocellulose.

In some embodiments, GH61 polypeptide of the present invention is used in combination with other optional ingredients such as at least one buffer, surfactant, and/or scouring agent. In some embodiments, at least one buffer is used with the GH61 polypeptide of the present invention (optionally combined with other enzymes) to maintain a desired pH within the solution in which the GH61 is employed. The exact concentration of buffer employed depends on several factors which the skilled artisan can determine. Suitable buffers are well known in the art. In some embodiments, at least one surfactant is used in with the GH61 of the present invention. Suitable surfactants include any surfactant compatible with the GH61 and, optionally, with any other enzymes being used in the mixture. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants also find use in the present invention, as is known in the art.

In some embodiments, the cellulase enzyme mixtures of the present invention are produced in a fermentation process in which the fungal cell described herein above is grown in submerged liquid culture fermentation. It is intended that any suitable fermentation medium and process will find use in the present invention. In some embodiments, submerged liquid fermentations of fungal cells are conducted as a batch, fed-batch and/or continuous process. It is not intended that the present invention be limited to any particular fermentation medium, protocol, process, and/or equipment. In some embodiments, the fermentation medium is a liquid comprising a carbon source, a nitrogen source, and other nutrients, vitamins and minerals which can be added to the fermentation media to improve growth and enzyme production of the host cell. In some embodiments, these other media components are added prior to, simultaneously with or after inoculation of the culture with the host cell. In some embodiments, the carbon source comprises a carbohydrate that induces the expression of the cellulase enzymes from the fungal cell. For example, in some embodiments, the carbon source comprises one or more of cellulose, cellobiose, sophorose, xylan, xylose, xylobiose and related oligo- or poly-saccharides known to induce expression of cellulases and beta-glucosidase in such fungal cells. In some embodiments, the media comprise cellulose, while in some other embodiments, the media do not comprise cellulose (i.e., measurable concentrations of cellulose). In some further embodiments, the media comprise carbon sources such as glucose, dextrose, etc. However, it is not intended that the present invention be limited to any specific carbon and/or nitrogen source, as any suitable carbon and/or nitrogen source finds use in the present invention. Indeed, it is not intended that the present invention be limited to any particular medium, as any suitable medium will find use in the desired setting.

In some embodiments utilizing batch fermentation, the carbon source is added to the fermentation medium prior to or simultaneously with inoculation. In some other embodiments utilizing fed-batch and/or continuous operations, the carbon source is also supplied continuously or intermittently during the fermentation process. For example, in some embodiments, the carbon source is supplied at a carbon feed rate of between about 0.2 and about 2.5 g carbon/L of culture/h, or any amount therebetween. In some additional embodiments, the carbon source is supplied at a feed rate of between about 0.1 and about 10 g carbon/L of culture/hour or at any suitable rate therebetween (e.g., about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, or about 10 g carbon/L of culture/h).

In some embodiments, the process for producing the enzyme mixture of the present invention is performed at a temperature from about 20° C. to about 80° C., or any temperature therebetween, for example from about 25° C. to about 65° C., or any temperature therebetween, or from about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., or any temperature therebetween.

In some embodiments, the methods for producing enzyme mixtures of the present invention are carried out at a pH from about 3.0 to about 8.0, or any pH therebetween, for example from about pH 3.5 to about pH 6.8, or any pH therebetween, for example from about pH 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, 6.5, about 6.6, about 6.7, about 6.8, about 6.9, about 7.0, about 7.1, about 7.2, about 7.3, about 7.4, 7.5, about 7.6, about 7.7, about 7.8, about 7.9, about 8.0, or any pH therebetween.

In some embodiments, the fermentation medium containing the fungal cells are used following fermentation, while in some other embodiments, the fermentation medium containing the fungal cells and the enzyme mixture are used, while in some additional embodiments, an enzyme mixture is separated from the fungal cells (e.g., by filtration and/or centrifugation), and the enzyme mixture in the fermentation medium is used, and in still additional embodiments, the fungal cells, enzyme(s), and/or enzyme mixtures are separated from the fermentation medium and then used. Low molecular solutes such as unconsumed components of the fermentation medium may be removed by ultrafiltration or any other suitable method. Any suitable method for separating cells, enzyme(s), and/or enzyme mixtures find use in the present invention. Indeed, it is not intended that the present invention be limited to any particular purification/separation method. In some additional embodiments, the fungal cells, enzyme(s) and/or enzyme mixtures are concentrated (e.g., by evaporation, precipitation, sedimentation and/or filtration). In some embodiments, stabilizers are added to the compositions comprising fungal cells, enzyme(s), and/or enzyme mixtures. In some embodiments, chemicals such as glycerol, sucrose, sorbitol and the like find use to stabilize the enzyme mixtures. In some additional embodiments, other chemicals (e.g., sodium benzoate and/or potassium sorbate), are added to the enzyme mixture to prevent growth of microbial contamination. In some additional embodiments, additional components are present in the compositions provided herein. It is not intended that the present invention be limited to any particular chemical and/or other components, as various components will find use in different settings. Indeed, it is contemplated that any suitable component will find use in the compositions of the present invention.

Methods for Generating Fermentable Sugars

The present invention provides methods for generating fermentable sugars, including but not limited to glucose. In some embodiments, the methods for generating glucose comprise contacting cellulose with fungal cells producing at least one enzyme, at least one enzyme, and/or at least one enzyme mixture described herein. For example, in some embodiments, the process comprises contacting cellulose with an enzyme mixture comprising two or more cellulose hydrolyzing enzymes, wherein at least one of the two or more cellulose hydrolyzing enzymes is produced by a fungal cell as described herein.

In some embodiments, the method for generating fermentable sugars such as glucose from cellulose using the enzyme mixture is batch hydrolysis, fed-batch hydrolysis, continuous hydrolysis, and/or a combination thereof. In some embodiments, the hydrolysis reaction is agitated, stirred, unmixed, and/or a combination thereof.

The methods for generating fermentable sugars such as glucose from cellulose are carried out at any suitable temperature known in the art. In some embodiments, a temperature of about 30° C. to about 80° C., or any temperature therebetween (e.g., a temperature of about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., or any temperature therebetween) find use.

In addition, any suitable pH finds use in the present invention. In some embodiments, a pH of about 3.0 to about 8.0, or any pH therebetween (e.g., about pH 3.5 to about pH 6.8, or any pH therebetween, for example from about pH 3.0, about 31, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, 6.5, about 6.6, about 6.7, about 6.8, about 6.9, about 7.0, about 7.1, about 7.2, about 7.3, about 7.4, 7.5, about 7.6, about 7.7, about 7.8, about 7.9, about 8.0, or any pH therebetween) finds use in the present invention, In some embodiments, the initial concentration of cellulose in the hydrolysis reactor, prior to the start of hydrolysis, is about 0% (w/w), to about 0.1% (w/w), to about 15% (w/w), or any amount therebetween, for example about 1%, about 2%, about 3%, about 4%, about 5%, about 6%, about 7%, about 8%, about 10%, about 11%, about 12%, about 13%, about 14%, or about 15% or any amount therebetween. However, it is not intended that the present invention be limited to any particular temperature, pH, time, nor cellulose concentration in the hydrolysis reaction, as any suitable temperature, pH, time, cellulose concentration, as well as other parameters find use in the present invention.

In some embodiments, the dosage of the cellulase enzyme and/or cellulase enzyme mixture used in the hydrolysis reaction is from about 0.1 to about 100 mg protein per gram cellulose, or any suitable amount therebetween (e.g., about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89%, about 90, about 91, about 100 mg protein per gram cellulose, or any amount therebetween. The hydrolysis is carried out for any suitable time period. In some embodiments, the hydrolysis is performed from about 0.5 hours to about 300 hours, from about 15 hours to 100 hours, or any time therebetween. In some embodiments, the hydrolysis reaction is performed for about 0.5, about 1, about 2, 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300 hours, or any time therebetween. It should be appreciated that the reaction conditions are not meant to limit the invention in any manner and may be adjusted as desired by those of skill in the art. Indeed, it is not intended that the present invention be limited to any particular hydrolysis reaction time, protein concentration, or any other specific reaction parameter, as various reaction parameters and components find use in the present invention.

In some embodiments, the enzymatic hydrolysis is carried out in a hydrolysis reactor. In some embodiments, the enzyme and/or enzyme mixture is added to the pretreated lignocellulosic feedstock (also referred to as the "substrate") prior to, during, or after the addition of the substrate to the hydrolysis reactor.

In some embodiments, various environmental conditions are adjusted according to any variety of methods known in the art in order to maximize the formation of a hydrolysis product such as glucose. For example, temperature, pH, % dissolved oxygen, stirring speed can each be independently adjusted. In some embodiments, the enzyme mixture is a cell-free mixture, as described herein.

In some embodiments, the methods for generating glucose utilizing enzymes and/or enzyme mixtures comprising reduced glucose oxidase and/or reduced cellobiose dehydrogenase activity, as described herein, provide higher yields of glucose from the enzymatically hydrolyzed cellulose than a corresponding method using an enzyme mixture with its full complement of glucose oxidase or cellobiose dehydrogenase activity. Further, some embodiments of the methods provided herein result in decreased conversion of the cellobiose and glucose products in the enzymatic hydrolyzate to oxidized products such as gluconolactone, gluconate, gluconic acid cellobionolactone, and/or cellobionic acid.

In some embodiments of the methods provided herein utilizing the genetically modified fungal cell(s), enzyme(s), and/or enzyme mixture(s) provided herein, improved glucose yield is measured and/or quantified. As described herein, glucose yield can be described in terms of the amount of generated glucose per theoretical maximum glucose yield, or in terms of Gmax.

For example, as described in U.S. Pat. Nos. 6,090,595 and 7,419,809, the cellulose content can be determined by acid hydrolysis of the cellulose, followed by determination of glucose concentration, taking into account the water necessary to hydrolyze the cellulose. In one specific example, a slurry of feedstock is centrifuged, washed with water, and suspended in sulfuric acid at a net sulfuric acid concentration of 70%. The slurry is incubated at 40° C. for 30 minutes, followed by diluting in deionized water to 2% sulfuric acid. At this time point, the samples are steam-autoclaved at 121° C. for 1 hour, to convert the oligomers to monomeric glucose. The glucose concentration is measured by HPLC or enzymatic assay as described below.

Alternatively, cellulose content can be analyzed by infrared spectroscopy as described in Example 1. For example, solids can be washed and placed on the detection crystal of an infrared spectrometer and their absorbance measured between 500-4000 $cm^{-1}$.

Glucose levels can be quantified by any of a variety of methods known in the art (See e.g., U.S. Pat. Nos. 6,090,595 and 7,419,809). For example, glucose concentrations can be determined using a coupled enzymatic assay based on glucose oxidase and horseradish peroxidase (See e.g., Trinder, Ann. Clin. Biochem., 6:24-27 [1969]). Additional methods of glucose quantification include chromatographic methods, for example by HPLC (See e.g., U.S. Pat. Nos. 6,090,595 and 7,419,809). Cellobiose levels can be measured by any number of HPLC methods known to those skilled in the art (See e.g., Kotiranta et al., Appl. Biochem. Biotechnol., 81: 81-90 [1999].

Similarly, decreased conversion of cellobiose and glucose products to oxidized products such as cellobionolactone and gluconolactone can be quantified using any suitable method known in the art. For example, products of glucose or cellobiose oxidation can be detected and quantified using infrared spectroscopy, or by chromatographic methodologies such as HPLC (See e.g., Rakotomanga et al., J. Chromatog. B. 4:277-284 [1991]; and Mansfield et al., App. Environ. Microbiol., 64:3804-3809 [1997]). Accordingly, total oxidation of glucose or cellobiose can be determined, for example, as a function of total oxidation products per theoretical maximum glucose yield, or as a function of Gmax.

The methods, fungal cells, enzymes, and enzyme mixtures provided herein include reduction or removal of glucose and/or cellobiose oxidizing enzyme activity from a cellulose hydrolyzing enzyme mixture, thereby improving the yield of fermentable sugars such as glucose, xylose, and/or cellobiose during hydrolysis of cellulose. Advantageously, the processes and enzyme mixtures provided herein result in an increased yield of glucose and/or cellobiose from the hydrolyzed cellulose and a decreased oxidation of the glucose and/or cellobiose to oxidized sugar products, such as gluconolactone, gluconate, gluconic acid, cellobionolactone, and/or cellobionic acid from the hydrolyzed cellulose, relative to an enzyme mixture with an unmodified amount of glucose and/or cellobiose oxidizing enzyme activity, or relative to a parental enzyme mixture.

In some embodiments, the methods provided herein comprise contacting a cellulose substrate with fungal cells producing at least one cellulose hydrolyzing enzyme, at least one cellulose hydrolyzing enzyme, and/or an enzyme mixture comprising two or more cellulose hydrolyzing enzymes. In some embodiments, the enzyme mixtures are characterized in that oxidation of cellobiose and/or glucose is reduced during hydrolysis of cellulose, as described in greater detail herein, relative to an enzyme mixture with an unmodified amount of glucose and/or cellobiose oxidizing enzyme activity, or relative to a parental enzyme mixture. In some embodiments, the processes provided herein comprise providing a cellulose substrate, typically as an aqueous slurry, and providing at least one enzyme mixture comprising at least two cellulose hydrolyzing enzymes, at least one cellulose hydrolyzing enzyme, and/or fungal cells producing at least one cellulose hydrolyzing enzyme. The cellulose-containing slurry is introduced into a reaction vessel such as a hydrolysis reactor, and the at least one enzyme mixture comprising at least two cellulose hydrolyzing enzymes, at least one cellulose hydrolyzing enzyme, and/or fungal cells producing at least one cellulose hydrolyzing enzyme is added to the vessel, in any order. After a period during which hydrolysis occurs, hydrolysis product in the form of fermentable sugars such as glucose and/or cellobiose is produced, and, if desired, is recovered.

In some embodiments, the cellulosic substrate is provided in an aqueous slurry and added to a reaction vessel. The concentration of cellulosic feedstock in the slurry depends on the material. In some embodiments, the concentration of cellulosic feedstock in the slurry is between about 1% to about 30% (w/w) undissolved solids, or any concentration therebetween, for example, from about 5% to about 20%, or from about 10% to about 20% undissolved solids, or any amount therebetween. In some embodiments, the concentration of cellulosic feedstock in the slurry comprises at least, at least about, up to, or about 1, about 2, about 3, about 4, about 5, about 6, about 7, about 8, about 9, about 10, about 11, about 12, 13, 14, about 15, about 16, about 17, about 18, about 19, about 20, about 21, about 22, about 23, about 24, about 25, about 26, about 27, about 28, about 29, or about 30% undissolved solids (w/w).

Any suitable method known in the art for generating glucose from cellulose using fungal cells producing at least one cellulose-hydrolyzing enzyme, at least one cellulose-hydrolyzing enzyme, and/or at least one enzyme mixtures find use in the present invention, including but not limited to batch hydrolysis, fed-batch hydrolysis, or continuous hydrolysis, as well as any suitable combination thereof. In some embodiments of batch processes, all the necessary materials are placed in a reactor at the start of the operation and the process is allowed to proceed until completion or until a desired endpoint, at which point the hydrolysis reaction is ended and in some embodiments, the product is harvested. In any batch process, one or more enzymes, the fungal cells producing at least one cellulose-hydrolyzing enzyme, and/or at least one enzyme mixture are added to the cellulose substrate before, during or after the introduction of the cellulose substrate to the reaction vessel. Thus, in some embodiments, the fungal cells, enzyme(s), and/or enzyme mixture(s) is added to the reaction vessel before introducing cellulosic substrate to the reaction vessel. In some other embodiments, the fungal cells, enzyme(s), and/or enzyme mixture(s) is added to the reaction vessel simultaneously with cellulosic substrate. In some other embodiments, the fungal cells, enzyme(s) and/or enzyme mixture(s) is added after introducing cellulosic substrate to the reaction vessel.

In some embodiments utilizing continuous process, cellulosic substrate is supplied and hydrolysis product is removed periodically or continuously at roughly volumetrically equal rates to maintain the hydrolysis reaction at a steady rate. Continuous processes can be performed according to any of a variety of methods known in the art, including but not limited to upflow hydrolysis processes (See e.g., U.S. Pat. No. 7,727, 746). However, it will be appreciated that any other suitable continuous process finds use in the present invention.

In some embodiments, following their withdrawal from the reactor, at least a portion of the unconverted solids are separated from the soluble hydrolysis liquor. Removal of the unconverted solids is accomplished using any suitable method, including but not limited to solids-liquid separation (e.g., by use of a filter press, belt filter, drum filter, vacuum filter, and/or membrane filter), centrifugation, settling (e.g., by use of a settling tank or an inclined settler for example, as disclosed in Knutsen and Davis, Appl., Biochem. Biotech., 98-100:1161-1172 [2002]; and Mores et al., Appl. Biochem. Biotech., 91-93:297-309 [2001]), clarification, or any other suitable process as would be known in the art. Clarification may be carried out using any suitable method known in the art. In some embodiments, a clarifier comprising a number of inclined plates to facilitate the separation of the solids and liquid or other features that are known in the art of solids-liquid separation find use. The soluble glucose, essentially free of undissolved solids, is then suitable for fermentation to ethanol. The unconverted solids are primarily lignin, which can be further utilized. For example, the unconverted solids can be burned and used as fuel or converted to generate electrical power.

In some embodiments, the unconverted solids comprise lignin, silica and/or other solid material. It is not intended that the present invention be limited to any particular unconverted solid(s). As the cellulose in the feedstock is hydrolyzed and released from the solid particles, the proportion of unconverted solids within the cellulose-containing solid particles increases. Depending on the density and particle size, the unconverted solids may be removed with the products at or settle to the bottom of the reaction vessel in a sediment or sludge. If a sludge layer forms at the bottom of the reactor due to very heavy particles, any means known in the art may be employed to remove the sludge or sediment. For example, in some embodiments, a scraper is used to remove the sludge. In some alternative embodiments, the bottom of the reactor is tapered to provide a path in which the heaviest solids settle, and then be removed and sent for processing, as desired.

In some embodiments, the fungal cells, enzyme(s), and/or enzyme mixture(s) are recovered and reused after the hydrolysis is completed or during the reaction. Recovery of the fungal cells, enzyme(s), and/or enzyme mixture(s) is accomplished using any suitable method known in the art. For example, in some embodiments, the fungal cells, enzyme(s), and/or enzyme mixture is removed from the hydrolysis liquor by precipitation (e.g., pH precipitation, salt precipitation, and/or temperature precipitation), extraction (e.g., solvent extraction), and/or filtration (e.g., ultrafiltration and/or microfiltration). It is not intended that the present invention be limited to any particular recovery method nor components. In some embodiments, the removed fungal cells, enzyme(s), and/or enzyme mixture(s) are added back to a hydrolysis reaction. In some embodiments utilizing ultrafiltration, the membrane has a molecular weight (MW) cut off of about 1,000, to about 20,000. In some embodiments, the MW cut off is from about 5,000 to about 10,000. In some embodiments, following recovery, the fungal cells, enzyme(s), and/or enzyme mixture(s) is recycled back into a reactor for further hydrolysis of additional feedstock. In some embodiments, the recycled enzyme(s) and/or enzyme mixture(s) are concentrated (e.g., by evaporation, precipitation, sedimentation and/or filtration). In some embodiments, chemicals such as glycerol, sucrose, sorbitol and the like are added to stabilize the enzyme mixture. In some additional embodiments, other chemicals, such as sodium benzoate or potassium sorbate, are added to the enzyme(s) and/or enzyme mixture(s) to prevent growth of microbial contamination.

In embodiments, the methods are conducted in a reaction volume within a suitable vessel. Any suitable vessel finds use in the present invention, including but not limited to flasks, bioprocess reactors, hydrolysis reactors, and the like. As used herein, the term "hydrolysis tower," "hydrolysis reactor," "bioprocess reactor," "hydrolysis tank," and the like refer to a reaction vessel of appropriate construction to accommodate the hydrolysis of cellulosic slurry by at least one cellulase enzyme. It should be appreciated that one or more hydrolysis reactors may be utilized, such as one or more batch or continuous stirred reactors. In some embodiments, in which more than one hydrolysis reactor is employed, the reactors are run in a series of two or more than two reactors, in which case the outlet of a first reactor feeds the inlet of a second reactor. Alternatively, in some embodiments, the reactors are run in parallel. Furthermore, in some embodiments, some of the reactors in the sequence are run in series, while others are run in parallel. Indeed, it is not intended that the present invention be limited to any particular reactor vessel, number of reactor vessels, nor any configuration of multiple reactors.

In some embodiments, the cellulose hydrolysis reaction volume is e greater than about 0.01 mL, about 0.1 mL, about 1 mL, about 10 mL, about 100 mL, about 1000 mL, or greater than about 5 L, about 10 L, about 25 L, about 50 L, about 75 L, about 100 L, about L, about 200 L, about 250 L, about 300 L, about 350 L, about 400 L, about 450 L, about 500 L, about 550 L, about 600 L, about 650 L, about 700 L, about 750 L, about 800 L, about 850 L, about 900 L, about 950 L, about 1000 L, about 5000 L, about 10,000 L, about 50,000 L, about 100,000 L, about 200,000 L, about 250,000 L, about 500,000 L, about 750,000 L, about 1,000,000 L, or greater than about 1,000,000 L. Indeed, it is not intended that the present invention be limited to any particular reaction volume, as any suitable/desired reaction volume funds use in the present invention. In some embodiments, the hydrolysis reaction mixture is agitated, unmixed, or a combination thereof. For example, in some embodiments in which the hydrolysis reaction mixture is agitated, one or more impellers, agitators, eductors, and the like are used to mix the slurry. In some other embodiments, the hydrolysis reaction mixture is "unmixed," in that no mixing (i.e., no agitation) of the reactor contents takes place during the hydrolysis reaction. In some additional embodiments, other factors, such as the percentage of dissolved oxygen and/or stirring speed are monitored and independently adjusted as needed.

Cellulosic Material

The cellulosic material used in the present invention can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of an hydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (See e.g., Wiselogel et al., in *Handbook on Bioethanol*, (Wyman, ed.), pp. 105-118, Taylor & Francis, Washington D.C. [1995]; Wyman, Biores. Technol., 50: 3-16 [1994]; Lynd, Appl. Biochem. Biotechnol., 24/25: 695-719 [1990]; Mosier et al., in *Advances in Biochemical Engineering/Biotechnology*, (Scheper, ed.), Vol. 65, pp. 23-40, Springer-Verlag, New York [1999]). It is understood herein that the cellulose used in the present invention may be in the form of lignocellulose, a plant cell wall material containing lignin, cellulose, and/or hemicellulose in a mixed matrix. In some embodiments, the cellulosic material is lignocellulose.

In some embodiments, the pretreated lignocellulose used in the methods of the present invention is a material of plant origin that, prior to pretreatment, contains at least about 10%, about 20%, about 30%, or about 40% cellulose (dry weight). In some embodiments, the lignocellulose comprises about 20, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 85, about 90% cellulose (dry weight) or any percent therebetween, and at least about 10% lignin (dry wt) to about at least 12% (dry weight). However, it is not intended that the present invention be limited to lignocellulosic material comprising any particular percentage of cellulose and/or lignin. In some embodiments, the lignocellulose is subjected to physical and/or chemical processes to make the fiber more accessible and/or receptive to the actions of cellulolytic enzymes. In some embodiments, the lignocellulosic feedstock contains higher levels of cellulose following pre-treatment, while in other embodiments, the cellulose level is not altered during the pretreatment process. For example, if acid pretreatment is employed, the hemicellulose component is hydrolyzed, which increases the relative level of cellulose. In this case, in some embodiments, the pretreated feedstock contains greater than about 20% cellulose and greater than about 12% lignin.

Lignocellulosic feedstocks that find use in the present the present invention include, but are not limited to, agricultural residues such as corn stover, wheat straw, barley straw, rice straw, oat straw, canola straw, sugarcane straw and soybean stover; fiber process residues such as corn fiber, sugar beet pulp, pulp mill fines and rejects or sugar cane bagasse; forestry residues such as aspen wood, other hardwoods, softwood, and sawdust; or grasses such as switch grass, miscanthus, cord grass, and reed canary grass. In some embodiments, the lignocellulosic feedstock is first subjected to size reduction by any of a variety of methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Glucose and Cellobiose Oxidation

Use of the compositions and methods provided herein result in hydrolysis reactions having decreased oxidation of cellobiose and/or glucose during hydrolysis of cellulose, relative to an enzyme mixture with an unmodified amount of glucose and/or cellobiose oxidizing enzyme activity, or relative to a parental enzyme mixture. Therefore, in some embodiments, the enzyme(s) and/or enzyme mixtures used herein are characterized in that oxidation of cellobiose and/or glucose is reduced or eliminated.

In some embodiments, in some methods and enzyme mixtures of the present invention, the enzyme mixture is characterized in that, when the enzyme mixture is contacted with cellobiose and/or cellulose and/or glucose (e.g., a cellobiose and/or cellulose and/or glucose substrate) no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized. For example, when the enzyme mixture is contacted with cellobiose or glucose no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose is oxidized to form cellobionolactone, cellobionic acid, gluconolactone, gluconate or gluconic acid. For example, no more than about 1%, about 2%, about 3%, about 4%, about 5%, about 6%, about 7%, about 8%, about 9%, about 10, about 11%, about 12%, about 13%, about 14%, about 15%, about 16%, about 17%, about 18%, about 19%, or about 20% (wt %) of cellobiose and/or glucose is oxidized after about 1, about 5, about 10, about 15, about 20, about 25, about 30, about 35, about 40, about 45, about 50, about 55, or about 60 minutes, or after about 1.5, about 2, about 3, about 4, about 5, about 6, about 7, about 8, about 9, about 10, about 11, about 12, about 14, about 15, about 16, about 71, about 18, about 19, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230 about 235, about 240, about 245, about 250, about 255, about 260, about 265, about 270, about 275, about 280, about 285, about 290, about 295, or about 300 hours or more. In some embodiments of the methods, the enzyme mixture is contacted with a cellulose and/or glucose substrate for a set period of time under reaction conditions at or about the optimal for enzymatic cellulose hydrolysis activity, In some embodiments in which the cellulose hydrolysis reaction is performed in batch mode, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose resulting from the hydrolysis of the cellulose substrate is oxidized after the termination of the batch mode cellulose hydrolysis reaction. In some embodiments in which the cellulose hydrolysis reaction is performed in continuous mode, no more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (wt %) of the cellobiose and/or glucose resulting from the hydrolysis of the cellulose substrate is oxidized at the time the cellulose hydrolysis reaction reaches steady state or quasi-steady state. In some embodiments, the initiation of the reaction can be the initial about 1, about 5, about 10, about 15, about 20, about 25, about 30, about 35, about 40, about 45, about 50, about 55, or 60 minutes, or about 1.5, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 hours, after the cellulose substrate and cellulase enzymes are first admixed.

Decreased conversion of cellobiose and glucose products to oxidized products such as cellobionolactone and gluconolactone can be quantified by any of a variety of suitable methods known in the art. For example, products of glucose or cellobiose oxidation can be detected and quantified using infrared spectroscopy and/or chromatographic methods such as those as described in the Examples (See also, Rakotomanga et al., J. Chromatog. B. 4:277-284 [1991]; and Mansfield et al., App. Environ. Microbiol., 64:3804-3809 [1997]). Thus, in some embodiments, total oxidation of glucose and/or cellobiose are determined, for example, as a function of total oxidation products per theoretical maximum glucose yield, or as a function of Gmax, as described herein.

In some embodiments, the assessment of the glucose and/or cellobiose oxidizing activity in an enzyme mixture is carried out under similar conditions of pH and temperature to those employed for the process of hydrolyzing cellulose as described above. For example, in some embodiments, the assessment of the glucose and/or cellobiose oxidizing activity of the enzyme mixture is carried out at a pH of about 3.0 to about 8.0, or at a pH of about 5.0 to 6.0; and at a temperature of about 30° C. to about 80° C., or at a temperature of about 50° C. to about 60° C. The concentration of glucose and/or cellobiose in the assessment is typically in a range of glucose and/or cellobiose concentrations that would be expected to be generated during the process of hydrolyzing cellulose as described herein. For example, in some embodiments, the glucose and/or cellobiose concentrations are from about 1 g/L to about 500 g/L, or from about 10 g/L to about 200 g/L, or from about 30 g/L to about 100 g/L. In some embodiments, an enzyme mixture is mixed with a solution containing both about 50% w/w glucose and about 5% w/w cellobiose or a solution containing about 50% w/w glucose alone, at about pH 5.0 and about 60° C. for about 24 hr, as set forth in the Examples, after which glucose and/or cellobiose oxidation products are quantified, for example by IR or by HPLC as described in the Examples. In some embodiments, an enzyme mixture is mixed with a solution containing about 100 g/L glucose at about pH 5.0 and about 55° C. for about 24 hr.

Additionally, when comparing the glucose and/or cellobiose oxidizing activity in an enzyme mixture to a reference (e.g., parental) enzyme mixture, the conditions of pH, temperature, and glucose/cellobiose concentration will depend upon such properties as the pH and temperature optima and stability, as well as the substrate affinity, of the particular glucose and/or cellobiose oxidizing enzymes that are present in the reference mixture and removed or inactivated in the enzyme mixture of interest. In some embodiments, the comparison is carried out at a pH and temperature range that is optimal for the reference enzyme mixture. In some other embodiments, the comparison is carried out at about pH and within temperature range that is optimal for cellulose hydrolysis reaction of the modified enzyme mixture. In some embodiments, the assessment of the glucose and/or cellobiose oxidizing activity of the enzyme mixture is carried out at a pH of about 3.0 to about 8.0, or at a pH of about 5.0 to about 6.0; and at a temperature of about 30° C. to about 80° C., or about 50° C. to about 60° C. Further, it will be appreciated that the concentration of cellobiose and/or glucose substrate in such a comparison will generally be within a range so as to readily detect oxidation products of the cellobiose and/or glucose substrate using the reference enzyme mixture. For example, in some embodiments, the concentration of cellobiose and/or glucose substrate is below a concentration that would cause substrate inhibition of the glucose and/or cellobiose oxidizing enzymes in the reference enzyme mixture. Thus, in some embodiments, the glucose and/or cellobiose concentrations generally range from about 1 g/L to about 300 g/L, or from about 10 g/L to about 100 g/L, or from about 30 g/L to about 70 g/L. In some embodiments, A analysis of glucose and/or cellobiose oxidizing activity in an enzyme mixture is carried out under similar conditions, including, pH, temperature and glucose and/or cellobiose concentrations, to those employed for the process of hydrolyzing cellulose. Further, it will be appreciated that identical conditions should be used to analyze the glucose and/or cellobiose oxidizing activity of both modified enzyme mixture and of a reference enzyme mixture.

In some embodiments, conversion of cellobiose and glucose products to oxidized products such as cellobionolactone and gluconolactone is indirectly quantified (e.g., by, measuring the total amount of glucose and cellobiose produced relative to the amount of cellulose consumed). In some cellulose hydrolysis reactions, the only significant by-products of the cellulose degradation reaction are oxidized products of cellobiose or glucose, or transglycosylation products. The presence of transglycosylation products can be distinguished from the presence of oxidized products of cellobiose or glucose using a variety of methods known in the art or otherwise provided in the Examples herein. For example in some embodiments, only transglycosylation products, but not oxidized products, are acid-hydrolyzed to form only glucose. Thus, in some embodiments, the difference between the amount of cellulose consumed and the amount of cellobiose and/or glucose present is determined, and reflects the amount of oxidized products of cellobiose or glucose, or reflects the amount of oxidized products of cellobiose or glucose and the amount of transglycosylation products. Methods of quantifying cellulose and glucose are known in the art or are otherwise provided elsewhere herein.

Cellulose Conversion to Cellobiose and/or Glucose

In some embodiments, the methods for generating glucose, as described herein, using the enzyme mixture with reduced or removed glucose and/or cellobiose oxidizing enzyme activity, and the enzyme mixture itself, are characterized as providing a higher yield of cellobiose and/or glucose from the enzymatically hydrolyzed cellulose than a corresponding process using an enzyme mixture, or an enzyme mixture itself, with an unmodified amount of glucose and/or cellobiose oxidizing enzyme activity. In some embodiments, the methods for generating glucose provided herein using the enzyme mixture with reduced or removed glucose and/or cellobiose oxidizing enzyme activity, and the enzyme mixture itself, are characterized in providing a higher yield of cellobiose and/or glucose from the enzymatically hydrolyzed cellulose than a corresponding process using a reference enzyme mixture under essentially the same pH, temperature and other conditions including, but not limited to, feedstock concentration, mineral concentration, stir rate, percent oxygenation, and other conditions relevant to those skilled in the art for reproducing cellulose hydrolysis reactions.

In reference to an "unmodified amount of glucose and/or cellobiose oxidizing enzyme activity," this phrase refers to an enzyme mixture obtained from a biological source organism in which the biological source organism has not been genetically modified or otherwise modified in such a way as to specifically target and thereby reduce the secretion, expression or activity of a glucose and/or cellobiose oxidizing enzyme, and/or the enzyme mixture has not been manipulated in such a way as to thereby reduce the amount or activity of a glucose and/or cellobiose oxidizing enzyme. In reference to a reference enzyme mixture, this term refers to an enzyme mixture obtained from a reference biological source organism that is the same biological source organism as the biological source organism that provides the enzyme mixture with reduced or removed glucose and/or cellobiose oxidizing enzyme activity, where the biological source organism has not been genetically modified in such a way as to specifically target and thereby reduce the secretion, expression or activity of a glucose and/or cellobiose oxidizing enzyme, and the enzyme mixture has not been manipulated in such a way as to thereby reduce the amount or activity of a glucose and/or cellobiose oxidizing enzyme.

As used herein in reference to a percentage of cellulose hydrolyzed by the enzyme mixture present in the form of cellobiose and/or glucose, these percentages reflect a weight percent based on the dry weight of the hydrolyzed cellulose.

Thus, in some embodiments of the methods provided herein, when the fungal cells producing at least one enzyme, at least one enzyme, and/or at least one enzyme mixture is contacted with cellulose, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% (wt %) of the cellulose hydrolyzed by the enzyme mixture is present in the form of cellobiose and/or glucose. In some embodiments, the fungal cells producing at least one enzyme, at least one enzyme, and/or at least one enzyme mixture is contacted with cellulose for a period of time of at least about 1, about 5 about 10, about 15, about 20, about 25, about 30, about 35, about 40, about 45, about 50, about 55, or about 60 minutes, or at least about 1.5, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, or about 300 hours or more.

In some embodiments in which the cellulose hydrolysis reaction is performed in batch mode, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, 9 about 8%, about 99%, or about 100% (wt %) of the cellulose hydrolyzed by the enzyme mixture is present in the form of cellobiose and/or glucose after the termination of the batch mode cellulose hydrolysis reaction. In some embodiments in which the cellulose hydrolysis reaction is performed in continuous mode, at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% (wt %) of the cellulose hydrolyzed by the enzyme mixture is present in the form of cellobiose and/or glucose at the time the cellulose hydrolysis reaction reaches steady state or quasi-steady state. In some embodiments, the initiation of the reaction can be the initial about 1, about 5, about 10, about 15, about 20, about 25, about 30, about 35, about 40, about 45, about 50, about 55, or about 60 minutes, or about 1.5, about 2, about 3, about 4, about 5, about 6, about 7, about 8, about 9, about 10, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 hours, after the cellulose substrate and cellulase enzymes are first admixed.

Enzyme Mixtures with Reduced Glucose and/or Cellobiose Oxidizing Enzyme Activity The present invention provides enzyme mixtures with reduced glucose and/or cellobiose oxidizing enzyme activity, which, when contacted with cellulose, result in a higher yield of glucose from the hydrolysis of cellulose than a corresponding method using an enzyme mixture with an unmodified amount of glucose and/or cellobiose oxidizing enzyme activity. In some embodiments, the enzyme mixture is characterized as providing a higher yield of cellobiose and/or glucose from the enzymatically hydrolyzed cellulose than a corresponding process using a reference enzyme mixture. In some embodiments, the enzyme mixture is characterized as causing decreased conversion of the cellobiose and glucose products in the enzymatic hydrolysate to oxidized products such as cellobionolactone and gluconolactone relative to an enzyme mixture with an unmodified amount of glucose and/or cellobiose oxidizing enzyme activity, or relative to a reference enzyme mixture.

In some embodiments, an enzyme mixture with reduced glucose and/or cellobiose oxidizing enzyme activity is treated to reduce the amount of glucose and/or cellobiose oxidizing enzyme in the enzyme mixture. It will be readily appreciated that any of a variety of technologies known in the art can be employed to reduce the amount of glucose and/or cellobiose oxidizing enzyme from the enzyme mixture, including but not limited to purification processes that selectively remove one or more glucose and/or cellobiose oxidizing enzyme activity from the enzyme mixture. In some embodiments, inhibitors of glucose and/or cellobiose oxidizing enzyme activity are added to the enzyme mixture. Additional embodiments include the use of genetically modified fungal cells to reduce the amount of one or more endogenous glucose and/or cellobiose oxidizing enzymes secreted by the fungal cell.

Purification Processes. In some embodiments, the enzyme mixture is subjected to a purification process to selectively separate one or more glucose and/or cellobiose oxidizing enzymes from the enzyme mixture. In some embodiments, the purification process comprises removing the glucose and/or cellobiose oxidizing enzyme from the enzyme mixture using an affinity-based stationary phase. Affinity-based purification technologies are well known in the art, and include any method to selectively bind a component of a biological mixture to a solid support based on a highly specific biological interaction such as that between antigen and antibody or enzyme and substrate. Thus, affinity-based methodologies include contacting the enzyme mixture with beads or any other suitable solid support that comprises antibodies or other molecules that selectively bind to and immobilize the glucose and/or cellobiose oxidizing enzyme, while the remaining components of the enzyme mixture remain in solution. Some examples include chromatography methods either in batch form or column form. The solid support can comprise individual particles (e.g., chromatography resin beads) or contiguous supports (e.g., arrays). Ligands immobilized on a solid support matrix can then be employed to purify targets from complex solutions. Conventional chromatography supports, as well as standard methods for grafting antibodies well known in the art and are described in numerous standard textbooks. These methods include the use of tubes, particles such as beads and any other suitable solid support. For example, particles are available in a large variety of different materials, including silica, glass, cellulose, agarose, and a wide variety of different polymers, including polystyrene polymethylmethacrylate, polyacrylamide, agarose, hydrogel, acrylic resins, and other types of gels used for electrophoresis. These supports may be purchased with ligands pre-attached or alternatively, the ligands can be indirectly attached or directly immobilized on the support using standard methods well known to those skilled in the art (See e.g., Biancala et al., Lett. Peptide Sci., 7:297 [2000]; MacBeath et al., Science, 289:1760-1763 [2000]; Cass et al., (eds.), Proc. Thirteenth Am. Peptide Symp., Leiden, Escom, 975-979 [1994]; U.S. Pat. No. 5,576,220; Cook et al, Tetrahed. Lett., 35:6777-6780 [1994]).

In some embodiments, the stationary phase comprises antibodies and/or any other molecule that selectively binds the glucose and/or cellobiose oxidizing enzyme, such an antibody fragments (e.g., a Fab, Fab' or F(ab')$_2$). Strategies for depletion of specific proteins in a complex mixture of proteins are well known (See e.g., Bjorhall et al. Proteomics 5:307-317 [2005]). In some embodiments, the stationary phase comprises antibodies directed toward glucose oxidase (EC 1.1.3.4), cellobiose dehydrogenase (EC 1.1.99.18), pyranose oxidase (EC1.1.3.10), glucooligosaccharide oxidase (EC 1.1.99.B3), pyranose dehydrogenase (EC 1.1.99.29) or glucose dehydrogenase (EC 1.1.99.10).

In embodiments, the stationary phase comprises molecules that selectively bind the glucose and/or cellobiose oxidizing enzyme(s). For example, in some embodiments, a binding protein, substrate, substrate analogue or other small molecule is coupled to the stationary phase to selectively bind the enzyme of interest. In some embodiments, the stationary phase comprises a glucose and/or cellobiose linked to the stationary phase. In some other embodiments, the stationary phase comprises a flavin adenine dinucleotide (FAD) linked to the stationary phase.

It will be appreciated that any of a variety of other purification methodologies are useful in the selective removal of one or more glucose and/or cellobiose oxidizing enzymes from the enzyme mixture. For example, in some embodiments, the purification methodology comprises fractionation methods including selective precipitation such as ammonium sulfate precipitation, isoelectric precipitation, selective thermal denaturation, or any other method which selectively precipitates glucose and/or cellobiose oxidizing enzymes from the enzyme mixture, while leaving other components of the enzyme mixture in solution, or vice versa. In some other embodiments, the purification methodologies comprise chromatographic methods including gel filtration, size exclusion, anionic exchange, cationic exchange, gel electrophoresis, and/or other chromatic separation method known in the art for physically separating proteins.

Oxidase Inhibitors. In some embodiments, reducing the amount of glucose and/or cellobiose oxidizing enzyme activity from the enzyme mixture employs the addition of one or more glucose and/or cellobiose oxidizing enzyme inhibitor(s) to the enzyme mixture Inhibitors of glucose and/or cellobiose oxidizing enzymes range from broad-spectrum oxidase inhibitors to specific inhibitors of glucose and/or cellobiose oxidizing enzymes, as described herein.

In some embodiments, a broad-spectrum oxidase inhibitor is added to the enzyme mixture. Broad-spectrum oxidase inhibitors are well-known in the art. Some examples include but are not limited to mercuric chloride, silver sulphate, hydrazine compounds such as aminoguanidine, semicarbazide, benserazide, oxalic dihydrazide, hydralazine, phenylhydrazine, carbidopa, diaminoguanidine, and copper chelators such as desferrioxamine, EDTA, sodium azide, potassium cyanide, triene 5, o-phenanthroline, histidine and a number of metal anions such as $Ag^+$, $Hg^{2+}$, and $Zn^{2+}$.

In some embodiments, a specific inhibitor of glucose and/or cellobiose oxidizing enzymes is added to the enzyme mixture. Specific inhibitors of cellobiose dehydrogenase include but are not limited to substrate analogues and other specific inhibitors such as cellobioimidazole, gentiobiose, lactobiono-1,5-lactone, celliobono-1,5-lactone, tri-N-acetylchitortriose, methyl-beta-D-cellobiosidase, 2,2-bipyridine, and/or cytochrome C. Specific inhibitors of glucose oxidase, pyranose oxidase, glucooligosaccharide oxidase, pyranose dehydrogenase, and glucose dehydrogenase include but are not limited to substrate analogues and other specific inhibitors.

Genetically Modified Fungal Cells. In some embodiments, the enzyme mixture is produced by a fungal cell that has been genetically modified to reduce the amount of the endogenous glucose and/or cellobiose oxidizing enzyme activity that is secreted by the fungal cell.

Genetic modifications contemplated herein reduce the enzymatic activity of glucose and/or cellobiose oxidizing enzymes produced by a fungal cell. Any glucose and/or cellobiose oxidizing enzyme known in the art can be targeted for reduction of activity by genetic modification. For example, glucose and/or cellobiose oxidizing enzymes include glucose oxidase (EC 1.1.3.4), cellobiose dehydrogenase (EC 1.1.99.18), pyranose oxidase (EC 1.1.3.10), glucooligosaccharide oxidase (EC 1.1.99.B3), pyranose dehydrogenase (EC 1.1.99.29), and glucose dehydrogenase (EC 1.1.99.10). Each of these glucose and/or cellobiose oxidizing enzymes are described in the four Provisional applications to which the present application claims priority (e.g., U.S. Prov. Patent Appln. Ser. Nos. 61/409,186, 61/409,217, 61/409,472, and 61/409,480, all of which were filed on Nov. 2, 2010 and are hereby incorporated by reference herein).

Pretreatment.

In some embodiments, a substrate of the enzyme mixture comprises pretreated cellulosic material. Thus, for example, in processes described herein, any pretreatment process known in the art can be used to disrupt plant cell wall components of cellulosic material (See e.g., Chandra et al., Adv. Biochem. Engin./Biotechnol., 108: 67-93 [2007]; Galbe and Zacchi, Adv. Biochem. Engin./Biotechnol., 108: 41-65 [2007]; Hendriks and Zeeman, Biores. Technol., 100:10-18 [2009]; Mosier et al., Biores. Technol., 96: 673-686 [2005];

Taherzadeh and Karimi, Int. J. Mol. Sci., 9:1621-1651 [2008]; and Yang and Wyman, Biofuels Bioprod. Bioref.-Biofpr. 2: 26-40 [2008]).

In some embodiments, the cellulosic material is subjected to particle size reduction, pre-soaking, wetting, washing, and/or conditioning prior to pretreatment, using any of a variety of methods known in the art.

In some embodiments, conventional pretreatments that find use in the present invention include, but are not limited to, steam pretreatment (with or without explosion), dilute acid pretreatment, hot water pretreatment, alkaline pretreatment, lime pretreatment, wet oxidation, wet explosion, ammonia fiber expansion, dilute ammonia pretreatment, organosolv pretreatment, and/or biological pretreatment. Additional pretreatments include, but are not limited to ammonia percolation, ultrasound, electroporation, microwave, supercritical $CO_2$, supercritical $H_2O$, ozone, and gamma irradiation pretreatments.

In some embodiments, the cellulosic material is pretreated before hydrolysis and/or fermentation. In some embodiments, pretreatment is performed prior to the hydrolysis. In some alternative embodiments, the pretreatment is carried out simultaneously with enzyme hydrolysis to release fermentable sugars, such as glucose, xylose, and/or cellobiose. In some embodiments, the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions (e.g., hemicelluloses), accessible to enzymes. Cellulosic material is passed to or through a reaction vessel where steam is injected to increase the temperature to the required temperature and pressure and is retained therein for the desired reaction time. Steam pretreatment is preferably done at about 140° C. to about 230° C., or from about 160° C. to about 200° C., or about 170° C. to about 190° C., where the optimal temperature range depends on any addition of a chemical catalyst. In some embodiments, residence time for the steam pretreatment is from about 1 to about 15 minutes, or about 3 to about 12 minutes, or about 4 to about 10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (See e.g., U.S. Pat. No. 4,451,648; Duff and Murray, Biores. Technol., 855: 1-33 [1996]; Galbe and Zacchi, Appl. Microbiol. Biotechnol., 59:618-628 [2002]; and U.S. Pat. Appln. Pub. No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (See e.g., Ballesteros et al., Appl. Biochem. Biotechnol., 129-132: 496-508 [2006]; Varga et al., Appl. Biochem. Biotechnol., 113-116:509-523 [2004]; Sassner et al., Enzyme Microb. Technol., 39:756-762 [2006]).

Chemical Pretreatment. Examples of suitable chemical pretreatment processes include, but are not limited to, dilute acid pretreatment, dilute alkali pretreatment (See e.g., U.S. Pat. Appln. Pub. Nos. 2007/0031918 and 2007/0037259), lime pretreatment, wet oxidation, ammonia fiber/freeze explosion or expansion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs (e.g., plug-flow reactors, counter-current reactors, or continuous counter-current shrinking bed reactors; See e.g., Duff and Murray, Biores. Technol., 855: 1-33 [1996]; Schell et al., Biores. Technol., 91:179-188 [2004]; and Lee et al., Adv. Biochem. Eng. Biotechnol., 65: 93-115 [1999]).

Any suitable methods for pretreatment under alkaline conditions also find use. These alkaline pretreatments include, but are not limited to, lime pretreatment, wet oxidation, ammonia percolation (APR), ammonia fiber/freeze expansion (AFEX) and dilute ammonia pretreatment.

Lime pretreatment is performed with calcium carbonate, sodium hydroxide, or ammonia at low temperatures of 85-150° C. and residence times from 1 hour to several days (See e.g., Wyman et al., Biores. Technol., 96:1959-1966 [2005]; Mosier et al., Biores. Technol., 96:673-686 [2005]; WO 2006/110891; WO 2006/11899; WO 2006/11900; and WO 2006/110901).

Wet oxidation is a thermal pretreatment performed typically at 180-200° C. for 5-15 minutes with addition of an oxidative agent such as hydrogen peroxide or over-pressure of oxygen (See e.g., Schmidt and Thomsen, Biores. Technol., 64:139-151 [1998]; Palonen et al., Appl. Biochem. Biotechnol., 117:1-17 [2004]; Varga et al., Biotechnol. Bioeng., 88:567-574 [2004]; Martin et al., J. Chem. Technol. Biotechnol., 81:1669-1677 [2006]). In some embodiments, the pretreatment is performed at about 1% to about 40% dry matter, or about 2% to about 30% dry matter, or about 5% to about 20% dry matter, and often the initial pH is increased by the addition of alkali such as sodium carbonate.

A modification of the wet oxidation pretreatment method, known as "wet explosion" (i.e., the combination of wet oxidation and steam explosion), can handle dry matter up to 30%. In wet explosion, the oxidizing agent is introduced during pretreatment after a certain residence time. The pretreatment is then ended by flashing to atmospheric pressure (See e.g., WO 2006/032282).

Ammonia fiber expansion (AFEX) involves treating cellulosic material with liquid or gaseous ammonia at moderate temperatures such as 90-100° C. and high pressure such as 17-20 bar for 5-10 minutes, where the dry matter content can be as high as 60% (See e.g., Gollapalli et al., Appl. Biochem. Biotechnol., 98:23-35 [2002]; Chundawat et al., Biotechnol. Bioeng., 96:219-231 [2007]; Alizadeh et al., Appl. Biochem. Biotechnol., 121:1133-1141 [2005]; Teymouri et al., Biores. Technol., 96:2014-2018 [2005]). AFEX pretreatment results in the depolymerization of cellulose and partial hydrolysis of hemicellulose. Lignin-carbohydrate complexes are cleaved. Dilute ammonia pretreatment utilizes more dilute solutions of ammonia than AFEX and may be conducted at a temperature of about 100-150° C., or any temperature therebetween (See e.g., U.S. Pat. Appln. Pub. Nos. 2007/0031918 and 2007/0037259). The duration of the dilute ammonia pretreatment may be 1-20 minutes, or any duration therebetween.

Organosolv pretreatment delignifies cellulosic material by extraction using aqueous ethanol (40-60% ethanol) at 160-

200° C. for 30-60 minutes (See e.g., Pan et al., Biotechnol. Bioeng., 90:473-481 [2005]; Pan et al., Biotechnol. Bioeng., 94:851-861 [2006]; and Kurabi et al., Appl. Biochem. Biotechnol., 121:219-230 [2005]). Sulphuric acid is usually added as a catalyst. In organosolv pretreatment, the majority of hemicellulose is removed.

There are various other suitable methods for pretreatment that find use in the present invention (See e.g., Schell et al., Appl. Biochem. Biotechnol., 105-108:69-85 [2003]; and Mosier et al., Biores. Technol., 96:673-686 [2005]; and U.S. Pat. Appln. Publ. No. 2002/0164730).

In some embodiments, the chemical pretreatment is carried out as an acid treatment. In some alternative embodiments, it is a continuous dilute and/or mild acid treatment. In some embodiments, the acid is sulfuric acid, but other acids also find use, including but not limited tonitric acid, phosphoric acid, hydrogen chloride, and/or mixtures thereof. Mild acid treatment is conducted in the pH range of about 1 to about 5, or about 1 to about 4, or about 1 to about 3. In some embodiments, the acid concentration is in the range from about 0.01 to about 20 wt % acid, or about 0.05 to about 10 wt % acid, or about 0.1 to about 5 wt % acid, or about 0.2 to about 2.0 wt % acid. The acid is contacted with cellulosic material and held at a temperature in the range of about 160° C. to about 220° C., or for about 165° C. to about 195° C., for periods ranging from seconds to minutes (e.g., about 1 second to about 60 minutes).

In some other embodiments, pretreatment is carried out as an ammonia fiber expansion step (AFEX pretreatment step).

In some embodiments, pretreatment takes place in an aqueous slurry. In some embodiments, cellulosic material is present during pretreatment in amounts between about 10 to about 80 wt %, or about 20 to about 70 wt %, or between about 30 to about 60 wt %, such as around 50 wt %. In some embodiments, the pretreated cellulosic material is unwashed, while in some other embodiments, it is washed using any method known in the art (e.g., washed with water).

Mechanical Pretreatment. Any suitable methods of mechanical pretreatment find use in the present invention.

Physical Pretreatment. As used herein, the term "physical pretreatment" refers to any pretreatment that promotes the separation and/or release of cellulose, hemicellulose, and/or lignin from cellulosic material. For example, in some embodiments, physical pretreatment involves irradiation (e.g., microwave irradiation), steaming/steam explosion, hydrothermolysis, and combinations thereof.

In some embodiments, physical pretreatment involves high pressure and/or high temperature (steam explosion). In some embodiments, "high pressure" means pressure in the range of about 300 to about 600 psi, or about 350 to about 550 psi, or about 400 to about 500 psi, such as around 450 psi. In some other embodiments, "high temperature" means temperatures in the range of about 100° C. to about 300° C., or about 140° C. to about 235° C. In some embodiments, mechanical pretreatment is performed in a batch-process, steam gun hydrolyzer system that uses high pressure and high temperature as defined above (e.g., a Sunds Hydrolyzer available from Sunds Defibrator AB, Sweden).

Combined Physical and Chemical Pretreatment. In some embodiments, cellulosic material is pretreated both physically and chemically. For instance, in some embodiments, the pretreatment step involves dilute or mild acid treatment and high temperature and/or pressure treatment. The physical and chemical pretreatments can be carried out sequentially or simultaneously, as desired. In some embodiments, a mechanical pretreatment is also included.

Accordingly, in some embodiments, cellulosic material is subjected to mechanical, chemical, and/or physical pretreatment, or any combination thereof, to promote the separation and/or release of cellulose, hemicellulose, and/or lignin.

Biological Pretreatment. In some embodiments, biological pretreatment processes find use in the present invention. Biological pretreatment techniques can involve applying lignin-solubilizing microorganisms (See e.g., Hsu, "Pretreatment of Biomass," in *Handbook on Bioethanol: Production and Utilization* (Wyman, ed.), Taylor & Francis, Washington, D.C., pp. 179-212 [1996]; Ghosh and Singh, Adv. Appl. Microbiol., 39:295-333 [1993]; McMillan, "Pretreating Lignocellulosic Biomass: a Review, in *Enzymatic Conversion of Biomass for Fuels Production* (Himmel et al. eds.), ACS Symposium Series 566, American Chemical Society, Washington, D.C., chapter 15 [1994]; Gong et al., 65: 207-241 [1999]; Olsson and Hahn-Hagerdal, Enz. Microb. Tech., 18:312-331 [1996]; and Vallander and Eriksson, Adv. Biochem. Eng./Biotechnol., 42:63-95 [1990]).

In some embodiments, the soluble compounds derived from pretreatment process are subsequently separated from the solids. For example, in some embodiments, the separation step comprises one or more of standard mechanical means such as screening, sieving, centrifugation, and/or filtration to achieve the separation. In some other embodiments, the soluble compounds are not separated from the solids following pretreatment. It will be appreciated that pretreatment may be conducted as a batch, fed-batch or continuous process. It will also be appreciated that pretreatment may be conducted at low, medium or high solids consistency (See e.g., WO 2010/022511).

Fermentation

In some embodiments, the methods for generating glucose provided herein further comprise fermentation of the resultant fermentable sugars (e.g., glucose) to an end product. Especially suitable fermenting organisms are able to ferment (i.e., convert), sugars, such as glucose, fructose, maltose, xylose, mannose and/or arabinose, directly or indirectly into at least one desired end product.

In some embodiments, yeast that find use in the present invention include, but are not limited to strains of the genus *Saccharomyces* (e.g., strains of *Saccharomyces cerevisiae* and *Saccharomyces uvarum*), strains of the genus *Pichia* (e.g., *Pichia stipitis*, such as *Pichia stipitis* CBS 5773 and *Pichia pastoris*), strains of the genus *Candida* (e.g., *Candida utilis, Candida arabinofermentans, Candida diddensii, Candida sonorensis, Candida shehatae, Candida tropicalis*, and *Candida boidinii*). Other fermenting organisms include, but are not limited to strains of *Zymomonas, Hansenula* (e.g., *Hansenula polymorphs* and *Hansenula anomala*), *Kluyveromyces* (e.g., *Kluyveromyces fragilis*), and *Schizosaccharomyces* (e.g., *Schizosaccharomyces pombe*).

Suitable bacterial fermenting organisms include, but are not limited to strains of *Escherichia* (e.g., *Escherichia coli*), strains of *Zymomonas* (e.g., *Zymomonas mobilis*), strains of *Zymobacter* (e.g., *Zymobactor palmae*), strains of *Klebsiella* (e.g., *Klebsiella oxytoca*), strains of *Leuconostoc* (e.g., *Leuconostoc mesenteroides*), strains of *Clostridium* (e.g., *Clostridium butyricum*), strains of *Enterobacter* (e.g., *Enterobacter aerogenes*), and strains of *Thermoanaerobacter* (e.g., *Thermoanaerobacter* BG1L1; See, Appl. Microbiol, Biotech. 77: 61-86; *Thermoanaerobacter ethanolicus, Thermoanaerobacter thermosaccharolyticum*, and *Thermoanaerobacter mathranii*). Strains of *Lactobacillus* also find use in the present invention, as well as strains of *Corynebacterium glutamicum* R, *Bacillus thermoglucosidaisus*, and *Geo-* bacillus thermoglucosidasius. Indeed, it is not intended that the present invention be limited to any particular fermenting organism.

The fermentation conditions depend on the desired fermentation product and can easily be determined by one of ordinary skill in the art. In some embodiments involving ethanol fermentation by yeast, the fermentation occurs for between about 1 and about 120 hours, or between about 12 and about 96 hours. In some embodiments, the fermentation is carried out at a temperature between about 20 to about 40° C., or about 26 to about 34° C., or about 32° C. In some embodiments, the fermentation pH is from pH about 3 to about 7, or about pH about 4 to about 6.

In some embodiments, enzymatic hydrolysis and fermentation are conducted in separate vessels so that each biological reaction can occur under its respective optimal conditions (e.g., temperature). In some other embodiments, the process for producing glucose from cellulose described herein is conducted simultaneously with fermentation in a simultaneous saccharification and fermentation (SSF). SSF is typically carried out at temperatures of about 28° C. to about 50° C., or about 30° C. to about 40° C., or about 35° C. to about 38° C., which is a compromise between the about 50° C. optimum for most cellulase enzyme mixtures and the about 28° C. to about 30° C. optimum for growth of most yeast.

Accordingly, in some embodiments, the methods for generating glucose further comprise fermentation of the glucose to at least one end product. It is not intended that the present invention be limited to any particular end product, as the methods of the present invention are suitable to produce a variety of end products. In some embodiments, the end products include, but are not limited to fuel alcohols and/or precursor industrial chemicals. For example, in some embodiments, the fermentation products include precursor industrial chemicals such as alcohols (e.g., ethanol, methanol, butanol); organic acids (e.g., butyric acid, citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, 812, beta-carotene); and/or hormones. In some embodiments, the end product is a fuel alcohol. Suitable fuel alcohols are known in the art and include, but are not limited to lower alcohols such as methanol, ethanol, butanol, and propyl alcohols.

Increased Expression of Saccharide Hydrolysis Enzymes

In some embodiments provided herein, the fungal cell is further genetically modified to increase its production of one or more saccharide hydrolysis enzymes. In some embodiments, the fungal cell overexpresses at least one homologous and/or heterologous gene encoding a saccharide hydrolysis enzyme (e.g., beta-glucosidase). It is not intended that the present invention be limited to any particular enzyme(s), as numerous enzymes find use in the present invention. In some embodiments, the enzyme is any one of a variety of endoglucanases, cellobiohydrolases, beta-glucosidases, endoxylanases, beta-xylosidases, arabinofuranosidases, alpha-glucuronidases, acetylxylan esterases, feruloyl esterases, alpha-glucuronyl esterases, and/or any other enzyme involved in saccharide hydrolysis. In some embodiments, the fungal cell is genetically modified to increase expression of beta-glucosidase. Thus, in some embodiments, a fungal cell comprises a polynucleotide sequence for increased expression of beta-glucosidase-encoding polynucleotide and further can be genetically modified to delete polynucleotides encoding one or more endogenous glucose and/or cellobiose oxidizing enzymes.

In some embodiments, the saccharide hydrolysis enzyme is endogenous to the fungal cell. In some embodiments, the saccharide hydrolysis enzyme is exogenous to the fungal cell. In some other embodiments, the enzyme mixture further comprises a saccharide hydrolysis enzyme that is heterologous to the fungal cell. Still further, in some embodiments, the process for generating glucose comprises contacting cellulose with an enzyme mixture that comprises a saccharide hydrolysis enzyme that is heterologous to the fungal cell.

In some embodiments, the fungal cells of the present invention are genetically modified to increase the expression of a saccharide hydrolysis enzyme using any of a variety of methods that are known to those of skill in the art. In some embodiments, the hydrolysis enzyme-encoding polynucleotide sequence is adapted for increased expression in a host fungal cell.

EXPERIMENTAL

The following examples, including experiments and results achieved, are provided for illustrative purposes only and are not to be construed as limiting the present invention.

In the experimental disclosure below, the following abbreviations apply: ppm (parts per million); M (molar); mM (millimolar); uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); HPLC (high pressure liquid chromatography); MES (2-N-morpholino ethanesulfonic acid); FIOPC (fold improvements over positive control); YPD (10 g/L yeast extract, 20 g/L peptone, and 20 g/L dextrose); SOE-PCR (splicing by overlapping extension PCR); ARS (ARS Culture Collection or NRRL Culture Collection, Peoria, Ill.); Axygen (Axygen, Inc., Union City, Calif.); Lallemand (Lallemand Ethanol Technology, Milwaukee, Wis.); Dual Biosystems (Dual Biosystems AG, Schlieven, Switzerland); Alphalyse (Alphalyse Inc., Palo Alto, Calif.); Dyadic (Dyadic International, Inc., Jupiter, Fla.); Promega (Promega, Inc., Madison, Wis.); Megazyme (Megazyme International Ireland, Ltd., Wicklow, Ireland); McMaster (McMaster Regional Centre for Mass Spectrometry in Hamilton, Ontario, Canada); Sigma-Aldrich (Sigma-Aldrich, St. Louis, Mo.); Dasgip (Dasgip Biotools, LLC, Shrewsbury, Mass.); Difco (Difco Laboratories, BD Diagnostic Systems, Detroit, Mich.); PCRdiagnostics (PCRdiagnostics, by E coli SRO, Slovak Republic); Agilent (Agilent Technologies, Inc., Santa Clara, Calif.); Molecular Devices (Molecular Devices, Sunnyvale, Calif.); Symbio (Symbio, Inc., Menlo Park, Calif.); Sartorius (Sartorius AG, Goettingen, Germany); Finnzymes (part of Thermo Fisher Scientific, Lafayette, Colo.); Dionex (now part of Thermo Fisher Scientific, Lafayette, Colo.); Idex (Idex Health and Science Group, Oak Harbor, Wash.); Microbeads (Microbeads A/S, Skedsmokorset, Norway); Calbiochem (Calbiochem-Novabiochem International, Inc., La Jolla, Calif.); Newport (Newport Scientific, Australia); and Bio-Rad (Bio-Rad Laboratories, Hercules, Calif.).

The following polynucleotide and polypeptide sequences find use in the present invention. As shown below, the polynucleotide sequence is followed by the encoded polypeptide.

*M. thermophila* G01:

(SEQ ID NO: 1)

ATGGGCTTCCTCGCCGCCACTCTTGTGTCCTGTGCCGCTCTCGCGAGCGCAGCAA
GCATCCCACGTCCCCATGCCAAGCGCCAGGTCTCCCAGCTTCGCGACGATTATGA
CTTCGTGATCGTTGGCGGTGGAACTAGCGGCCTCACTGTAGCCGATCGGCTGACA
GAGGCCTTTCCAGCCAAGAACGTCCTTGTCATTGAGTATGGAGACGTCCACTACG
CCCCGGGAACCTTCGATCCGCCGACGGACTGGATCACACCTCAGCCTGATGCCC
CCCCTTCCTGGTCTTTCAATTCCCTCCCCAACCCAGACATGGCAAACACAACAGC
GTTTGTGCTAGCCGGCCAAGTGGTGGGTGGAAGCAGTGCCGTGAACGGCATGTT
CTTTGACCGCGCATCCCGCCACGACTACGATGCGTGGACCGCGGTCGGCGGGTC
CGGGTTCGAACAGTCCAGCCACAAGTGGGACTGGGAGGGGCTGTTCCCTTTCTTC
CAGAAGAGCGTCACGTTCACGGAACCGCCGGCCGACATCGTCCAGAAGTATCAC
TACACCTGGGACCTGTCTGCCTACGGCAATGGCTCAACCCCCATCTACAGCAGCT
ATCCGGTCTTCCAGTGGGCCGACCAGCCGTTACTTAACCAGGCATGGCAGGAGA
TGGGAATCAATCCGGTGACCGAATGCGCCGGCGGCGACAAGGAGGGTGTCTGCT
GGGTTCCCGCCTCGCAGCACCCTGTCACGGCGAGGAGGTCGCACGCCGGGCTCG
GCCACTACGCCGATGTGCTCCCGCGAGCCAATTACGACCTCCTCGTTCAACACCA
GGTTGTCAGGGTAGTATTCCCCAATGGGCCGAGCCACGGACCGCCGCTTGTCGA
GGCGCGGTCCCTGGCCGACAACCACCTGTTCAACGTGACTGTGAAGGGCGAAGT
CATCATCTCGGCGGGCGCTCTGCACACCCCGACCGTCCTTCAACGGAGCGGCATC
GGCCCGGCATCCTTCTTGGACGACGCCGGGATCCCCGTGACGCTTGACCTGCCGG
GCGTCGGCGCCAACCTCCAGGACCACTGCGGTCCGCCCGTCACGTGGAACTACA
CCGAGCCCTACACCGGCTTCTTCCCGCTCCCCTCCGAGATGGTCAACAACGCGAC
CTTCAAAGCCGAAGCCATCACCGGCTTCGACGAGGTCCCGGCCCGCGGCCCCTA
CACGCTCGCCGGGGGCAACAACGCCATCTTCGTATCGCTCCCACACCTCACGGCC
GACTACGGCGCCATCACCGCAAATATCCGCGCCATGGTCGCCGACGGAACCGCC
GCCTCCTATCTCGCGGCCGACGTCCGCACCATCCCGGGGATGGTGGCCGGCTAC
GAGGCCCAGCTCCTCGTGCTCGCCGACCTGCTCGACAACCCGGAGGCGCCCAGC
CTGGAGACGCCGTGGGCGACGAGCGAGGCGCCGCAGACGTCGTCGGTCCTGGCC
TTCCTGCTGCACCCGCTCAGCCGCGGCAGCGTGCGGCTCAACCTCAGCGACCCGC
TCGCGCAGCCCGTGCTCGACTACGCTCCGGGTCCAACCCGGTCGACATCGACCT
GCACCTCGCCCACGTGCGCTTCCTGCGCGGCCTGCTCGACACGCCCACCATGCAG
GCCCGCGGGCGCTCGAGACGGCCCCCGGCTCGGCCGTGGCCGACAGCGACGAG
GCGCTGGGGGAGTACGTGCGCTCGCACAGCACGCTGTCCTTCATGCACCCGTGCT
GCACGGCCGCCATGCTGCCCGAGGACCGGGGCGGCGTCGTCGGGCCGGACCTCA
AGGTGCACGGGGCCGAGGGCCTGAGGGTCGTGGACATGAGCGTGATGCCGCTGT
TGCCGGGGGCGCACCTGAGCGCCACTGCTTATGCGGTGGGGGAGAAAGCTGCGG
ATATTATCATCCAGGAGTGGATGGACAAGGAGCAGTGA (SEQ ID NO: 2)

MGFLAATLVSCAALASAASIPRPHAKRQVSQLRDDYDFVIVGGGTSGLTVADRLTE
AFPAKNVLVIEYGDVHYAPGTFDPPTDWITPQPDAPPSWSFNSLPNPDMANTTAFVL
AGQVVGGSSAVNGMFFDRASRHDYDAWTAVGGSGFEQSSHKWDWEGLFPFFQKS

-continued

VTFTEPPADIVQKYHYTWDLSAYGNGSTPIYSSYPVFQWADQPLLNQAWQEMGINP

VTECAGGDKEGVCWVPASQHPVTARRSHAGLGHYADVLPRANYDLLVQHQVVRV

VFPNGPSHGPPLVEARSLADNHLFNVTVKGEVIISAGALHTPTVLQRSGIGPASFLDD

AGIPVTLDLPGVGANLQDHCGPPVTWNYTEPYTGFFPLPSEMVNNATFKAEAITGFD

EVPARGPYTLAGGNNAIFVSLPHLTADYGAITANIRAMVADGTAASYLAADVRTIPG

MVAGYEAQLLVLADLLDNPEAPSLETPWATSEAPQTSSVLAFLLHPLSRGSVRLNLS

DPLAQPVLDYRSGSNPVDIDLHLAHVRFLRGLLDTPTMQARGALETAPGSAVADSD

EALGEYVRSHSTLSFMHPCCTAAMLPEDRGGVVGPDLKVHGAEGLRVVDMSVMPL

LPGAHLSATAYAVGEKAADIIIQEWMDKEQ

*M. thermophila* GO2:

(SEQ ID NO: 3)
ATGGAGCTGCTTCGAGTCTCCCTCGCCGCTGTTGCACTCTCCCCATTAATATTATT

CGGCGTTGCAGCCGCCCACCCTACCGCCCGATCCATTGCCCGCTCCACGATTCTT

GACGGAGCCGATGGCCTTCTTCCGGAGTATGACTACATCATCATCGGGGGCGGC

ACGTCCGGATTGACTGTCGCCGACAGACTCACGGAGAATAGAAAGCGCAAGTTT

TCCCGCTCTCCCCTCCCAACGTCACCCGCCCGATCGTCACCGGCGTGGTGTTATT

CTGTTCTTGTTTTGGAAAGAGGCATTTTCCAGAACTCTAGCTCGGTGACCACCAT

TTCTGGGGGAAGCAGAGGCCTCTTCGATCCAAGTCTGACCTTCAACATCAACTCC

GTTCCCCAAGCTGGGCTGGACAACCGCAGCATTGCCGTCATTGGCGGGTTGATCC

TCGGCGGCAGCTCCGGCGTCAACGGGCTTCAAGTCCTCCGTGGACAAAGAGAAG

ACTATGACCGCTGGGGATCGTACTTTGGGCCAAACTCTGACTGGAGTTGGAAAG

GTCTCCTGCCGTATTTCAAGAAGGCATGGAATTTCCATCCGCCCAGGCCAGAGCT

GGTCAGTCAGTTCGACATCAAGTACGACCCCAGCTACTGGGGCAACACGTCTGA

CGTGCACGCATCTTTCCCAACCACTTTCTGGCCGGTGCTCAAATTGGAGATGGCT

GCATTTGGTGACATCCCTGGGGTCGAATATCCGCCCGACTCTGCTTCTGGCGAGA

CCGGGGCGTATTGGCACCCAGCGTCCGTTGACCCAGCGACAGTCCTCCGCTCCTT

CGCTCGGCCCGCGCATTGGGACAACATTGAGGCGGCACGTCCCAATTACCACAC

CCTGACCGGGCAACGCGTATTGAAGGTCGCATTTGATGGCAATCGAGCGACCAG

CGTCGTCTTCGTGCCGGCGAATGCAACGGATCACAGCACTGCCAGGTCCGTGAA

GGCCAAGAAGGAGATCGTCTTGGCCGCCGGCGCCATTCACACGCCCCAAATCCT

ACAGGCGAGCGGAGTAGGGCCGAAGCAGGTCCTGAAGGAAGCAGGCGTGCCGC

TTGTCGTTGACGCTCCCGGTGTCGGCAGCAATTTCCAAGACCAGCCGTATGTGGT

TGCTCCCACCTTCAATTTTACCAAGTTCCCCTTCCACCCGGACTTCTACGACATGA

TTCTGAACCAGACTTTTATCGCCGAGGCTCAGGCCCAGTTTGAAAAGGACCGTAC

CGGACCTCACACCATCGCATCCGGCTATTGCGGCAGCTGGCTCCCCCTCCAGATC

ATTGCCCCAAATTCGTGGAAGGACATCGCTAGGCGGTACGAATCCCAAGACCCA

GCCGCCTACCTCCCCGCCGGCACCGATGAGACCGTCATCGAGGGGTACAGGGCG

CAGCAGAAAGCACTAGCGAGGTCCATGAGGAGCAAGCAATCGGCAATGTATAA

CTTCTTCCTGAGGGGCGGCTACGAAGAGGGTTCTGTCGTCTACTTGCACCCAACC

AGCCGTGGCACCGTTCGCATCAACCGATCCGACCCCTTCTTCTCGCCGCCCGAGG

TCGACTACAGGGCACTGAGCAACCCTACCGACCTGGAGGTCCTGCTCGAATTCA

CTCCCCTTCACCCGCAGGTACTTCTTGGAGACGAGGTTGAAGTCCCTCGACCCGGT

-continued

CGAGCTGTCGCCCGGTGCCAACGTCACGGCGCCCGCCGACATCGAGGCCTGGCT

TCGCAGCGTCATGATCCCGTCCTCCTTCCATCCCATCGGCACGGCCGCCATGTTG

CCTAGGCACCTCGGTGGTGTCGTGGACGAGAACCTTCTGGTGTACGGGGTCGAA

GGCTTGAGTGTCGTCGACGCCAGCGTCATGCCCGACTTGCCGGGCTCATACACGC

AGCAGACCGTGTATGCTATTGCTGAGAAGGCCGCGGATCTCATTAAGAGCAGGG

CTTGA (SEQ ID NO: 4)
MELLRVSLAAVALSPLILFGVAAAHPTARSIARSTILDGADGLLPEYDYIIGGGTSGL

TVADRLTENRKRKFSRSPLPTSPARSSPAWCYSVLVLERGIFQNSSSVTTISGGSRGLF

DPSLTFNINSVPQAGLDNRSIAVIGGLILGGSSGVNGLQVLRGQREDYDRWGSYFGP

NSDWSWKGLLPYFKKAWNFHPPRPELVSQFDIKYDPSYWGNTSDVHASFPTTFWPV

LKLEMAAFGDIPGVEYPPDSASGETGAYWHPASVDPATVLRSFARPAHWDNIEAAR

PNYHTLTGQRVLKVAFDGNRATSVVFVPANATDHSTARSVKAKKEIVLAAGAIHTP

QILQASGVGPKQVLKEAGVPLVVDAPGVGSNFQDQPYVVAPTFNFTKFPFHPDFYD

MILNQTFIAEAQAQFEKDRTGPHTIASGYCGSWLPLQIIAPNSWKDIARRYESQDPAA

YLPAGTDETVIEGYRAQQKALARSMRSKQSAMYNFFLRGGYEEGSVVYLHPTSRGT

VRINRSDPFFSPPEVDYRALSNPTDLEVLLEFTPFTRRYFLETRLKSLDPVELSPGANV

TAPADIEAWLRSVMIPSSFHPIGTAAMLPRHLGGVVDENLLVYGVEGLSVVDASVM

PDLPGSYTQQTVYAIAEKAADLIKSRA

*M. thermophila* CDH1:

(SEQ ID NO: 5)
ATGAGGACCTCCTCTCGTTTAATCGGTGCCCTTGCGGCGGCACTCTTGCCGTCTG

CCCTTGCGCAGAACAACGCGCCGGTAACCTTCACCGACCCGGACTCGGGCATTA

CCTTCAACACGTGGGGTCTCGCCGAGGATTCTCCCCAGACTAAGGGCGGTTTCAC

TTTTGGTGTTGCTCTGCCCTCTGATGCCCTCACGACAGACGCCAAGGAGTTCATC

GGTTACTTGAAATGCGCGAGGAACGATGAGAGCGGTTGGTGCGGTGTCTCCCTG

GGCGGCCCCATGACCAACTCGCTCCTCATCGCGGCCTGGCCCCACGAGGACACC

GTCTACACCTCTCTCCGCTTCGCCACCGGCTATGCCATGCCGGATGTCTACCAGG

GGGACGCCGAGATCACCCAGGTCTCCTCCTCTGTCAACTCGACGCACTTCAGCCT

CATCTTCAGGTGCGAGAACTGCCTGCAATGGAGTCAAAGCGGCGCCACCGGCGG

TGCCTCCACCTCGAACGGCGTGTTGGTCCTCGGCTGGGTCCAGGCATTCGCCGAC

CCCGGCAACCCGACCTGCCCCGACCAGATCACCCTCGAGCAGCACGACAACGGC

ATGGGTATCTGGGGTGCCCAGCTCAACTCCGACGCCGCCAGCCCGTCCTACACC

GAGTGGGCCGCCCAGGCCACCAAGACCGTCACGGGTGACTGCGGCGGTCCCACC

GAGACCTCTGTCGTCGGTGTCCCCGTTCCGACGGGCGTCTCGTTCGATTACATCG

TCGTGGGCGGCGGTGCCGGTGGCATCCCCGCCGCCGACAAGCTCAGCGAGGCCG

GCAAGAGTGTGCTGCTCATCGAGAAGGGCTTTGCCTCGACCGCCAACACCGGAG

GCACTCTCGGCCCCGAGTGGCTCGAGGGCCACGACCTTACCCGCTTTGACGTGCC

GGGTCTGTGCAACCAGATCTGGGTTGACTCCAAGGGGATCGCTTGCGAGGATAC

CGACCAGATGGCTGGCTGTGTCCTCGGCGGCGGTACCGCCGTGAATGCCGGCCT

GTGGTTCAAGCCCTACTCGCTCGACTGGGACTACCTCTTCCCTAGTGGTTGGAAG

TACAAAGACGTCCAGCCGGCCATCAACCGCGCCCTCTCGCGCATCCCGGGCACC

```
GATGCTCCCTCGACCGACGGCAAGCGCTACTACCAACAGGGCTTCGACGTCCTCT

CCAAGGGCCTGGCCGGCGGCGGCTGGACCTCGGTCACGGCCAATAACGCGCCAG

ACAAGAAGAACCGCACCTTCTCCCATGCCCCCTTCATGTTCGCCGGCGGCGAGC

GCAACGGCCCGCTGGGCACCTACTTCCAGACCGCCAAGAAGCGCAGCAACTTCA

AGCTCTGGCTCAACACGTCGGTCAAGCGCGTCATCCGCCAGGGCGGCCACATCA

CCGGCGTCGAGGTCGAGCCGTTCCGCGACGGCGGTTACCAAGGCATCGTCCCCG

TCACCAAGGTTACGGGCCGCGTCATCCTCTCTGCCGGTACCTTTGGCAGTGCAAA

GATCCTGCTGAGGAGCGGTATCGGTCCGAACGATCAGCTGCAGGTTGTCGCGGC

CTCGGAGAAGGATGGCCCTACCATGATCAGCAACTCGTCCTGGATCAACCTGCC

TGTCGGCTACAACCTGGATGACCACCTCAACACCGACACTGTCATCTCCCACCCC

GACGTCGTGTTCTACGACTTCTACGAGGCGTGGGACAATCCCATCCAGTCTGACA

AGGACAGCTACCTCAACTCGCGCACGGGCATCCTCGCCCAAGCCGCTCCCAACA

TTGGGCCTATGTTCTGGGAAGAGATCAAGGGTGCGGACGGCATTGTTCGCCAGC

TCCAGTGGACTGCCCGTGTCGAGGGCAGCCTGGGTGCCCCCAACGGCAAGACCA

TGACCATGTCGCAGTACCTCGGTCGTGGTGCCACCTCGCGCGGCCGCATGACCAT

CACCCCGTCCCTGACAACTGTCGTCTCGGACGTGCCCTACCTCAAGGACCCCAAC

GACAAGGAGGCCGTCATCCAGGGCATCATCAACCTGCAGAACGCCCTCAAGAAC

GTCGCCAACCTGACCTGGCTCTTCCCCAACTCGACCATCACGCCGCGCCAATACG

TTGACAGCATGGTCGTCTCCCCGAGCAACCGGCGCTCCAACCACTGGATGGGCA

CCAACAAGATCGGCACCGACGACGGGCGCAAGGGCGGCTCCGCCGTCGTCGACC

TCAACACCAAGGTCTACGGCACCGACAACCTCTTCGTCATCGACGCCTCCATCTT

CCCCGGCGTGCCCACCACCAACCCCACCTCGTACATCGTGACGGCGTCGGAGCA

CGCCTCGGCCCGCATCCTCGCCCTGCCCGACCTCACGCCCGTCCCCAAGTACGGG

CAGTGCGGCGGCCGCGAATGGAGCGGCAGCTTCGTCTGCGCCGACGGCTCCACG

TGCCAGATGCAGAACGAGTGGTACTCGCAGTGCTTGTGA
```

(SEQ ID NO: 6)

```
MRTSSRLIGALAAALLPSALAQNNAPVTFTDPDSGITFNTWGLAEDSPQTKGGFTFG

VALPSDALTTDAKEFIGYLKCARNDESGWCGVSLGGPMTNSLLIAAWPHEDTVYTS

LRFATGYAMPDVYQGDAEITQVSSSVNSTHFSLIFRCENCLQWSQSGATGGASTSNG

VLVLGWVQAFADPGNPTCPDQITLEQHDNGMGIWGAQLNSDAASPSYTEWAAQAT

KTVTGDCGGPTETSVVGVPVPTGVSFDYIVVGGGAGGIPAADKLSEAGKSVLLIEKG

FASTANTGGTLGPEWLEGHDLTRFDVPGLCNQIWVDSKGIACEDTDQMAGCVLGG

GTAVNAGLWFKPYSLDWDYLFPSGWKYKDVQPAINRALSRIPGTDAPSTDGKRYY

QQGFDVLSKGLAGGGWTSVTANNAPDKKNRTFSHAPFMFAGGERNGPLGTYFQTA

KKRSNFKLWLNTSVKRVIRQGGHITGVEVEPFRDGGYQGIVPVTKVTGRVILSAGTF

GSAKILLRSGIGPNDQLQVVAASEKDGPTMISNSSWINLPVGYNLDDHLNTDTVISHP

DVVFYDFYEAWDNPIQSDKDSYLNSRTGILAQAAPNIGPMFWEEIKGADGIVRQLQ

WTARVEGSLGAPNGKTMTMSQYLGRGATSRGRMTITPSLTTVVSDVPYLKDPNDK

EAVIQGIINLQNALKNVANLTWLFPNSTITPRQYVDSMVVSPSNRRSNHWMGTNKIG
```

TDDGRKGGSAVVDLNTKVYGTDNLFVIDASIFPGVPTTNPTSYIVTASEHASARILAL

PDLTPVPKYGQCGGREWSGSFVCADGSTCQMQNEWYSQCL

*M. thermophila* CDH2:

(SEQ ID NO: 7)

ATGAAGCTACTCAGCCGCGTTGGGGCGACCGCCCTAGCGGCGACGTTGTCACTG

CAGCAATGTGCAGCCCAGATGACCGAGGGGACCTACACCGATGAGGCTACCGGT

ATCCAATTCAAGACGTGGACCGCCTCCGAGGGCGCCCCTTTCACGTTTGGCTTGA

CCCTCCCCGCGGACGCGCTGGAAAAGGATGCCACCGAGTACATTGGTCTCCTGC

GTTGCCAAATCACCGATCCCGCCTCGCCCAGCTGGTGCGGTATCTCCCACGGCCA

GTCCGGCCAGATGACGCAGGCGCTGCTGCTGGTCGCCTGGGCCAGCGAGGACAC

CGTCTACACGTCGTTCCGCTACGCCACCGGCTACACGCTCCCCGGCCTCTACACG

GGCGACGCCAAGCTGACCCAGATCTCCTCCTCGGTCAGCGAGGACAGCTTCGAG

GTGCTGTTCCGCTGCGAAAACTGCTTCTCCTGGGACCAGGATGGCACCAAGGGC

AACGTCTCGACCAGCAACGGCAACCTGGTCCTCGGCCGCGCCGCCGCGAAGGAT

GGTGTGACGGGCCCCACGTGCCCGGACACGGCCGAGTTCGGTTTCCATGATAAC

GGTTTCGGACAGTGGGGTGCCGTGCTTGAGGGTGCTACTTCGGACTCGTACGAG

GAGTGGGCTAAGCTGGCCACGACCACGCCCGAGACCACCTGCGATGGCACTGGC

CCCGGCGACAAGGAGTGCGTTCCGGCTCCCGAGGACACGTATGATTACATCGTT

GTCGGTGCCGGCGCCGGTGGTATCACCGTCGCCGACAAGCTCAGCGAGGCCGGC

CACAAGGTCCTTCTCATCGAGAAGGGACCCCCTTCGACCGGCCTGTGGAACGGG

ACCATGAAGCCCGAGTGGCTCGAGAGCACCGACCTTACCCGCTTCGACGTTCCC

GGCCTGTGCAACCAGATCTGGGTCGACTCTGCCGGCATCGCCTGCACCGATACC

GACCAGATGGCGGGCTGCGTTCTCGGCGGTGGCACCGCTGTCAACGCTGGTTTGT

GGTGGAAGCCCCACCCCGCTGACTGGGATGAGAACTTCCCCGAAGGGTGGAAGT

CGAGCGATCTCGCGGATGCGACCGAGCGTGTCTTCAAGCGCATCCCCGGCACGT

CGCACCCGTCGCAGGACGGCAAGTTGTACCGCCAGGAGGGCTTCGAGGTCATCA

GCAAGGGCCTGGCCAACGCCGGCTGGAAGGAAATCAGCGCCAACGAGGCGCCC

AGCGAGAAGAACCACACCTATGCACACACCGAGTTCATGTTCTCGGGCGGTGAG

CGTGGCGGCCCCCTGGCGACGTACCTTGCCTCGGCTGCCGAGCGCAGCAACTTC

AACCTGTGGCTCAACACTGCCGTCCGGAGGGCCGTCCGCAGCGGCAGCAAGGTC

ACCGGCGTCGAGCTCGAGTGCCTCACGGACGGTGGCTTCAGCGGGACCGTCAAC

CTGAATGAGGGCGGTGGTGTCATCTTCTCGGCCGGCGCTTTCGGCTCGGCCAAGC

TGCTCCTTCGCAGCGGTATCGGTCCTGAGGACCAGCTCGAGATTGTGGCGAGCTC

CAAGGACGGCGAGACCTTCACTCCCAAGGACGAGTGGATCAACCTCCCCGTCGG

CCACAACCTGATCGACCATCTCAACACTGACCTCATTATCACGCACCCGGATGTC

GTTTTCTATGACTTCTATGCGCCTGGGACGAGCCCATCACGGAGGATAAGGAG

GCCTACCTGAACTCGCGGTCCGGCATTCTCGCCCAGGCGGCGCCCAATATCGGCC

CTATGATGTGGGATCAAGTCACGCCGTCCGACGGCATCACCCGCCAGTTCCAGT

GGACATGCCGTGTTGAGGGCGACAGCTCCAAGACCAACTCGACCCACGCCATGA

CCCTCAGCCAGTACCTCGGCCGTGGCGTCGTCTCGCGCGGCCGGATGGGCATCA

CCTCCGGGCTGAGCACGACGGTGGCCGAGCACCCGTACCTGCACAACAACGGCG

ACCTGGAGGCGGTCATCCAGGGGATCCAGAACGTGGTGGACGCGCTCAGCCAGG

-continued

TGGCCCGACCTCGAGTGGGTGCTCCCGCCGCCCGACGGGACGGTGGCCGACTACG

TCAACAGCCTGATCGTCTCGCCGGCCAACCGCCGGGCCAACCACTGGATGGGCA

CGGCCAAGCTGGGCACCGACGACGGCCGCTCGGGCGGCACCTCGGTCGTCGACC

TCGACACCAAGGTGTACGGCACCGACAACCTGTTCGTCGTCGACGCGTCCGTCTT

CCCCGGCATGTCGACGGGCAACCCGTCGGCCATGATCGTCATCGTGGCCGAGCA

GGCGGCGCAGCGCATCCTGGCCCTGCGGTCTTAA (SEQ ID NO: 8)
MKLLSRVGATALAATLSLQQCAAQMTEGTYTDEATGIQFKTWTASEGAPFTFGLTL

PADALEKDATEYIGLLRCQITDPASPSWCGISHGQSGQMTQALLLVAWASEDTVYTS

FRYATGYTLPGLYTGDAKLTQISSSVSEDSFEVLFRCENCFSWDQDGTKGNVSTSNG

NLVLGRAAAKDGVTGPTCPDTAEFGFHDNGFGQWGAVLEGATSDSYEEWAKLATT

TPETTCDGTGPGDKECVPAPEDTYDYIVVGAGAGGITVADKLSEAGHKVLLIEKGPP

STGLWNGTMKPEWLESTDLTRFDVPGLCNQIWVDSAGIACTDTDQMAGCVLGGGT

AVNAGLWWKPHPADWDENFPEGWKSSDLADATERVFKRIPGTSHPSQDGKLYRQE

GFEVISKGLANAGWKEISANEAPSEKNHTYAHTEFMFSGGERGGPLATYLASAAERS

NFNLWLNTAVRRAVRSGSKVTGVELECLTDGGFSGTVNLNEGGGVIFSAGAFGSAK

LLLRSGIGPEDQLEIVASSKDGETFTPKDEWINLPVGHNLIDHLNTDLIITHPDVVFYD

FYAAWDEPITEDKEAYLNSRSGILAQAAPNIGPMMWDQVTPSDGITRQFQWTCRVE

GDSSKTNSTHAMTLSQYLGRGVVSRGRMGITSGLSTTVAEHPYLHNNGDLEAVIQGI

QNVVDALSQVADLEWVLPPPDGTVADYVNSLIVSPANRRANHWMGTAKLGTDDG

RSGGTSVVDLDTKVYGTDNLFVVDASVFPGMSTGNPSAMIVIVAEQAAQRILALRS

Aspergillus oryzae pyranose oxidase:

(SEQ ID NO: 9)
ATGTCCATGACATCAGGACGTCAAGCGTTTACTTCCGAGTGCAGAGATTCAAATA

CCACAAATTCATTTTGGTTGGCTAATTCACCGACTCTCACACTTGGCTCTACGAT

GCAGGTCGTGGGGTCCGGCCCCATCGGCGCCACCTATGCCAAGATTCTAGCTGA

CGCCGGCAAGGATGTCCTCATGGTTGAGACTGGCACCCAGGAAAGTAAGATTGC

TGGAGAGCATAAGAAGAATGCTATCAACTACCAGAAAGATATCGATGCCTTTGT

GCATGTCATTAAGGTAATCAGCTCAAGAATTAGCACCTTTGAGTGTATTTCTCTA

ACTTTCGATCTTCTCCTCTTTCAGGGAAGTCTACACTACACGTCTGTACCGACCA

ACAAAGCCGCCGTTCCTACACTGGCTCCGATCTCCTGGAAAGCGAACGGCCAAA

TTTTCAACGGACAGAATCCCCGCCAGGATCCAAACGTAAACCTGGATGCCAATG

GTGTGGCACGTAATGTGGGCGGCATGTCTACCCACTGGACTTGTGCGACTCCCCG

ACAGAAAGAGAAGGTTGAACGCAGCGATATATTCAGTGGTGACGAATGGGATA

GCCTGTACAAGGAGGCAGAAAAGTTGATCGGAACCAGCAAGACTGTGCTGAATG

ACTCGATCCGGCAAGAATTGGTCATGGAGATTCTGAATGACGAGTACGGGAAGC

GATCAGCCGAACCACTACCTTTGGCTGCAAAGAGGAATGGCAATACGGCCTACA

TCACTTGGTCATCCTCGTCAACTATCCTTGACGCGATGAACTGTAAGAAGAAATT

TACACTATGGCCCGAGCACCACTGTGAGAAGTTTAAAGTCGAGGAAACAGATAA

CGGGCCACAGGTCACCAAGGCTATAATCCGCAAACTCGCCACAGATAAACTGAT

TACAGTTAAGGCGAAAGTATTTATCGCTTGCGGGGGGCCTATACTTACACCCCAG

CTACTTTTCAATTCGGGCTTCGTGCCGACAAAGCCCAACAGGGATCCCAGAACCC

```
AAATACCATTAGAAGACGACGAGAAAGGCATCCCACCTCCACCGGATACTCTGG

AGCATCTCAAGCTTCCTGCTCTAGGACGCTATCTGACAGAGCAAAGCATGTGCTT

CTGCCAAATTGTTCTGAAAAAAGAATGGATTGAGGCAGTGGCTAATCCAAAAAA

GAACCCTTATCAAAGCGATGGGGTGAAACGCAAAAAGTGGGAGAAGCTCAAGG

AAGGGTGGAAGGAAAGGGTCCAGGAACATATGAAAAGGTTTAATGACCCTATTC

CCTTCCCGTTCGATGATTTGGACCCTCAGGTTACTCTACCCTTGGACTATCACCAT

CCGTGGCATACCCAAATCCATCGCGATGCCTTCTCCTATGGCGCAGCACCCCCAG

CCATTGATAAGCGGACCATTGTTGACCTCCGATTCTTCGGAACGGTTGAGCCGGA

CTGGAAGAACTATGTGACCTTTGAAACCGACATCAGGGATGCGTACGGCATGCC

CCAGCCCACCTTCCGCTACAAGCTGAACGATGAGGATCGCAAACGGTCGCACCA

GATGATGAAAGATATGGAAGAGGCCGCTGGTGCTCTGGGTGGCTACCTCCCAGG

GTCGGAGCCTCAATTTCTAGCTCCTGGCCTTGCACTGCACGTCTGTGGTACCACT

AGAGCTCAGAAGAAGGAGAAAGAGTGTGACCCTGATCCCAAAGAGACCTCGTG

CTGCGATGAGAACTCCAAGATCTGGGGTATCCACAACCTGTACGTGGGTGGGTT

AAATGTGATCCCTGGTGCCAATGGGTCCAACCCTACCTTGACAGCAATGTGCTTC

GCCATCAAAAGCGCGAAGAGTATCCTTGAAGGGAATTCTTAG (SEQ ID NO: 10)
MSMTSGRQAFTSECRDSNTTNSFWLANSPTLTLGSTMQVVGSGPIGATYAKILADA

GKDVLMVETGTQESKIAGEHKKNAINYQKDIDAFVHVIKVISSRISTFECISLTFDLLL

FQGSLHYTSVPTNKAAVPTLAPISWKANGQIFNGQNPRQDPNVNLDANGVARNVGG

MSTHWTCATPRQKEKVERSDIFSGDEWDSLYKEAEKLIGTSKTVLNDSIRQELVMEI

LNDEYGKRSAEPLPLAAKRNGNTAYITWSSSSTILDAMNCKKKFTLWPEHHCEKFK

VEETDNGPQVTKAIIRKLATDKLITVKAKVFIACGGPILTPQLLFNSGFVPTKPNRDPR

TQIPLEDDEKGIPPPPDTLEHLKLPALGRYLTEQSMCFCQIVLKKEWIEAVANPKKNP

YQSDGVKRKKWEKLKEGWKERVQEHMKRFNDPIPFPFDDLDPQVTLPLDYHHPWH

TQIHRDAFSYGAAPPAIDKRTIVDLRFFGTVEPDWKNYVTFETDIRDAYGMPQPTFR

YKLNDEDRKRSHQMMKDMEEAAGALGGYLPGSEPQFLAPGLALHVCGTTRAQKK

EKECDPDPKETSCCDENSKIWGIHNLYVGGLNVIPGANGSNPTLTAMCFAIKSAKSIL

EGNS

Acremonium strictum glucooligosaccharide oxidase:
                                            (SEQ ID NO: 11)
ATGGTGCGCATCCAAGAGCTCACCGCGGCCTTGAGCCTCGCCTCAGTGGTCCAG

GCTTCATGGATCCAGAAGCGCAACTCAATCAACGCCTGTCTCGCCGCCGCCGAC

GTCGAGTTCCACGAGGAAGACTCTGAAGGCTGGGACATGGACGGCACAGCCTTC

AACCTCCGCGTCGACTACGACCCAGCTGCCATTGCCATCCCTGCTCCACCGAGG

ATATCGCTGCTGCTGTCCAGTGCGGTCTTGATGCTGGTGTGCAGATCTCCGCCAA

GGGTGGTGGTCACAGTTACGGTTCTTATGGGTTCGGTGGTGAGGATGGTCATCTT

ATGTTGGAGCTGGATCGTATGTACCGTGTGTCGGTTGATGATAATAATGTGGCGA

CTATTCAGGGCGGTGCTCGTCTTGGATACACTGCTCTCGAGCTTCTTGACCAGGG

TAACCGTGCACTTTCTCACGGTACTTGCCCTGCCGTCGGTGTCGGCGGTCACGTC

CTCGGCGGTGGTTACGGTTTCGCAACCCACACCCACGGTCTGACCCTCGACTGGC

TGATCGGCGCCACCGTCGTTCTCGCTGATGCCTCCATCGTGCACGTCTCCGAGAC
```

-continued

```
CGAGAACGCCGATCTCTTCTGGGCCCTCCGTGGCGGCGGCGGTGGTTTCGCCATC

GTCTCCGAGTTCGAGTTCAACACCTTCGAGGCCCCCGAGATCATCACCACTTACC

AGGTCACCACCACCTGGAACCGGAAGCAGCACGTTGCCGGTCTCAAGGCTCTCC

AGGACTGGGCTCAGAACACCATGCCCAGGGAGCTCAGCATGCGTCTTGAGATCA

ACGCCAACGCTCTCAACTGGGAGGGTAACTTCTTCGGTAACGCCAAGGACCTCA

AGAAGATTCTTCAGCCTATCATGAAGAAGGCGGGTGGCAAGTCTACCATTTCCA

AGCTCGTTGAGACCGATTGGTATGGCCAGATCAACACCTACCTCTACGGTGCTGA

CTTGAACATCACCTACAACTACGACGTCCACGAGTACTTCTACGCCAACAGCTTG

ACCGCTCCCCGTCTCTCCGACGAAGCCATCCAAGCCTTCGTCGACTACAAGTTCG

ACAACTCCTCCGTCCGCCCCGGCCGCGGCTGGTGGATTCAATGGGACTTCCACGG

CGGCAAGAACTCTGCCCTGGCCGCCGTCTCCAACGACGAAACCGCCTACGCCCA

CCGCGACCAGCTCTGGCTCTGGCAGTTCTACGACAGCATCTATGACTACGAGAA

CAACACCTCTCCCTACCCGGAGAGCGGTTTCGAGTTCATGCAGGGCTTCGTCGCT

ACCATCGAGGACACTCTCCCTGAGGACAGGAAGGGCAAGTACTTCAACTACGCC

GACACCACGCTTACCAAGGAGGAGGCGCAGAAGTTGTACTGGAGGGGCAACCTT

GAGAAGTTGCAGGCTATCAAGGCCAAGTACGATCCTGAGGATGTGTTTGGTAAT

GTTGTCTCTGTTGAGCCCATTGCCTAG
```

(SEQ ID NO: 12)
```
MVRIQELTAALSLASVVQASWIQKRNSINACLAAADVEFHEEDSEGWDMDGTAFNL

RVDYDPAAIAIPRSTEDIAAAVQCGLDAGVQISAKGGGHSYGSYGFGGEDGHLMLE

LDRMYRVSVDDNNVATIQGGARLGYTALELLDQGNRALSHGTCPAVGVGGHVLGG

GYGFATHTHGLTLDWLIGATVVLADASIVHVSETENADLFWALRGGGGGFAIVSEF

EFNTFEAPEIITTYQVTTTWNRKQHVAGLKALQDWAQNTMPRELSMRLEINANALN

WEGNFFGNAKDLKKILQPIMKKAGGKSTISKLVETDWYGQINTYLYGADLNITYNY

DVHEYFYANSLTAPRLSDEAIQAFVDYKFDNSSVRPGRGWWIQWDFHGGKNSALA

AVSNDETAYAHRDQLWLWQFYDSIYDYENNTSPYPESGFEFMQGFVATIEDTLPED

RKGKYFNYADTTLTKEEAQKLYWRGNLEKLQAIKAKYDPEDVFGNVVSVEPIA
```

*Agaricus bisporus* pyranose dehydrogenase:

(SEQ ID NO: 13)
```
ATGATACCTCGAGTGGCCAAATTCAACTTTCGACTCTTGTCTCTCGCATTATTGG

GGATTCAGGTTGCACGCAGTGCCATCACATACCAAAACCCGACCGATTTACCTG

GTGACGTTGACTATGATTTCATCGTTGCTGGCGGTGGAACTGCAGGTTTAGTTGT

GGCCTCTCGTCTCAGTGAGAATCCGGAATGGAATGTACTGGTCATCGAGGCCGG

GCCTTCCAACAAGGACGTCTTCGAAACACGGGTCCCTGGCCTTTCTTCGGAACTC

CGGCCACGTTTTGATTGGAATTATACAACGATTCCTCAAGATGCTCTCGGTGGCA

GGAGCCTGAATTACTCGAGGGCGAAGCTCTTAGGCGGTTGCAGTAGCCATAATG

GGATGGTTTACACACGATGTTCGAGAGACGATTGGGACAATTATGCCGAAATCA

CCGGTAATCAAGCATTTAGCTGGGACAGCATCCTACCTGTCATGAAGAGGGCTG

AGAAATTCAGTAAAGATTCCTCTCATAAACCGGTAAAGGGCCATATTGACCCCTC

CGTGCACGGTGGTGACGGAAAATTGTCCGTGGTCGCATCATACACCAACGCCTC

TTTCAATGACTTATTACTTGAAACCGCGAAAGAATTAAGCGGTGAATTTCCGTTC

AAATTGGATATGAATGACGGGCGGCCTCTTGGATTAACTTGGACTCAGTATACG
```

-continued

```
ATTGATCAACGCGGGGAGCGGAGCAGCTCTGCAACAGCGTATTTAGAGGGTACT

GGAAATAACGTCCATGTCTTGGTTAACACTCTTGTTACCCGTATAGTCTCAGCAG

AAAATGGGACCGACTTCCGAAGCGTCGAGTTTGCTACTGATGCCGACAGCCCAA

AGATCCAATTACGAGCGAAAAAGGAAGTCATTGTATCTGGAGGAGTCATCAATT

CGCCTCAGATCCTCATGAATTCCGGCATTGGGGGCCGAGAGGTGCTTGGAGCTA

ATGGAATTGACACATTGGTGGATAATCCGAGTGTCGGGAAAAATTTATCGGACC

AGGCTGCAACAATTATAATGCTCGATACAACACTCCCTATTACTGATTATGATGT

TGATGCAGCGCTTATTGAATGGAAGAAGTCGCACACTGGACCTCTAGCCCAAGG

AGGTCGCCTAAACCACCTTACATGGGTACGATTGCCTGATGACAAGCTGGATGG

ACTTGATCCTTCAAGTGGCGAAAATTCGCCACATATTGAGTTCCAATTCGGGCAA

ATTAGCCACCAGCTCCCTCCCAGTGGTCTAACACGTTTTAGCTTCTATCGACACT

GTTCTCCAATTCCGCCGTTGATCAACCTCTACACTGTTTCGCGGGGTTCTATTTCT

CTCAGTAACAACGATCCGTTCTCCCACCCACTCATCGATCTCAACATGTTTGGAG

AGGAAATAGATCCCGCTATTCTGCGTGAGGGTATTCGCAGTGCCCGAAGAATGC

TTTCTTCCCAAGCATTCAAAGGCTTTGTCGGTGAAACGGTGTTTCCTCCAAGCGA

CGCTACCTCTGATGAAGATTTGGATACCTTCCTCAAAACGTCAACGTTTTCTTAC

GTGCATGGTGTGGGAACGTTGTCTATGTCTCCTCAGAGTGCCTCGTGGGGTGTCG

TTAACCCTGATTTCCGTGTCAAAGGAACCAGTGGCCTGCGGGTTGTCGACGCGTC

TGTGATTCCATTCGCTCCGGCGGGCACACTCAAGAACCTGTTTATGCATTTGCT

GAGCATGCAAGTGTGTTAATAGCGAAGAGCTACAGCTAA
```

```
                                            (SEQ ID NO: 14)
MIPRVAKFNFRLLSLALLGIQVARSAITYQNPTDLPGDVDYDFIVAGGGTAGLVVAS

RLSENPEWNVLVIEAGPSNKDVFETRVPGLSSELRPRFDWNYTTIPQDALGGRSLNY

SRAKLLGGCSSHNGMVYTRCSRDDWDNYAEITGNQAFSWDSILPVMKRAEKFSKD

SSHKPVKGHIDPSVHGGDGKLSVVASYTNASFNDLLLETAKELSGEFPFKLDMNDG

RPLGLTWTQYTIDQRGERSSSATAYLEGTGNNVHVLVNTLVTRIVSAENGTDFRSVE

FATDADSPKIQLRAKKEVIVSGGVINSPQILMNSGIGGREVLGANGIDTLVDNPSVGK

NLSDQAATIIMLDTTLPITDYDVDAALIEWKKSHTGPLAQGGRLNHLTWVRLPDDKL

DGLDPSSGENSPHIEFQFGQISHQLPPSGLTRFSFYRHCSPIPPLINLYTVSRGSISLSNN

DPFSHPLIDLNMFGEEIDPAILREGIRSARRMLSSQAFKGFVGETVFPPSDATSDEDLD

TFLKTSTFSYVHGVGTLSMSPQSASWGVVNPDFRVKGTSGLRVVDASVIPFAPAGHT

QEPVYAFAEHASVLIAKSYS
```

*Talaromyces stipitatus* (ATCC 10500) glucose dehydrogenase:
```
                                            (SEQ ID NO: 15)
ATGCGACTTGGCTCTATCGGCGCAGGCCTCGCTCTCCTCGCTGCCCTCGCTGTCC

TCGCTGCCCACGTGCACGCCTTGGCACCGCGCACCCAGATTGCCGAGGAATACG

ATTTTGTCGTCGTTGGCGGCGGCCAGGCTGGTCTCGTGATCGGAGCTCGTCTGTC

GGAGATTGCAAATTATACAGTTCTCGTGCTGGAGGCAGGGACGAATGGAGACGA

ATTTCGAGAACGAATAGGCACGTACAACTTTTATACTCCCGCATATTCCTACTAC

GAGTCACTATGGACGACACCAATGAATTGGGCATACTATACTGTGCCTCAATCCC
```

-continued

```
ATGCCGAGAATCGTCAAATTGAGTGGACCCGTGGTAAGGGGCTGGGCGGAAGTT
CTGCGATCAACGGATTGTACCTGACTCGCCCCGGTAAAGAGGAGATCAATGCAT
GGAAAGACCTGCTAGGAGACATGGACGGGGCGGACAATTGGTCGTGGGATTCGT
TCTATGCTGCAATGAAGAAGAGCGAGACTTTTACTCCCCCGTCGAATGAGATTGC
TACAGAAGGGAACATTACATGGACCTTTCTACTCGTGGTATTCAGGGACCGATT
CAGGCAACGTATCCCGGCTATACCTTCCCCCAAGTCGGCGAATGGGTCATGTCTC
TGGAAGCAATGGGCATTGCTAGTTCTAACGATATGTACGGTGGTGAGGTGTATG
GCGCCGAAGTCTCGACGTCGAGTATCAATCCCACGAACTGGACACGCTCGTACA
GCCGGACGGGATATCTCGACCCGCTCGCAGACAACGGCAATTACGACGTTGTGG
CCGATGCGTTTGTCACGCGCATTCTCTTTGATGCTTCTTCTCCGTCGAATAATCTG
ACAGCAAACGGCGTGCAGTATACTCTTGACAACGGCAAGACAAACTGCACGGTC
AAGGTCAAGAAAGAGGTGATCTTATCAGCTGGGACGGTTGGCAGTCCTGCGGTA
CTGCTCCACAGCGGTGTCGGTCCGAAAGATGTTCTTTCAGATGCTGGAGTTGAGC
TGGTGTCTGAACTTCCTGGTGTGGGTCACCACCTTCAGGATCATTTTAACAACAC
CCTTTATCTCTCCTACATCGATTCAGCCATCGCCTACATCAATTCCACGCTGATGT
ACGGCGATAATCTGGACGCACTACAGAAGAACATCACCACTCAAATCAACCAAT
TCGTGCTGAACACGACTTACGATGCTGGTGTCATTGCAGGATACAAAGCAATTGC
AAATATGACCGCAACCACAATCCTCAGTAGTTCTATCGGGCAAATTGAGCTCTTG
TTCATGAATAGTGACTTAAACGGCGATATTGGTATCACTGCTGCTCTTCAACATC
CTTACAGCCATGGACGCATATACATCAATTCCTCGAATCCGTTGGACTATCCCGT
CATTGATCCGAATTATCTTGCTGTTTCTGCTGACTATGAAATCCTCCGCGACGGC
CTCAATCTAGCCCGCCAACTCGGCAACACACAACCCCTAAGCAGCTGTCTAATA
GCCGAAACAATCCCCGGTCCCAGCGTCAAAACCGACGACGACTGGCTTGAATGG
ATCCGCGAAGCGACGGGGACAGAGTTCCACCCTTCATCGTCCTGTGCGATGCTA
CCCCGAGAGCAAGGCGGAGTAGTCGATGCCAACCTGCGCGTCTACGGTCTTGCC
AATGTTCGTGTTGCGGATGCCAGCGTTGTCCCGATTTCATTGTCGACGCATCTTAT
GGCGTCGACGTATGGAGTCGCAGAACAGGCTAGTAATATCATTCGTGCGCACTA
CACGGATAGTAGGACTACAGGCACGAGTAGTTCCGATCCTGGCTCTGCGTCGTC
ACCGACAAGCAGTGCATTGGGCGCTGAAGGGACTACTGGGGCGATTAGTGCTCA
TACAGCGCCTTCTGGTGGTGTACGAAGCGTTTCTGCGGTATCCGCTTGGGTTGCT
GTTGTGTTCGCTGCAGCTGTTTCCATTTTCCATTCCTTGCATTGA
```

(SEQ ID NO: 16)
MRLGSIGAGLALLAALAVLAAHVHALAPRTQIAEEYDFVVVGGGQAGLVIGARLSEI
ANYTVLVLEAGTNGDEFRERIGTYNFYTPAYSYYESLWTTPMNWAYYTVPQSHAE
NRQIEWTRGKGLGGSSAINGLYLTRPGKEEINAWKDLLGDMDGADNWSWDSFYAA
MKKSETFTPPSNEIATEGNITWDLSTRGIQGPIQATYPGYTFPQVGEWVMSLEAMGIA
SSNDMYGGEVYGAEVSTSSINPTNWTRSYSRTGYLDPLADNGNYDVVADAFVTRIL
FDASSPSNNLTANGVQYTLDNGKTNCTVKVKKEVILSAGTVGSPAVLLHSGVGPKD
VLSDAGVELVSELPGVGHHLQDHFNNTLYLSYIDSAIAYINSTLMYGDNLDALQKNI
TTQINQFVLNTTYDAGVIAGYKAIANMTATTILSSSIGQIELLFMNSDLNGDIGITAAL
QHPYSHGRIYINSSNPLDYPVIDPNYLAVSADYEILRDGLNLARQLGNTQPLSSCLIAE

-continued

TIPGPSVKTDDDWLEWIREATGTEFHPSSSCAMLPREQGGVVDANLRVYGLANVRV

ADASVVPISLSTHLMASTYGVAEQASNIIRAHYTDSRTTGTSSSDPGSASSPTSSALGA

EGTTGAISAHTAPSGGVRSVSAVSAWVAVVFAAAVSIFHSLH

Example 1

Fungal Strains and Methods

As described below, variants of fungal strain C1 were prepared. In addition, the *Trichoderma reesei* cellulase enzyme mixture ("Turbo") used in the following Examples is produced by a strain modified to produce and secrete high levels of the TrCel3A beta-glucosidase, encoded by *T. reesei* bgl1, as described in U.S. Pat. No. 6,015,703.

Strains and Nomenclature

Strain CF-400 (Δcdh1) is a derivative of C1 strain ("UV18#100fΔalp1Δpyr5") further modified with a deletion of cdh1, wherein cdh1 comprises the polynucleotide sequence of SEQ ID NO:5. Strain CF-401 (Δcdh1Δcdh2), is a derivative of the C1 strain further modified with a deletion of both a cdh1 and a cdh2, wherein cdh2 comprises the polynucleotide sequence of SEQ ID NO:7. Strain CF-402 (+Bgl1) is a derivative of the C1 strain further modified for overexpression of an endogenous beta-glucosidase 1 enzyme (Bgl1). Strain CF-403 is a derivative of the C1 strain modified with a deletion of cdh1 and further modified to overexpress bgl1. Strain CF-404 is a derivative of the C1 strain further modified to overexpress bgl1 with a deletion of both cdh1 and cdh2.

Cellulolytic enzymes from strain CF-400, CF-401, CF-402, CF-403 and CF-404, were produced by submerged liquid culture fermentation using methods well-known in the art.

The *T. reesei* Turbo cellulose was produced by submerged liquid culture fermentation using methods described in U.S. Pat. Appln. Publ. No. 2010/0304438. The filtered fermentation broth was desalted using Biospin columns (Biorad) following the manufacturer's protocol. Total protein concentration of the desalted enzyme was assayed using a BCA kit (Sigma) with a bovine serum albumin (Sigma) control.

Hydrolysis Reaction Conditions

Wheat straw ("WS") was pretreated using the methods described in U.S. Pat. No. 4,461,648. Following pretreatment, sodium benzoate was added at a concentration of 0.5% as a preservative. The pretreated material was then washed with six volumes of lukewarm (~35° C.) tap water using a Buchner funnel and filter paper to produce the substrate for subsequent hydrolysis reactions ("pretreated WS").

The cellulosic portion of the pretreated WS was hydrolyzed using the cellulolytic enzyme systems obtained as described above. Pretreated WS was hydrolyzed with 30 mg of cellulase per g of cellulose in reactions with 50 g/L cellulose at 50° C. and pH 5.0, with 250 rpm orbital shaking, in total reaction volumes of 50 mL unless specified. For hydrolysis reactions containing the cellulase enzyme mixtures produced by C1 strains CF-400 and CF-401, beta-glucosidase purified from the Turbo or CF-402 cellulases was added at a dose of 125 IU per gm cellulose.

Detection of Glucose Yield in Hydrolysis Reaction

In this reaction, 1 mL aliquots of reaction mixture were sampled periodically from reaction flasks. Each reaction was well mixed during sampling to avoid removing a disproportionate amount of solid or supernatant. The reaction was stopped by incubating the aliquot in a 100° C. hot block for at least 5 minutes. The supernatants of each reaction were analyzed for glucose concentration to determine the extent of conversion. The conversion calculation included correction terms for the effect of glucose on the density of the solution and the volume exclusion effect of non-hydrolyzable lignin present in the reaction. Glucose concentration was determined using a coupled enzymatic assay based on glucose oxidase and horseradish peroxidases using methods known in the art (See e.g., Trinder, Ann. Clin. Biochem., 6:24-27 [1969]).

Detection of Cellulose Conversion

Residual solids from each of the 50 mL reactions were recovered, washed and analyzed by infrared spectroscopy. Aliquots of the samples were centrifuged at 2500 rpm for 5 min in an Eppendorf microfuge to sediment the solids, the supernatant was decanted, and the solids were resuspended back to the original volume in water. This procedure was repeated 5 times. Washed solids were placed on the detection crystal of a Golden Gate ATR cell installed on a Bruker Vertex 70 infrared spectrometer and absorbance was measured between 500-4000 $cm^{-1}$.

Example 2

Purification of C1 CDH1

First, 400 mL of C1 supernatant was concentrated to 140 mL using a rotary evaporator. Then, 63 mL of the concentrate was buffer-exchanged into 20 mM MOPS buffer pH 7.0 using 4 in-line Hi-Prep 26/10 desalting columns (GE Healthcare, 17-5087-02). The resulting buffer-exchanged supernatant (~150 g/L total protein) was loaded onto a column containing 500 mL DEAE Fast Flow resin (GE Healthcare, 17-0709-01) pre-equilibrated with 20 mM pH7.0 MOPS buffer. The column was rinsed with 1 column volume (CV) of 20 mM MOPS (pH7.0) and then a 0-300 mM sodium chloride gradient was run over 12 column volumes. Fractions were collected and analyzed by NuPage® Novex® Bis-tris SDS-PAGE gels (Invitrogen, NP0322BOX). The SDS-PAGE bands corresponding to the apparent molecular weight of CDH1 were analyzed by MS (performed by Alphalyse). The mass-mapping analysis confirmed the presence of CDH1 in late-eluting fractions. Fractions containing CDH1, as demonstrated by SDS-PAGE gel, and confirmed by MS were pooled and concentrated by ultrafiltration using Sartorius centrifugal 10 kDa filter (Sartorius-Stedim, VS2002). Then, 10 mL 500 mM piperazine (pH 5.6) and 45 mL saturated ammonium sulfate were added to 45 mL of the CDH1-containing pool and the resulting mixture was loaded onto a Phenyl FF (high sub) 16/10 column (GE Healthcare, 28-9365-45) pre-equilibrated with 1.6 M ammonium sulfate in 50 mM piperazine, pH 5.6. A gradient of 1.6 M to 0 M ammonium sulfate in 50 mM piperazine, pH 5.6, was run over 30 CV. Fractions were collected and SDS-PAGE gel analysis was performed on the selected fractions as described above, revealing CDH1 eluted in the final rinse step with approximately 80-90% purity.

CDH1 activity was measured using a DCPIP (2,6-dichlorophenolindophenol) reduction assay similar to that described by Schou et. al. (Schou et al., Biochem J., 330:565-71 [1998]). Briefly, In a UV-transparent flat-bottom 96-well plate, 50 μL CDH1-containing fractions were added to 150 μL of a solution of 1.0 g/L cellobiose and 100 μM DCPIP in 100 mM sodium acetate, pH 5.0. Samples were agitated briefly at room temperature and then absorbance at 530 nm ($A_{530}$) was measured for 10 minutes. C1 CDH1-containing fractions displayed a rapid drop in absorbance at 530 nm. DCPIP assays were performed using varying amounts of glucose or cellobiose with purified CDH1. Serial dilutions of cellobiose (1.0 g/L to 7.8 mg/L) and glucose (10 g/L to 78 mg/L) were prepared in a 96-well shallow-well plate. 20 μL glucose and cellobiose standards were added to 160 μL/well 200 mM DCPIP (in 100 mM pH 5.0 sodium acetate). Reactions were initiated by addition of 20 μL CDH1 solution. Absorbance at 530 nm was monitored for 30 minutes. Comparisons of the rates of decrease in absorbance at 530 nm indicate that C1 CDH1 is approximately 10-fold more active on cellobiose than glucose.

Example 3

Making of CDH1 Split Marker Deletion Constructs

Genomic DNA was isolated from the C1 strain using standard procedures. Briefly, hyphal inoculum was seeded into a growth medium and allowed to grow for 72 hours at 35° C. The mycelial mat was collected by centrifugation, washed, and 50 μL DNA extraction buffer (200 mM Tris, pH 8.0; 250 mM NaCl; 125 mM EDTA; 0.5% SDS) was added. The mycelia were ground with conical grinder, re-extracted with 250 μL extraction buffer, and the suspension was centrifuged. The supernatant was transferred to a new tube containing 300 μL isopropanol. DNA was collected by centrifugation, washed twice with 70% ethanol, and diluted in 100 μL of water.

Genomic DNA fragments flanking the cdh1 gene were cloned using primers cf09067 and cf09068 (cdh1 upstream homology) and primers cf09069 and cf09070 (cdh1 downstream homology). PCR reactions were performed by using the GoTaq® Polymerase (Promega) following the manufacturer's instructions using 0.2 μM of each primer. Amplification conditions were 95° C. 2 minutes, followed by 35 cycles of 95° C. for 30 seconds, 55° C. for 30 seconds (for upstream homology) or 53° C. for 30 seconds (for downstream homology), and 72° C. for 1 minute, and followed by final extension at 72° C. for 5 minutes. The pyr5 gene was PCR amplified as a split marker from a vector using primers cf09024 and cf09025 (for the 5' portion of the gene) and cf09026 and cf09027 (for the 3' portion of the gene). PCR reactions were performed using the GoTaq® Polymerase (Promega) following the manufacturer's instructions using 0.2 μM of each primer. Amplification conditions were 95° C. for 2 minutes, followed by 35 cycles of 95° C. for 30 seconds, 53° C. for 30 seconds, and 72° C. for 1 minute, followed by a final extension at 72° C. for 5 minutes. Primers are shown in Table 3-1. In separate strand overlap extension reactions (Horton et al., Meth. Enzymol., 217:270-279 [1993]), the PCR products resulting from primers cf09067 and cf09068 and primers cf09026 and cf09027 were fused as were the PCR products resulting from primers cf09069 and cf09070 and primers cf09024 and cf09025. PCR reactions were performed by using Finnzymes' Phusion® DNA Polymerases following the manufacturer's instructions including 3% DMSO and using 0.2 μM of each primer. Amplification conditions were 98° C. for 1 minute, followed by 35 cycles of 98° C. for 10 seconds, 62° C. for 20 seconds, 72° C. for 2 minutes, and followed by final extension at 72° C. for 5 minutes. The strand overlap extension products were used for cdh1 deletion.

TABLE 3-1

Primer Sequences

| Primer Name | Sequence (5'-3') |
|---|---|
| cf09067 | CACGCGGGGTTCTTTCTCCATCTC (SEQ ID NO: 17) |
| cf09068 | TGAGGAAAACGCCGAGACTGAGCTCGACTCTGCCGGCCT ACCTACGA (SEQ ID NO: 18) |
| cf09069 | ATCAGTTGGGTGCACGAGTGGGTTTTGATGGGGAGTTGA GTTTGTGAA (SEQ ID NO: 19) |
| cf09070 | GGATGGATGAGGTTGTTTTTGAGC (SEQ ID NO: 20) |
| cf09024 | AACCCACTCGTGCACCCAACTGAT (SEQ ID NO: 21) |
| cf09025 | GACCACGATGCCGGCTACGATACC (SEQ ID NO: 22) |
| cf09026 | ACATGGCCCCACTCGCTTCTTACA (SEQ ID NO: 23) |

Example 4

Transformation Method

C1 cells and derivative strains were inoculated into 100 mL growth medium in a 500 mL Erlenmeyer flask using $10^6$ spores/mL. The culture was incubated for 48 hours at 35° C., 250 rpm. To harvest the mycelia, the culture was filtered over a sterile Myracloth filter (Calbiochem) and washed with 100 mL 1700 mM NaCl/CaCl$_2$ solution (0.6 M NaCl, 0.27 M CaCl$_2$*H$_2$O). The washed mycelia were transferred into a 50 mL tube and weighed. Caylase (20 mg/gram mycelia) was dissolved in 1700 mM NaCl/CaCl$_2$ and UV-sterilized for 90 sec. Then 3 mL of sterile Caylase solution was added into the tube containing washed mycelia and mixed. Then 15 mL of 1700 mM NaCl/CaCl$_2$ solution was added into the tube and mixed. The mycelium/Caylase suspension was incubated at 30° C., 70 rpm for 2 hours. Protoplasts were harvested by filtering through a sterile Myracloth filter into a sterile 50 mL tube. 25 mL cold STC (1.2 M sorbitol, 50 mM CaCl$_2$*H$_2$O, 35 mM NaCl, 10 mM Tris-HCl) was added to the flow through and spun down at 2720 rpm (1500×g) for 10 min at 4° C. The pellet was resuspended in 50 mL STC and centrifuged again. After the washing steps the pellet was resuspended in 1 mL STC.

Into the bottom of a 15 mL sterile tube, 2 μg DNA of each pyr5::Δcdh1 strand overlap extension product was pipetted and 1 μL aurintricarboxylic acid and 100 μL protoplasts were added. The content was mixed and the protoplasts with the DNA were incubated at room temperature for 25 min. 1.7 mL PEG4000 solution (60% PEG4000 (polyethylene glycol, average molecular weight 4000 daltons), 50 mM CaCl$_2$.H$_2$O, 35 mM NaCl, 10 mM Tris-HCl) was added and mixed thoroughly. The solution was kept at room temperature for 20 min. The tube was filled with STC, mixed and centrifuged at 2500 rpm (1250×g) for 10 min at 4° C. The STC was poured off and the pellet was resuspended in the remaining STC and plated on minimal selective media plates, lacking uracil, but containing 0.67 M sucrose as an osmotic stabilizer. The plates were incubated for 5 days at 35° C. Colonies were restreaked and checked for the deletion of cdh1, designated as strain "CF-400."

Example 5

Confirmation of CDH1 Deletion

Genomic DNA was prepared as described in Example 3. Primer pairs cf09112 and cf09113 (PCR reactions were performed by using the GoTaq® Polymerase (Promega) following the manufacturer's instructions using 0.2 μM of each primer. Amplification conditions were 95° C. for 2 minutes, followed by 35 cycles of 95° C. for 30 seconds, 54° C. for 30 seconds, 72° C. for 30 seconds, and followed by final extension at 72° C. for 5 minutes) as well as cf09110 and cf09111 (reactions were performed by using the GoTaq® Polymerase (Promega) following the manufacturer's instructions using 0.2 μM of each primer. Amplification conditions were 95° C. for 2', followed by 35 cycles of 95° C. for 30", 55.4° C. for 30", 72° C. for 30", and followed by final extension at 72° C. for 5') were used in separate PCR reactions to confirm absence of the cdh1 gene. Primers cf09181 and cf09091 were used in PCR to confirm proper junction structure and targeting of the pyr5 marker construct (See, Table 5-1). The PCR reaction was performed by using the GoTaq® Polymerase (Promega) following the manufacturer's instructions using 0.2 μM of each primer. Amplification conditions were 95° C. for 2 minutes, followed by 35 cycles of 95° C. for 30 seconds, 54.4° C. for 30 seconds, 72° C. for 3 minutes 30 seconds, and followed by final extension at 72° C. for 5 minutes. PCR products were run on agarose gel to confirm a banding pattern indicative of cdh1 deletion.

TABLE 5-1

Primer Sequences

| Primer Name | Sequence (5'-3') |
|---|---|
| cf09110 | AAGCGTGCCGATTTTCCTGATTTC (SEQ ID NO: 24) |
| cf09111 | GCATTTCTGGGGCGGTTAGCA (SEQ ID NO: 25) |
| cf09112 | TCATCGACGCCTCCATCTTCC (SEQ ID NO: 26) |
| cf09113 | TTTCGGTTGTCGTGTTTCCATTAT (SEQ ID NO: 27) |
| cf09181 | GGAGATCCTGGAGGATTTCC (SEQ ID NO: 28) |
| cf09091 | CAGGCGGTGTGCGTTATCAAAA (SEQ ID NO: 29) |

A colorimetric dichlorophenolindophenol (DCPIP) assay was used to test for deletion of cdh1 in CF-400. Deletion of cdh1 was determined by decreased ability to reduce the DCPIP substrate compared to a cellulase enzyme mixture (or culture filtrate) produced by the parent strain. Cells of the parental C1 strain and putative cdh1 delete strain were grown and supernatant tested for DCPIP activity. Combined in microtiter plates were 160 μL of freshly made DCPIP reagent solution (0.2 mM DCPIP in 100 mM sodium acetate, pH 5.0), 20 μL cellobiose solution (1 g/L cellobiose in deionized water), and 20 mLs of undiluted cell supernatant. The absorbance of the solution was immediately measured over time at 530 nm in kinetic mode for 30 minutes to track loss of absorbance as a result of DCPIP reduction. Supernatant from strains displaying decreased ability to reduce the DCPIP substrate were run on SDS-PAGE to confirm the absence of CDH1.

Proteins from culture supernatants of submerged liquid culture fermentations of CF-400 and the untransformed parent were separated by SDS-PAGE using standard protocols. The proteins were visualized by staining with Simply Blue Safe Stain (Invitrogen), as per manufacturer's instructions. The Cdh1 protein was observed as a ~90 kD band in the untransformed parent but was absent in CF-400.

Example 6

Deletion of CDH2

Genomic DNA was isolated as described in Example 3. Genomic DNA fragments flanking the cdh2 gene were cloned using primers cf10340 and cf10341 (cdh2 upstream homology) and primers cf10342 and cf10343 (cdh2 downstream homology). PCR reactions were performed by using the GoTaq® Polymerase (Promega) following the manufacturer's instructions using 0.2 μM of each primer. Amplification conditions were 95° C. for 2 minutes, followed by 35 cycles of 95° C. for 30 seconds, 58° C. for 30 seconds (for upstream homology) or 58.4° C. for 30 seconds (for downstream homology), 72° C. for 1 minute, and followed by final extension at 72° C. for 5 minutes. The hygromycin gene was PCR amplified as a split marker from a vector using primers cf10176 and cf10177 (for the 5' region of the gene) and cf10178 and cf10179 (for the 3' region of the gene). PCR reactions were performed by using the GoTaq® Polymerase (Promega) following the manufacturer's instructions using 0.2 μM of each primer. Amplification conditions were 95° C. for 2 minutes, followed by 35 cycles of 95° C. for 30 seconds, 56.3° C. for 30 seconds, 72° C. for 1 minute 30 seconds, and followed by final extension at 72° C. for 5 minutes. Primers are shown in Table 5. In separate strand overlap extension reactions (Example 3) the PCR products resulting from primers cf10340 and cf10341 and primers cf10178 and cf10179 were fused as were the PCR products resulting from primers cf10342 and cf10343 and primers cf10176 and cf10177. PCR reactions were performed by using Phusion® DNA Polymerases (Finnzymes) following the manufacturer's instructions and including 3% DMSO and 0.2 μM of each primer. Amplification conditions were 98° C. 1 minute, 35 cycles of 98° C. 10 seconds, 62° C. 20 seconds, 72° C. 2 minutes and final extension at 72° C. 5 minutes. The strand overlap extension products were used for cdh2 deletion.

TABLE 5-1

Primer Sequences

| Primer Name | Sequence (5'-3') |
|---|---|
| cf10340 | TTCAGCACGGCCGGGGATTTTATCCA (SEQ ID NO: 30) |
| cf10341 | GTAACACCCAATACGCCGGCCGAACATAAGAGCGGAGGTCAG GAATAA (SEQ ID NO: 31) |
| cf10342 | CCGTCTCTCCGCATGCCAGAAAGAGCTGTCAACGCTGGTTTGT GGTGG (SEQ ID NO: 32) |
| cf10343 | AATGCCGGACCGCGAGTTCAGGTA (SEQ ID NO: 33) |
| cf10176 | TCTTTCTGGCATGCGGAGAGACGG (SEQ ID NO: 34) |
| cf10177 | TGTTGGCGACCTCGTATTGGGAAT (SEQ ID NO: 35) |
| cf10178 | TCTCGGAGGGCGAAGAATCTCGTG (SEQ ID NO: 36) |
| cf10179 | TTCGGCCGGCGTATTGGGTGTTAC (SEQ ID NO: 37) |

Strain CF-401 cells were grown and transformed as described in Example 4. Transformed colonies of CF-401 were restreaked and checked for deletion of cdh2.

Genomic DNA was prepared as described in Example 3. Deletion of cdh2 in CF-401 was confirmed by PCR. Primers cf10326 and cf10327 were used in PCR to confirm absence of the cdh2 gene. The PCR reaction was performed by using the GoTaq® Polymerase (Promega) following the manufacturer's instructions using 0.2 μM of each primer. Amplification conditions were 95° C. for 2 minutes, followed by 35 cycles of 95° C. for 30 seconds, 59.3° C. for 30 seconds, 72° C. for 30 seconds and followed by final extension at 72° C. for 5 minutes. Primers cf10364 and cf10295 were used in PCR to confirm proper junction structure and targeting of the hygromycin marker construct (Table 6-2). The PCR reaction was performed by using the GoTaq® Polymerase (Promega) following the manufacturer's instructions using 0.2 μM of each primer. Amplification conditions were 95° C. 2 minutes, 35 cycles of 95° C. 30 seconds, 56° C. 30 seconds, 72° C. 3 minutes and final extension at 72° C. 5 minutes. PCR products were run on agarose gel to confirm a banding pattern indicative of cdh2 deletion. Dichlorophenolindophenol (DCPIP) assay and SDS-PAGE confirmation of cdh2 deletion were performed as described in Example 5. Deletion of cdh2 from strain CF-401 was determined by decreased ability of the resulting culture filtrate (or cellulase enzyme mixture) to reduce the DCPIP substrate compared to that produced by the parent strain CF-400.

TABLE 6-2

Primer Sequences

| Primer Name | Sequence (5'-3') |
|---|---|
| cf10326 | GCGCTGGAAAAGGATGCCACCGAGT (SEQ ID NO: 38) |
| cf10327 | GCACCCCACTGTCCGAAACCGTTA (SEQ ID NO: 39) |
| cf10295 | AGCGCGTCTGCTGCTCCATACAAG (SEQ ID NO: 40) |
| cf10364 | CAAAGCCACGTCCAGGTTGATAGA (SEQ ID NO: 41) |

Example 7

Hydrolysis of Pretreated Wheat Straw by an Enzyme Mixture Lacking CDH1

The ability of CF-402 and CF-403 enzyme mixtures to saccharify the cellulose present in pretreated wheat straw (WS) as measured by glucose and gluconate production was compared in a hydrolysis assay as described in Example 1. Each enzyme mixture was assessed using both a single enzyme dose of 30 mg enzyme/g cellulose and in parallel using a second 30 mg enzyme/g cellulose dose added after a 24 hr hydrolysis to the original 30 mg/g enzyme load. The preparation of pretreated WS used in these experiments had a maximum convertibility of 95%; conversions of all enzymes were normalized. Hydrolysis assay results are depicted in FIG. 1.

In the single dose experiment, the total soluble products measured, equaled a cellulose conversion of 79% and 87% of theoretical maximum glucose yield with enzyme mixtures from CF-402 and CF-403 respectively. About 5% of soluble products were measured to be gluconate for CF-403 as compared to 10% for CF-402. The results demonstrate that removing the CDH1 enzyme from the cellulase mixture produced by C1 derived strains improves glucose yield.

In the multidose experiments, the total soluble products measured with enzyme mixtures from CF-402 indicated a 90% cellulose conversion as compared to 95% with enzyme mixtures from CF-403. The conversion of glucose to gluconate was higher for CF-402 (14%) compared to CF-403 (7%).

Example 8

Hydrolysis of Pretreated Wheat Straw by an Enzyme Mixture Lacking Both CDH1 and CDH2

The ability of enzyme mixtures to saccharify the cellulose present in pretreated WS was compared for enzyme mixtures obtained from CF-401, CF-400, and CF-402 in the following hydrolysis assay.

Enzyme mixtures derived from CF-400, CF-401 and CF-402 were produced by fermentation as described in Example 1. Enzyme mixtures derived from CF-400, CF-401 and CF-402 were added to the pretreated wheat straw at enzyme loads of 3.83-6% w.r.t cellulose. The cellulose concentration was 110 g/L. Aspergillus niger beta-glucosidase (ANBG, Sigma) at an enzyme load of 2% w.r.t cellulose, was supplemented to CF-400 and CF-401 enzyme mixtures as these strains lack added beta-glucosidase activity. Glucose and gluconate yields were compared for the sample withdrawn at 48-70 hrs.

For glucose analysis, the samples were diluted 1:10 using 10 mM $H_2SO_4$ and then analyzed using an Agilent HPLC 1200 equipped with HPX-87H Ion exclusion column (300 mm×7.8 mm) with 5 mM $H_2SO_4$ as a mobile phase at a flow rate of 0.6 mL/min at 65° C. The retention time of the glucose was 9.1 minutes. The gluconate analysis was carried out using LC-MS. The LC/MS/MS used was a API2000 triple quadrupole system (AB Sciex) equipped with Agilent 1100 HPLC, and CTC PAL autosampler. The column used was a HYPERCARB 50×2.1 mm, 3 μm at 80° C. temperature. The chromatography method was a 2 minutes isocratic (95% A) run with a flow rate of 350 μL/min. The two mobile phases contained 1.5% $NH_4OH$. The mobile phase A was aqueous, and the B phase was a 50:50 solution of $CH_3CN$:IPA. The MS/MS transition monitored for gluconate was 194.99/161.10. The analytical methods and controls for measuring gluconate and glucose were slightly different for CF-402. However, the methods and controls used are well known in the art.

Figure 2:
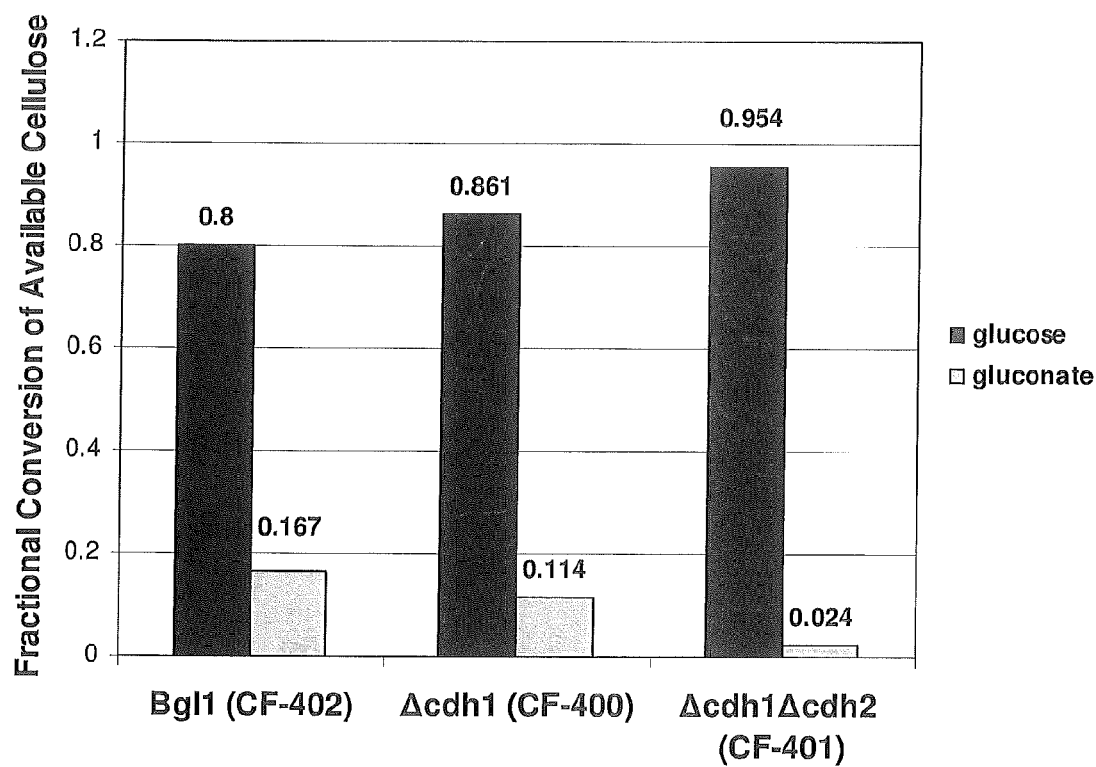
FIG. 2 is a chart that shows the products of cellulose hydrolysis using enzyme mixtures produced by strain CF-400 (comprising a cdh1 deletion); strain CF-401 (comprising the deletions of cdh1 and cdh2) and strain CF-402 (comprising cdh1 and cdh2), as further described in Example 8.

The results are provided in FIG. 2 and in Table 7-1 below.

TABLE 7.1

| Glucose Conversion | | | |
|---|---|---|---|
| | Fractional Conversion of Available Cellulose | | |
| Enzyme Mixture | Glucose | Gluconate | Sum |
| Bgl1 (CF-402) | 0.800 | 0.167 | 0.967 |
| Δcdh1 (CF-400) | 0.861 | 0.114 | 0.974 |
| Δcdh1Δcdh2 (CF-401) | 0.954 | 0.024 | 0.978 |

Results from the experiments show the total soluble products obtained from the enzyme mixtures derived from strains CF-400, CF-401 and CF-402 were similar. However the ratios of glucose:gluconate were different in the soluble products produced by the enzyme mixtures from the different strains. CF-402-derived enzyme mixtures produced about 23 g/L of gluconate. In comparison, CF-400-derived enzyme mixtures (the deletion of the cdh1 gene) reduced the gluconate production to about 16 g/L. The enzyme mixture resulting from the additional deletion of the cdh2 gene in CF-401 significantly reduced (3.3 g/L) the gluconate production. This reduction in gluconate production represented an 86% reduction compared to the enzyme mixtures derived from CF-402 strain. Correspondingly the glucose yields increased from 112 g/L with CF-402 to 133.6 g/L with CF-401-derived enzyme mixtures. The results demonstrate that the removal of CDH1 and CDH2 enzymes by deletion of both cdh1 and cdh2 genes significantly increases glucose yield with a concomitant decrease in gluconate production in the saccharification reaction.

Example 9

Enzymatic Hydrolysis of Cellulose

The cellulosic portion of pretreated WS was hydrolyzed according to the methods described in Example 1 using enzyme mixture derived from CF-402. In each reaction, an initial 30 mg/g dose of CF-402 was allowed to react with the pretreated WS substrate. After 24 hours, an additional dose of 30 mg/g of CF-402 enzyme mixture was added to one reaction flask.

Figure 11:
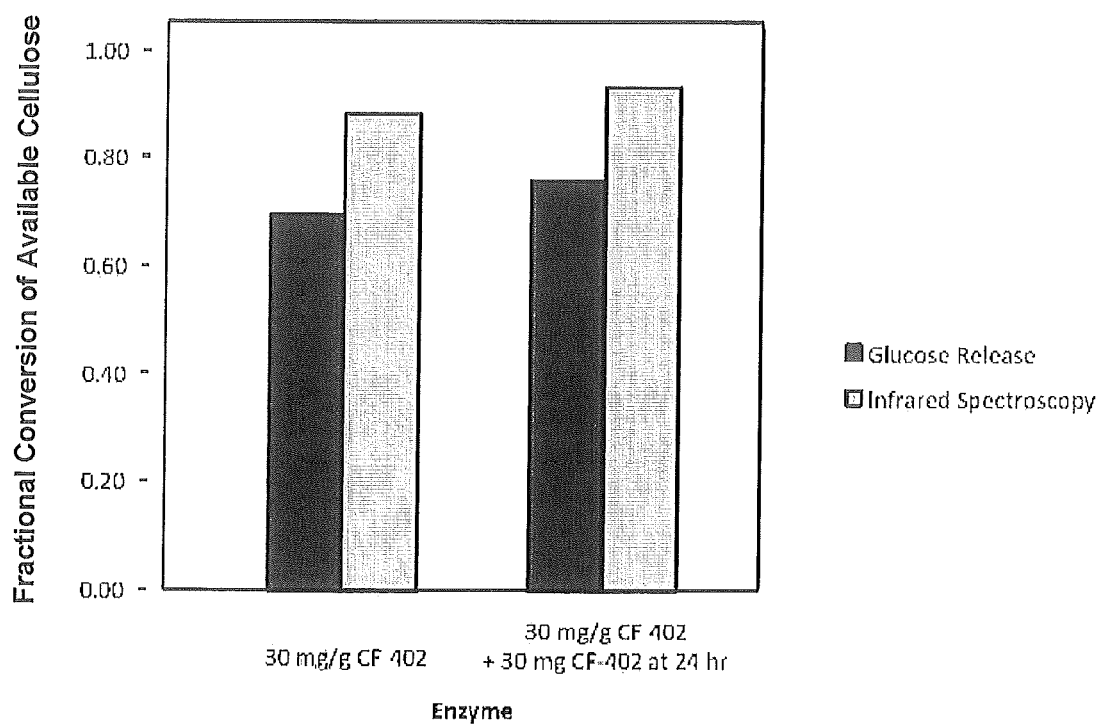
FIG. 11 provides a chart showing fractional recovery of available cellulose using an enzyme mixture containing cellobiose dehydrogenase activity. Dark bars represent glucose yield as measured using a horseradish peroxidase coupled enzymatic assay described in Example 1. Light bars represent expected glucose yield calculated using the IR method for determining cellulose conversion described in Example 9.

Aliquots of 1 mL were sampled periodically from all these flasks, and glucose concentrations were determined using a coupled enzymatic assay as described in Example 1. By glucose yield, a single 30 mg/g dose of the CF-402 enzyme mixture produces 69.5% of theoretical maximum glucose yield (Gmax). Dosing additional CF-402 increased this yield to 75.6% as shown in FIG. 11.

Example 10

Conversion of Glucose by C1-Derived Enzyme Mixtures

Fifty-two mg of the C1-derived CF-402 enzyme mixture or the *T. reesei* "Turbo" enzyme mixture was mixed with a solution containing both 50% w/w glucose and 5% w/w cellobiose or a solution containing 50% w/w glucose alone, at pH 5.0 and 60° C. for 24 hr and 48 hr.

An unknown species (detected in HPLC chromatograms as described in more detail herein) was produced in a time-dependent manner in these reactions (Table 2). The peak areas of the unknown species are normalized to the peak area of the unknown species in the 24 hr reaction of the CF-402 enzyme mixture and glucose only. These data indicate that the insoluble cellulose substrate, primarily comprising cellulose and lignin, need not be present for the formation of this species. The presence of glucose alone was sufficient for the formation of the species, although production of the species was enhanced by the addition of cellobiose.

TABLE 10-1

Production of Unknown Compound by Enzyme Mixtures

| [Glucose] (w/w) | [Cellobiose] (w/w) | Enzyme | Peak Area of Unknown (normalized) | |
|---|---|---|---|---|
| | | | 24 h | 48 h |
| 50% | — | Turbo | 0.08 | 0.09 |
| | | CF-402 | 1.00 | 1.44 |
| | 5% | Turbo | 0.13 | 0.14 |
| | | CF-402 | 1.32 | 1.70 |

Example 11

Analysis of Cellulose Hydrolysis Products Using Concentrated Acid Hydrolysis

Figure 12:
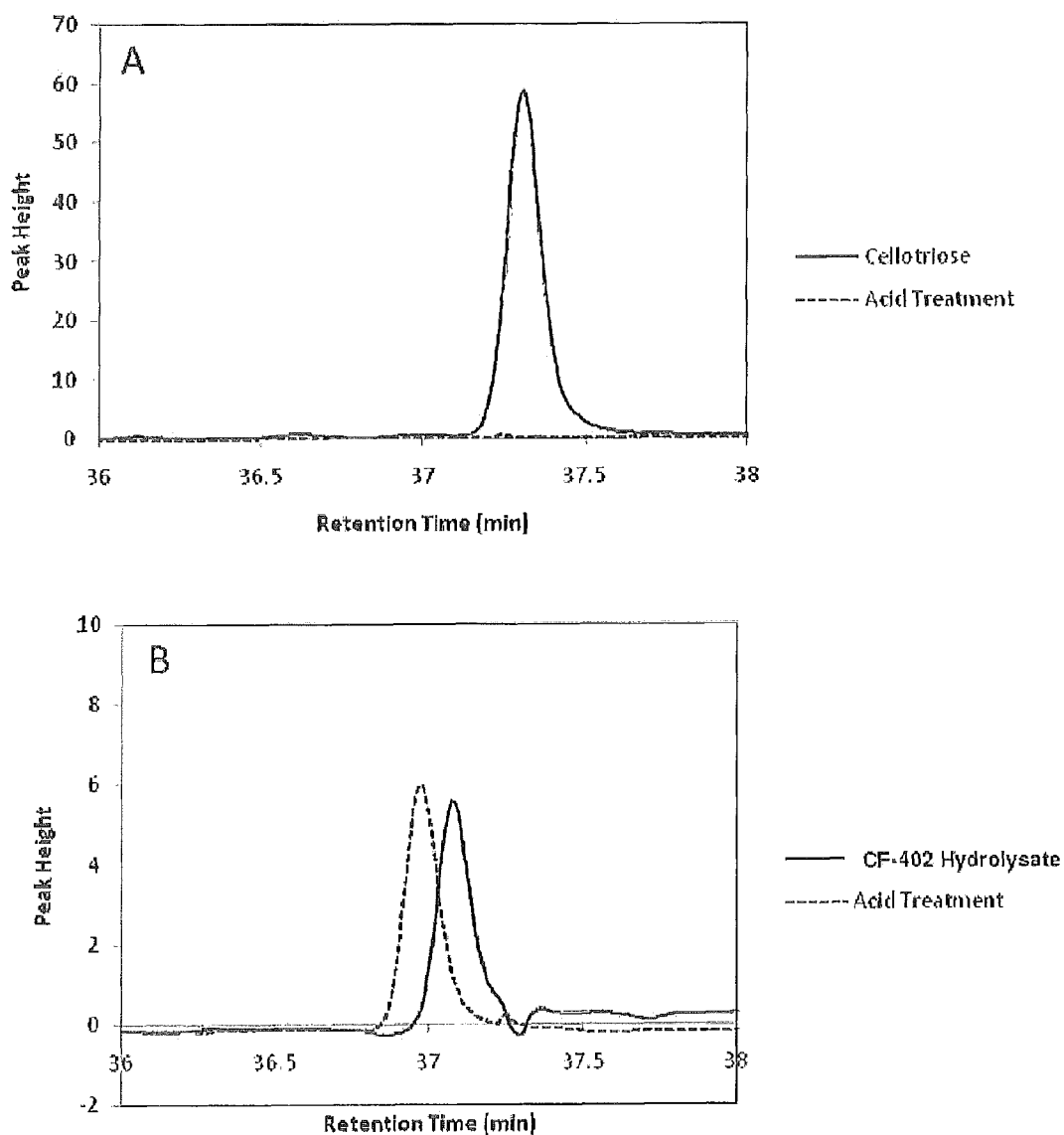
FIGS. 12A and 12B are HPLC chromatograms showing the effect of acid hydrolysis of cellotriose (FIG. 12A) or of cellulose hydrolysis products produced by an enzyme mixture containing cellobiose dehydrogenase (FIG. 12B) as described in Example 11.

The unknown species observed in Example 10 was subjected to acid conditions known to hydrolyse oligosaccharides to test if it represented a glucose oligomer. Such a glucose oligomer could be present as either a direct product of cellulose hydrolysis or from synthesis reaction of the direct products through a reaction such as transglycosylation. Cellotriose, a beta 1-4 trimer of glucose, was used as a positive control. Acid hydrolysis was performed by mixing an equal volume of a sample and 98% sulphuric acid. Acid hydrolysis completely abolished the cellotriose peak in a HPLC chromatogram collected using the method described herein (FIG. 12A) but it did not significantly alter the peak area of the unknown species, though it did have a minor effect on its retention time (FIG. 12B). These results indicate that the unknown species is not a glucose oligomer.

Example 12

Infrared (IR) Spectroscopy of Lignocellulosic Hydrolysate

Figure 13:
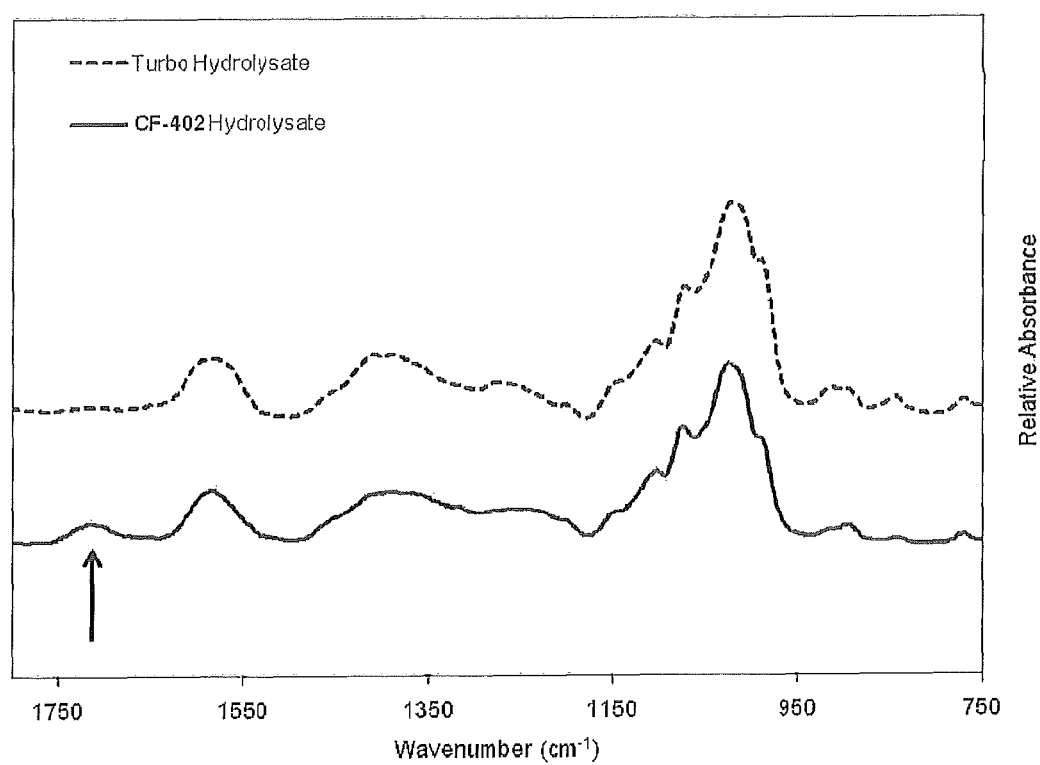
FIG. 13 provides an IR spectrum of cellulose hydrolysate obtained using enzyme mixtures lacking (Turbo) or containing (CF-402) cellobiose dehydrogenase activity. The vertical arrow indicates the carbonyl peak at $1715\ cm^{-1}$ unique to the hydrolysate produced by the CF-402 enzyme mixture.

IR spectroscopy was used to analyze the hydrolysate from reactions with pretreated wheat straw in Example 11. Hydrolysates were selected from reactions which had reached their endpoint (i.e. no additional glucose formation was observed). Hydrolysate was applied dropwise to the ATR detection crystal of a Bruker Vertex 70 Infrared spectrometer, and each drop was allowed to evaporate to form a cast film. A peak at a wavenumber of 1715 $cm^{-1}$ in the spectrum of CF-402 hydrolysate was not observed in the Turbo hydrolysate (FIG. 13). This wavenumber is associated with a vibrational mode of a carbonyl group. In conjunction with other observations described herein that the unknown species can be produced by the CF-402 enzyme mixture from glucose alone, this indicates that the unknown species is an oxidized form of glucose.

Example 13

Identification and Quantification of Glucono-Lactone in Enzymatic Cellulose Hydrolysates There are three forms of oxidized glucose: gluconic acid formed by oxidation at carbon 1, glucuronic acid formed by oxidation at carbon 6 and glucaric acid which is oxidized at carbons 1 and 6. Gluconic acid exists in pH-dependent equilibrium with its lactone form (gluconolactone or 1,5-glucono-lactone, or D-glucono-1,5-lactone) produced via esterification. High-performance liquid chromatography (HPLC) was performed to characterize these compounds in enzymatic cellulose hydrolysates.

Glucuronic acid, glucaric acid and the lactone form of gluconic acid were analyzed by anion-exchange HPLC. The HPLC system was a Dionex DX-500 modular chromatography system consisting of a GP50 gradient pump, a Rheodyne (Idex) six port sampling valve, an AS40 automated sampler, an ED40 or ED50 electrochemical detector with a gold working electrode and Ag/AgCl reference electrode for pulsed amperometric detection (PAD). The CarboPac™ PA1 column (4×250 mm; Dionex) and guard (4×50 mm) consist of a 10 μm diameter polystyrene/divinylbenzene substrate agglomerated with 580 nm MicroBead quaternary ammonium functionalized latex (2% cross linkage; Microbeads).

Samples of glucuronic acid, glucaric acid and gluconolactone were diluted in water to bring them within range of the standards (0.003-0.030 g/L) and injected in a volume of 25 μL. Samples were subjected to an isocratic separation in a solution of 6 mM NaOH for 28 minutes after injection. A 6 minute gradient, raising the NaOH concentration linearly from 10 mM to 300 mM, was then applied. Next, a 5 minute gradient, raising the NaOH concentration from 300 mM to 1 M, was applied. The column was then re-equilibrated with 6 mM NaOH prior to the next run. Peak integration and quantification of standards and unknowns was performed with CHROMELEON® software (Dionex).

Glucose was mixed with a secreted enzyme mixture harvested from CF-402. Specifically, fifty-two mg of the CF-402 enzyme mixture was mixed with a solution containing both 50% w/w glucose, at pH 5.0 and 60° C. for 24 hr and 48 hr. The product of this reaction was analyzed using the above HPLC conditions. One component from the product of this reaction co-eluted with both glucaric acid and gluconolactone (FIG. 14A).

A second HPLC method was used to analyze the glucaric acid, gluconic acid lactone, and the product of the reaction of glucose with the secreted enzyme mixture harvested from CF-402. This method employs a IonPac®AS11-HC column (4×250 mm; Dionex) and AG11-HC guard (4×50 mm) consisting of a 9 μm diameter ethylvinylbenzene polymer cross linked with 55% divinylbenzene polymer agglomerated with a 70 nm alkanol quaternary ammonium latex (6% latex cross linkage) and a capacity of 290 μeq/column (4×250 mm). The HPLC system used for this method comprised a dual gradient pump (DP) with vacuum degassing, dual Rheodyne (Idex) six port sampling valves and an AS automated sampler with diverter valve. The system was equipped with both electrochemical and conductivity detectors. An anion trap column (ATC) was installed in-line between the serial pump and the DC injection valve to remove any anionic species in the eluent and a carbonate removal device which was installed between the chemical suppressor and the conductivity detector to partially remove any carbonate in the mobile phase.

Samples of glucaric acid, gluconic acid lactone, and the product of the reaction of glucose with the secreted enzyme mixture harvested from CF-402 were diluted in water to bring them within range of the standards (0.003-0.030 g/L) and injected in a volume of 25 μL. The samples were subjected to an isocratic separation in a solution of 1 mM NaOH for 6 minutes after injection. A six-minute gradient, raising the NaOH concentration linearly from 1 mM to 60 mM was then applied. The column was subsequently cleaned with a short 1 M NaOH step prior to requilibration in 1 mM NaOH. Peak integration and quantification of standards and unknowns was performed with CHROMELEON® software (Dionex).

Using this second HPLC method, gluconolactone, but not glucaric acid, co-elutes with a component of the product of the reaction of glucose with the secreted enzyme mixture harvested from CF-402 (FIG. 14B). Therefore, the unknown species is gluconolactone, which is produced by the action of one or more enzymes within the C-1 enzyme system.

Example 14

Decrease in Glucose Yield from Cellulose Hydrolysis in the Presence of Oxidoreductases Wheat straw was pretreated and washed as described in Example 1. The cellulose in this pretreated material was hydrolysed by 30 mg *T. reesei* Turbo cellulase per gram of cellulose. The reaction was performed at 50° C. and pH 5.0, with 250 rpm orbital shaking.

Enzymes from the E.C. 1 group of enzymes, the oxidoreductases, were added to the hydrolysate of this reaction in separate reactions. Glucose oxidase from *Aspergillus niger* (E.C. 1.1.3.4), pyranose oxidase from *Coriolus* sp. (E.C. 10.1.3.10) and glucose dehydrogenase from *Pseudomonas* sp. (10.1.1.47), all purchased from Sigma-Aldrich, were tested. Enzymatic reactions were carried out over 72 h at the pH and temperature optima of each enzyme: pH 8.0 and 37° C. for glucose oxidase and glucose dehydrogenase; pH 7.0 and 37° C. for pyranose oxidase. For glucose dehydrogenase, a supplement of one equivalent (with respect to glucose) of beta-nicotinamide adenine dinucleotide hydrate (Sigma) was added to the reaction mixture. Enzymes were dosed at 0.45 mg per gram of starting cellulose. This dose corresponds to 1.5% of the full dose of 30 mg/g, simulating the presence of a low-abundance oxidative enzyme in a mixed enzyme system. The glucose concentrations were determined in each reaction flask and in no-enzyme controls by HPLC (Dionex ICS5000 with a CarboPac™ PA1, 4×250 mm column (Dionex), with an eluent of 6% 200 mM NaOH in degassed ddH$_2$O, run time of 25 minutes at a rate of 1.5 ml/min in which glucose retention time is 11.2 minutes) to determine the glucose yield loss. P-values were determined from a t-statistic calculated for the case of unequal sample sizes and equal variances; there were two to four plus-enzyme and one to two no-enzyme flasks.

TABLE 14-1

Glucose Yield Loss Due to Enzymatic Action of Oxidoreductases

| Enzyme | Glucose Yield Loss | P-value |
|---|---|---|
| Glucose Oxidase | 4.38% | <0.01 |
| Pyranose Oxidase | 3.81% | <0.01 |
| Glucose Dehydrogenase | 2.27% | <0.05 |

These data indicate that a significant decrease in glucose yield can be produced by oxidoreductases present in very low abundance in a cellulolytic enzyme system. Elimination or reduction of these enzymatic activities by any means would therefore result in improved glucose recovery.

Example 15

Saccharification of Acid-Pretreated Corn Stover

In this Example, experiments conducted using CF-404 on acid-pretreated corn stover are described. In these experiments, 0.81% to 6% CF-404 (with regard to glucan concentration) was added to a mixture of water and pre-treated corn stover (NREL) (90 g/kg glucan) at a cellulose concentration of 9% and pH 5. The mixture was incubated at 55° C., with shaking for 73 hours. During this incubation, samples were periodically taken and the sugar concentration determined using by HPLC, using methods known in the art. Cellulose and residual xylan were found to have been converted to their monomeric sugars in high yield.

What is claimed is:

1. A *Myceliophthora thermophile* fungal cell that has been genetically modified to reduce the amount of endogenous cellobiose oxidizing enzyme activity that is produced by the fungal cell, wherein the fungal cell has been genetically modified by deleting endogenous cellobiose dehydrogenase enzymes having at least about 90% or at least about 95% sequence identity to the sequences of SEQ ID NOS:6 and 8.

2. The fungal cell of claim 1, wherein the fungal cell has been genetically modified to reduce the amount of endogenous cellobiose dehydrogenase produced by the fungal cell and to increase the production of at least one saccharide hydrolyzing enzyme, wherein said at least one saccharide hydrolyzing enzyme is selected from beta-glucosidases, endoglucanases, cellobiohydrolases, esterases, beta-xylosidases, xylanases, arabinofuranosidases, alpha-glucuronidases, acetylxylan esterases, feruloyl esterases, alpha-glucuronyl esterases, and GH61 enzymes.

3. The fungal cell of claim 2, wherein said at least one saccharide hydrolyzing enzyme is a *Myceliophthora thermophila* enzyme.

4. The fungal cell of claim 2, wherein said at least one saccharide hydrolyzing enzyme is overexpressed by said fungal cell.

5. The fungal cell of claim 2, wherein said overexpressed saccharide hydrolyzing enzyme is beta-glucosidase.

* * * * *